US009556426B2

(12) United States Patent
Singh et al.

(10) Patent No.: US 9,556,426 B2
(45) Date of Patent: Jan. 31, 2017

(54) PROTEIN KINASE CONJUGATES AND INHIBITORS

(75) Inventors: Juswinder Singh, Ashland, MA (US); Russell Colyn Petter, Stow, MA (US); Deqiang Niu, Lexington, MA (US); Lixin Qiao, Andover, MA (US); Arthur Kluge, Lincoln, MA (US); Roy Lobb, Westwood, MA (US); Shomir Ghosh, Brookline, MA (US); Zhendong Zhu, Westborough, MA (US)

(73) Assignee: Celgene Avilomics Research, Inc., Cambridge, MA (US)

( * ) Notice: Subject to any disclaimer, the term of this patent is extended or adjusted under 35 U.S.C. 154(b) by 1026 days.

(21) Appl. No.: 12/882,484

(22) Filed: Sep. 15, 2010

(65) Prior Publication Data

US 2011/0117073 A1 May 19, 2011

Related U.S. Application Data

(60) Provisional application No. 61/242,988, filed on Sep. 16, 2009.

(51) Int. Cl.

| | |
|---|---|
| ***C12N 9/96*** | (2006.01) |
| ***C07D 401/14*** | (2006.01) |
| ***C07D 403/04*** | (2006.01) |
| ***C07D 403/06*** | (2006.01) |
| ***C07D 403/12*** | (2006.01) |
| ***A61K 47/48*** | (2006.01) |
| ***C07D 213/74*** | (2006.01) |
| ***C07D 213/81*** | (2006.01) |
| ***C07D 213/82*** | (2006.01) |
| ***C07D 215/22*** | (2006.01) |
| ***C07D 231/12*** | (2006.01) |
| ***C07D 239/42*** | (2006.01) |
| ***C07D 239/48*** | (2006.01) |
| ***C07D 333/68*** | (2006.01) |
| ***C07D 401/12*** | (2006.01) |
| ***C07D 403/14*** | (2006.01) |
| ***C07D 409/04*** | (2006.01) |
| ***C07D 409/12*** | (2006.01) |
| ***C07D 409/14*** | (2006.01) |
| ***C07D 413/12*** | (2006.01) |
| ***C07D 413/14*** | (2006.01) |
| ***C07D 417/12*** | (2006.01) |
| ***C07D 417/14*** | (2006.01) |
| ***C07D 471/04*** | (2006.01) |
| ***C07D 471/10*** | (2006.01) |
| ***C07D 487/04*** | (2006.01) |
| ***C07D 495/04*** | (2006.01) |
| ***C07D 498/04*** | (2006.01) |
| ***C12N 9/12*** | (2006.01) |

(52) U.S. Cl.

CPC .......... *C12N 9/96* (2013.01); *A61K 47/48061* (2013.01); *A61K 47/48238* (2013.01); *C07D 213/74* (2013.01); *C07D 213/81* (2013.01); *C07D 213/82* (2013.01); *C07D 215/22* (2013.01); *C07D 231/12* (2013.01); *C07D 239/42* (2013.01); *C07D 239/48* (2013.01); *C07D 333/68* (2013.01); *C07D 401/12* (2013.01); *C07D 401/14* (2013.01); *C07D 403/04* (2013.01); *C07D 403/06* (2013.01); *C07D 403/12* (2013.01); *C07D 403/14* (2013.01); *C07D 409/04* (2013.01); *C07D 409/12* (2013.01); *C07D 409/14* (2013.01); *C07D 413/12* (2013.01); *C07D 413/14* (2013.01); *C07D 417/12* (2013.01); *C07D 417/14* (2013.01); *C07D 471/04* (2013.01); *C07D 471/10* (2013.01); *C07D 487/04* (2013.01); *C07D 495/04* (2013.01); *C07D 498/04* (2013.01); *C12N 9/1205* (2013.01)

(58) Field of Classification Search

CPC ........................................................ C12N 9/96

See application file for complete search history.

(56) References Cited

U.S. PATENT DOCUMENTS

| | | | |
|---|---|---|---|
| 3,710,795 | A | 1/1973 | Higuchi et al. |
| 4,650,750 | A | 3/1987 | Giese |
| 4,709,016 | A | 11/1987 | Giese |
| 5,262,564 | A | 11/1993 | Kun et al. |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |

(Continued)

FOREIGN PATENT DOCUMENTS

| | | | | |
|---|---|---|---|---|
| CN | 101054380 A | | 10/2007 | |
| EP | 1939625 | | 7/2008 | |
| JP | 2000508657 | | 7/2000 | |
| JP | 2005534286 | | 11/2005 | |
| JP | 2006517959 | | 8/2006 | |
| JP | 2010504324 | | 2/2010 | |
| WO | WO 97/38983 | | 10/1997 | |
| WO | WO99/06378 | | 2/1999 | |
| WO | WO 00/18895 | * | 4/2000 | ............... C12N 9/12 |
| WO | WO 03/081210 | | 10/2003 | |

(Continued)

OTHER PUBLICATIONS

Denny, 2002, Irreversible inhibitors of the erbB family of protein tyrosine kinases, Pharmacology & Therapeutics, 93: 253-261.*

(Continued)

*Primary Examiner* — Amber D Steele
(74) *Attorney, Agent, or Firm* — Jones Day

(57) ABSTRACT

The invention relates to protein conjugates that contain a protein kinase containing a cysteine residue in the ATP binding site and an inhibitor that is covalently and irreversibly bonded to said cysteine residue, such that the activity of the protein kinase is irreversibly inhibited. The invention also relates to compounds that irreversibly inhibit protein kinases.

48 Claims, 4 Drawing Sheets

(56) References Cited

U.S. PATENT DOCUMENTS

| | | | |
|---|---|---|---|
| 5,610,020 A | 3/1997 | Giese et al. | |
| 5,650,270 A | 7/1997 | Giese et al. | |
| 5,756,466 A | 5/1998 | Bemis et al. | |
| 5,760,041 A | 6/1998 | Wisser et al. | |
| 5,856,116 A | 1/1999 | Wilson et al. | |
| 6,002,008 A | 12/1999 | Wissner et al. | |
| 6,025,147 A | 2/2000 | Bemis et al. | |
| 6,057,119 A | 5/2000 | Wilson et al. | |
| 6,162,613 A | 12/2000 | Su et al. | |
| 6,251,912 B1 | 6/2001 | Wissner et al. | |
| 6,288,082 B1 | 9/2001 | Wissner et al. | |
| 6,335,155 B1 | 1/2002 | Wells et al. | |
| 6,344,455 B1 | 2/2002 | Bridges et al. | |
| 6,384,051 B1 | 5/2002 | Frost et al. | |
| 6,552,216 B1 | 4/2003 | Singh et al. | |
| 6,569,876 B1 | 5/2003 | Cheronis et al. | |
| 6,602,863 B1 | 8/2003 | Bridges et al. | |
| 6,664,247 B2 | 12/2003 | Bebbington et al. | |
| 6,686,350 B1 | 2/2004 | Zheng et al. | |
| 6,849,267 B2 | 2/2005 | Bemis et al. | |
| 6,919,178 B2 | 7/2005 | Erlanson et al. | |
| 6,949,534 B2 | 9/2005 | Zheng et al. | |
| 6,974,809 B2 | 12/2005 | Golec et al. | |
| 7,202,033 B2 | 4/2007 | Prescott et al. | |
| 7,235,576 B1 | 6/2007 | Riedl et al. | |
| 7,383,135 B1 | 6/2008 | Xie et al. | |
| 7,407,939 B2 * | 8/2008 | Livnah et al. | 514/6.9 |
| 7,504,410 B2 | 3/2009 | Bryant et al. | |
| 7,528,143 B2 | 5/2009 | Noronha et al. | |
| 7,792,665 B2 | 9/2010 | Alessi et al. | |
| 7,982,036 B2 | 7/2011 | Singh et al. | |
| 7,989,465 B2 | 8/2011 | Singh et al. | |
| 8,188,137 B2 | 5/2012 | Niu et al. | |
| 8,242,271 B2 * | 8/2012 | Singh et al. | 544/317 |
| 8,293,705 B2 | 10/2012 | Niu et al. | |
| 8,309,685 B2 | 11/2012 | Petter et al. | |
| 8,329,901 B2 | 12/2012 | Singh et al. | |
| 8,338,439 B2 | 12/2012 | Singh et al. | |
| 8,445,498 B2 | 5/2013 | Singh et al. | |
| 8,450,335 B2 | 5/2013 | Singh et al. | |
| 8,524,760 B2 | 9/2013 | Niu et al. | |
| 8,563,568 B2 | 10/2013 | Witowski et al. | |
| 8,586,600 B2 | 11/2013 | Singh et al. | |
| 8,603,737 B2 | 12/2013 | Hagel et al. | |
| 8,609,679 B2 | 12/2013 | Singh et al. | |
| 8,710,222 B2 | 4/2014 | Singh et al. | |
| 8,741,837 B2 | 6/2014 | Niu et al. | |
| 8,748,606 B2 | 6/2014 | Singh et al. | |
| 8,778,877 B2 | 7/2014 | Niu et al. | |
| 8,980,935 B2 | 3/2015 | Niu et al. | |
| 9,040,541 B2 | 5/2015 | Singh et al. | |
| 9,067,929 B2 | 6/2015 | Singh et al. | |
| 9,163,061 B2 | 10/2015 | Petter et al. | |
| 2002/0058809 A1 | 5/2002 | Emmanuel et al. | |
| 2004/0009890 A1 | 1/2004 | Erickson et al. | |
| 2004/0023957 A1 | 2/2004 | Wang et al. | |
| 2004/0049032 A1 | 3/2004 | Charrier et al. | |
| 2004/0229937 A1 | 11/2004 | Dumas et al. | |
| 2004/0235829 A1 | 11/2004 | Scott et al. | |
| 2005/0026933 A1 | 2/2005 | Greenberger et al. | |
| 2005/0032798 A1 | 2/2005 | Boyer et al. | |
| 2005/0038031 A1 | 2/2005 | Dumas et al. | |
| 2005/0059703 A1 | 3/2005 | Wilhelm et al. | |
| 2005/0186630 A1 | 8/2005 | Erlanson et al. | |
| 2006/0003317 A1 | 1/2006 | Perni et al. | |
| 2006/0030553 A1 | 2/2006 | Zheng et al. | |
| 2006/0079494 A1 | 4/2006 | Santi et al. | |
| 2006/0174816 A1 | 8/2006 | Acharya et al. | |
| 2006/0235046 A1 | 10/2006 | Zacharchuk et al. | |
| 2006/0247262 A1 | 11/2006 | Baenteli et al. | |
| 2007/0020684 A1 | 1/2007 | Bledsoe et al. | |
| 2007/0020704 A1 | 1/2007 | Wilhelm et al. | |
| 2007/0082884 A1 | 4/2007 | Taunton et al. | |
| 2007/0179083 A1 | 8/2007 | Paul et al. | |
| 2007/0249031 A1 | 10/2007 | Binch et al. | |
| 2007/0259869 A1 | 11/2007 | Binch et al. | |
| 2007/0299092 A1 | 12/2007 | Floyd et al. | |
| 2008/0032963 A1 | 2/2008 | Binch et al. | |
| 2008/0108636 A1 | 5/2008 | Honigberg et al. | |
| 2008/0269140 A1 | 10/2008 | Wang et al. | |
| 2008/0300268 A1 * | 12/2008 | Singh et al. | 514/275 |
| 2009/0137588 A1 | 5/2009 | Singh et al. | |
| 2009/0306085 A1 | 12/2009 | Petter et al. | |
| 2010/0185419 A1 | 7/2010 | Singh et al. | |
| 2011/0117073 A1 | 5/2011 | Singh et al. | |
| 2011/0230476 A1 | 9/2011 | Niu et al. | |
| 2011/0269244 A1 | 11/2011 | Petter et al. | |
| 2013/0065879 A1 | 3/2013 | Singh et al. | |
| 2013/0072469 A1 | 3/2013 | Singh et al. | |
| 2013/0131105 A1 | 5/2013 | Petter et al. | |
| 2014/0057929 A1 | 2/2014 | Witowski et al. | |
| 2014/0213574 A1 | 7/2014 | Singh et al. | |
| 2014/0303165 A1 | 10/2014 | Singh et al. | |
| 2014/0323465 A1 | 10/2014 | Niu et al. | |
| 2015/0031106 A1 | 1/2015 | Niu et al. | |
| 2015/0175657 A1 | 6/2015 | Niu et al. | |
| 2015/0252019 A1 | 9/2015 | Singh et al. | |

FOREIGN PATENT DOCUMENTS

| | | | |
|---|---|---|---|
| WO | WO 2004/000833 | 12/2003 | |
| WO | WO 2004/048343 | 6/2004 | |
| WO | WO 2004/069791 | 8/2004 | |
| WO | WO 2004/072261 * | 8/2004 | |
| WO | WO2004/078128 | 9/2004 | |
| WO | WO2004/078746 | 9/2004 | |
| WO | WO2004/078747 | 9/2004 | |
| WO | WO2004/113274 | 12/2004 | |
| WO | WO2005/000197 A2 | 1/2005 | |
| WO | WO2005/000284 | 1/2005 | |
| WO | WO2005/026158 | 3/2005 | |
| WO | WO 2005/034840 A2 | 4/2005 | |
| WO | WO 2005/069894 | 8/2005 | |
| WO | WO 2005/075425 * | 8/2005 | C07D 213/00 |
| WO | WO2005/114219 A2 | 12/2005 | |
| WO | WO 2006/021544 | 3/2006 | |
| WO | WO2006/040056 | 4/2006 | |
| WO | WO2006/084058 A2 | 8/2006 | |
| WO | WO2006/117567 A2 | 11/2006 | |
| WO | WO2006/117570 A1 | 11/2006 | |
| WO | WO2006/125539 | 11/2006 | |
| WO | WO 2006/132739 A2 | 12/2006 | |
| WO | WO 2006/132739 A3 | 12/2006 | |
| WO | WO 2007/038613 A2 | 4/2007 | |
| WO | WO2007/062459 A1 | 6/2007 | |
| WO | WO 2007/085833 | 8/2007 | |
| WO | WO 2007/117215 A1 | 10/2007 | |
| WO | WO 2007/120339 | 10/2007 | |
| WO | WO 2007/133352 A2 | 11/2007 | |
| WO | WO 2007/136790 * | 11/2007 | |
| WO | WO2007/136790 A2 | 11/2007 | |
| WO | WO 2008/039218 A2 | 4/2008 | |
| WO | WO 2008/049123 | 4/2008 | |
| WO | WO 2008/073687 | 6/2008 | |
| WO | WO 2008/079719 | 7/2008 | |
| WO | WO2008/092199 A1 | 8/2008 | |
| WO | WO 2008/144463 | 11/2008 | |
| WO | WO 2008/144464 | 11/2008 | |
| WO | WO 2008/151183 A1 | 12/2008 | |
| WO | WO 2009/030890 | 3/2009 | |
| WO | WO 2009/051822 | 4/2009 | |
| WO | WO 2009/082697 | 7/2009 | |
| WO | WO 2009/082701 | 7/2009 | |
| WO | WO 2009/091550 A2 | 7/2009 | |
| WO | WO 2009/091550 A8 | 7/2009 | |
| WO | WO 2009/158571 | 12/2009 | |
| WO | WO 2010/028236 | 3/2010 | |
| WO | WO 2010/123870 | 10/2010 | |
| WO | WO 2011/002807 | 1/2011 | |
| WO | WO 2011/002808 | 1/2011 | |
| WO | WO 2011/031896 | 3/2011 | |
| WO | WO 2011/034907 | 3/2011 | |

(56) References Cited

FOREIGN PATENT DOCUMENTS

| | | |
|---|---|---|
| WO | WO 2011/082285 | 7/2011 |
| WO | WO 2011/090760 | 7/2011 |
| WO | WO 2012/021444 | 2/2012 |

OTHER PUBLICATIONS

Atwell et al., "A Novel Mode of Gleevec Binding is Revealed by the Structure of Spleen Tyrosine Kinase," The Journal of Biological Chemistry, 279:55827-55832 (2004).
Bantscheff et al. "Quantitative Chemical Proteomics Reveals Mechanisms of Action of Clinical ABL Kinase Inhibitors," Nature Biotechnology, 25:1035-1044 (2007).
Bilodeau et al., "Potent *N*-(1,3-Thiazol-2-yl)Pyridine-2-Amine Vascular Endothelial Growth Factor Receptor Tyrosine Kinase Inhibitors with Excellent Pharmacokinetics and Low Affinity for the hERG Ion Channel," J. Med. Chem., 47:6363-6372 (2004).
Braselmann et al., "R406, An Orally Available Spleen Tyrosine Kinase Inhibitor Blocks Fc Receptor Signaling and Reduces Immune Complex-Mediated Inflammation," J Pharmacol Exp Ther., 319:998-1008 (2006).
Cohen et al., "Structural Bioinformatics-Based Design of Selective, Irreversible Kinase Inhibitors," Science, 308:1318-1321 (2005).
Dragovich et al., "Structure-Based Design, Synthesis, and Biological Evaluation of Irreversible Human Rhinovirus 3C Protease Inhibitors. 6. Structure-Activity Studies of Orally Bioavailable, 2-Pyridone-Containing Peptidomimetics," J. Med. Chem., 45:1607-1623 (2002).
Fradera et al., "Unsupervised Guided Docking of Covalently Bound Ligands," Journal of Computer-Aided Molecular Design, 18:635-650 (2004).
Fry et al., "Specific, Irreversible Inactivation of the Epidermal Growth Factor Receptor and erbB2, by a New Class of Tyrosine Kinase Inhibitor," Proc. Natl. Acad. Sci. USA, 95:12022-12027 (1998).
Gaspar et al., "Cysteine 116 Participates in Intermolecular Bonding of the Human $VEGF_{121}$ Homodimer," Archives of Biochemistry and Biophysics, 404:126-135 (2002).
Heredia et al., "In Situ Preparation of Protein—"Smart" Polymer Conjugates with Retention of Bioactivity," J. Am. Chem. Soc., 127:16955-16960 (2005).
Johnson et al., "Structure-Based Design of a Parallel Synthetic Array Directed Toward the Discovery of Irreversible Inhibitors of Human Rhinovirus 3C Protease," J. of Med. Chem. 45:2016-2023 (2002).
Kwak et al., "Irreversible Inhibitors of the EGF Receptor may Circumvent Acquired Resistance to Gefitinib," Proc. Natl. Acad. Sci., 102:7665-7670 (2005).
Pan et al., "Discovery of Selective Irreversible Inhibitors for Bruton's Tyrosine Kinase," ChemMedChem, 2:58-61 (2007).
Powers et al., "SAR and Mode of Action of Novel Non-Nucleoside Inhibitors of Hepatitis C NS5b RNA Polymerase," J. Med Chem., 49:1034-1046 (2006).
Ray et al., "Design of Novel Synthetic MTS Conjugates of Bile Acids for Site-Directed Sulfhydrl Labeling of Cysteine Residues in Bile Acid Binding and Transporting Proteins," Bioorganic & Medicinal Chemistry Letters, 16:1473-1476 (2006).
Schirmer et al., "Targeted Covalent Inactivation of Protein Kinases by Resorcylic Acid Lactone Polyketides," Proc. Natl. Acad. Sci., 103:4232-4239 (2006).
Singh et al., Structure-Based Design of a Potent, Selective, and Irreversible Inhibitor of the Catalytic Domain of the erbB Receptor Subfamily of Protein Tyrosine Kinases, J. Med. Chem., 40:1130-1135 (1997).
Toth et al., "Computational Approach to Site-Directed Ligand Discovery," Proteins, 68:551-560 (2007).
Wissner et al., "2-(Quinazolin-4-Ylamino)-[1,4] Benzoquinones as Covalent-Binding, Irreversible Inhibitors of the Kinase Domain of Vascular Endothelial Growth Factor Receptor-2," J. Med. Chem., 48:7560-7581 (2005).
Wood et al., "6-Ethynylthieno[3,2-d]- and 6-Ethynylthieno[2,3-d]Pyrimidin-4-Anilines as Tunable Covalent Modifers of ErbB Kinases," Proc. Natl. Acad. Sci., 105:2773-2778 (2008).
Zhang et al., "Targeting Cancer with Small Molecule Kinases Inhibitors," Nature Reviews Cancer, 9:28-39 (2009).
Boggon, 2005, "Crystal structure of the Jak3 kinase domain in complex with a staurosporine analog", Blood, 106(3):996-1002.
European Search Report of European Application No. 10817748.6-1453, dated Apr. 17, 2014.
International Search Report and Written Opinion of PCT Application No. PCT/US09/056025, mailed Feb. 2, 2010.
International Search Report and Written Opinion of PCT Application No. PCT/US10/048916, mailed Mar. 15, 2011.
Baker, "Factors in Design of Active-Site Directed Irreversible Inhibitors", J. Pharmaceutical Sciences, 1964, 53(4), 347-364.
Barbas et al., "Immune Versus Natural Selection: Antibody Aldolases with Enzymic Rates But Broader Scope;" Science; vol. 278, Dec. 19, 1997; www.sciencemag.org; pp. 2085-2092.
Baskin et al., Copper-free click chemistry for dynamic in vivo imaging; PNAS: Proceedings of the National Academy of Sciences of the United States of America, The Geography of poverty, vol. 104, No. 43, Oct. 23, 2007; www.pnas.org/cgi/doi/10.1073/pnas.0707090104; pp. 16793-16797.
Blight et al., "Molecular virology of hepatitis C virus: an update with respect to potential antiviral targets;" Antiveral Therapy 3 (Supplement 3); Second International Conference on Therapies for Viral Hepatitis; Copyright 1998 International Medical Press; pp. 71-81.
Choi et al., "Chemoselective small molecules that covalently modify one lysine in a non-enzyme protein in plasma;" Natural Chemical Biology; vol. 6, Feb. 2010; www.nature.com/naturechemicalbiology; pp. 133-139.
Dal Maso and Franceschi, "Epidemiology of non-Hodgkin lymphomas and other haemolymphopoietic neoplasms in people with AIDS;" The Lancet Oncology, vol. 4, Feb. 2003; hllp:l/oncology.thelancel.com; pp. 110-119.
De Biase et al., "Chemistry of the Inactivation of 4-Aminobutyrate Aminotransferase by the Antiepileptic Drug Vigabatrin;" The Journal of Biological Chemistry; Copyright 1991 by The American Society for Biochemistry and Molecular Biology, Inc.; vol. 266, No. 30, Oct. 25, 1991; pp. 20056-20061.
Denny, 2002, "Irreversible inhibitors of the erbB family of protein tyrosine kinases", Pharmacol Ther; 93:253-261.
Dewitte et al. 1996, "SMoG: de novo design method based on simple, fast, and accurate free energy estimates. 1. Methology and supporting evidence", J Am Chem Soc; 118:11733-11744.
Doppalapudi et al. "Chemically programmed antibodies: Endothelin receptor targeting CovX-Bodies;" Bioorganic & Medicinal Chemistry Letters 17, The Tetrahedron Journal for Research at the Interface of Chemistry and Biology; www.sciencedirect.com; Copyright 2006 Elsevier Ltd.; (2007); pp. 501-506.
Ekicki et al., 2003, "Design, synthesis and evaluation of novel irreversible inhibitors for caspases", Ph.D. Thesis, Georgia Institute of Technology, Chapter 4.
European Search Opinion and Supplementary European Search Report dated Feb. 6, 2014, from European Application No. 10841710.6.
Feldman et al., J. Biol. Chem., vol. 280, No. 20, pp. 19867-19874, 2005.
Fretheim et al. Int. J. Protein Res. 14, pp. 451-456, 1979.
Fry et al. 1999, "Inhibition of the Epidermal Growth Factor Receptor Family of Tyrosine Kinases as an Approach to Cancer Chemotherapy: Progression from Reversible to Irreversible Inhibitors", Pharmacol. Ther.; 82(2-3):207-218.
Gordon and Ford, 1972, "The Chemist's Companion", John Wiley and Sons, Inc., p. 108.
Graupera et al., "Angiogenesis selectively requires the p1 OOa isoform of P13K to control endothelial cell migration;" The International Weekly Journal of Science: Nature, A Gut Issue: Bacterial symbiosis shapes a healthy immune response, vol. 453, No. 7195, May 29, 2008; pp. 662-666.

(56) References Cited

OTHER PUBLICATIONS

Guillerm et al., "Inactivation of S-Adenosyi-Lhomocysteine Hydrolase by 6'-Cyano-5', 6'-didehydro-6'-deoxyhomoadenosine and 6'-Chloro-6'-cyano-5', 6'-didehydro-6'-deoxyhomoadenosine. Antiviral and Cytotoxic Effects;" Journal of Medicinal Chemistry, vol. 49, No. 4, Feb. 23, 2006; Copyright 2006 by The American Chemical Society; Published on the web Jan. 27, 2006; pp. 1223-1226.
Guo et al., "Breaking the one antibody-one target axiom;" Proceedings of the National Academy of Sciences of the United States of America; vol. 103, No. 29, Jul. 18, 2006; www.pnas.org/cgi/doi/10.1073/pnas.0603822103; pp. 11009-11014.
Hagel et al., 2011, "Selective irreversible inhibition of a protease by targeting a noncatalytic cysteine", Nat Chem Biol; 7(1):22-24.
Hansen et al., 2005, "Allosteric inhibition of PTP1B activity by selective modification of a non-active site cysteine residue", Biochemistry; 44(21):7704-7712.
Hermann and Niedobilek, "Epstein-Barr virus-associated carcinomas: facts and fiction;" Journal of Pathology, The Journal of the Pathological Society of Great Britain and Ireland, vol. 199, No. 2, Feb. 2003; Published online in Wiley InterScience (www.interscience.wiley.com); Copyright 2003 John Wiley & Sons, Ltd.; pp. 140-145.
Hernandez-Avila et al., "Human Papilloma Virus 16-18 Infection and Cervical Cancer in Mexico: A Case-Control Study;" Archives of Medical Research, vol. 28, No. 2; 1997; pp. 265-271.
Huang et al., The role of thyroid autoantibodies in the development of thyroid dysfunction in Taiwanese chronic hepatitis C patients with interferon-alpha and ribavirin combination therapy; Journal of Viral Hepatitis, vol. 13, No. 6, Jun. 2006; Copyright 2006 Blackwell Publishing Ltd; pp. 396-401.
Huang, "Fluorescence Polarization Competition Assay: The Range of Resolvable Inhibitor Potency is Limited by the Affinity of the Fluorescent Ligand;" Biojournal of Biomolecular Screening, The Official Journal of the Society for Biomolecular Screening, vol. 8, No. 1, Feb. 2003; Copyright 2003 The Society for Biomolecular Screening; www.sbsonline.org; pp. 34-38.
Hung et al., "Long-term effect of interferon alpha-2b plus ribavirin therapy on incidence of hepatocellular carcinoma in patients with hepatitis C virus-related cirrhosis"; Journal of Viral Hepatitis, vol. 13, No. 6, Jun. 2006; Copyright 2006 Blackwell Publishing Ltd., pp. 409-414.
Hur et al., 2008, "Clinical stage EGFR inhibitors irreversibly alkylate Bmx kinase", Bioorg Med Chem Lett; 18(22):5916-5919.
International Preliminary Report on Patentability of International Application No. PCT/US2009/056025, dated Mar. 8, 2011.
International Preliminary Report on Patentability of International Application No. PCT/US2010/048916, issued Mar. 20, 2012.
International Preliminary Report on Patentability of International Application No. PCT/US2010/062473, dated Jul. 4, 2012.
International Search Report and Written Opinion from International Application No. PCT/US2010/062473, mailed May 24, 2011.
Johnson et al., 2003, "Inhibitors tethered near the acetylcholinesterase active site serve as molecular rulers of the peripheral and acylation sites", J Biol Chem; 278:38948-38955.
Lawate et al., "Trifiuoromethylacetylenic Alcohols as Affinity Labels: Inactivation of Estradiol Dehydrogenase by a Triftuoromethylacetylenic Secoestradiol;" Journal of Medicinal Chemistry; vol. 33, No. 9, Sep. 1990; Copyright 1990 American Chemical Society; pp. 2319-2321.
Leite et al. 2007, "Frog: a Free Online drug 3D conformation generator", Nucleic Acids Res; 35:W568-W572.
Levitsky et al., 2003, "Selective inhibition of engineered receptors via proximity-accelerate alkylation", Org Lett; 5(5):693-696.
Li et al. 2004, "Chemical Adaptor Immunotherapy: Design, Synthesis, and Evaluation of Novel Integrin-Targeting Devices;" Journal of Medicinal Chemistry, vol. 47, pp. 5630-5640.
Lima et al., 2005, "Bioisosterism: A Useful Strategy for Molecular Modification and Drug Design", Curr Med Chem; 12:23-49.
Lyne, 2002, "Structure-based virtual screening: an overview", Drug Discovery Today; 7 (20):1047-1055.
Marone et al., "Targeting phosphoinosilide 3-kinase—Moving towards therapy;" Biochimica et Biophysica Acta (BBA), Proteins and Proteomics, vol. 1784, No. 1, Jan. 2008; Copyright 2007 Elsevier B.V.; pp. 159-185.
Marrano et al., 2001, "Evaluation of novel dipeptide-bound α,β-unsaturated amides and epoxides as irreversible inhibitors of guinea pig liver transglutaminase", Bioorganic & Medicinal Chemistry; 9:1923-1928.
Moll et al., 2005, "BALLView: An object-oriented molecular visualization and modeling framework", Journal of Computer-Aided Molecular Design; 19:791-800.
Moradpour and Blum, "Current and evolving therapies for hepatitis C;" European Journal of Gastroenterology & Hepatology; Official Journal of the European Association for Gastroenterology and Endoscopy, vol. 11, No. 11; Copyright 1999 Lippincott Williams & Wilkins; pp. 1199-1202.
Mortreux et al., "Molecular and cellular aspects of HTLV-1 associated leukemogenesis in vivo;" Leukemia, Normal and Malignant Hemopoiesis, vol. 17, No. 1, Jan. 2003; www.nature.com/leu; Official Journal of the Leukaemia Research Fund, UK; Copyright 2003 Nature Publishing Group; pp. 26-38.
Nango et al., "Active Site Mapping of 2-Deoxy-scyllo-inosose Synthase, the Key Starter Enzyme for the Biosynthesis of 2-Deoxystreptamine. Mechanism-Based Inhibition and Identification of Lysine-141 as the Entrapped Nucleophile;" Journal of the American Chemical Society, JOC Articles published on the web Sep. 23, 2003; Copyright 2004 American Chemical Society; J. Org. Chem. 2004, vol. 69, No. 3, Feb. 6, 2004, pp. 593-600.
Nonaka et al., "FLAG-tag selective covalent protein labeling via a binding-induced acyl-transfer reaction;" Bioorganic & Medicinal Chemistry Letters 19, The Tetrahedron Journal for Research at the Interface of Chemistry and Biology; www.sciencedirect.com; Copyright 2009 Elsevier Ltd.; (2009); pp. 6696-6699.
Notification of Transmittal of the International Search Report and the Written Opinion of the International Searching Authority, or the Declaration for International Application No. PCT/US2010/062473 mailed on May 24, 2011.
Office Action mailed Apr. 30, 2013 for U.S. Appl. No. 12/982,352, filed Dec. 30, 2010.
Office Action mailed Dec. 10, 2012 for U.S. Appl. No. 12/982,352, filed Dec. 30, 2010.
Office Action mailed Dec. 31, 2014 for U.S. Appl. No. 12/982,352, filed Dec. 30, 2011.
Office Action mailed Jan. 20, 2015 for U.S. Appl. No. 12/882,484, filed Sep. 15, 2010.
Office Action mailed Jun. 26, 2014 for U.S. Appl. No. 12/554,433, filed Sep. 4, 2009.
Office Action mailed Jun. 5, 2014 for U.S. Appl. No. 12/882,484, filed Sep. 15, 2010.
Office Action mailed Mar. 27, 2012 for U.S. Appl. No. 12/554,433, filed Sep. 4, 2009.
Office Action mailed Nov. 21, 2014 for U.S. Appl. No. 12/554,433, filed Sep. 4, 2009.
Office Action mailed Nov. 26, 2012 for U.S. Appl. No. 12/554,433, filed Sep. 4, 2009.
Office Action mailed Sep. 12, 2014 for U.S. Appl. No. 12/982,352, filed Dec. 30, 2010.
Ploeman et al., 1996, "Irreversible inhibition of cytosolic glutathione-S-transferases", Glutathione S-Transferases Structure, Function and Clinical Implications, Taylor and Francis Ltd. London, Chapter 13:143-152.
Popkov et al., "Instant immunity through chemically programmable vaccination and covalent self-assembly;" Proceedings of the National Academy of Sciences of the United States of America, Signaling networks and body shape; vol. 106, No. 11, Mar. 17, 2009; www.pnas.org/cgi/doi/10.1073/pnas.09001471 06; pp. 4378-4383.

(56) References Cited

OTHER PUBLICATIONS

Rader et al., "Chemically programmed monoclonal antibodies for cancer therapy: Adaptor immunotherapy based on a covalent antibody catalyst;" Proceedings of the National Academy of Sciences of the United States of America, Fungal susceptibility caused by apoptosis inhibitors; vol. 100, No. 9, Apr. 29, 2003; www.pnas.org/cgi/doi/10.1073/pnas.0931308100; pp. 5396-5400.
Reynolds et al., "Phospholipase A2 Inhibition and Modification by Manoalogue;" Journal of the American Chemical Society; Copyright 1988 American Chemical Society; J. Am. Chem. Soc 1998, 110, pp. 5172-5177.
Rostovtsev et al., "A Stepwise Huisgen Cycloaddition Process: Copper(I)-Catalyzed Regioselective "Litigation" of Azides and Terminal Alkynes;" Angewandte Cheme, A Journal of the Gesellschaft Deutscher Chemiker; International Edition 2002, vol. 41, No. 14, Jul. 15, 2002; Copyright 2002 Wiley-VCH Verlag GmbH, 69451 Weinheim, Germany 2002; pp. 2596-2599.
Shimada et al., 2000, "Analysis of knowledge-based protein-ligand potentials using a self-consistent method", Protein Sci., 9(4)765-75.
Singh et al., 2010, "Targeted covalent drugs of the kinase family", Curr Opin Chem Biol; 14:475-480.
Singh et al., 2011, "The resurgence of covalent drugs", Nat Rev Drug Discovery; 10:307-317.
Statsuk et al., "Tuning a Three-Component Reaction for Trapping Kinase Substrate Complexes;" Journal of the American Chemical Society, JACS Articles published on web Nov. 20, 2008; Copyright 2008 American Chemical Society; J. Am. Chem. Soc., vol. 130, No. 51,2008, 130, pp. 17568-17574.
Sun et al, Structure-Based Design, Synthesis, Evaluation, and Crystallographic Studies of Conformationally Constrained Smac Mimetics as Inhibitors of the X-linked Inhibitor of Apoptosis Protein (XIAP); Journal of Medicinal Chemistry, vol. 51, No. 22, Nov. 27, 2008; J. Med. Chem. 2008; Copyright 2008 American Chemical Society; Published on Web Oct. 28, 2008; pp. 7169-7180.
Sun et al., "Carbohydrate and Protein Immobilization onto Solid Surfaces by Sequential Diels-Aider and Azide-Aikyne Cycloadditons;" Bioconjugate Chemistry, vol. 17, No. 1, Jan./Feb. 2006; Bioconjugate Chem. 2006; Copyright 2006 American Chemical Society; Published on Web Dec. 21, 2005; pp. 52-57.
Sun et al., "Design, Synthesis, and Evaluation of Potent, Nonpeptidic Mimetics of Second Mitochondria-Derived Activator of Caspases;" Journal of Medicinal Chemistry, vol. 52, No. 3, Feb. 12, 2009; J. Med. Chem. 2009; Copyright 2009 American Chemical Society; Published on the web Jan. 12, 2009; pp. 593-596.
Tsou et al., 2005, "Optimization of 6,7-disubstituted-4-(arylamino)quinoline-3-carbonitriles as orally active, irreversible inhibitors of human epidermal growth factor receptor-2 kinase activity", Journal of Medicinal Chemistry; 48:1107-1131.
Walker, "Hepatitis C virus: an overview of current approaches and progress;" Drug Discovery Today, vol. 4, No. 11, Nov. 11, 1999; Copyright 1999 Elsevier Science Ltd.; pp. 518-529.
Wang et al., "Characterization of HKI-272 Covalent Binding to Human Serum Albumin;" Drug and Metabolism and Disposition, vol. 38, No. 7, Jul. 2010; Copyright 2010 by the American Society for Pharmacology and Experimental Therapeutics, pp. 1083-1093.
Weiland, "Interferon therapy in chronic hepatitis C virus infection;" FEMS Microbiology Reviews, Special Issue, Papers presented at the Fems Symposium on the Hepatitis C Virus and its Infection; Istanbul, Turkey, Jun. 29-Jul. 1, 1993; Copyright 1994 Federation of European Microbiological Societies; pp. 279-288.
Wissner et al., 2003, "Synthesis and structure-activity relationships of 6,7-disubstituted 4-anilinoquinoline 3-carbonitriles. The design of an orally active, irreversible inhibitor of the tyrosine kinase activity of the epidermal growth factor receptor (EGFR) and the human epidermal growth factor receptor-2 (HER-2)", Journal of Medicinal Chemistry; 46:49-63.
Wymann et al., 1996, "Wortmannin inactivates phosphoinositide 3-kinase by covalent modification of Lys-802, a residue involved in the phosphate transfer reaction", Mol Cell Biol; 16(4):1722-1733.
Yang et al., "Importance of Ligand Reorganization Free Energy in Protein-Ligand Binding-Affinity Prediction:" National Institutes of Health; J. Am. Chem. Soc. 2009; Sep. 30, 2009; 131(38): pp. 13709-13721.
Abdulhameed et al., "Microscopic Modes and Free Energies of 3-Phosphinoditide-Dependent Kinase-1 (PDK-1) Binding with Celecoxib and Other Inhibitors," J. Phys. Chem. B, 2006, 110:26365-26374.
Abdulhameed, "Computational Design of 3-Phosphoinositide-dependent Kinase-1 Inhibitors as Potential Anti-Cancer Agents," University of Kentucky Doctoral Dissertations, paper 757, Jul. 13, 2009.
Bain et al., "The Selectivity of Protein Kinase Inhibitors: a further update," Biochem. J. 2007, 408:297-315 & Supplementary Figures.
Del Rio et al., "A computational workflow for the design of irreversible inhibitors of protein kinases," J. Comput. Aided Mol. Des., 2010, 24:183-194.
Govindan et al., "New cycloartanol sulfates from the algo Tydemania expeditionis: inhibitors of the protein kinase pp60v-src," Journal of Natural Products, 1994, 57:74-78.
Institute of Molecular Function, Docking Study with HyperChem (online), Sep. 4, 2007, ftp://ftp.molfunction.com/molfuncrelease/pamphletDS.pdf, Date of search: Mar. 11, 2015 (with partial English translation).
Kitahara et al., "Synthesis of -tumeronol A, an inhibitor of soybean lipoxygenase, and -ar-turmerone," Bioscience Biotechnology & Biochemistry, 1993, 57:1137-1140.
Mitsuhhi et al., "Tautomycetin Is a Novel and Specific Inhibitor of Serine/Threonine Protein Phosphatase Type 1, as PP1," Biochemical and Biophysical Research Communications, 2001, 287:328-331.
Nakamura, Pharmacia, 2005, 41(12):1144-1148 (with partial English translation).
Nurtjahja-Tjendraputra et al., "Effective anti-platelet and COX-1 enzyme inhibitors from pungent constituents of ginger," Thrombosis Research, 2003, 111:259-265.
Office Action mailed Apr. 27, 2015 for U.S. Appl. No. 12/554,433, filed Sep. 4, 2009.
Steindl et al., "Human Rhinovirus 3C Protease: Generation of Pharmacophore Models for Peptidic and Nonpeptidic Inhibitors and Their Application in Virtual Screening," J. Chem. Inf. Model., 2005, 45:716-724.
Tsuji, "Development of the Structure-based Drug Design Systems, HMHC and DSHC," Molecular Science (online), 2007, 1(1), NP004, http://j-molsci.jp/np/NP004.pdf, Date of search: Mar. 11, 2015 (with partial English translation).
Office Action mailed Oct. 22, 2016 for U.S. Appl. No. 12/982,352, filed Dec. 30, 2010.
Smaill et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J. Med. Chem., 2000, 43:1380-1397.
Palmer et al., "Tyrosine Kinase Inhibitors. 11. Soluble Analogues of Pyrrolo- and Pyrazoloquinazolines as Epidermal Growth Factor Receptor Inhibitors: Synthesis, Biological Evaluation, and Modeling of the Mode of Binding," J. Med. Chem., 1997, 40:1519-1529.
Thompson et al., "Mechanistic Studies on b-Ketoacyl Thiolase from Zoogloea ramigera: Identification of the Active-Site Nucleophile as Cys89, Its Mutation to Ser89 and Kinetic and Thermodynamic Characterization of Wild-Type and Mutant Enzymes," Biochemistry, 1989, 28:5735-5742.
Doorn et al., "Inhibition of Human Mitochondrial Aldehyde Dehydrogenase by 4-Hydroxynon-2-enal and 4-Oxonon-2-enal," Chem. Res. Toxicol., 2006, 19:102-110.
Lee et al., "Irreversible Inactivation of Trypanothione Reductase by Unsaturated Mannich Bases: A Divinyl Ketone as Key Intermediate," J. Med. Chem., 2005, 48:7400-7410.
Schulz, "Metabolism of 4-Pentenoic Acid and Inhibition of Thiolase by Metabolites of 4-Pentenoic Acid," Biochemistry, 1983, 22:1827-1832.
CAS Registry Number 1026864-16-3; STN entry date Jun. 10, 2008.

(56) References Cited

OTHER PUBLICATIONS

Opposition No. 2016-700411 filed against Japanese Patent No. 5806670 on May 10, 2016; dispatched on Jun. 24, 2016 (with English Translation).
Zhang et al., "Targeting cancer with small molecule kinase inhibitors", Nature Reviews Cancer, 9:28-39 (2009), Supplementary Information S1.
Zhang et al., "Targeting cancer with small molecule kinase inhibitors", Nature Reviews Cancer; 9:28-39 (2009), Supplementary Information S2.
Zhang et al., "Targeting cancer with small molecule kinase inhibitors", Nature Review Cancer, 9:28-39 (2009), Supplementary Information S3.
Blair et al., "Structure-guided development of affinity probes for tyrosine kinases using chemical genetics," Nature Chemical Biology; 3(4):229-238 (Apr. 2007).
Powers et al., "Irreversible Inhibitors of Serine, Cysteine, and Threonine Proteases," Chem. Rev.; 102:4639-4750 (2002).
Soyaku kagaku (Drug-Production Chemistry), Approaches from Organic Synthesis (2004) Tokyo Kagaku Dojin, North Yasuyuki and Hiraoka Tetsuo, eds., p. 116 (with English Translation).
Hur et al., 2008, "Clinical staqe EGFR inhibitors irreversibly alkylate Bmx kinase", Bioorg Med Chem Lett; 18(22):5916-5919; Supplemental Data.
Response to Communication pursuant to Art. 94(3) EPC dated Dec. 6, 2013 for EP 08770044.9 based on PCT/US2008/065646 (WO 2008/151183), submitted Jun. 16, 2014.
Mast/stem cell growth factor receptor Kit, Homo sapiens, http://www.uniprot.org/blast/!about=P10721[546-976]&key=Topologicaldomein, accessed Jul. 12, 2016.
CSFIR—Macrophage colony-stimulating factor 1 receptor, Homo sapiens, http://www.uniprot.org/uniprot/P07333, accessed Jul. 12, 2016.
Notice of Grounds for Revocation (in connection with Opposition No. 2016-700411) against Japanese Patent No. 5806670 mailed on Sep. 1, 2016; Dispatching No. 078712 (with English Translation).
Notification of submission of Third Party Observation regarding Japanese Patent Application No. 2015-174949 mailed on Oct. 6, 2016 (with Concise Explanation of Revelance).
Third Party Observation regarding Japanese Patent Application No. 2015-174949 submitted to the Japanese Patent Office on Sep. 12, 2016 (with Concise Explanation of Revelance).
Third Party Observation regarding Japanese Patent Application No. 2015-174949 submitted to the Japanese Patent Office on Sep. 12, 2016 (English Translation).
Notice of Grounds for Rejection regarding Japanese Patent Application No. 2015-174949 dispatched from the Japanese Patent Office on Nov. 4, 2016 (with English translation).

* cited by examiner

Irreversible Inhibitors Demonstrate Prolonged PD Relative to Sorafenib in EOL-1 cells with FIL1P1-PDGFR alpha fusion protein

PROTEIN KINASE CONJUGATES AND INHIBITORS

RELATED APPLICATION

This application claims the benefit of U.S. Patent Application No. 61/242,988, filed on Sep. 16, 2009, the entire teachings of which are incorporated herein by reference.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

Protein conjugates in which a protein of interest is covalently bonded to an inhibitor of the protein can be used for several purposes. For example, the conjugates can be used to study protein structure and function. In addition, if the inhibitor has therapeutic potential determining the presence or amount of conjugate in a sample obtained from a patient can provide information about inhibitor efficacy and target protein metabolism. Accordingly, there remains a need for new protein conjugates.

SUMMARY OF THE INVENTION

It has been determined that protein kinases can be grouped based on the presence of certain non-conserved cysteines that are present in or near the ATP binding site. The common non-conserved cysteines are referred to herein as CYS1-CYS13 and are targets for covalent modification to form protein kinase conjugates. Irreversible inhibitors that form a covalent bond with one of the target Cys residues can selectively form conjugates with protein kinases that contain the target cysteine residue. Irreversible inhibitors that are suitable for forming a conjugate of the invention comprise a binding moiety that binds in or near the ATP binding site of a protein kinase, and a warhead moiety.

In general, the conjugates have the formula:

$$X\text{-}M\text{-}S\text{—}CH_2\text{-Prot}$$

wherein Prot is a protein kinase or portion thereof that contains a cysteine in or near the ATP binding site;

$S—CH_2$ is the sulfur atom and methylene group from the side chain of the cysteine residue;

M is a modifier moiety that is formed by the covalent bonding of a warhead group with the side chain of the cysteine residue; and X is a chemical moiety that binds in or near the ATP binding site of the protein kinase.

The invention also relates to compounds disclosed herein that irreversibly inhibit a protein kinases.

DETAILED DESCRIPTION OF THE INVENTION

Definitions

Figure 1:
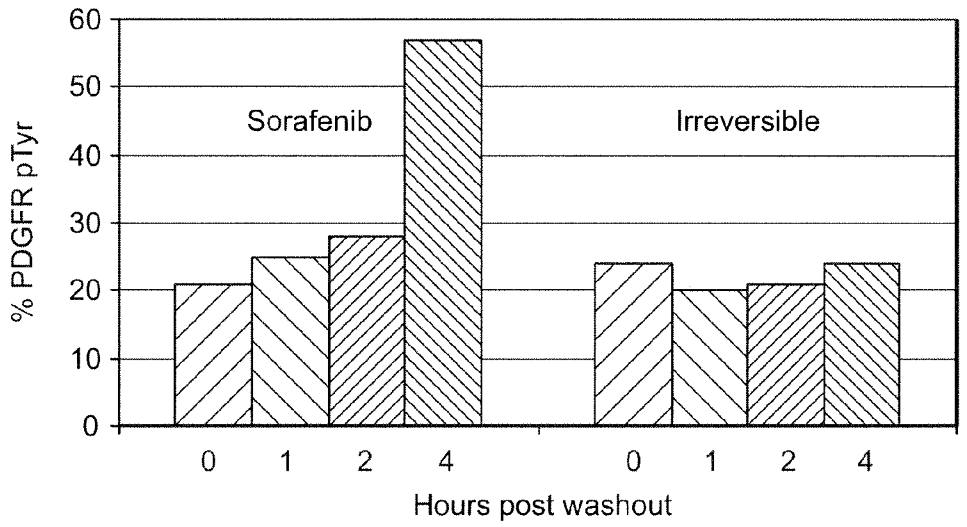
FIG. 1 is a histogram showing the inhibition of PDGFR with reference compound sorafenib and an irreversible inhibitor (XVIII-11) in a "washout" experiment using EOL-1 cells.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

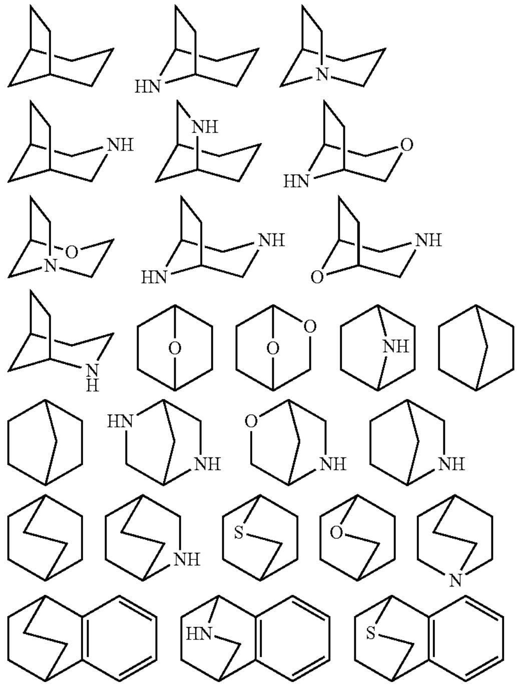

-continued

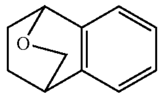

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "lower cycloalkyl" refers to a $C_{3-5}$ saturated cyclic group, and includes cyclopropyl, cyclobutyl, and cyclopentyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$, $C_{2-8}$, $C_{2-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer from 1 to 8, from 1 to 6, from 1 to 4, from 1 to 3, from 1 to 2, from 2 to 8, from 2 to 6, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

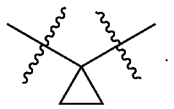 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to fourteen or five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein, the term "solubilizing group" refers to a chemical moiety that promotes the solubility of a compound to which it is attached. Suitable solubilizing groups include, for example, saturated heterocyclic rings, such as morpholino, piperazinyl, and piperadinyl, and amino group, such as dimethyl amino and methoxypropylamino.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; —CH═CHPh, which may be substituted with $R^\circ$; $—(CH_2)_{0-4}O(CH_2)_{0-1}$-pyridyl which may be substituted with $R^\circ$; $—NO_2$; —CN; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched)alkylene)O—N(R°$_2$; or $—(C_{1-4}$ straight or branched)alkylene)C(O)O—N(R°)$_2$, wherein each R° may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6 membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$. —($C_{1-4}$ straight or branched alkylene)C(O)OR$^•$, or —SSR$^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6 membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═$NNR^*_2$, ═NNHC(O)R*, ═NNHC(O)OR*, ═$NNHS(O)_2R^*$, ═NR*, ═NOR*, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6 membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6 membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —$NH_2$, —NHR$^•$, —$NR^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6 membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —R$^•$, -(haloR$^•$), —OH, —OR$^•$, —O(haloR$^•$), —CN, —C(O)OH, —C(O)OR$^•$, —$NH_2$, —NHR$^•$, —$NR^•_2$, or —$NO_2$, wherein each R$^•$ is unsubstituted or where preceded by "halo" is substituted only with one or more halogens, and is independently $C_{1-4}$aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^3$, of a provided compound comprises one or more deuterium atoms.

As used herein, the term "irreversible" or "irreversible inhibitor" refers to an inhibitor (i.e. a compound) that is able to be covalently bonded to a cysteine residue in a target protein kinase in a substantially non-reversible manner. That is, whereas a reversible inhibitor is able to bind to (but is generally unable to form a covalent bond with) a target protein kinase, and therefore can become dissociated from the target protein kinase an irreversible inhibitor will remain substantially bound to the target protein kinase once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to target protein kinase once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with target protein kinase, the use of mass spectrometry of the protein drug target modified in the presence of the inhibitor compound, discontinuous exposure, also known as "washout" studies, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein. It will be appreciated that the -L-Y group, as defined and described herein, provides such warhead groups for covalently, and irreversibly, inhibiting the protein.

As used herein, the term "inhibitor" is defined as a compound that binds to and/or inhibits a target protein kinase with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a protein kinase activity between a sample comprising a compound of the present invention, or composition thereof, and protein, and an equivalent sample comprising the protein kinase, in the absence of said compound, or composition thereof.

Protein Kinase Conjugates

The invention relates to a conjugate comprising a protein kinase that contains a cysteine residue in the ATP binding site and an inhibitor that binds to the ATP binding site. In the conjugate of the invention, the inhibitor is covalently and irreversibly bonded to the cysteine residue in the ATP binding site of the protein kinase such that the activity of the protein kinase is irreversibly inhibited.

The conjugates described herein have a variety of uses. For example, the amount of conjugated target polypeptide relative to unconjugated target polypeptide in a biological sample obtained from a patient that has been treated with an irreversible inhibitor can be used as a biomarker to monitor dosing and efficacy in inhibiting polypeptide activity. Thus, when irreversible inhibitors are used therapeutically, the conjugates can be used to tailor dosing of irreversible inhibitors (e.g., quantity administered and/or time interval between administrations) to obtain the desired therapeutic effect.

As described herein, it has been determined that protein kinases can be grouped based on the presence of certain non-conserved cysteines that are present in or near the ATP binding site. The common non-conserved cysteines are referred to herein as CYS1-CYS13 and are targets for covalent modification in the conjugates of the invention. Table 1 presents protein kinases that have a target CYS, the sequence code for the amino acid sequence of the protein kinase, the amino acid sequence encompassing the cysteine of interest, and the residue number of the cysteine of interest in the amino acid sequence. For example, as is apparent from Table 1 CYS1 refers to Cys945 of JAK3, Cys619 of FGFR1, Cys622 of FGFR2, Cys613 of FGFR3, CYS607 of FGFR4, Cys788 of CKIT, Cys744 of CSFR1, Cys814 of PDGRF-A, Cys545 of FAK2, Cys807 of FLT3, Cys680 of FER, Cys679 of FES, Cys122 of CDKL1, Cys122 of CDKL4, Cys1033 of FLT4, Cys1024 of KDR, Cys1018 of FLT1 and Cys822 of PDGFR-B. Similarly, CYS2, CYS3, CYS4, CYS5, CYS6, CYST, CYS8, CYS11, CYS12 and CYS13 refer to particular cystiene residues in particular protein kinases as set forth in Table 1. The cysteines identified in Table 1 that are used to group protein kinases are not conserved in the protein kinase family, but the identified cysteines are common to and found in the particular proteins that make up the protein kinase groups identified in Table 1, such as the CYS1 kinases.

TABLE 1

| CYS | Kinase | SEQ CODE | SEQUENCE | RESIDUE NUMBER |
|---|---|---|---|---|
| CYS1 | JAK3 | P52333 | RCVHRDL (SEQ ID NO: 1) | 945 |
| CYS1 | FGFR1 | P11362 | KCIHRDL (SEQ ID NO: 2) | 619 |
| CYS1 | FGFR2 | P21802 | KCIHRDL (SEQ ID NO: 2) | 622 |
| CYS1 | FGFR3 | P22607 | KCIHRDL (SEQ ID NO: 2) | 613 |
| CYS1 | FGFR4 | P22455 | KCIHRDL (SEQ ID NO: 2) | 607 |
| CYS1 | KIT | P10721 | NCIHRDL (SEQ ID NO: 3) | 788 |
| CYS1 | CSF1R | P07333 | NCIHRDL (SEQ ID NO: 4) | 744 |
| CYS1 | PDGFR-A | P16234 | NCVHRDL (SEQ ID NO: 5) | 814 |
| CYS1 | FAK2 | Q14289 | NCVHRDI (SEQ ID NO: 6) | 545 |
| CYS1 | FLT3 | P36888 | SCVHRDL (SEQ ID NO: 7) | 807 |
| CYS1 | FER | P16591 | NCIHRDL (SEQ ID NO: 3) | 680 |
| CYS1 | FES | P07332 | CCIHRDL (SEQ ID NO: 8) | 679 |
| CYS1 | CDKL1 | Q00532 | NCIHRDV (SEQ ID NO: 4) | 122 |
| CYS1 | CDKL4 | Q5MAI5 | NCIHRDI (SEQ ID NO: 9) | 122 |
| CYS1 | FLT4 | P35916 | KCIHRDL (SEQ ID NO: 2) | 1033 |

TABLE 1-continued

| CYS | Kinase | SEQ CODE | SEQUENCE | RESIDUE NUMBER |
|---|---|---|---|---|
| CYS1 | KDR | P35968 | KCIHRDL (SEQ ID NO: 2) | 1024 |
| CYS1 | FLT1 | P17948 | SCIHRDL (SEQ ID NO: 2) | 1018 |
| CYS1 | PDGFR-B | P09619 | NCVHRDL (SEQ ID NO: 5) | 822 |
| CYS2 | KDR | P35968 | ICDFG (SEQ ID NO: 10) | 1045 |
| CYS2 | MEK1 | Q02750 | LCDFG (SEQ ID NO:11 ) | 207 |
| CYS2 | FLT3 | P36888 | ICDFG (SEQ ID NO: 10) | 828 |
| CYS2 | KIT | P10721 | ICDFG (SEQ ID NO: 10) | 809 |
| CYS3 | JAK3 | P52333 | SGCLRDF (SEQ ID NO: 12) | 909 |
| CYS3 | BLK | P51451 | RGCLLDF (SEQ ID NO: 13) | 319 |
| CYS3 | MAP2K7 | O14733 | GTCAEKL (SEQ ID NO: 14) | 202 |
| CYS3 | ITK | Q08881 | HGCLSDY (SEQ ID NO: 15) | 442 |
| CYS3 | BMX | P51813 | NGCLLNY (SEQ ID NO: 16) | 496 |
| CYS3 | TEC | P42680 | RGCLLNFL (SEQ ID NO: 17) | 449 |
| CYS3 | BTK | Q06187 | NGCLLNYL (SEQ ID NO: 18) | 481 |
| CYS3 | TXK | P42681 | NGCLLNYL (SEQ ID NO: 18) | 350 |
| CYS3 | EGFR | P00533 | FGCLLDYV (SEQ ID NO: 10) | 797 |
| CYS3 | ERBB2_ErbB2 | P04626 | YGCLLDHV (SEQ ID NO: 20) | 805 |
| CYS3 | ERBB4_ErbB4 | Q15303 | HGCLLEYV (SEQ ID NO: 21) | 803 |
| CYS4 | NEK2 | P51955 | YGRCQK (SEQ ID NO: 22) | 22 |
| CYS4 | PLK3 | Q9H4B4 | FARCYE (SEQ ID NO: 23) | 76 |
| CYS4 | PLK2 | Q9NYY3 | FAKCYE (SEQ ID NO: 24) | 96 |
| CYS4 | PLK1_HUMAN | P53350 | FAKCFE (SEQ ID NO: 25) | 67 |
| CYS4 | MSK2-b | | | |
| CYS4 | MSK1-b | | | |
| CYS4 | MAP3K1 | | | |
| CYS5 | PFTAIRE1 | O94921 | DLCQYMD (SEQ ID NO: 26) | 218 |
| CYS5 | JNK2 | P45984 | NLCQVIH (SEQ ID NO: 27) | 116 |

TABLE 1-continued

| CYS | Kinase | SEQ CODE | SEQUENCE | RESIDUE NUMBER |
|---|---|---|---|---|
| CYS5 | JNK1 | P45938 | NLCQVIQ (SEQ ID NO: 28) | 116 |
| CYS5 | JNK3 | P53779 | NLCQVIQ (SEQ ID NO: 28) | 154 |
| CYS5 | BMPR2 | Q13873 | SLCKYLSL (SEQ ID NO: 28) | 288 |
| CYS6 | TNKQ | Q13470 | SGCFGV (SEQ ID NO: 30) | 126 |
| CYS6 | YES | P07947 | QGCFGE (SEQ ID NO: 31) | 287 |
| CYS6 | FGR | P09769 | TGCFGD (SEQ ID NO: 32) | 273 |
| CYS6 | SRC | P12931 | QGCFGE (SEQ ID NO: 31) | 280 |
| CYS6 | LIMK1 | P53667 | KGCFGQ (SEQ ID NO: 33) | 349 |
| CYS6 | FGFR2 | P21802 | EGCFGQ (SEQ ID NO: 34) | 491 |
| CYS6 | FGFR3 | P22607 | EGCFGQ (SEQ ID NO: 34) | 482 |
| CYS6 | FGFR1 | P11362 | EGCFGQ (SEQ ID NO: 34) | 488 |
| CYS6 | FGFR4 | P22455 | EGCFGQ (SEQ ID NO: 34) | 477 |
| CYS7 | FAK | Q05397 | GRCIGEGQFGD (SEQ ID NO: 35) | 427 |
| CYS7 | ALK1 | P37023 | VECVGKGRYG (SEQ ID NO: 36) | 207 |
| CYS7 | ALK2 | Q04771 | LECVGKGRYG (SEQ ID NO: 37) | 313 |
| CYS8 | ZAP70 | P43403 | GCGNF (SEQ ID NO: 38) | 346 |
| CYS8 | CRIK | O14578 | GCGHF (SEQ ID NO: 39) | 105 |
| CYS8 | Erk3 | Q16659 | GCGGN (SEQ ID NO: 40) | 28 |
| CYS8 | CK1g1 | Q9HCP0 | GCGNF (SEQ ID NO: 38) | 52 |
| CYS8 | CK1g2 | P78368 | GCGNF (SEQ ID NO: 38) | 54 |
| CYS8 | CK1g3 | Q9YGM4 | GCGNF (SEQ ID NO: 38) | 51 |
| CYS9 | ROR1 | | | |
| CYS10 | MELK | | | |
| CYS11 | KIT | P10721 | YCCYG (SEQ ID NO: 41) | 674 |
| CYS11 | FMS | P07333 | YCCYG (SEQ ID NO: 41) | 667 |
| CYS11 | RON | Q04912 | YMCHG (SEQ ID NO: 42) | 1165 |
| CYS11 | FGR | P09769 | FMCHG (SEQ ID NO: 43) | 338 |

TABLE 1-continued

| CYS Kinase | SEQ CODE | SEQUENCE | RESIDUE NUMBER |
|---|---|---|---|
| CYS11ALK KINASE | Q9UM73 | AARNCLLT**C**PG PGRVAKIGD (SEQ ID NO: 44) | 1259 |
| CYS13B-RAF | P15056 | TKPQLAIVTQW **C**EGGSSLYHH (SEQ ID NO: 45) | 532 |

The conjugates of the invention contain a protein kinase or portion thereof. Preferably the protein kinase or portion thereof is a human protein kinase or portion thereof. However, the invention encompasses conjugates that contain a protein kinase or portion thereof from any desired species, such as a rodent (mouse, rat) or primate (macaque, chimpanzee). The sequence codes for human protein kinases are provided in Table 1. The invention is not limited to conjugates that contain protein kinases or portion thereof that have the same sequences as the database sequences provided in Table 1. It is well-known in the art that there may be two or more sequences for a particular kinase that differ in amino acid sequence in sequence databases. These proteins are nonetheless recognized as being the same kinase. The sequence variation may be due to natural sequence variation, such as allelic variants or naturally arising mutations. The conjugates of the invention encompass all forms of protein kinases, including allelic variants and mutant proteins.

Irreversible inhibitors that form a covalent bond with one of the target Cys residues (CYS1-CYS13) can selectively form conjugates with protein kinases that contain the target cysteine residue. Irreversible inhibitors that are suitable for forming a conjugate of the invention comprises a binding moiety that binds in or near the ATP binding site of a protein kinase, and a warhead moiety. As described herein, the warhead moiety can react with a target cysteine of the protein kinase, and is provided by the group -L-Y.

In general the conjugates have the formula:

$X\text{-}M\text{-}S\text{—}CH_2\text{-}Prot$

Prot is a protein kinase or portion thereof that contains a cysteine in or near the ATP binding site;

S—$CH_2$ is the sulfur atom and methylene group from the side chain of the cysteine residue;

M is a modifier moiety that is formed by the covalent bonding of a warhead group with the side chain of the cysteine residue; and X is a chemical moiety that binds in or near the ATP binding site of the protein kinase.

The modifier moiety is formed by the covalent binding of a warhead group (-L-Y) with the side chain of the cysteine residue. The modifier moiety can be provided by reaction of any of the warheads described herein with a target cysteine. It is to be understood that the L and Y components described herein can be variously combined to provide a warhead of formula -L-Y, and that conjugates of the invention encompass the reaction product of a cysteine and any combination of the L and Y groups described herein. In one example, the modifier moiety is provided by the reaction of -L-Y with a target cysteine, wherein L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(=S)—, —C(=NR)—, —N=N—, or —C(=$N_2$)—;

Y is hydrogen, nitrile, $C_{1-6}$ aliphatic optionally substituted with one or more OH, NRxRy, oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and Rx and Ry are independently hydrogen, lower alkyl, lower haloalkyl, or lower cycloalkyl;

each $R^e$ is independently selected from -Q-Z, OH, oxo, $NO_2$, halogen, CN, a suitable leaving group, or a $C_{1-6}$ aliphatic optionally substituted with oxo, halogen, $NO_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

Further examples and embodiments of -L-Y that can react with a cysteine to form a modifier moiety are described in detail herein. Table 2 presents the structures of a number of non-limiting examples of modifier moieties that are bonded to the side chain of cysteine (S—$CH_2$ in the structures shown in Table 2). In some embodiments, the modifier moiety is selected from the non-limiting exemplary modifier moieties that are bonded to the side chain of cysteine (S—$CH_2$) presented in Table 2. In some embodiments, the conjugate comprises a structure selected from those presented in Table 2.

TABLE 2

Exemplary Modifiers:

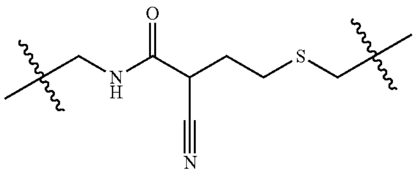

a

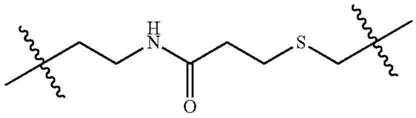

b

TABLE 2-continued
Exemplary Modifiers:
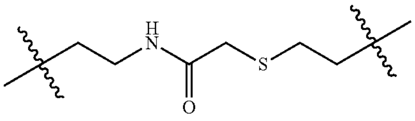
c
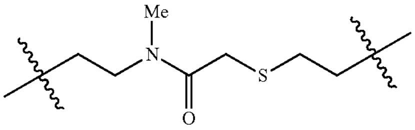
d
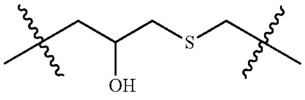
e
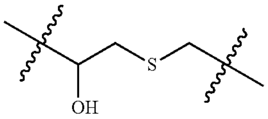
f
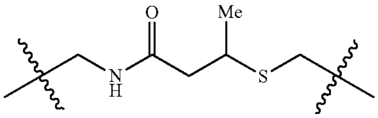
g
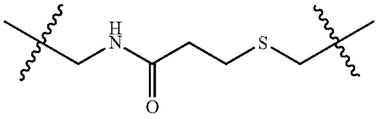
h
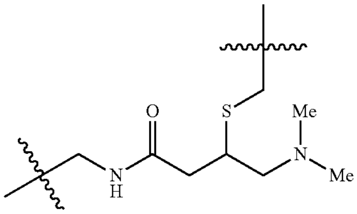
i
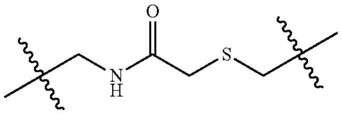
j
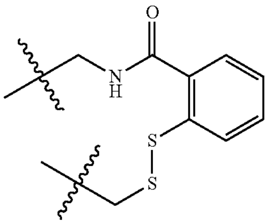
k
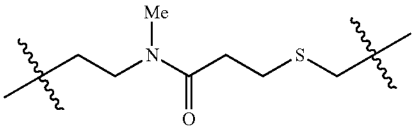
l
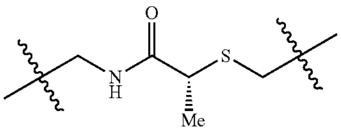
m
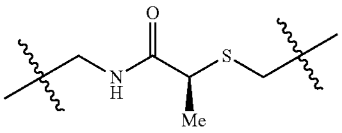
n
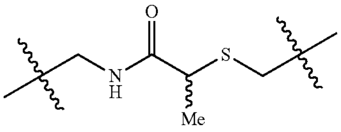
o
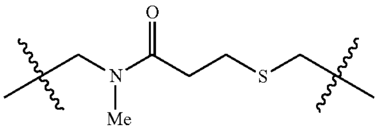
p TABLE 2-continued
Exemplary Modifiers:
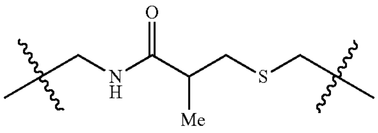
q
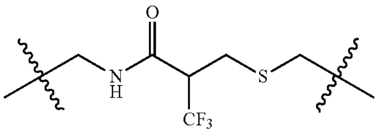
r
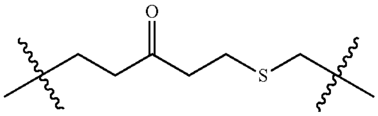
s
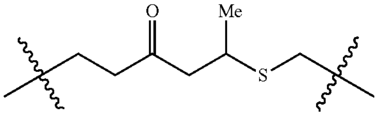
t
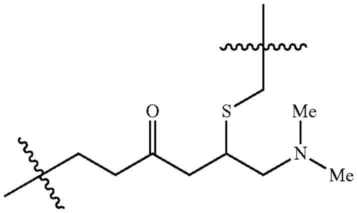
u
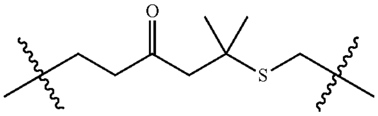
v
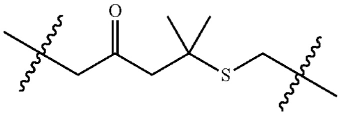
w
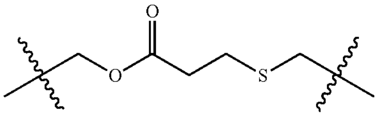
x
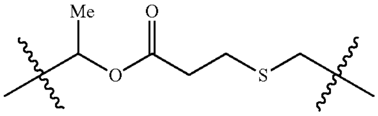
y
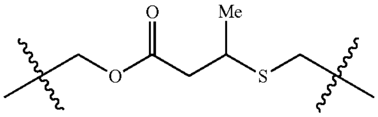
z
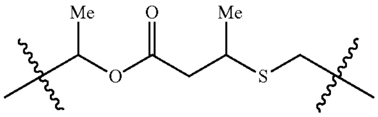
aa
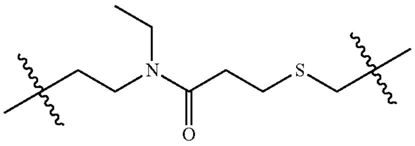
bb
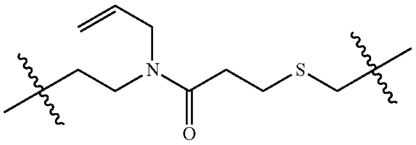
cc
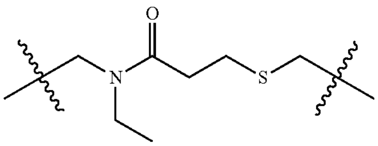
dd TABLE 2-continued
| Exemplary Modifiers: |
| --- |
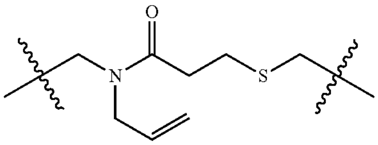
ee
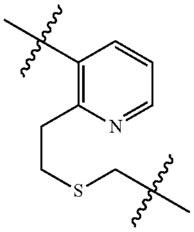
ff
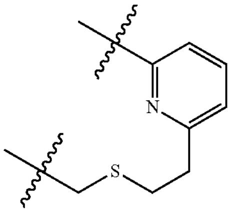
gg
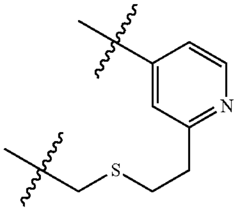
hh
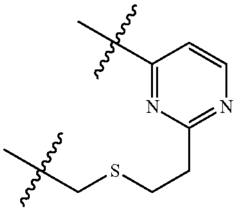
ii
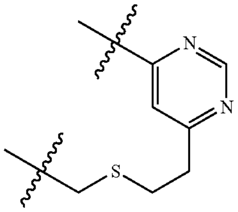
jj
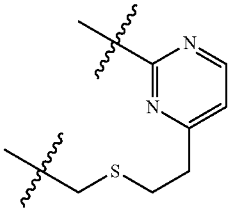
kk
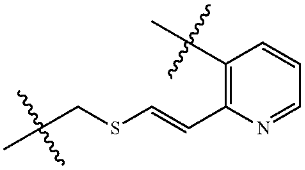
ll
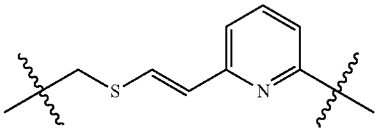
mm
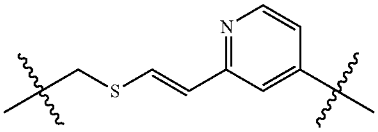
nn
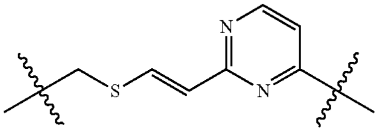
oo
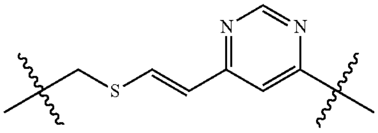
pp TABLE 2-continued
| Exemplary Modifiers: | |
| --- | --- |
| 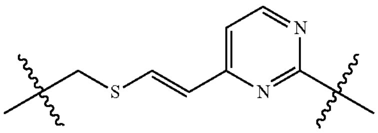 qq | 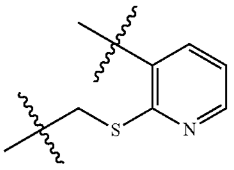 rr |
| 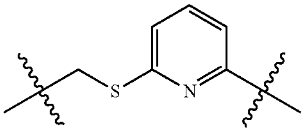 ss | 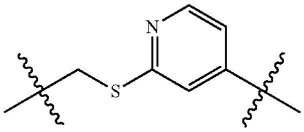 tt |
| 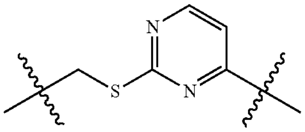 uu | 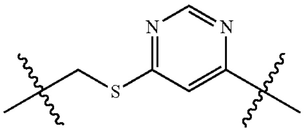 vv |
| 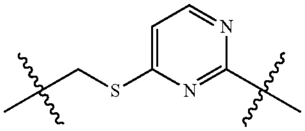 ww | 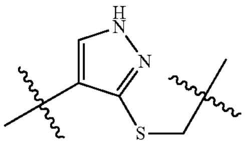 xx |
| 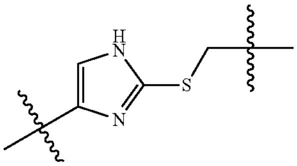 yy | 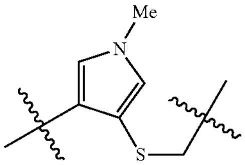 zz |
| 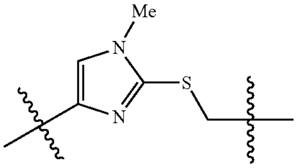 aaa | 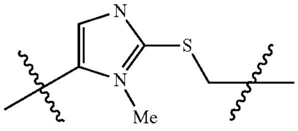 bbb |
| 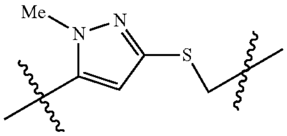 ccc | 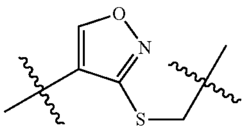 ddd |
| 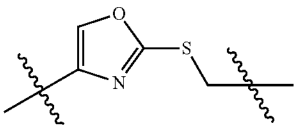 eee | 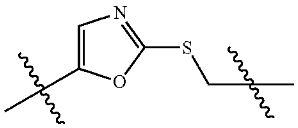 fff |

TABLE 2-continued
| Exemplary Modifiers: | |
|---|---|
| 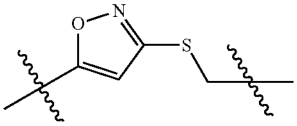<br>ggg | 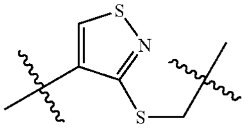<br>hhh |
| 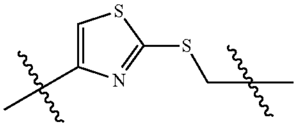<br>iii | 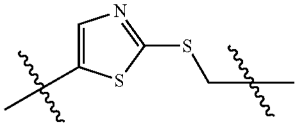<br>jjj |
| 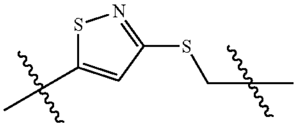<br>kkk | 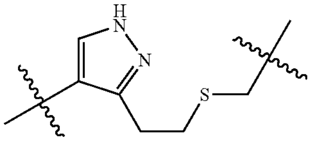<br>lll |
| 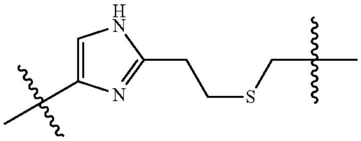<br>mmm | 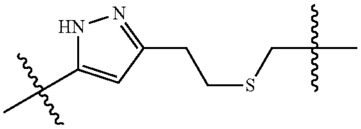<br>nnn |
| 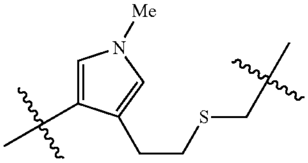<br>ooo | 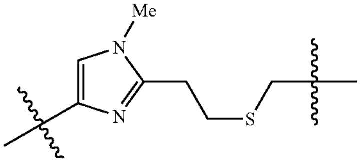<br>ppp |
| 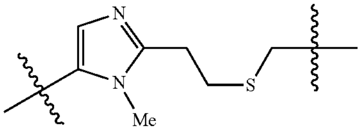<br>qqq | 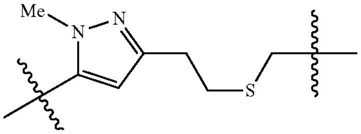<br>rrr |
| 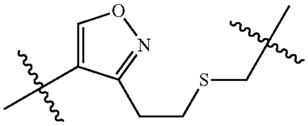<br>sss | 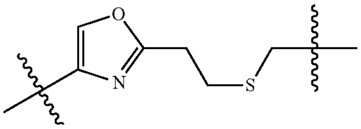<br>ttt |
| 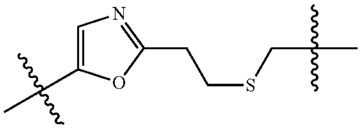<br>uuu | 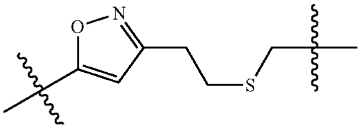<br>vvv |

TABLE 2-continued
Exemplary Modifiers:
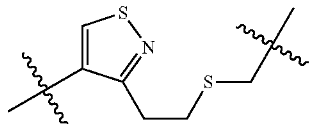
www
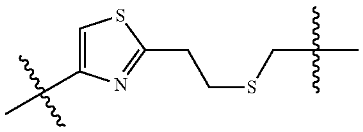
xxx
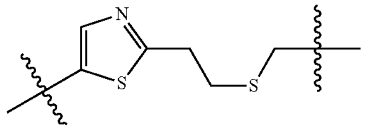
yyy
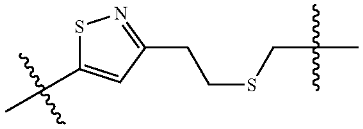
zzz
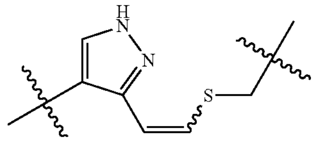
aaaa
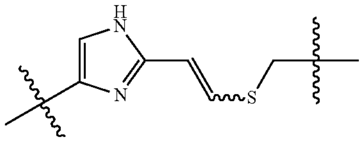
bbbb
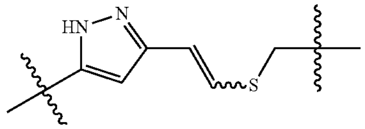
cccc
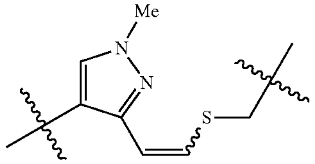
dddd
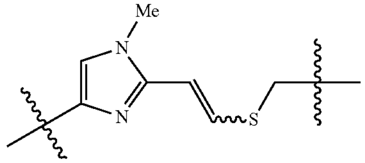
eeee
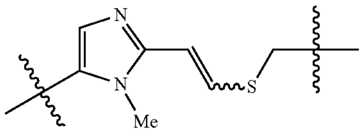
ffff
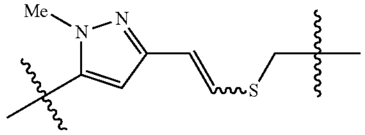
gggg
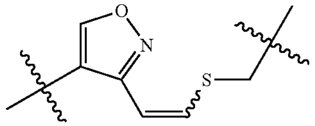
hhhh
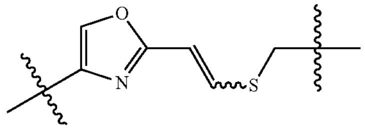
iiii
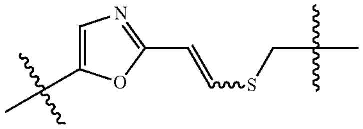
jjjj
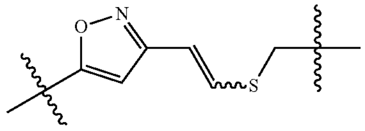
kkkk
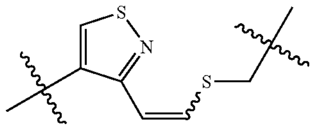
llll TABLE 2-continued
Exemplary Modifiers:
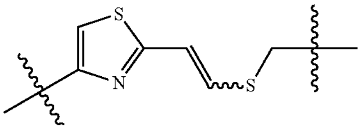
mmmm
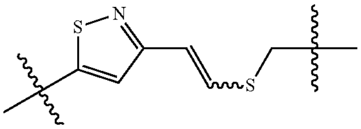
nnnn
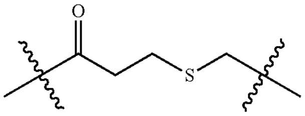
oooo
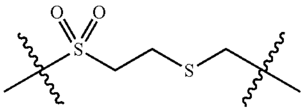
pppp
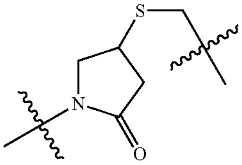
qqqq
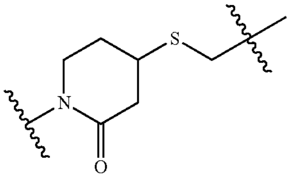
rrrr
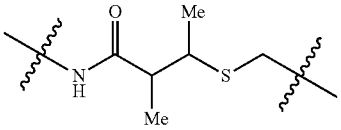
ssss
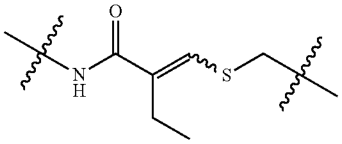
tttt
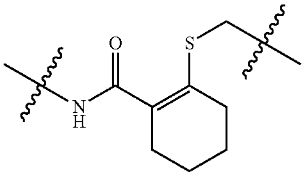
uuuu
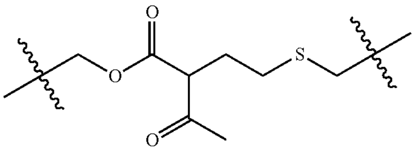
vvvv
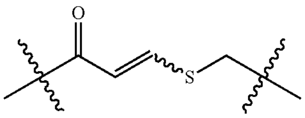
wwww
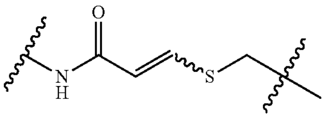
xxxx
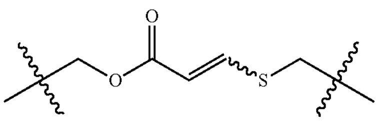
yyyy
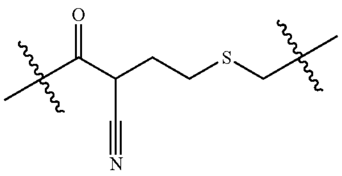
zzzz
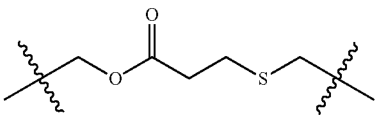
aaaaa
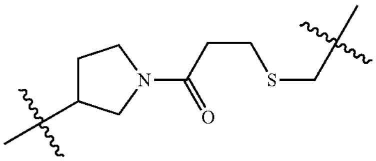
bbbbb TABLE 2-continued Exemplary Modifiers:

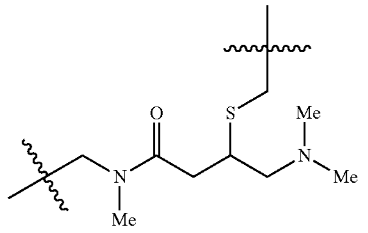

ccccc

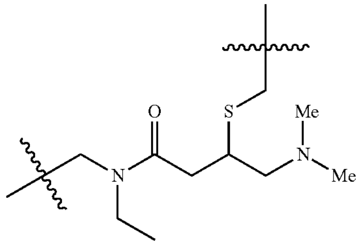

ddddd

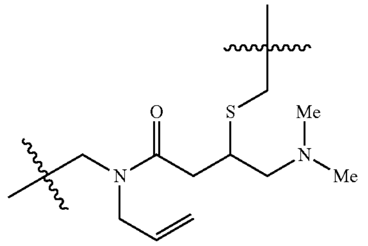

eeeee

As described above, the conjugates have the general formula:

X-M-S—$CH_2$-Prot.

Prot is a protein kinase or portion thereof that contains a cysteine in or near the ATP binding site;

S—$CH_2$ is the sulfur atom and methylene group from the side chain of the cysteine residue;

M is a modifier moiety that is formed by the covalent bonding of a warhead group with the side chain of the cysteine residue; and X is a chemical moiety that binds in or near the ATP binding site of the protein kinase.

In one aspect, the conjugate comprises a CYS1 kinase, CYS5 kinase, CYS6 kinase, CYST kinase, CYS8 kinase, CYS9 kinase, CYS10 kinase, CYS11 kinase, CYS12 kinase, CYS13 kinase or a portion of any of the forgoing that contains the target cysteine (i.e., CYS1 or CYS5-CYS13).

The conjugate can comprise any suitable chemical moiety that binds in or near the ATP binding site of the protein kinase. Many suitable chemical moieties that bind the ATP binding site of kinases are well-known in the art. In addition, the binding modes of many such chemical moieties are known and can be used to design additional moieties that bind the ATP binding site using conventional methods of structure based design. For example, nilotinib, imatinib, sorafenib (U.S. Pat. No. 7,235,576), VX-680 (U.S. Pat. No. 6,664,247), BI2536 (US2006/018182), TAE226 (US2008/01322504), PF-573,228, CP-562,271-26, CPP690550, and the like are well-known compounds that bind to the ATP binding site of protein kinases. These compounds, portions thereof and derivatives thereof can be used as a chemical moiety that binds to the ATP binding site of a protein kinase, for example, by attaching a warhead to the compound, portion thereof or derivative thereof.

The invention relates to a conjugate comprising a protein kinase that comprises CYS1 and an inhibitor that binds to the ATP binding site of the CYS1 kinase. In the conjugate of the invention, the inhibitor is covalently and irreversibly bonded to CYS1 such that the activity of the protein kinase is irreversibly inhibited.

In some embodiments, the conjugate has the formula

X-M-S—$CH_2$-Prot wherein Prot is a protein kinase or portion thereof that contains CYS1;

S—$CH_2$ is the sulfur atom and methylene group from the side chain of CYS1;

M is a modifier moiety that is formed by the covalent bonding of a warhead group with the side chain of CYS1; and X is a chemical moiety that binds in or near the ATP binding site of the protein kinase that contains CYS1.

In these embodiments, Prot is selected from the group consisting of JAK3, FGFR (e.g., FGFR1, FGFR2, FGFR3, FGFR4), CKIT, CSFR1, FAK2, FLT3, FER, FES, CDKL1, CDKL4, FLT4, KDR, FLT1, PDGFR (e.g., PDGRF-A, PDGFR-B), and a portion of any one of the foregoing that comprises CYS1.

The conjugate can comprise substantially the entire mature protein kinase or a portion thereof that comprises CYS1. Generally, Prot comprises at least a portion of the protein kinase that has an amino acid sequence selected from the group consisting of RC*VHRDL (SEQ ID NO:1), KC*IHRDL (SEQ ID NO:2), NC*IHRDL (SEQ ID NO:3), NC*IHRDV (SEQ ID NO:4), NC*VHRDL (SEQ ID NO:5), NC*VHRDI (SEQ ID NO:6), SC*VHRDL (SEQ ID NO:7), CC*IHRDL (SEQ ID NO:8), or NC*IHRDI (SEQ ID NO:9), wherein C* is CYS1.

Some conjugates of these embodiments, contain a modifier moiety that is selected from the moieties shown in Table 2.

The conjugate can comprise any suitable chemical moiety that binds in or near the ATP binding site of the protein kinase. Many suitable chemical moieties that bind the ATP binding site of kinases are well-known in the art. In addition, the binding modes of many such chemical moieties are known and can be used to design additional moieties that bind the ATP binding site using conventional methods of structure based design. For example, nilotinib, imatinib and sorafenib are well-know inhibitors of protein kinases that contain CYS1, such as C-KIT, PDGFR (PDGFRA, PDGFRB), FLT3, CSF1R and/or KDR. In some embodiments of conjugates in which a warhead is covalently and irreversibly bonded to CYS1, Prot is C-KIT, PDGFR (PDGFRA, PDGFRB), FLT3, CSF1R, or KDR and X is nilotinib, imatinib, sorafenib or a portion thereof or derivative thereof that binds C-KIT, PDGFR (PDGFRA, PDGFRB), FLT3, CSF1R, or KDR.

If desired, a compound of Formula I, II or III disclosed in U.S. Ser. No. 12/132,537, filed Jun. 3, 2008, can be used as a chemical moiety that binds in or near the ATP binding site of a CYS1 kinase, such as C-KIT or PDGFR. The entire teachings of U.S. Ser. No. 12/132,537, including Formulas I, II and III and the descriptions thereof, are incorporated herein by reference. Other suitable chemical moieties for binding to the ATP binding site of a CYS1 kinase include compounds of Formulas XVIII-XX described herein.

The invention relates to a conjugate comprising a protein kinase that comprises CYS1 and an inhibitor that binds to the ATP binding site of the CYS1 kinase. In the conjugate of the invention, the inhibitor is covalently and irreversibly bonded to CYS1 such that the activity of the protein kinase is irreversibly inhibited.

In some embodiments, the conjugate has the formula $$X\text{-}M\text{-}S\text{—}CH_2\text{-}Prot$$

wherein Prot is a protein kinase or portion thereof that contains CYS5;

S—$CH_2$ is the sulfur atom and methylene group from the side chain of CYS5;

M is a modifier moiety that is formed by the covalent bonding of a warhead group with the side chain of CYS5; and X is a chemical moiety that binds in or near the ATP binding site of the protein kinase that contains CYS5.

In these embodiments, Prot is selected from the group consisting of PFTAIRE1, a JNK (e.g., JNK1, JNK2, JNK3) and BMPR2, and a portion of any one of the foregoing that comprises CYS5.

The conjugate can comprise substantially the entire mature protein kinase or a portion thereof that comprises CYS5. Generally, Prot comprises at least a portion of the protein kinase that has an amino acid sequence selected from the group consisting of DLC*QYMD (SEQ ID NO:26), NLC*QVIH (SEQ ID NO:27), NLC*QVIQ (SEQ ID NO:28), and SLC*KYLSL (SEQ ID NO:29), wherein C* is CYS5.

Some conjugates of these embodiments, contain a modifier moiety that is selected from the moieties shown in Table 2.

The conjugate can comprise any suitable chemical moiety that binds in or near the ATP binding site of the protein kinase. Suitable chemical moieties for binding to the ATP binding site of a CYS5 kinase include, for example, compounds of Formulas VI-VIII, IX, IX-a, X, X-a, XI, XII and XII-a described herein.

In some embodiments, the conjugate has the formula $$X\text{-}M\text{-}S\text{—}CH_2\text{-}Prot$$

wherein Prot is a protein kinase or portion thereof that contains CYS6;

S—$CH_2$ is the sulfur atom and methylene group from the side chain of CYS6;

M is a modifier moiety that is formed by the covalent bonding of a warhead group with the side chain of CYS6; and X is a chemical moiety that binds in or near the ATP binding site of the protein kinase that contains CYS6.

In these embodiments, Prot is selected from the group consisting of TNK1, YES, FGR, SRC, LIMK1, FGFR (e.g., FGFR1, FGFR2, FGFR3, and FGFR4), and a portion of any one of the foregoing that comprises CYS6.

The conjugate can comprise substantially the entire mature protein kinase or a portion thereof that comprises CYS6. Generally, Prot comprises at least a portion of the protein kinase that has an amino acid sequence selected from the group consisting of SGC*FGV (SEQ ID NO:30), QGC*FGE (SEQ ID NO:31), TGC*FGD (SEQ ID NO:32), KGC*FGQ (SEQ ID NO:33), and EGC*FGQ (SEQ ID NO:34), wherein C* is CYS6.

Some conjugates of these embodiments contain a modifier moiety that is selected from the moieties shown in Table 2.

The conjugate can comprise any suitable chemical moiety that binds in or near the ATP binding site of the protein kinase.

In some embodiments, the conjugate has the formula $$X\text{-}M\text{-}S\text{—}CH_2\text{-}Prot$$

wherein Prot is a protein kinase or portion thereof that contains CYS7;

S—$CH_2$ is the sulfur atom and methylene group from the side chain of CYS7;

M is a modifier moiety that is formed by the covalent bonding of a warhead group with the side chain of CYS7; and X is a chemical moiety that binds in or near the ATP binding site of the protein kinase that contains CYS7.

In these embodiments, Prot is selected from the group consisting of FAK, ALK (e.g., ALK1, ALK2), and a portion of any one of the foregoing that comprises CYS7.

The conjugate can comprise substantially the entire mature protein kinase or a portion thereof that comprises CYS7. Generally, Prot comprises at least a portion of the protein kinase that has an amino acid sequence selected from the group consisting of GRC*IGEGQFGD (SEQ ID NO:35), VEC*VGKGRYG (SEQ ID NO:36), and LEC*VGKGRYG (SEQ ID NO:37), wherein C* is CYS7.

Some conjugates of these embodiments contain a modifier moiety that is selected from the moieties shown in Table 2.

The conjugate can comprise any suitable chemical moiety that binds in or near the ATP binding site of the protein kinase. Suitable chemical moieties for binding to the ATP binding site of a CYS7 kinase include, for example, compounds of Formula IV described herein, and the well-known compounds TAE226 (US2008/01322504), PF-573,228, and CP-562,271-26.

In some embodiments, the conjugate has the formula $$X\text{-}M\text{-}S\text{—}CH_2\text{-}Prot$$

wherein Prot is a protein kinase or portion thereof that contains CYS8;

S—$CH_2$ is the sulfur atom and methylene group from the side chain of CYS8;

M is a modifier moiety that is formed by the covalent bonding of a warhead group with the side chain of CYS8; and X is a chemical moiety that binds in or near the ATP binding site of the protein kinase that contains CYS8.

In these embodiments, Prot is selected from the group consisting of ZAP70, CRIK, ERK3, CK1g1, CK1g2, and CK1g3, and a portion of any one of the foregoing that comprises CYS8.

The conjugate can comprise substantially the entire mature protein kinase or a portion thereof that comprises CYS8. Generally, Prot comprises at least a portion of the protein kinase that has an amino acid sequence selected from the group consisting of GC*GNF (SEQ ID NO:38), GC*GHF (SEQ ID NO:39), and GC*GGN (SEQ ID NO:40), wherein C* is CYS8.

Some conjugates of these embodiments contain a modifier moiety that is selected from the moieties shown in Table 2.

The conjugate can comprise any suitable chemical moiety that binds in or near the ATP binding site of the protein kinase. Suitable chemical moieties for binding to the ATP binding site of a CYS8 kinase include, for example, compounds of Formula I-a, I-b, I-c, I-d, I-e, and I-f described herein, and the well-known compounds imatinib, nilotinib, and CP-562,271-26 and the compounds disclosed in US 2006/0247246, in particular the compound of Example 6.

In some embodiments, the conjugate has the formula $$X\text{-}M\text{-}S\text{—}CH_2\text{-}Prot$$

wherein Prot is a protein kinase or portion thereof that contains CYS9;

S—$CH_2$ is the sulfur atom and methylene group from the side chain of CYS9;

M is a modifier moiety that is formed by the covalent bonding of a warhead group with the side chain of CYS9; and X is a chemical moiety that binds in or near the ATP binding site of the protein kinase that contains CYS9.

In these embodiments, Prot can be ROR1 or a portion thereof that comprises CYS9.

The conjugate can comprise substantially the entire mature protein kinase or a portion thereof that comprises CYS9.

Some conjugates of these embodiments contain a modifier moiety that is selected from the moieties shown in Table 2.

The conjugate can comprise any suitable chemical moiety that binds in or near the ATP binding site of the protein kinase.

In some embodiments, the conjugate has the formula $$X\text{-}M\text{-}S\text{—}CH_2\text{-}Prot$$

wherein Prot is a protein kinase or portion thereof that contains CYS10;

S—$CH_2$ is the sulfur atom and methylene group from the side chain of CYS10;

M is a modifier moiety that is formed by the covalent bonding of a warhead group with the side chain of CYS10; and X is a chemical moiety that binds in or near the ATP binding site of the protein kinase that contains CYS10.

In these embodiments, Prot can be MELK or a portion thereof that comprises CYS10.

The conjugate can comprise substantially the entire mature protein kinase or a portion thereof that comprises CYS10.

Some conjugates of these embodiments contain a modifier moiety that is selected from the moieties shown in Table 2.

The conjugate can comprise any suitable chemical moiety that binds in or near the ATP binding site of the protein kinase.

In some embodiments, the conjugate has the formula $$X\text{-}M\text{-}S\text{—}CH_2\text{-}Prot$$

wherein Prot is a protein kinase or portion thereof that contains CYS11;

S—$CH_2$ is the sulfur atom and methylene group from the side chain of CYS11;

M is a modifier moiety that is formed by the covalent bonding of a warhead group with the side chain of CYS11; and X is a chemical moiety that binds in or near the ATP binding site of the protein kinase that contains CYS11.

In these embodiments, Prot is selected from the group consisting of c-KIT, FMS, RON, FLT3, and FGR, and a portion of any one of the foregoing that comprises CYS11.

The conjugate can comprise substantially the entire mature protein kinase or a portion thereof that comprises CYS11. Generally, Prot comprises at least a portion of the protein kinase that has an amino acid sequence selected from the group consisting of YCC*YG (SEQ ID NO:41), YMC*HG (SEQ ID NO:42), and FMC*HG (SEQ ID NO:43), wherein C* is CYS11.

Some conjugates of these embodiments, contain a modifier moiety that is selected from the moieties shown in Table 2.

The conjugate can comprise any suitable chemical moiety that binds in or near the ATP binding site of the protein kinase. Suitable chemical moieties for binding to the ATP binding site of a CYS11 kinase include, for example, compounds of Formula XIII-a, XIII-b, XIII-c, XIII-d, and XIV-XVII described herein.

In some embodiments, the conjugate has the formula $$X\text{-}M\text{-}S\text{—}CH_2\text{-}Prot$$

wherein Prot is a protein kinase or portion thereof that contains CYS12;

S—$CH_2$ is the sulfur atom and methylene group from the side chain of CYS12;

M is a modifier moiety that is formed by the covalent bonding of a warhead group with the side chain of CYS12; and X is a chemical moiety that binds in or near the ATP binding site of the protein kinase that contains CYS12.

In these embodiments, Prot can be ALK kinase or a portion thereof that comprises CYS12.

The conjugate can comprise substantially the entire mature protein kinase or a portion thereof that comprises CYS12. Generally, Prot comprises at least a portion of the protein kinase that has the amino acid sequence AARNCLLTC*PGPGRVAKIGD (SEQ ID NO:44), wherein C* is CYS12.

Some conjugates of these embodiments, contain a modifier moiety that is selected from the moieties shown in Table 2.

The conjugate can comprise any suitable chemical moiety that binds in or near the ATP binding site of the protein kinase.

In some embodiments, the conjugate has the formula $$X\text{-}M\text{-}S\text{—}CH_2\text{-}Prot$$

wherein Prot is a protein kinase or portion thereof that contains CYS13;

S—$CH_2$ is the sulfur atom and methylene group from the side chain of CYS13;

M is a modifier moiety that is formed by the covalent bonding of a warhead group with the side chain of CYS13; and X is a chemical moiety that binds in or near the ATP binding site of the protein kinase that contains CYS13.

In these embodiments, Prot can be B-RAF or a portion thereof that comprises CYS13.

The conjugate can comprise substantially the entire mature protein kinase or a portion thereof that comprises CYS13. Generally, Prot comprises at least a portion of the protein kinase that has the amino acid sequence TKPQLAIVTQWC*EGSSLYHH (SEQ ID NO:45), wherein C* is CYS13.

Some conjugates of these embodiments, contain a modifier moiety that is selected from the moieties shown in Table 2.

The conjugate can comprise any suitable chemical moiety that binds in or near the ATP binding site of the protein kinase.

The invention also relates to conjugates comprising a protein kinase that contains a cysteine residue in the ATP binding site and an inhibitor disclosed herein, wherein the inhibitor is covalently and irreversibly bonded to the cysteine residue in the ATP binding site of the protein kinase such that the activity of the protein kinase is irreversibly inhibited. In one embodiment, the conjugate comprises an inhibitor disclosed herein and a protein kinase, wherein the inhibitor is covalently and irreversibly bonded to a cysteine residue in the ATP binding site of the protein kinase.

In some embodiments, the conjugate comprises C-KIT or a portion thereof comprising CYS1 of C-KIT (Cys788) and a compound of formula XVIII, XIX, XIX-a, XIX-b, XIX-c, XX or XX-a that is covalently and irreversible bonded to CYS1 of C-KIT (Cys788), such that C-KIT is irreversibly inhibited.

In some embodiments, the conjugate comprises KDR or a portion thereof comprising CYS1 of KDR (Cys1024) and a compound of formula XVIII, XIX, XIX-a, XIX-b, XIX-c, XX or XX-a that is covalently and irreversible bonded to CYS1 of KDR (Cys1024), such that KDR is irreversibly inhibited.

In some embodiments, the conjugate comprises PDGFRA or a portion thereof comprising CYS1 of PDGFRA (Cys814) and a compound of formula XVIII, XIX, XIX-a, XIX-b, XIX-c, XX or XX-a that is covalently and irreversible bonded to CYS1 of PDGFRA (Cys814), such that PDGFRA is irreversibly inhibited.

In some embodiments, the conjugate comprises PDGFRB or a portion thereof comprising CYS1 of PDGFRB (Cys822) and a compound of formula XVIII, XIX, XIX-a, XIX-b, XIX-c, XX or XX-a that is covalently and irreversible bonded to CYS1 of PDGFRB (Cys822), such that PDGFRB is irreversibly inhibited.

In some embodiments, the conjugate comprises FLT3 or a portion thereof comprising CYS1 of FLT3 (Cys807) and a compound of formula XVIII, XIX, XIX-a, XIX-b, XIX-c, XX or XX-a that is covalently and irreversible bonded to CYS1 of FLT3 (Cys807), such that FLT3 is irreversibly inhibited.

In some embodiments, the conjugate comprises CSF1R or a portion thereof comprising CYS1 of CSF1R (Cys744) and a compound of formula XVIII, XIX, XIX-a, XIX-b, XIX-c, XX or XX-a that is covalently and irreversible bonded to CYS1 of CSF1R (Cys744), such that CSF1R is irreversibly inhibited.

In some embodiments, the conjugate comprises B-RAF or a portion thereof comprising CYS13 of B-RAF (Cys532) and a compound of formula XVIII, XIX, XIX-a, XIX-b, XIX-c, XX or XX-a that is covalently and irreversible bonded to CYS13 of B-RAF (Cys532), such that B-RAF is irreversibly inhibited.

In some embodiments, the conjugate comprises FLT3 or a portion thereof comprising CYS2 of FLT3 (Cys828) and a compound of formula II-a, II-b, II-c or II-d that is covalently and irreversible bonded to CYS2 of FLT3 (Cys828), such that FLT3 is irreversibly inhibited.

In some embodiments, the conjugate comprises MEK1 or a portion thereof comprising CYS2 of MEK1 (Cys207) and a compound of formula II-a, II-b, II-c or II-d that is covalently and irreversible bonded to CYS2 of MEK1 (Cys207), such that MEK1 is irreversibly inhibited.

In some embodiments, the conjugate comprises JAK3 or a portion thereof comprising CYS3 of JAK3 (Cys909) and a compound of formula V that is covalently and irreversible bonded to CYS3 of JAK3 (Cys909), such that JAK3 is irreversibly inhibited.

In some embodiments, the conjugate comprises PLK1 or a portion thereof comprising CYS4 of PLK1 (Cys67) and a compound of formula III that is covalently and irreversible bonded to CYS4 of PLK1 (Cys67), such that PLK1 is irreversibly inhibited.

In some embodiments, the conjugate comprises FAK or a portion thereof comprising CYS7 of FAK (Cys427) and a compound of formula IV, IVa or IVb that is covalently and irreversible bonded to CYS7 of FAK (Cys427), such that FAK is irreversibly inhibited.

In some embodiments, the conjugate comprises JNK1 or a portion thereof comprising CYS5 of JNK1 (Cys116) and a compound of formula V1, VII, VIII, IX, IX-a, X, X-a, XI, XII or XII-a that is covalently and irreversible bonded to CYS5 of JNK1 (Cys116), such that JNK1 is irreversibly inhibited.

In some embodiments, the conjugate comprises ZAP70 or a portion thereof comprising CYS8 of ZAP70 (Cys346) and a compound of formula I-a, I-b, I-c, I-d, I-e, and I-f that is covalently and irreversible bonded to CYS8 of ZAP70 (Cys346), such that ZAP70 is irreversibly inhibited.

In some embodiments, the conjugate comprises RON or a portion thereof comprising CYS11 of RON (Cys1165) and a compound of formula XIII-a, XIII-b, XIII-c, XIII-d, XIV, XV, XVI, or XVII that is covalently and irreversible bonded to CYS11 of RON (Cys1165), such that RON is irreversibly inhibited.

3. Compounds that Irreversibly Inhibit Protein Kinases

The invention relates to compounds that irreversibly inhibit one or more protein kinases and to pharmaceutically acceptable salt and compositions thereof. Without wishing to be bound by any particular theory, it is believed that the warhead groups in the compounds described herein are particularly suitable for covalently binding to a key cysteine residue in the binding site of certain protein kinases. The compounds disclosed herein are inhibitors of at lease one protein kinase and for descriptive convenience are referred to as inhibitors of a particular kinase.

A. Warheads

The compounds of the invention comprise a warhead group that is provided by -L-Y in the formulas described herein. The following detailed description of the warhead groups provided by -L-Y apply to each of the compounds and formulas described herein. It is to be understood that L and Y can be variously combined to provide a warhead. The particular L and Y groups described herein can be combined in any desired combination to provide a warhead for any of the embodiments of compounds described herein.

In general, a warhead is provided by -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(═S)—, —C(═NR)—, —N═N—, or —C(═$N_2$)—;

Y is hydrogen, nitrile, $C_{1-6}$ aliphatic optionally substituted with one or more OH, NRxRy, oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and Rx and Ry are independently hydrogen, lower alkyl, lower haloalkyl, or lower cycloalkyl;

each $R^e$ is independently selected from -Q-Z, OH, oxo, $NO_2$, halogen, CN, a suitable leaving group, or a $C_{1-6}$ aliphatic optionally substituted with oxo, halogen, $NO_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, L is a covalent bond.

In certain embodiments, L is a bivalent $C_{1-8}$ saturated or unsaturated, straight or branched, hydrocarbon chain. In certain embodiments, L is —$CH_2$—.

In certain embodiments, L is a covalent bond, —$CH_2$—, —NH—, —$CH_2$NH—, —NH$CH_2$—, —NHC(O)—, —NHC(O)$CH_2$OC(O)—, —$CH_2$NHC(O)—, —NH$SO_2$—, —NH$SO_2$$CH_2$—, —NHC(O)$CH_2$OC(O)—, or —$SO_2$NH—.

In some embodiments, L is a bivalent $C_{2-8}$ straight or branched, hydrocarbon chain wherein L has at least one double bond and one or two additional methylene units of L are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, or —C(O)—.

In certain embodiments, L is a bivalent $C_{2-8}$ straight or branched, hydrocarbon chain wherein L has at least one double bond and at least one methylene unit of L is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of L are optionally and independently replaced by cyclopropylene, —O—, —N(R)—, or —C(O)—.

In some embodiments, L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—.

As described above, in certain embodiments, L is a bivalent $C_{2-8}$ straight or branched, hydrocarbon chain wherein L has at least one double bond. One of ordinary skill in the art will recognize that such a double bond may exist within the hydrocarbon chain backbone or may be "exo" to the backbone chain and thus forming an alkylidene group. By way of example, such an L group having an alkylidene branched chain includes —$CH_2$C(═$CH_2$)$CH_2$—. Thus, in some embodiments, L is a bivalent $C_{2-8}$ straight or branched, hydrocarbon chain wherein L has at least one alkylidenyl double bond. Exemplary L groups include —NHC(O)C(═$CH_2$)$CH_2$—.

In certain embodiments, L is a bivalent $C_{2-8}$ straight or branched, hydrocarbon chain wherein L has at least one double bond and at least one methylene unit of L is replaced by —C(O)—. In certain embodiments, L is —C(O)CH═CH($CH_3$)—, —C(O)CH═CH$CH_2$NH($CH_3$)—, —C(O)CH═CH($CH_3$)—, —C(O)CH═CH—, —$CH_2$C(O)CH═CH—, —$CH_2$C(O)CH═CH($CH_3$)—, —$CH_2$$CH_2$C(O)CH═CH—, —$CH_2$$CH_2$C(O)CH═CH$CH_2$—, —$CH_2$$CH_2$C(O)CH═CH$CH_2$NH($CH_3$)—, or —$CH_2$$CH_2$C(O)CH═CH($CH_3$)—, or —CH($CH_3$)OC(O)CH═CH—.

In certain embodiments, L is a bivalent $C_{2-8}$ straight or branched, hydrocarbon chain wherein L has at least one double bond and at least one methylene unit of L is replaced by —OC(O)—.

In some embodiments, L is a bivalent $C_{2-8}$ straight or branched, hydrocarbon chain wherein L has at least one double bond and at least one methylene unit of L is replaced by —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of L are optionally and independently replaced by cyclopropylene, —O—, —N(R)—, or —C(O)—. In some embodiments, L is —$CH_2$OC(O)CH═CH$CH_2$—, —$CH_2$—OC(O)CH═CH—, or —CH(CH═$CH_2$)OC(O)CH═CH—.

In certain embodiments, L is —NRC(O)CH═CH—, —NRC(O)CH═CH$CH_2$N($CH_3$)—, —NRC(O)CH═CH$CH_2$O—, —$CH_2$NRC(O)CH═CH—, —NR$SO_2$CH═CH—, —NR$SO_2$CH═CH$CH_2$—, —NRC(O)(C═$N_2$)C(O)—, —NRC(O)CH═CH$CH_2$N($CH_3$)—, —NR$SO_2$CH═CH—, —NR$SO_2$CH═CH$CH_2$—, —NRC(O)CH═CH$CH_2$O—, —NRC(O)C(═$CH_2$)$CH_2$—, —$CH_2$NRC(O)—, —$CH_2$NRC(O)CH═CH—, —$CH_2$$CH_2$NRC(O)—, or —$CH_2$NRC(O)cyclopropylene-, wherein each R is independently hydrogen or optionally substituted $C_{1-6}$ aliphatic.

In certain embodiments, L is —NHC(O)CH═CH—, —NHC(O)CH═CH$CH_2$N($CH_3$)—, —NHC(O)CH═CH$CH_2$O—, —$CH_2$NHC(O)CH═CH—, —NH$SO_2$CH═CH—, —NH$SO_2$CH═CH$CH_2$—, —NHC(O)(C═$N_2$)C(O)—, —NHC(O)CH═CH$CH_2$N($CH_3$)—, —NH$SO_2$CH═CH—, —NH$SO_2$CH═CH$CH_2$—, —NHC(O)CH═CH$CH_2$O—, —NHC(O)C(═$CH_2$)$CH_2$—, —$CH_2$NHC(O)—, —$CH_2$NHC(O)CH═CH—, —$CH_2$$CH_2$NHC(O)—, or —$CH_2$NHC(O)cyclopropylene-.

In some embodiments, L is a bivalent $C_{2-8}$ straight or branched, hydrocarbon chain wherein L has at least one triple bond. In certain embodiments, L is a bivalent $C_{2-8}$ straight or branched, hydrocarbon chain wherein L has at least one triple bond and one or two additional methylene units of L are optionally and independently replaced by —NRC(O)—, —C(O)NR—, —S—, —S(O)—, —$SO_2$—, —C(═S)—, —C(═NR)—, —O—, —N(R)—, or —C(O)—. In some embodiments, L has at least one triple bond and at least one methylene unit of L is replaced by —N(R)—, —N(R)C(O)—, —C(O)—, —C(O)O—, or —OC(O)—, or —O—.

Exemplary L groups include —C≡C—, —C≡C$CH_2$N(isopropyl)-, —NHC(O)C≡C$CH_2$$CH_2$—, —$CH_2$—C≡C—$CH_2$—, C≡C$CH_2$O—, —$CH_2$C(O)C≡C—, —C(O)C≡C—, or —$CH_2$OC(═O)C≡C—.

In certain embodiments, L is a bivalent $C_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)$SO_2$—, or —$SO_2$N(R)—. Exemplary L groups include —NHC(O)-cyclopropylene-$SO_2$— and —NHC(O)-cyclopropylene-.

As defined generally above, Y is hydrogen, $C_{1-6}$ aliphatic optionally substituted with oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 $R^e$ groups, each $R^e$ is independently selected from -Q-Z, oxo, $NO_2$, halogen, CN, or $C_{1-6}$ aliphatic, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and, Z is hydrogen or $C_{1-6}$ aliphatic optionally substituted with oxo, halogen, $NO_2$, or CN.

In certain embodiments, Y is hydrogen.

In certain embodiments, Y is $C_{1-6}$ aliphatic optionally substituted with oxo, halogen, $NO_2$, or CN. In some embodiments, Y is $C_{2-6}$ alkenyl optionally substituted with oxo, halogen, $NO_2$, or CN. In other embodiments, Y is $C_{2-6}$ alkynyl optionally substituted with oxo, halogen, $NO_2$, or CN. In some embodiments, Y is $C_{2-6}$ alkenyl. In other embodiments, Y is $C_{2-4}$ alkynyl.

In other embodiments, Y is $C_{1-6}$ alkyl substituted with oxo, halogen, $NO_2$, or CN. Such Y groups include —$CH_2F$, —$CH_2Cl$, —$CH_2CN$, and —$CH_2NO_2$.

In certain embodiments, Y is a saturated 3-6 membered monocyclic ring having 0-3 heteroatoms independently selected from nitrogen, oxygen, or sulfur, wherein Y is substituted with 1-4 $R^e$ groups, wherein each $R^e$ is as defined above and described herein.

In some embodiments, Y is a saturated 3-4 membered heterocyclic ring having 1 heteroatom selected from oxygen or nitrogen wherein said ring is substituted with 1-2 $R^e$ groups, wherein each $R^e$ is as defined above and described herein. Exemplary such rings are epoxide and oxetane rings, wherein each ring is substituted with 1-2 $R^e$ groups, wherein each $R^e$ is as defined above and described herein.

In other embodiments, Y is a saturated 5-6 membered heterocyclic ring having 1-2 heteroatom selected from oxygen or nitrogen wherein said ring is substituted with 1-4 $R^e$ groups, wherein each $R^e$ is as defined above and described herein. Such rings include piperidine and pyrrolidine, wherein each ring is substituted with 1-4 $R^e$ groups, wherein each $R^e$ is as defined above and described herein. In certain embodiments, Y is

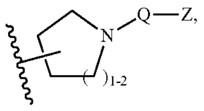 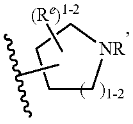 , or

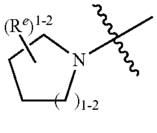 , wherein each R, Q, Z, and $R^e$ is as defined above and described herein.

In some embodiments, Y is a saturated 3-6 membered carbocyclic ring, wherein said ring is substituted with 1-4 $R^e$ groups, wherein each $R^e$ is as defined above and described herein. In certain embodiments, Y is cyclopropyl, cyclobutyl, cyclopentyl, or cyclohexyl, wherein each ring is substituted with 1-4 $R^e$ groups, wherein each $R^e$ is as defined above and described herein.

In certain embodiments, Y is

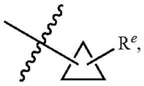

wherein $R^e$ is as defined above and described herein. In certain embodiments, Y is cyclopropyl optionally substituted with halogen, CN or $NO_2$.

In certain embodiments, Y is a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein.

In some embodiments, Y is a partially unsaturated 3-6 membered carbocyclic ring, wherein said ring is substituted with 1-4 $R^e$ groups, wherein each $R^e$ is as defined above and described herein. In some embodiments, Y is cyclopropenyl, cyclobutenyl, cyclopentenyl, or cyclohexenyl wherein each ring is substituted with 1-4 $R^e$ groups, wherein each $R^e$ is as defined above and described herein. In certain embodiments, Y is

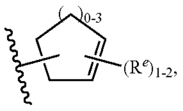

wherein each $R^e$ is as defined above and described herein.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein. In certain embodiments, Y is selected from:

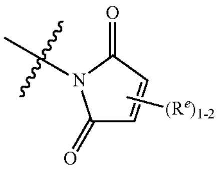 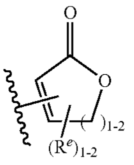 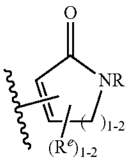

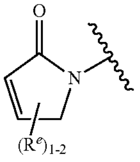

wherein each R and $R^e$ is as defined above and described herein.

In certain embodiments, Y is a 6-membered aromatic ring having 0-2 nitrogens wherein said ring is substituted with 1-4 $R^e$ groups, wherein each $R^e$ group is as defined above and described herein. In certain embodiments, Y is phenyl, pyridyl, or pyrimidinyl, wherein each ring is substituted with 1-4 $R^e$ groups, wherein each $R^e$ is as defined above and described herein.

In some embodiments, Y is selected from:

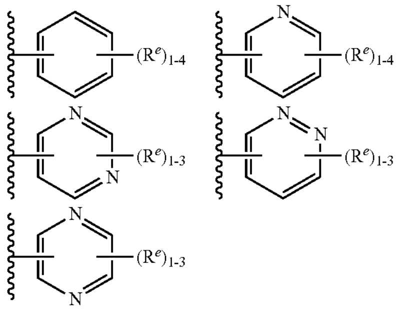

wherein each $R^e$ is as defined above and described herein.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above and described herein. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above and described herein. In certain embodiments, Y is selected from:

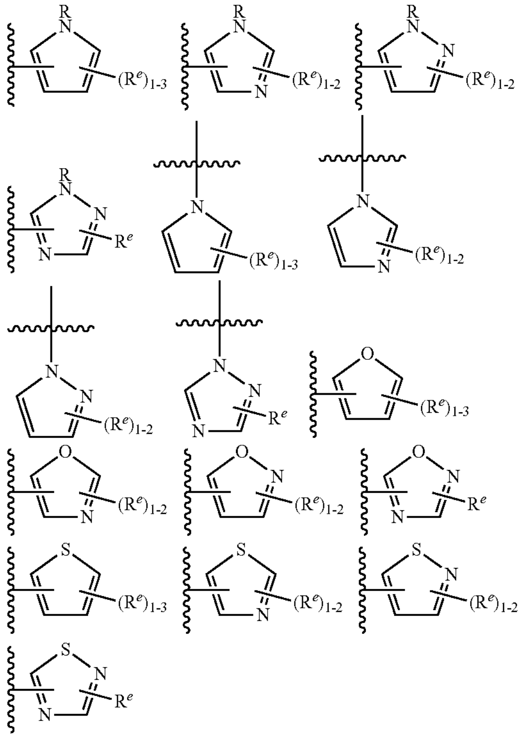

wherein each R and $R^e$ is as defined above and described herein.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein $R^e$ is as defined above and described herein. Exemplary such bicyclic rings include 2,3-dihydrobenzo[d]isothiazole, wherein said ring is substituted with 1-4 $R^e$ groups, wherein $R^e$ is as defined above and described herein.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —$SO_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —$SO_2$—. In certain embodiments, the Z moiety of the $R^e$ group is hydrogen. In some embodiments, -Q-Z is —NHC(O)CH═$CH_2$ or —C(O)CH═$CH_2$.

In certain embodiments, each $R^e$ is independently selected from oxo, $NO_2$, CN, fluoro, chloro, —NHC(O)CH═$CH_2$, —C(O)CH═$CH_2$, —$CH_2$CH═$CH_2$, —C≡CH, —C(O)O$CH_2$Cl, —C(O)O$CH_2$F, —C(O)O$CH_2$CN, —C(O)$CH_2$Cl, —C(O)$CH_2$F, —C(O)$CH_2$CN, or —$CH_2$C(O)$CH_3$, In certain embodiments, $R^e$ is a suitable leaving group, ie a group that is subject to nucleophilic displacement. A "suitable leaving" is a chemical group that is readily displaced by a desired incoming chemical moiety such as the thiol moiety of a cysteine of interest. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetyl, methanesulfonyloxy (mesyloxy), tosyloxy, triflyloxy, nitro-phenylsulfonyloxy (nosyloxy), and bromo-phenylsulfonyloxy (brosyloxy).

In certain embodiments, the following embodiments and combinations of -L-Y apply:

(a) L is a bivalent $C_{2-8}$ straight or branched, hydrocarbon chain wherein L has at least one double bond and one or two additional methylene units of L are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, or —C(O)—; and Y is hydrogen or $C_{1-6}$ aliphatic optionally substituted with oxo, halogen, $NO_2$, or CN; or (b) L is a bivalent $C_{2-8}$ straight or branched, hydrocarbon chain wherein L has at least one double bond and at least one methylene unit of L is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (c) L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (d) L is a bivalent $C_{2-8}$ straight or branched, hydrocarbon chain wherein L has at least one double bond and at least one methylene unit of L is replaced by —C(O)—; and Y is hydrogen or $C_{1-6}$ aliphatic optionally substituted with oxo, halogen, $NO_2$, or CN; or (e) L is a bivalent $C_{2-8}$ straight or branched, hydrocarbon chain wherein L has at least one double bond and at least one methylene unit of L is replaced by —OC(O)—; and Y is hydrogen or $C_{1-6}$ aliphatic optionally substituted with oxo, halogen, $NO_2$, or CN; or (f) L is —NRC(O)CH═CH—, —NRC(O)CH═CHCH$_2$N(CH$_3$)—, —NRC(O)CH═CHCH$_2$O—, —CH$_2$NRC(O)CH═CH—, —NRSO$_2$CH═CH—, —NRSO$_2$CH═CHCH$_2$—, —NRC(O)(C═N$_2$)—, —NRC(O)(C═N$_2$)C(O)—, —NRC(O)CH═CHCH$_2$N(CH$_3$)—, —NRSO$_2$CH═CH—, —NRSO$_2$CH═CHCH$_2$—, —NRC(O)CH═CHCH$_2$O—, —NRC(O)C(═CH$_2$)CH$_2$—, —CH$_2$NRC(O)—, —CH$_2$NRC(O)CH═CH—, —CH$_2$CH$_2$NRC(O)—, or —CH$_2$NRC(O)cyclopropylene-; wherein R is H or optionally substituted $C_{1-6}$ aliphatic; and Y is hydrogen or $C_{1-6}$ aliphatic optionally substituted with oxo, halogen, $NO_2$, or CN; or (g) L is —NHC(O)CH═CH—, —NHC(O)CH═CHCH$_2$N(CH$_3$)—, —NHC(O)CH═CHCH$_2$O—, —CH$_2$NHC(O)CH═CH—, —NHSO$_2$CH═CH—, —NHSO$_2$CH═CHCH$_2$—, —NHC(O)(C═N$_2$)—, —NHC(O)(C═N$_2$)C(O)—, —NHC(O)CH═CHCH$_2$N(CH$_3$)—, —NHSO$_2$CH═CH—, —NHSO$_2$CH═CHCH$_2$—, —NHC(O)CH═CHCH$_2$O—, —NHC(O)C(═CH$_2$)CH$_2$—, —CH$_2$NHC(O)—, —CH$_2$NHC(O)CH═CH—, —CH$_2$CH$_2$NHC(O)—, or —CH$_2$NHC(O)cyclopropylene-; and Y is hydrogen or $C_{1-6}$ aliphatic optionally substituted with oxo, halogen, $NO_2$, or CN; or (h) L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (i) L is a bivalent $C_{2-8}$ straight or branched, hydrocarbon chain wherein L has at least one triple bond and one or two additional methylene units of L are optionally and independently replaced by —NRC(O)—, —C(O)NR—, —N(R)$SO_2$—, —$SO_2$N(R)—, —S—, —S(O)—, —$SO_2$—, —OC(O)—, or —C(O)O—, and Y is hydrogen or $C_{1-6}$ aliphatic optionally substituted with oxo, halogen, $NO_2$, or CN; or (j) L is —C≡C—, —C≡CCH$_2$N(isopropyl)-, —NHC(O)C≡CCH$_2$CH$_2$—, —CH$_2$—C≡C—CH$_2$—, —C≡CCH$_2$O—, —CH$_2$C(O)C≡C—, —C(O)C≡C—, or —CH$_2$OC(═O)C≡C—; and Y is hydrogen or $C_{1-6}$ aliphatic optionally substituted with oxo, halogen, $NO_2$, or CN; or (k) L is a bivalent $C_{2-8}$ straight or branched, hydrocarbon chain wherein one methylene unit of L is replaced by cyclopropylene and one or two additional methylene units of L are independently replaced by —NRC(O)—, —C(O)NR—, —N(R)$SO_2$—, —$SO_2$N(R)—, —S—, —S(O)—, —$SO_2$—, —OC(O)—, or —C(O)O—; and Y is hydrogen or $C_{1-6}$ aliphatic optionally substituted with oxo, halogen, $NO_2$, or CN; or (l) L is a covalent bond and Y is selected from:

(i) $C_{1-6}$ alkyl substituted with oxo, halogen, $NO_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

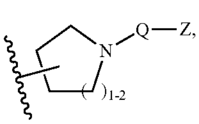
, 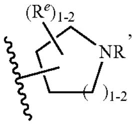
, or

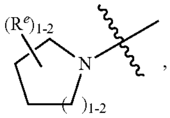
, wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein;

or (x)

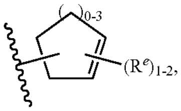
, wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

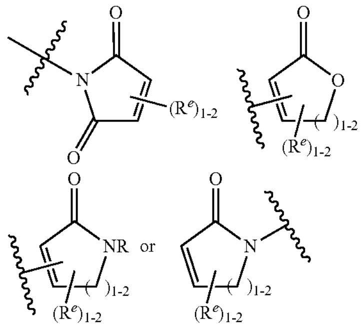

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

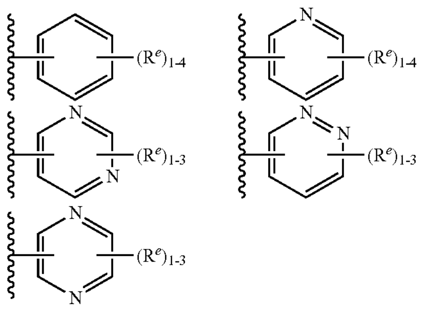

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

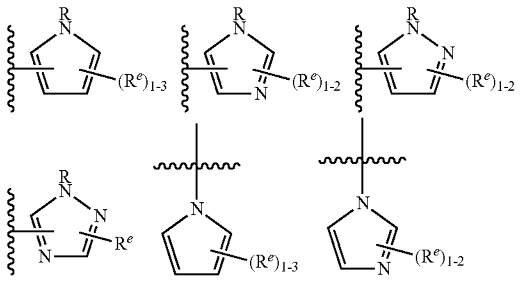

-continued

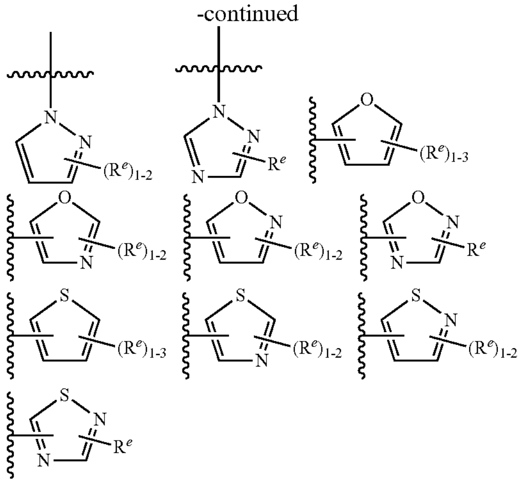

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(m) L is —C(O)— and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

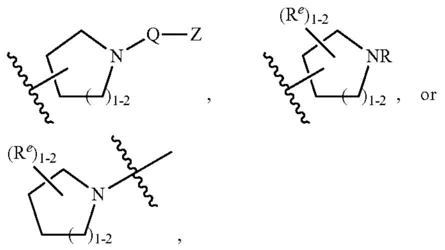

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein;

(x)

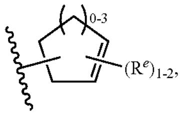

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

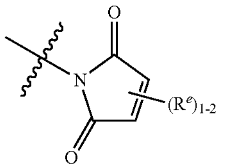 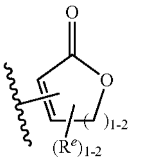

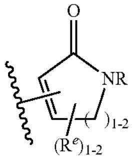 or 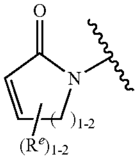

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

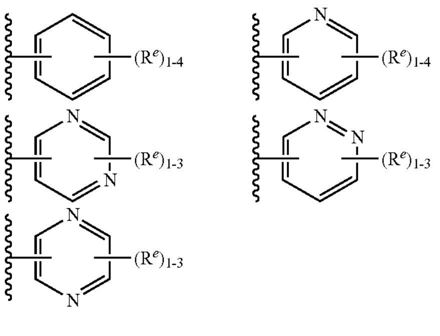

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

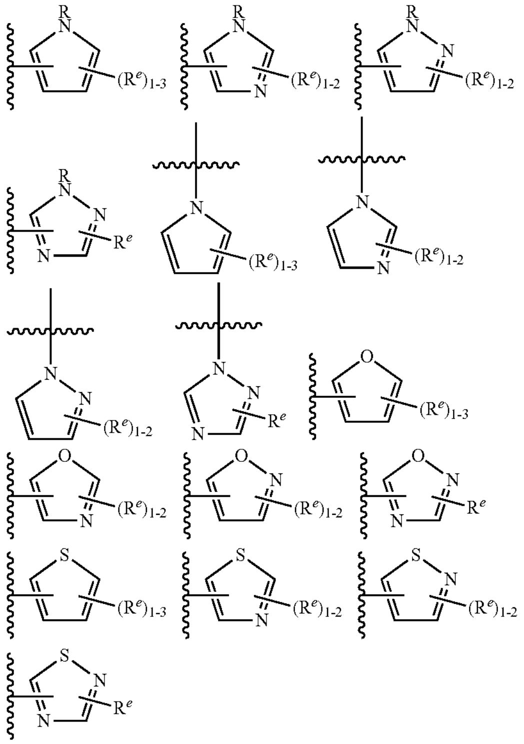

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(n) L is —N(R)C(O)— and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

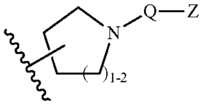 , 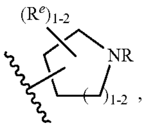 , or

-continued

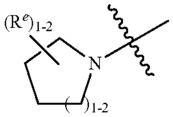

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein;

(x)

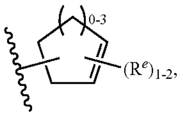

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

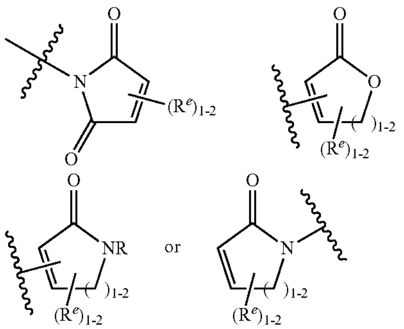

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

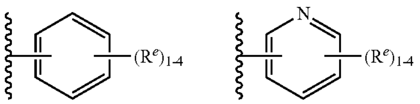

-continued

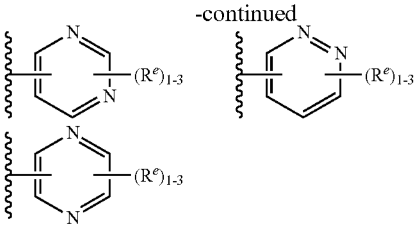

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

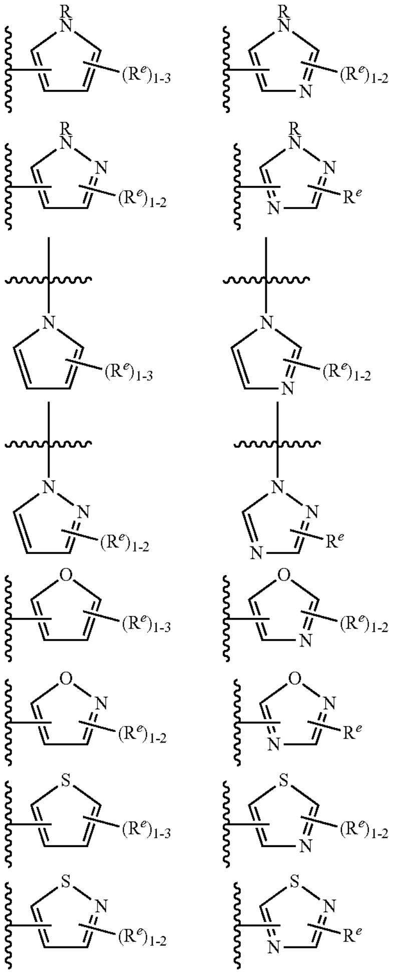

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(o) L is a bivalent $C_{3-8}$ saturated or unsaturated, straight or branched, hydrocarbon chain; and Y is selected from:

(i) $C_{1-6}$ alkyl substituted with oxo, halogen, $NO_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

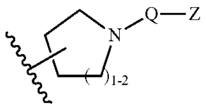

,

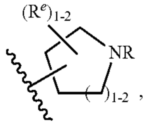

, or

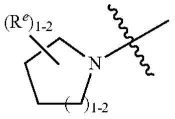

, wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein;

(x)

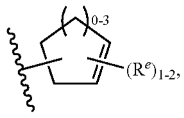

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

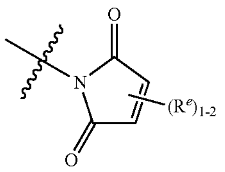

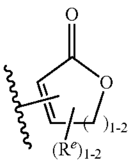

-continued

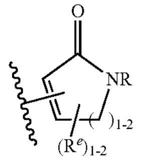

or

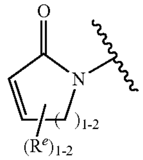

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

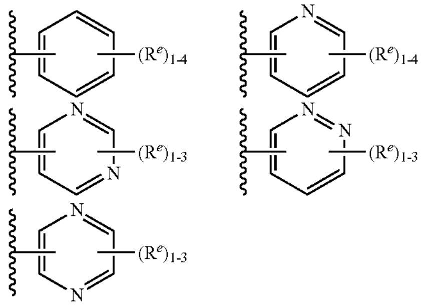

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

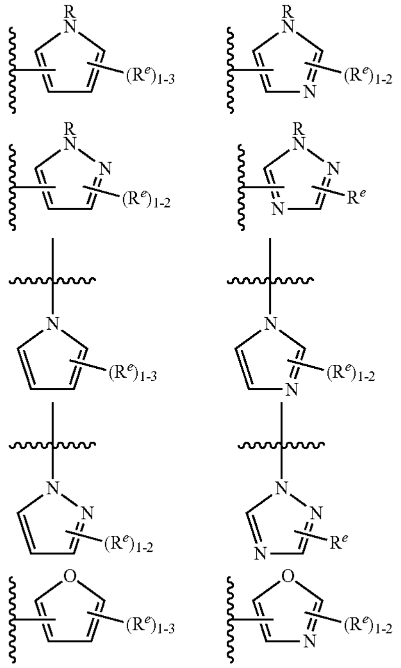

-continued

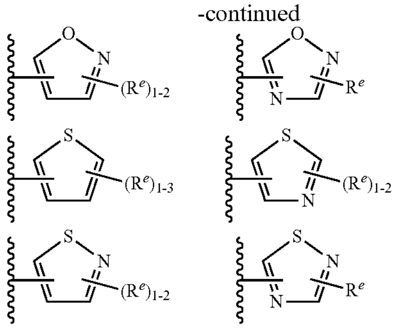

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(p) L is a covalent bond, $—CH_2—$, —NH—, —C(O)—, $—CH_2NH—$, $—NHCH_2—$, —NHC(O)—, $—NHC(O)CH_2OC(O)—$, $—CH_2NHC(O)—$, $—NHSO_2—$, $—NHSO_2CH_2—$, $—NHC(O)CH_2OC(O)—$, or $—SO_2NH—$; and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

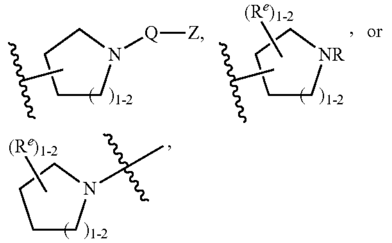

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein;

(x)

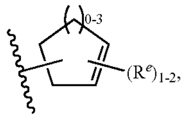

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

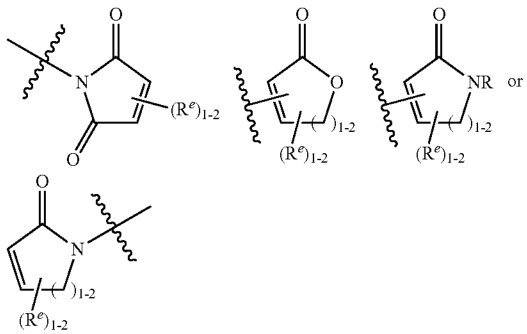

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

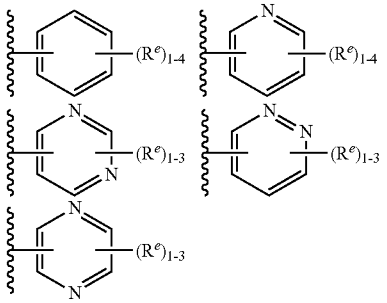

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

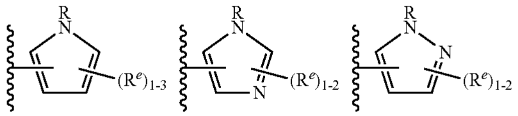

-continued

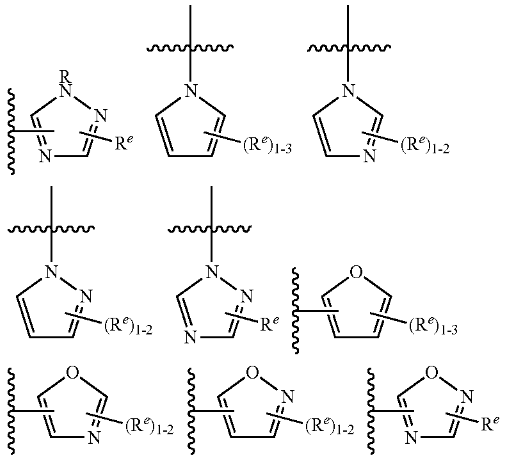

-continued

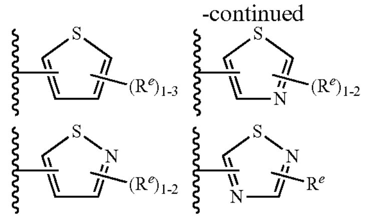

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein.

In certain embodiments, the Y group is selected from those set forth in Table 3, below, wherein each wavy line indicates the point of attachment to the rest of the molecule.

TABLE 3

| Exemplary Y groups: | | | |
|---|---|---|---|
| 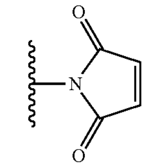 | 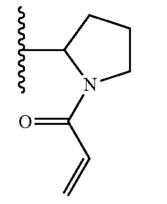 | 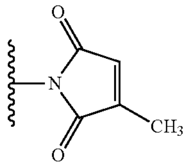 | 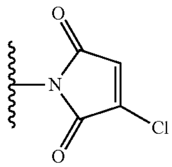 |
| a | b | c | d |
| 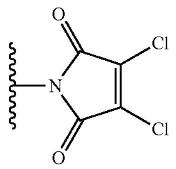 | 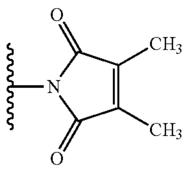 | 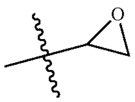 | 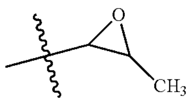 |
| e | f | g | h |
| 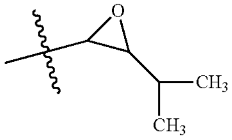 | 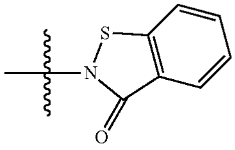 | 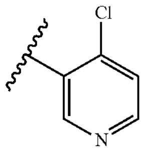 | 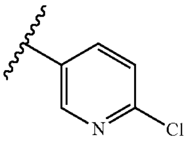 |
| i | j | k | l |
| 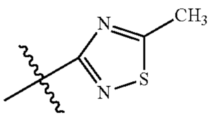 | 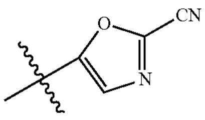 | 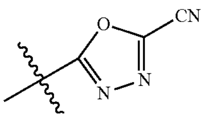 | 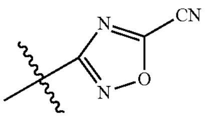 |
| m | n | o | p |
| 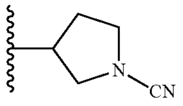 | 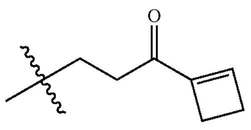 | 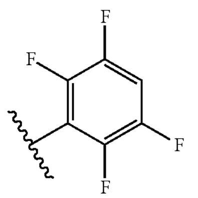 | 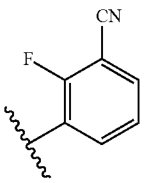 |
| q | r | s | t |

TABLE 3-continued
Exemplary Y groups:
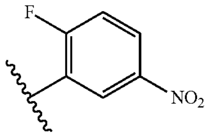
u
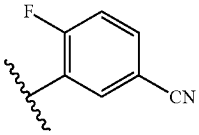
v
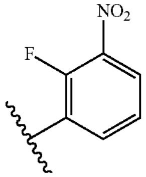
w
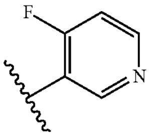
x
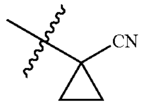
y
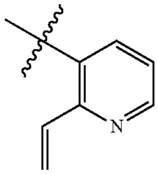
z
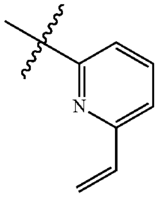
aa
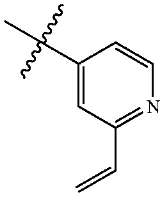
bb
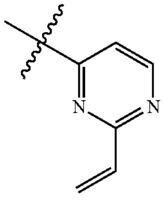
cc
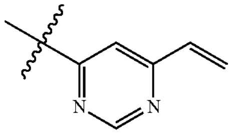
dd
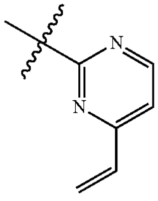
ee
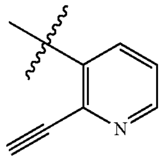
ff
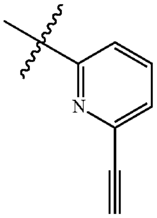
gg
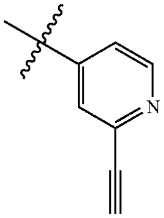
hh
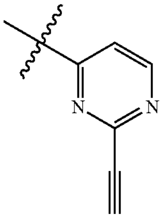
ii
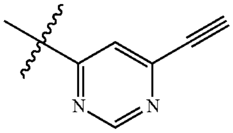
jj
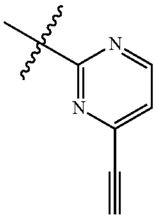
kk
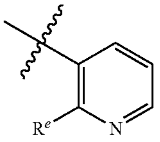
ll
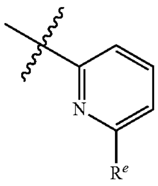
mm
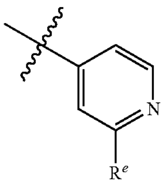
nn
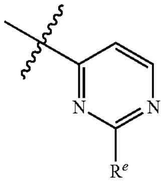
oo
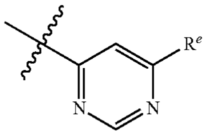
pp
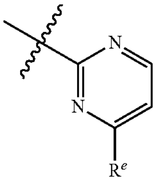
qq
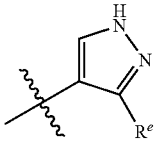
rr TABLE 3-continued
| Exemplary Y groups: | | | |
|---|---|---|---|
| 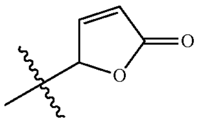 | 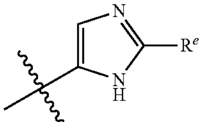 | 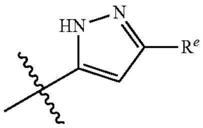 | 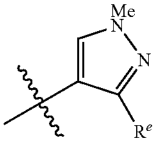 |
| ss | tt | uu | vv |
| 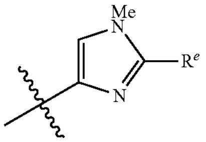 | 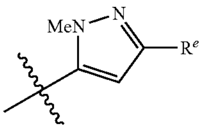 | 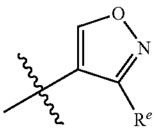 | 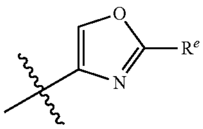 |
| ww | xx | yy | zz |
| 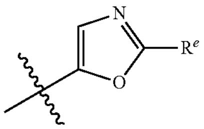 | 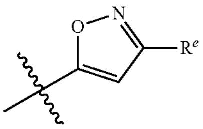 | 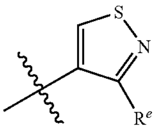 | 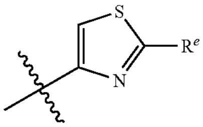 |
| aaa | bbb | ddd | ddd |
| 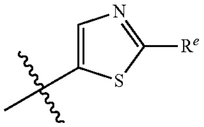 | 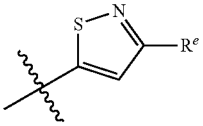 | 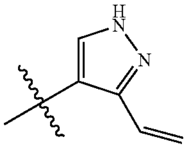 [SMILES: *c1c[nH]nc1C=C] | 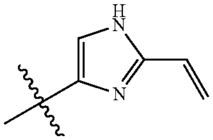 |
| eee | fff | ggg | hhh |
| 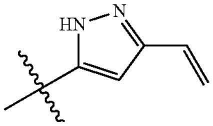 | 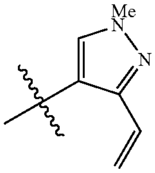 | 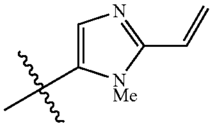 | 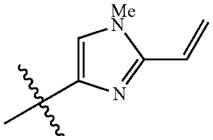 |
| iii | jjj | kkk | lll |
| 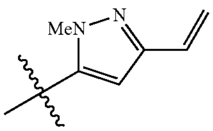 | 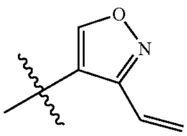 | 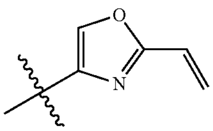 | 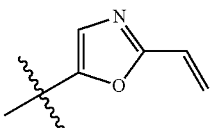 |
| mmm | nnn | ooo | ppp |
| 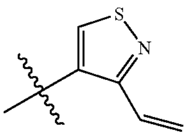 | 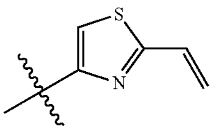 | 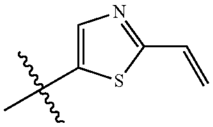 | 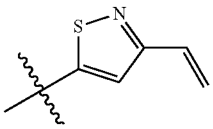 |
| qqq | rrr | sss | ttt |

TABLE 3-continued
Exemplary Y groups:
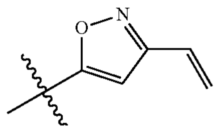
uuu
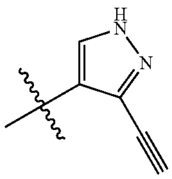
vvv
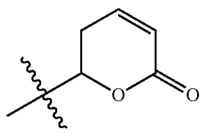
qqq
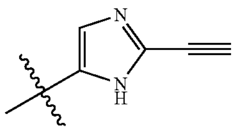
www
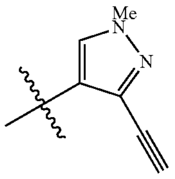
xxx
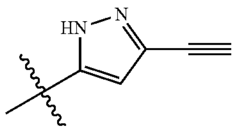
yyy
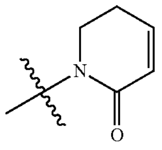
zzz
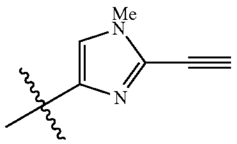
aaaa
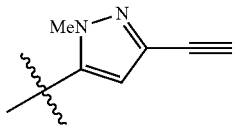
bbbb
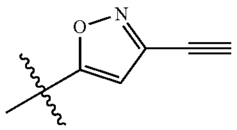
cccc
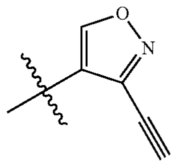
dddd
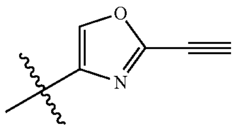
eeee
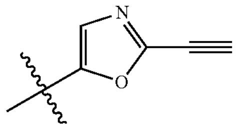
ffff
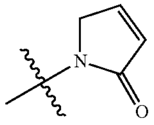
gggg
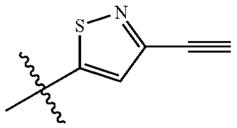
hhhh
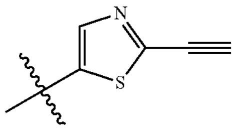
iiii
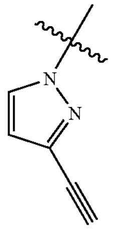
jjjj
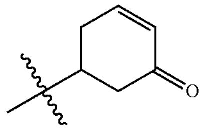
kkkk
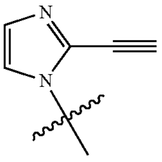
llll
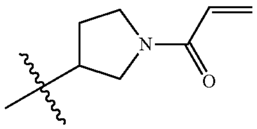
mmmm
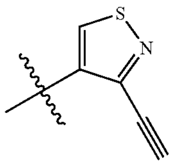
nnnn
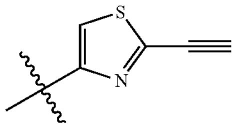
oooo
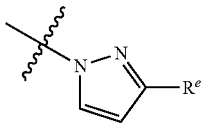
pppp
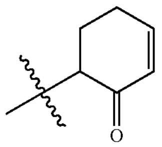
qqqq
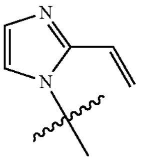
rrrr
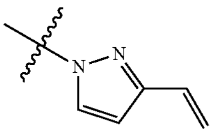
ssss
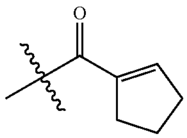
tttt
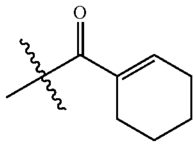
uuuu TABLE 3-continued

| Exemplary Y groups: | | | |
|---|---|---|---|
| 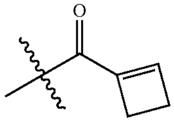 vvvv | 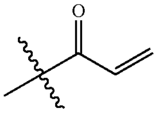 wwww | 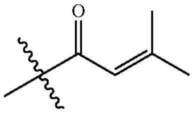 xxxx | 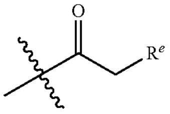 yyyy |
| 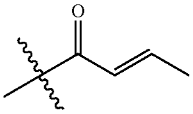 zzzz | 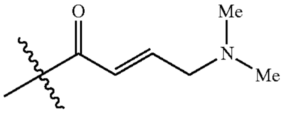 aaaaa | 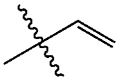 bbbbb | 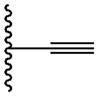 ccccc |

wherein each $R^e$ group depicted in Table 2 is independently selected from halogen. In certain embodiments, $R^1$ is $—C{\equiv}CH$, $—C{\equiv}CCH_2NH$(isopropyl), $—NHC(O)C{\equiv}CCH_2CH_3$, $—CH_2—C{\equiv}C—CH_3$, $—C{\equiv}CCH_2OH$, $—CH_2C(O)C{\equiv}CH$, $—C(O)C{\equiv}CH$, or $—CH_2OC({=}O)C{\equiv}CH$. In some embodiments, $R^1$ is selected from $—NHC(O)CH{=}CH_2$, $—NHC(O)CH{=}CHCH_2N(CH_3)_2$, or $—CH_2NHC(O)CH{=}CH_2$.

In certain embodiments, $R^1$ is selected from those set forth in Table 4, below, wherein each wavy line indicates the point of attachment to the rest of the molecule.

TABLE 4

| Exemplary $R^1$ Groups | | |
|---|---|---|
| 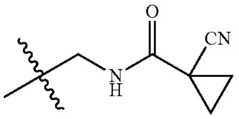 a | 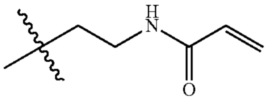 b | 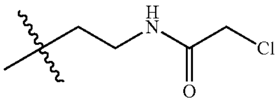 c |
| 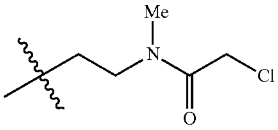 d | 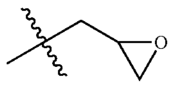 e | 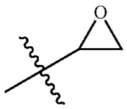 f |
| 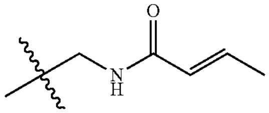 g | 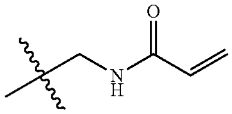 h | 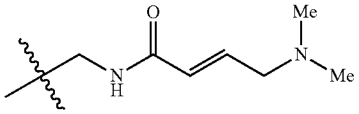 i |
| 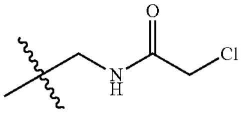 j | 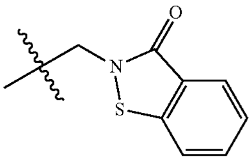 k | 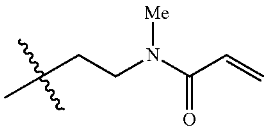 l |
| 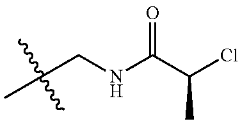 m | 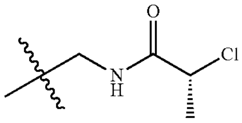 n | 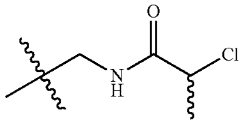 o |

TABLE 4-continued
Exemplary R[1] Groups
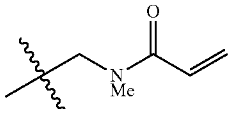
p
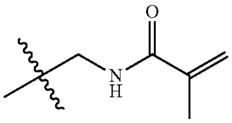
q
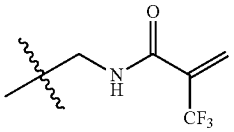
r
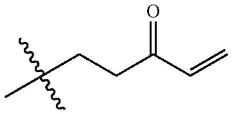
s
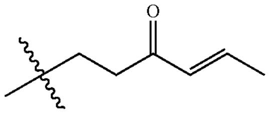
t
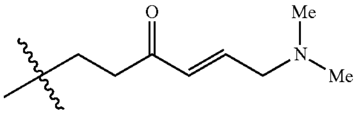
u
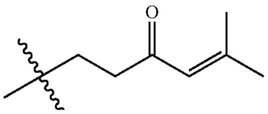
v
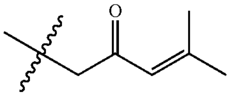
w
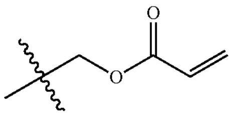
x
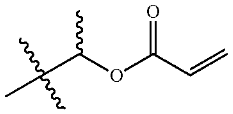
y
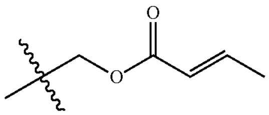
z
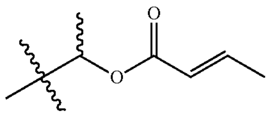
aa
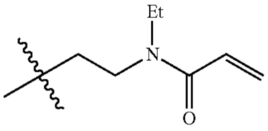
bb
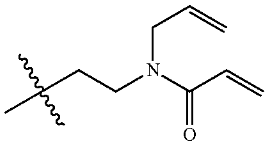
cc
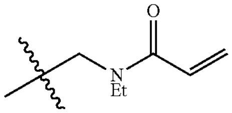
dd
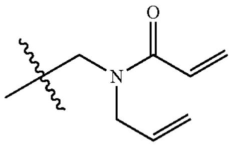
ee
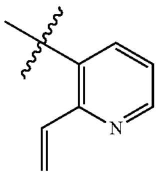
ff
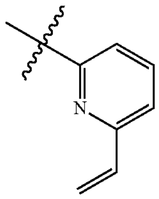
gg
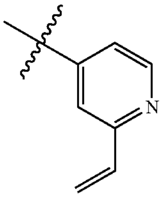
hh
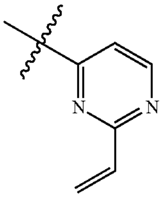
ii
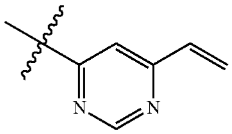
jj TABLE 4-continued
Exemplary $R^1$ Groups
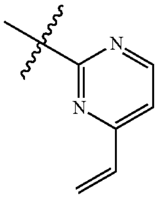
kk
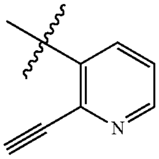
ll
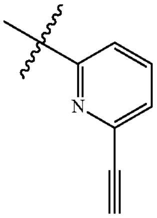
mm
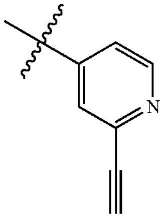
nn
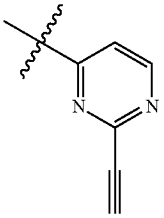
oo
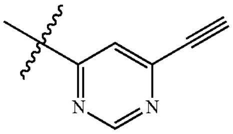
pp
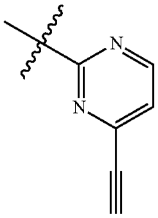
qq
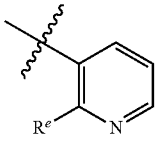
rr
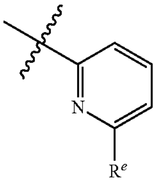
ss
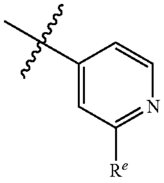
tt
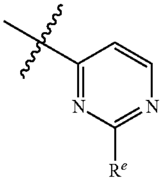
uu
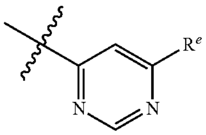
vv
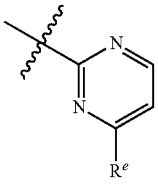
ww
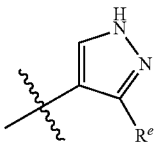
xx
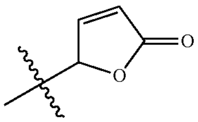
yy
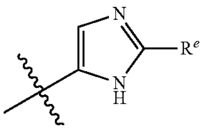
zz
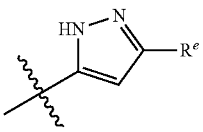
aaa
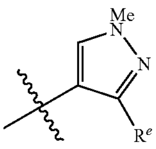
bbb TABLE 4-continued
Exemplary $R^1$ Groups
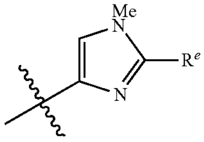
ccc
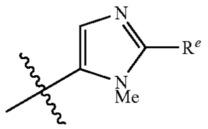
ddd
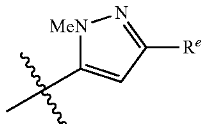
eee
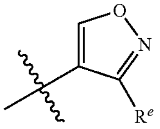
fff
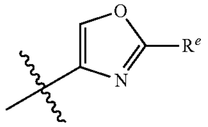
ggg
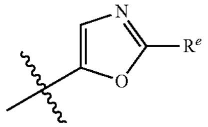
hhh
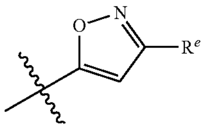
iii
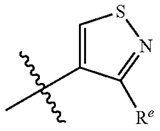
jjj
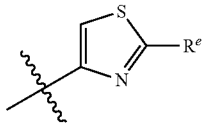
kkk
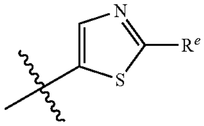
lll
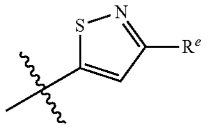
mmm
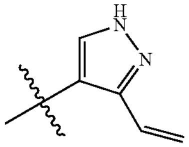
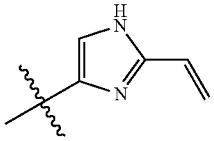
nnn
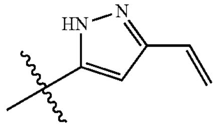
ooo
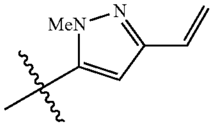
ppp
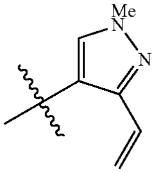
qqq
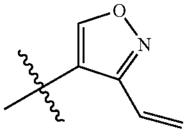
rrr
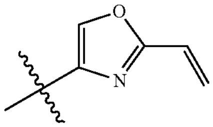
sss
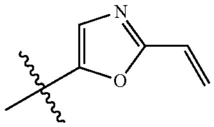
ttt
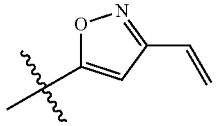
uuu
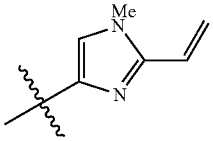
vvv
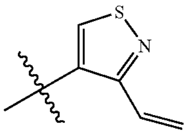
www
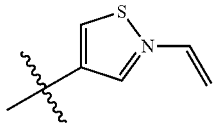
xxx
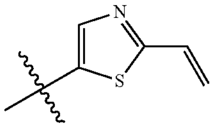
yyy TABLE 4-continued
Exemplary $R^1$ Groups
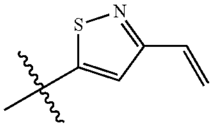
zzz
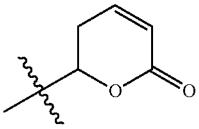
aaaa
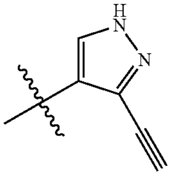
bbbb
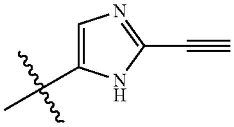
cccc
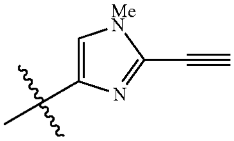
dddd
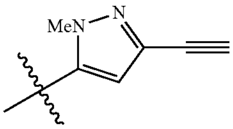
eeee
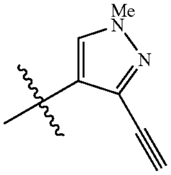
ffff
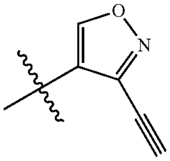
gggg
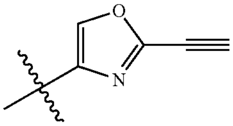
hhhh
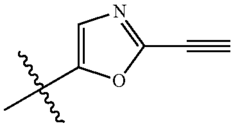
iiii
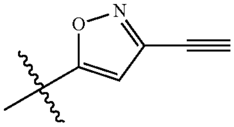
jjjj
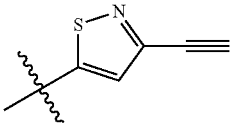
kkkk
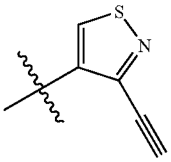
llll
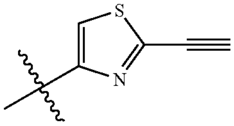
mmmm
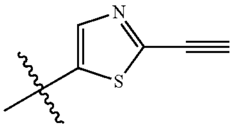
nnnn
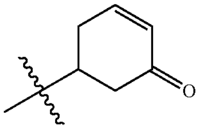
oooo
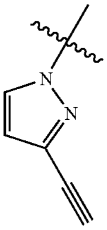
pppp
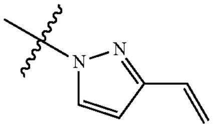
qqqq
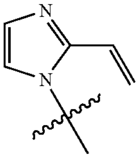
rrrr
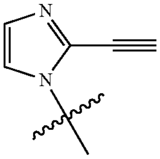
ssss
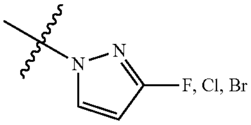
tttt TABLE 4-continued
Exemplary R1 Groups
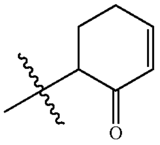
uuuu
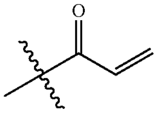
vvvv
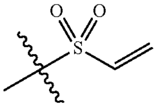
wwww
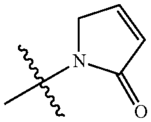
xxxx
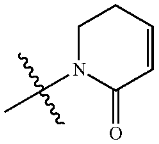
yyyy
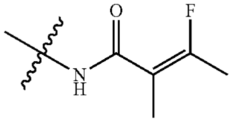
zzzz
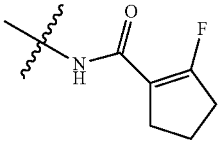
aaaaa
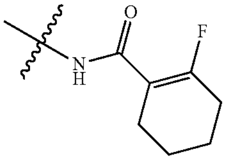
bbbbb
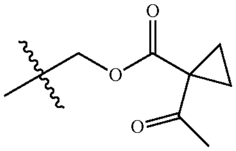
ccccc
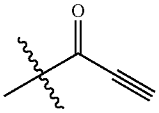
ddddd
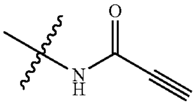
eeeee
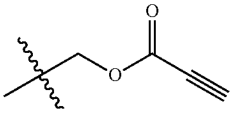
fffff
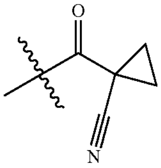
ggggg
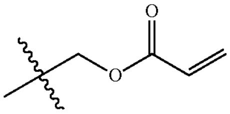
hhhhh
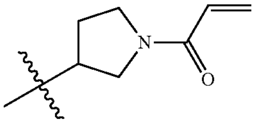
iiiii
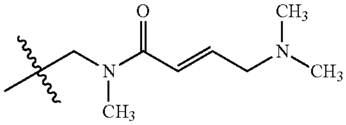
jjjjj
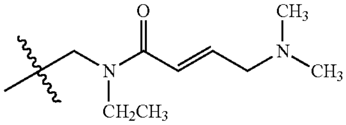
kkkkk
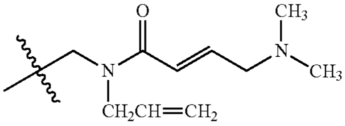
lllll
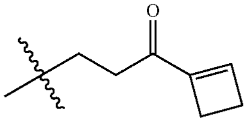
mmmmm
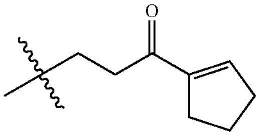
nnnnn
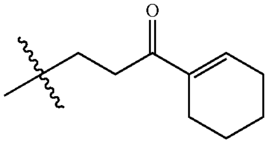
ooooo
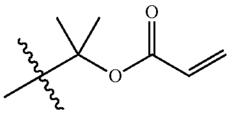
ppppp
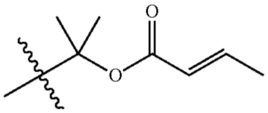
qqqqq
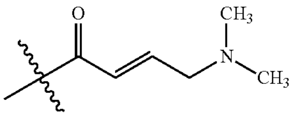
rrrrr TABLE 4-continued
Exemplary R[1] Groups
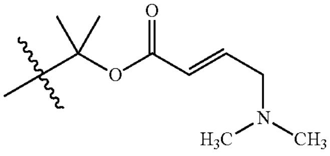
sssss
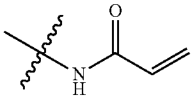
ttttt
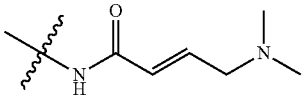
uuuuu
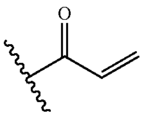
vvvvv
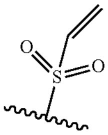
wwwww
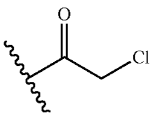
xxxxx
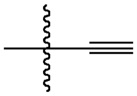
yyyyy
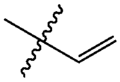
zzzzz
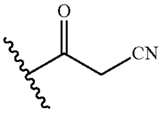
aaaaaa
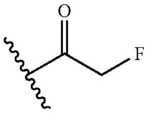
bbbbbb
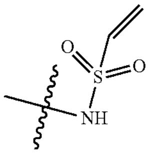
cccccc
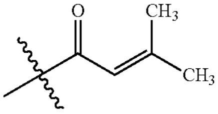
dddddd
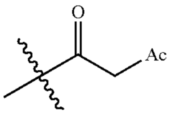
eeeeee
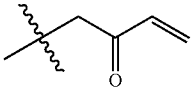
ffffff
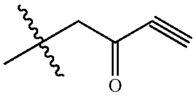
gggggg
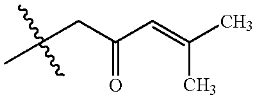
hhhhhh
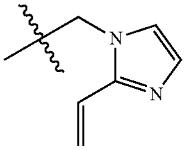
iiiii
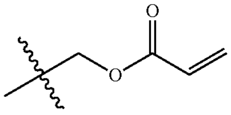
jjjjj
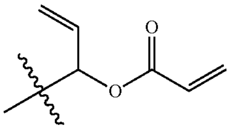
kkkkkk
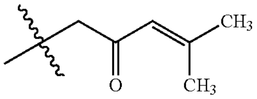
lllll
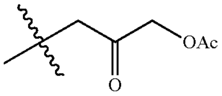
mmmmmm
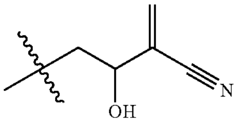
nnnnnn
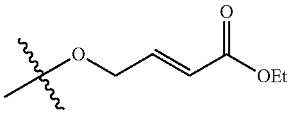
oooooo
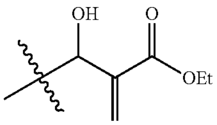
pppppp TABLE 4-continued

| Exemplary $R^1$ Groups | | |
|---|---|---|
| 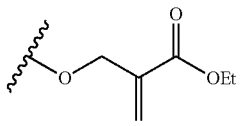 qqqqqq | 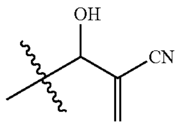 rrrrrr | 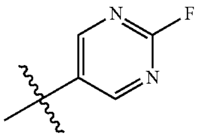 ssssss |
| 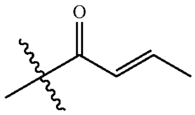 tttttt | 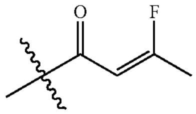 uuuuuu | 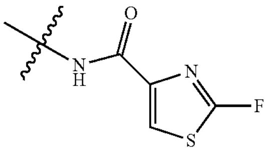 vvvvvv |
| 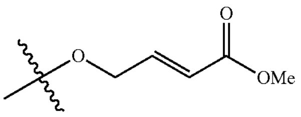 or wwwwww | 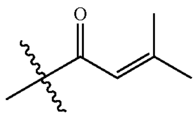 xxxxxx | |

wherein each $R^e$ is independently a suitable leaving group, $NO_2$, CN, or oxo.

B. ZAP70 Inhibitors

In one aspect, the invention is a compound of formula I-a, I-b or I-c:

I-a

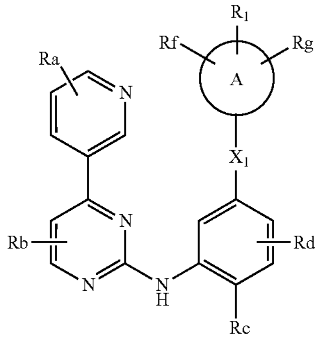

I-b

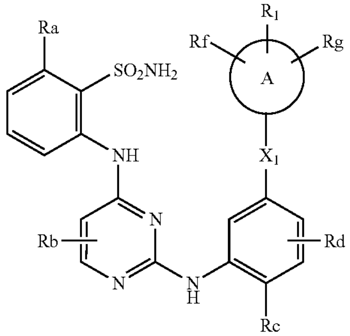

-continued

I-c

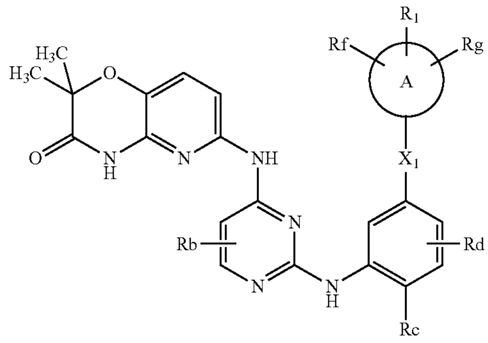

or a pharmaceutically acceptable salt thereof, wherein:

each of Ra Rb, Rc, Rd, and Rf are independently selected from R, OR, halogen, —$CF_3$, —CN, —C≡C—R or —C(O)NHRz;

Rg is selected from R, OR, halogen, —$CF_3$ and a 5-10 membered monocyclic or bicyclic, saturated, partially unsaturated, or aryl ring containing 0-3 heteroatoms independently selected from the group consisting of nitrogen, oxygen, and sulfur that is optionally substituted with R, OR, halogen or —$CF_3$;

each R is independently hydrogen, lower alkyl, lower haloalkyl or lower cycloalkyl;

each Rz is independently hydrogen, aliphatic or aryl;

$X_1$ is —NH—C(O)— or —C(O)—NH—;

Ring A is a 4-10 membered monocyclic or bicyclic, saturated, partially unsaturated, or aryl ring containing 0-3 heteroatoms independently selected from the group consisting of nitrogen, oxygen, and sulfur; and $R_1$ is -L-Y. The group -L-Y is as described herein in the detailed description of the warheads.

In some embodiments, Rb is bonded to the 5 position of the pyrimidinyl ring, and the compound is of formula I-d, I-e or I-f.

I-d

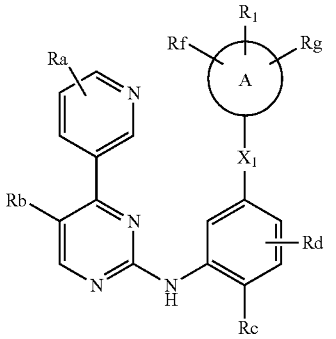

I-e

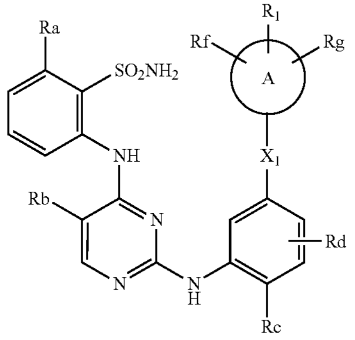

I-f

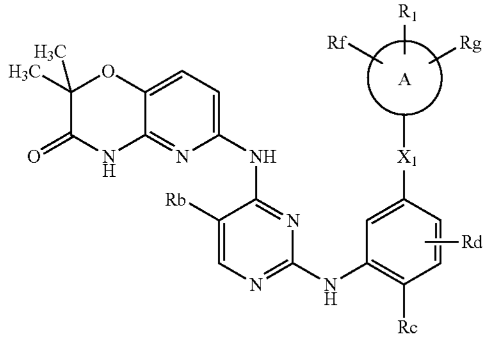

In some embodiments of compound of formula I-a, I-b, I-c, I-d, I-e or I-f, Ring A is selected from the group consisting of:

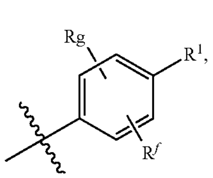

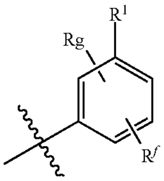

,

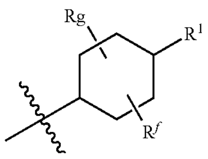

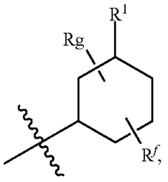

-continued

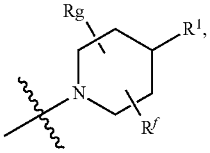

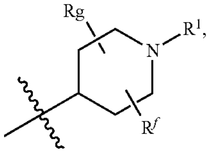

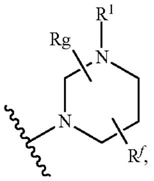

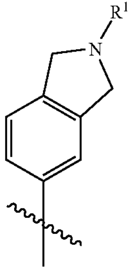

,

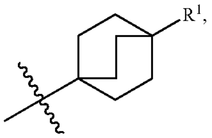

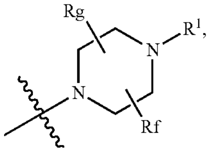

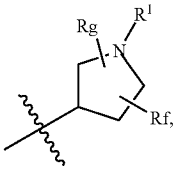

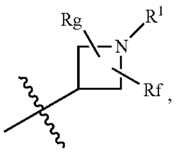

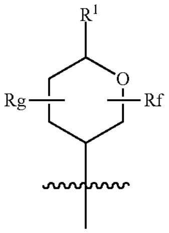

and

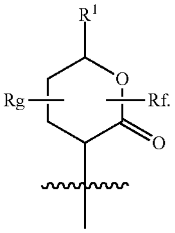

In particular embodiments, $R^1$ is characterized in that the -L-Y moiety is capable of covalently binding to Cys 346 of ZAP70, thereby irreversibly inhibiting the enzyme.

Exemplary ZAP70 Compounds

I-1

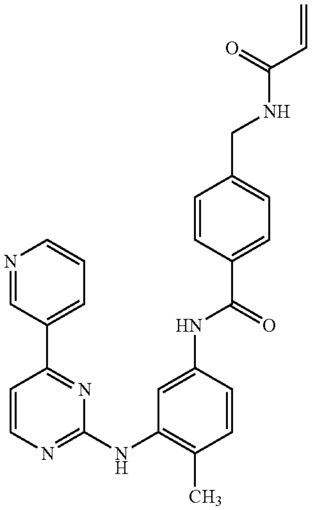

-continued
I-2
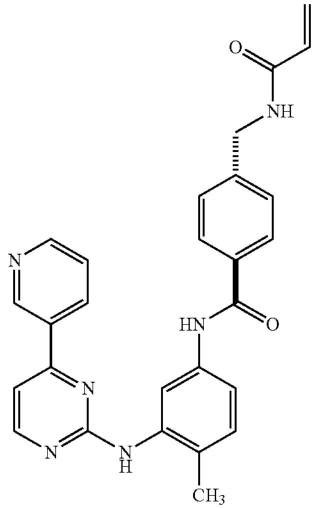
I-3
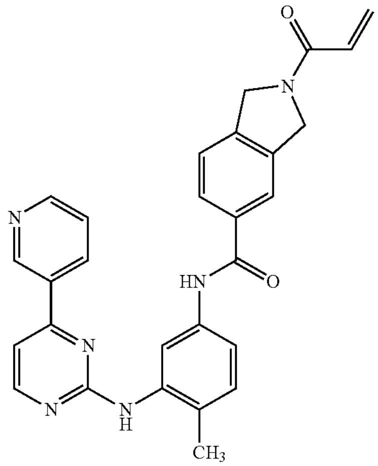
I-4
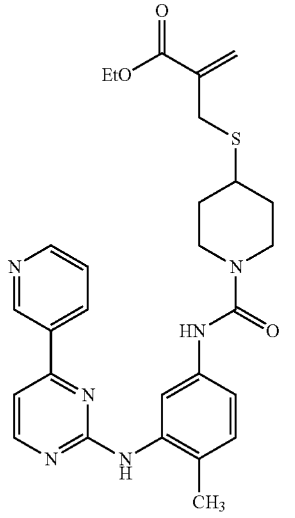
-continued
I-5
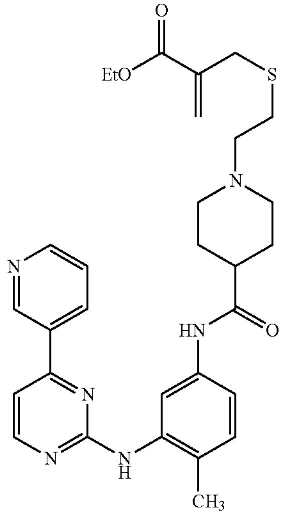
I-6
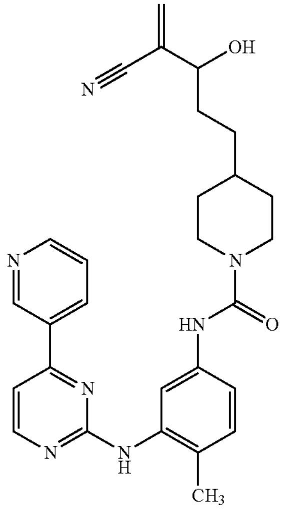
I-7
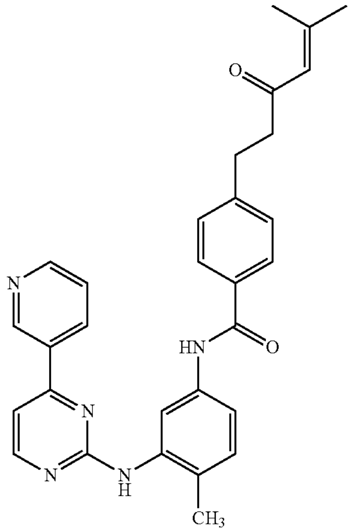

-continued
I-8
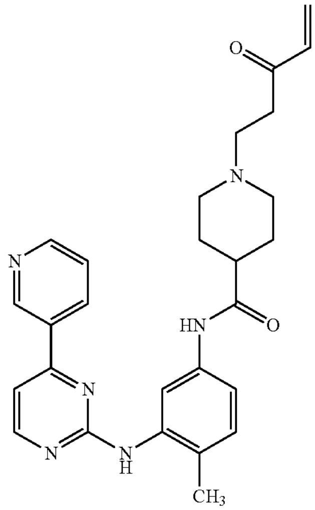
I-9
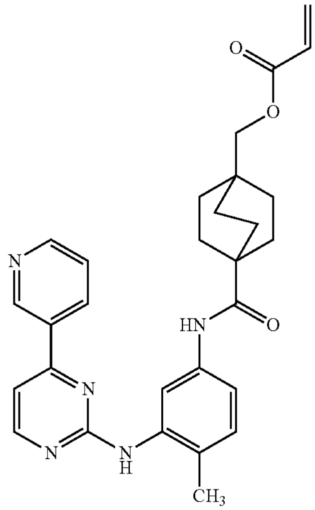
I-10
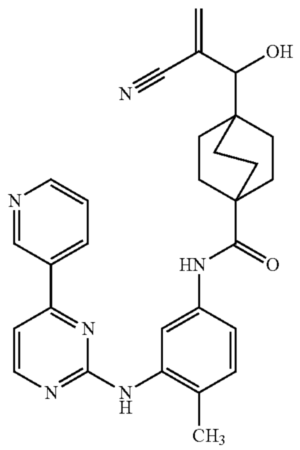
-continued
I-11
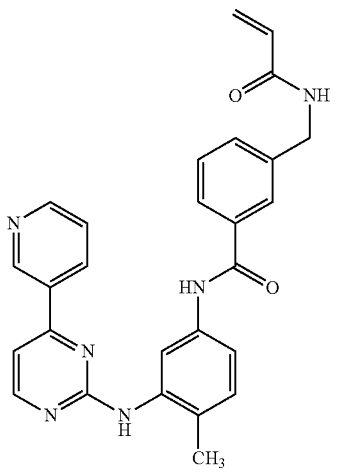
I-12
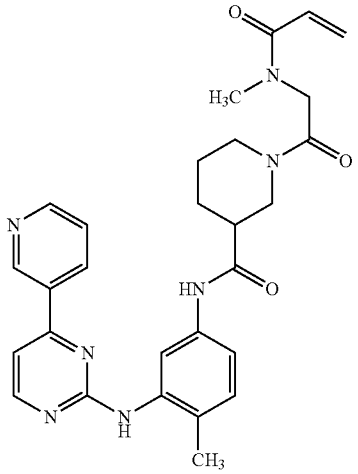
I-13
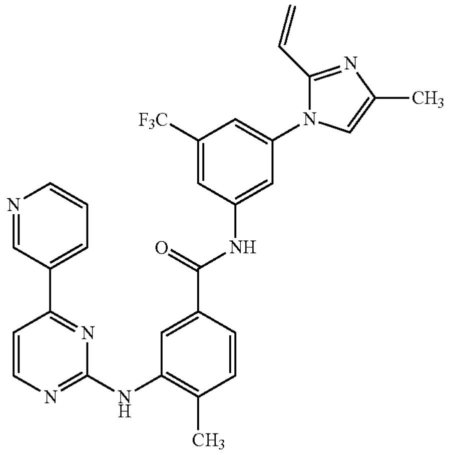

-continued
I-14
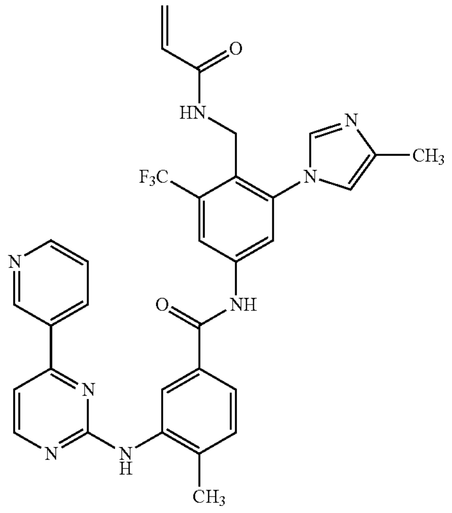
I-15
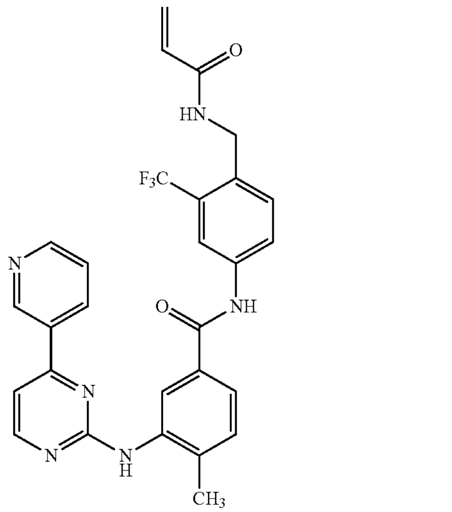
I-16
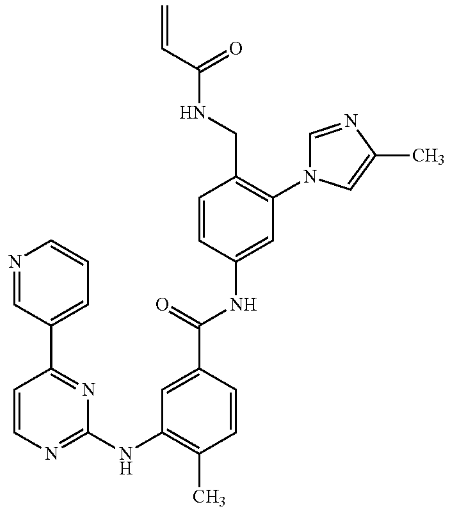
-continued
I-17
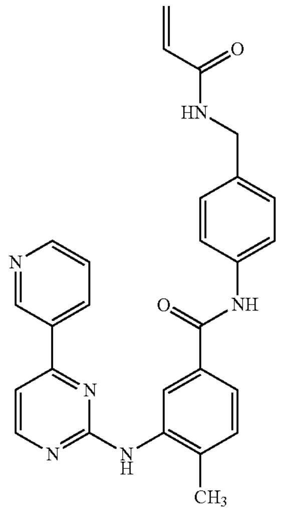
I-18
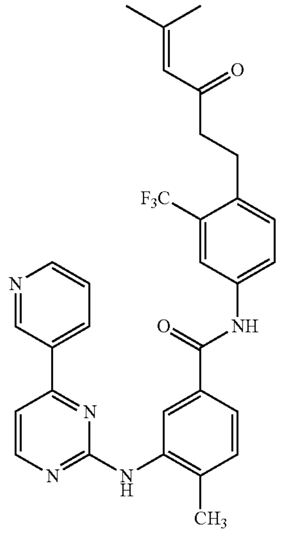
I-19
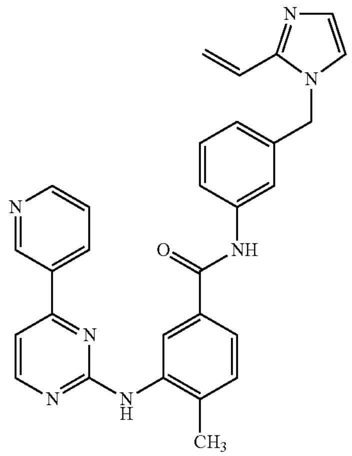

-continued
I-20
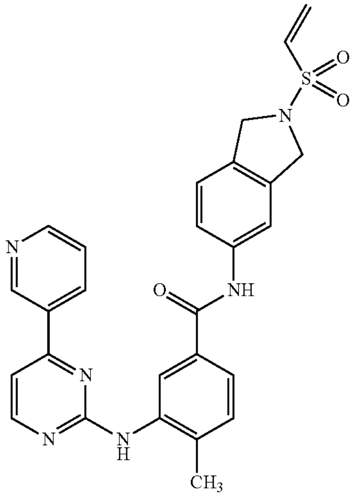
I-21
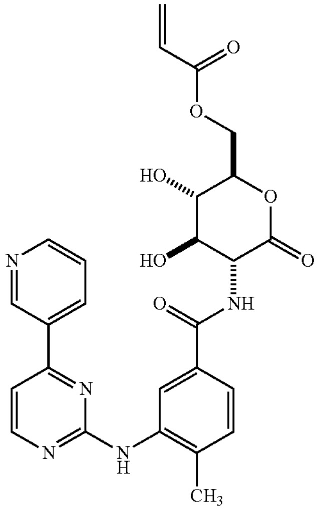
I-22
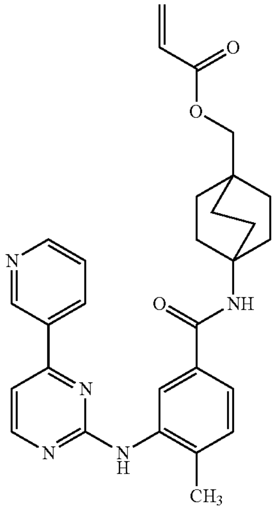
-continued
I-23
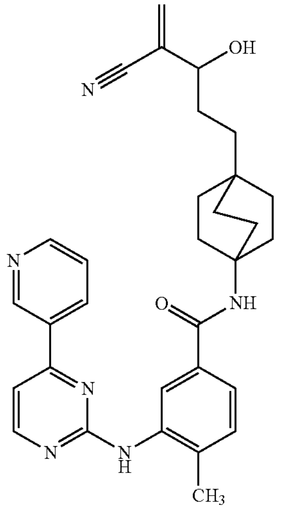
I-24
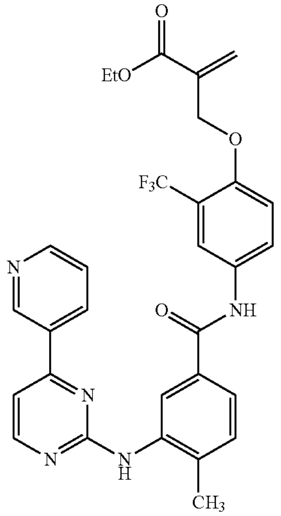
I-25
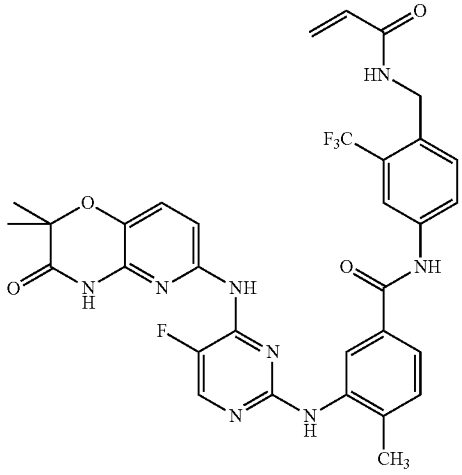

-continued
I-26
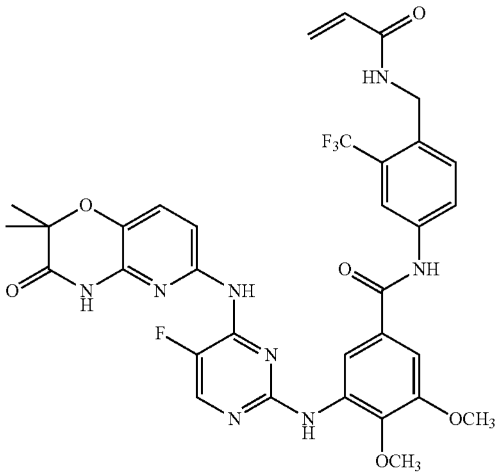
I-27
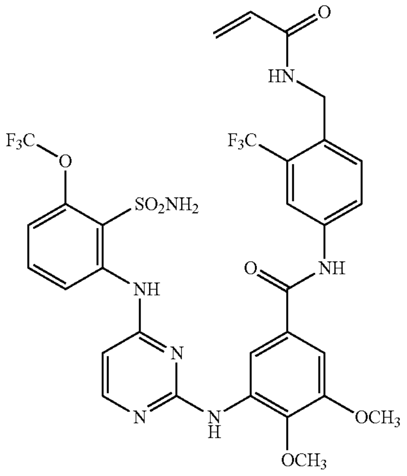
I-28
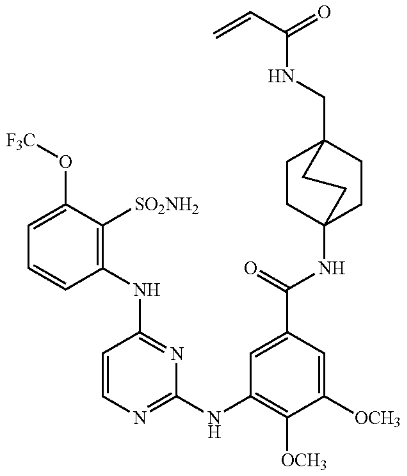
-continued
I-29
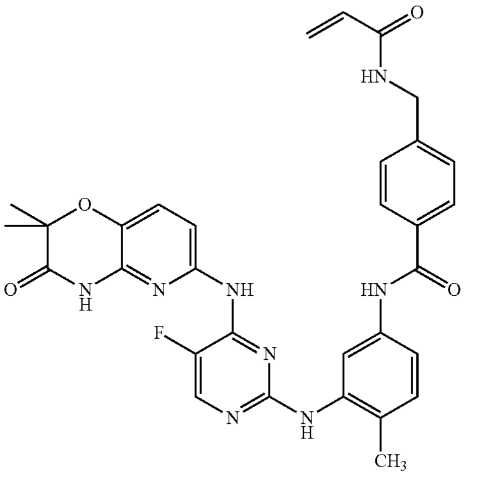
I-30
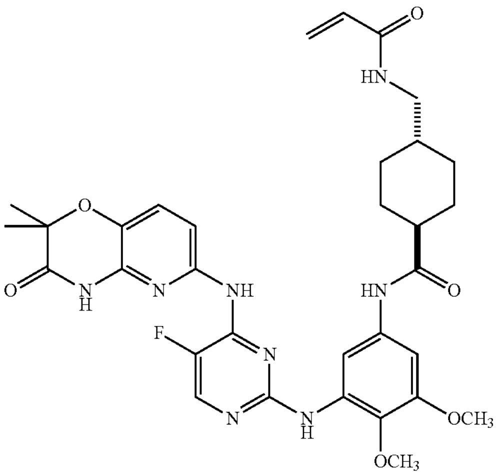
I-31
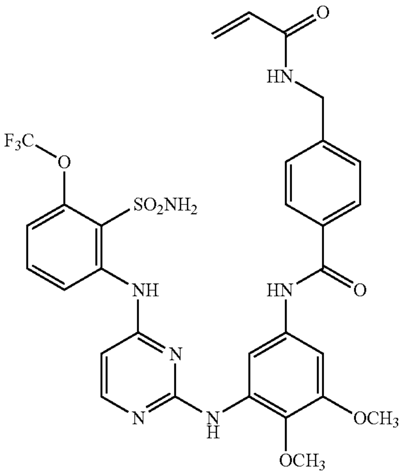

-continued

I-32

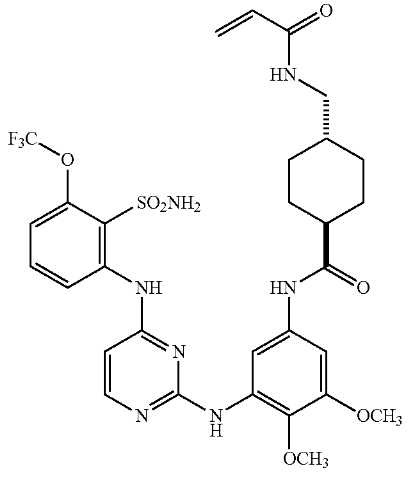

C. FLT3 Inhibitors

In another aspect, the invention is a compound of formula II-a, II-b, II-c or II-d:

II-a

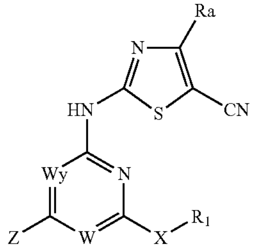

II-b

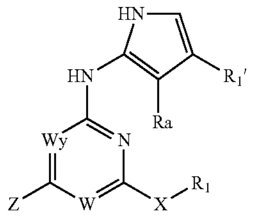

II-c

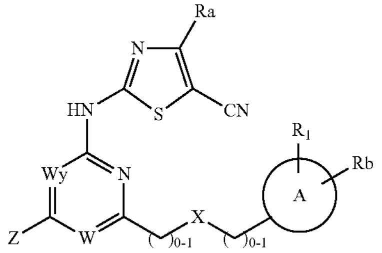

II-d

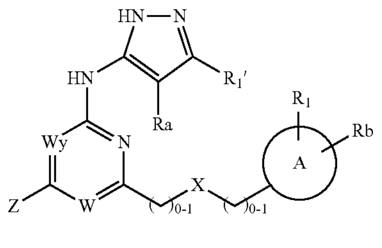

or a pharmaceutically acceptable salt thereof, wherein:

Wy is N or C—Rb;

W is N or CH;

X is NH, $CH_2$, O or S;

each of Ra and Rb are independently selected from R, OR, halogen, —$CF_3$, —CN, —C≡C—R, —NRxRy, or —C(O)NHRz;

each R, Rx and Ry is independently hydrogen, lower alkyl, lower haloalkyl, or lower cycloalkyl;

each Rz is independently hydrogen, aliphatic, or aryl;

Z is hydrogen or a solubilizing group;

Ring A is a 4-10 membered monocyclic or bicyclic, saturated, partially unsaturated, or aryl ring containing 0-3 heteroatoms independently selected from the group consisting of nitrogen, oxygen, and sulfur;

$R_1$ or $R_{1'}$ is -L-Y, with the proviso that when $R_1$ is -L-Y, $R_{1'}$ is R, OR, halogen, —$CF_3$—CN, —C≡C—R or —C(O)NHRz, and when $R_{1'}$ is -L-Y, $R_1$ is R, OR, halogen, —$CF_3$, —CN, —C≡C—R or —C(O)NHRz. The group -L-Y is as described herein in the detailed description of the warheads.

In some embodiments, the compound is of Formula II-a, II-b, II-c or II-d, and Z is methoxypropylamino, dimethyl amino or is selected from the group consisting of

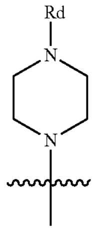 , 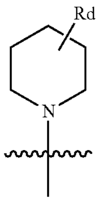 and 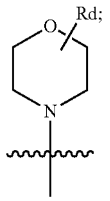

wherein Rd is hydrogen, R, OR, halogen, —$CF_3$, —CN, —C≡C—R or —C(O)NHRz.

In certain embodiments, the compound is of Formula II-c or II-d, and Ring A is selected from the group consisting of:

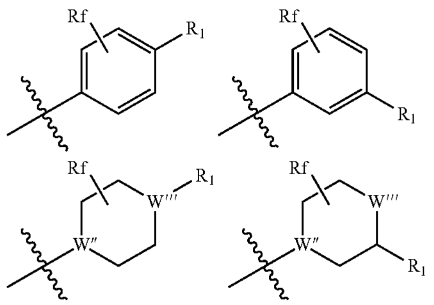

wherein W" and W"' are independently nitrogen or carbon atoms. In these embodiments, Z is methoxypropylamino, dimethyl amino or is selected from the group consisting of

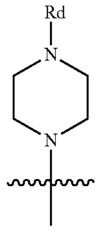 , 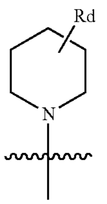 and 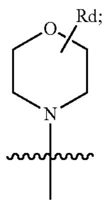

wherein Rd is hydrogen, R, OR, halogen, —$CF_3$, —CN, —C≡C—R or —C(O)NHRz.

In certain embodiments, $R_1$ is characterized in that the -L-Y moiety is capable of covalently binding to a Cys2 residue in a protein kinase selected from FLT3 (Cys 828) and MEK1 (Cys 207), thereby irreversibly inhibiting the enzyme. In particular embodiments, $R_1$ is characterized in that the -L-Y moiety is capable of covalently binding to Cys 828 of FLT3, thereby irreversibly inhibiting the enzyme.

Exemplary FLT3 inhibitors

II-1

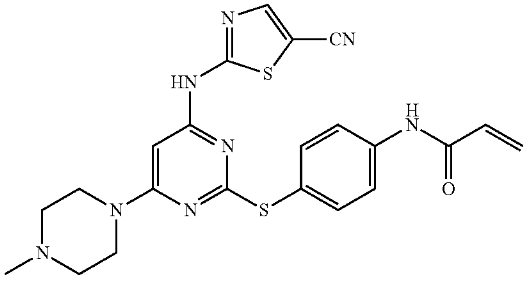

II-2

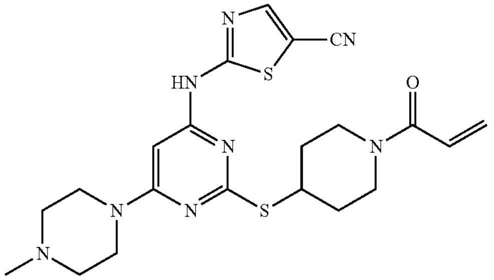

II-3

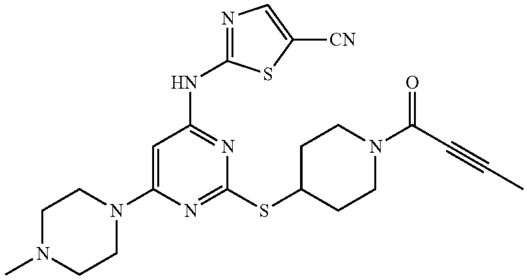

II-4

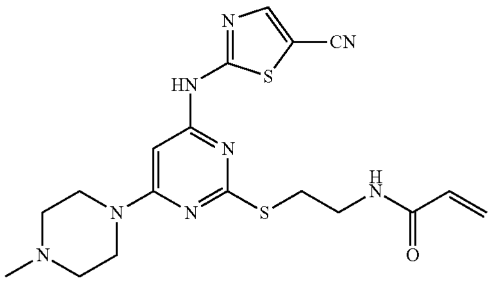

-continued

II-5

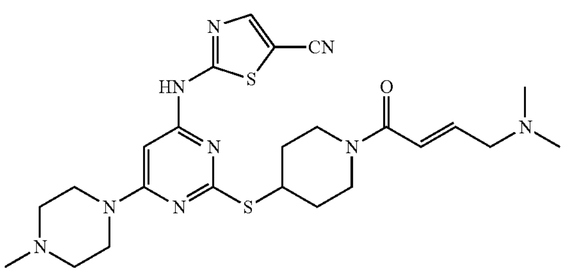

II-6

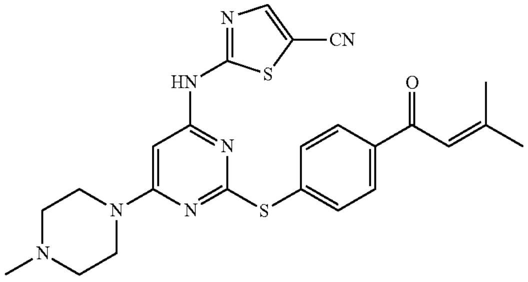

II-7

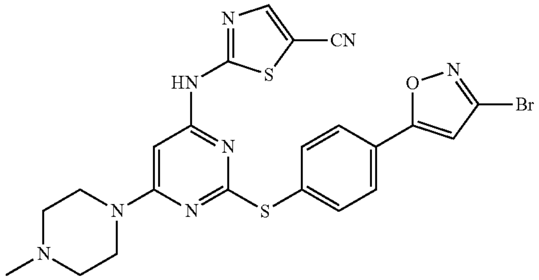

II-8

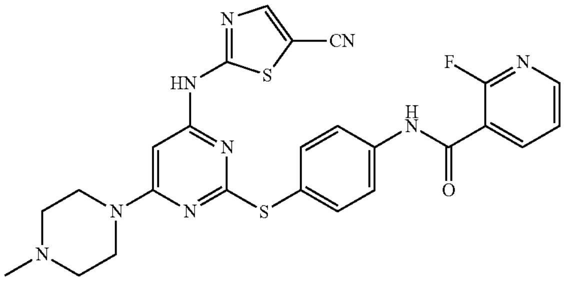

II-9

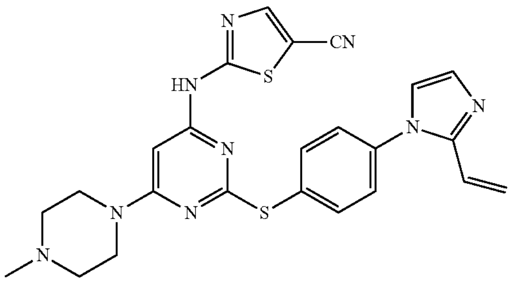

-continued
II-10
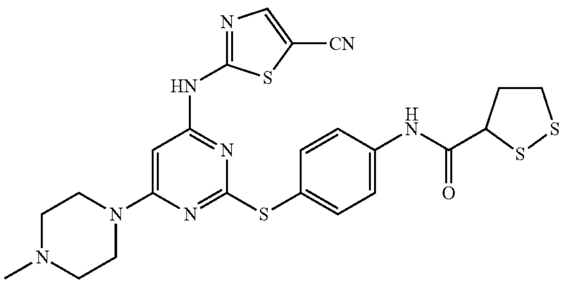
II-11
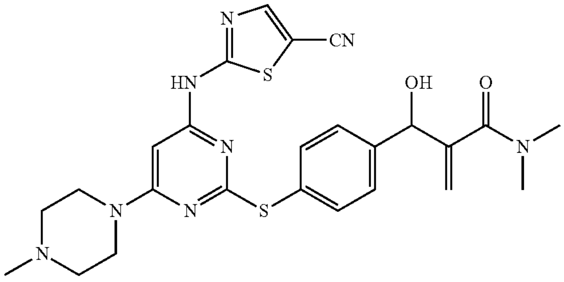
II-12
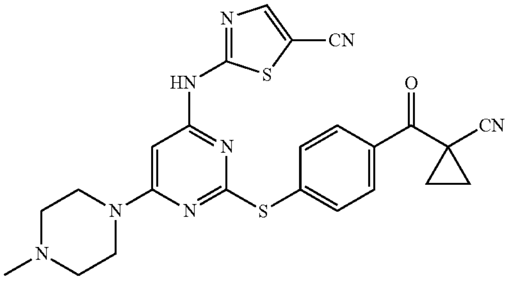
II-13
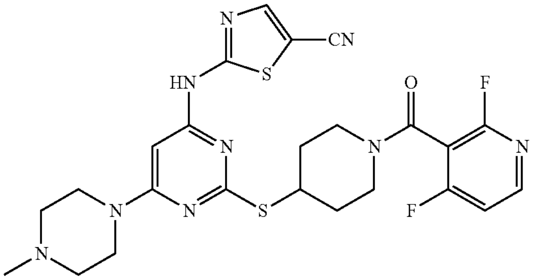
II-14
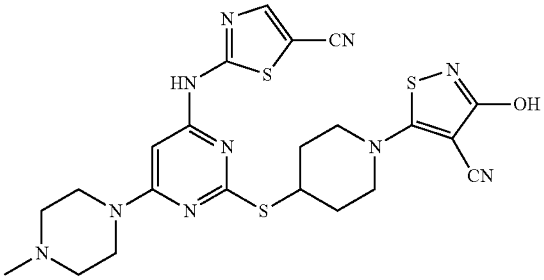
-continued
II-15
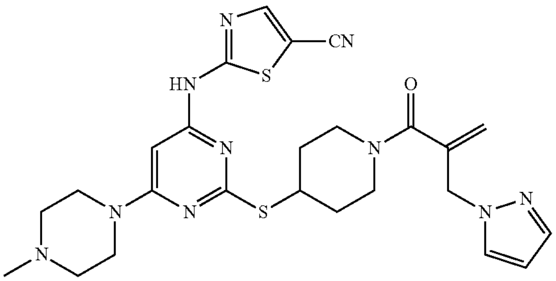
II-16
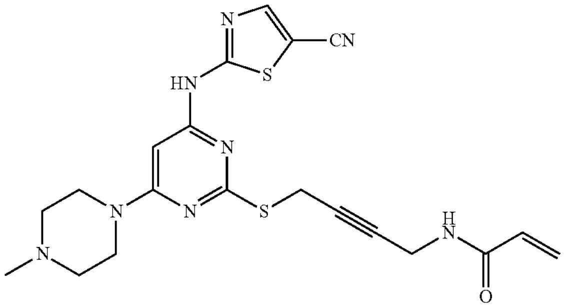
II-17
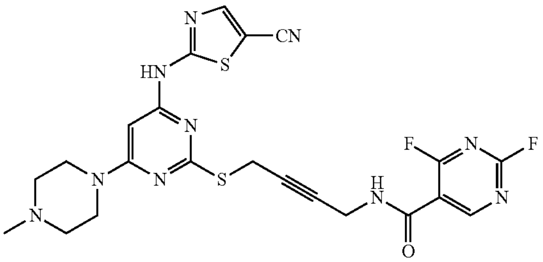
II-18
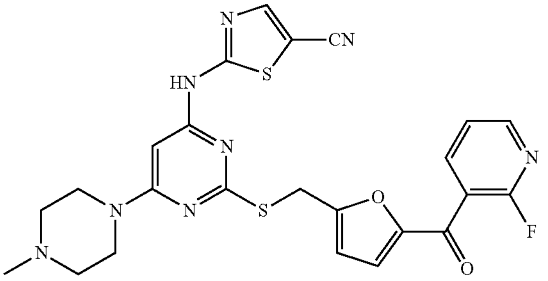
II-19
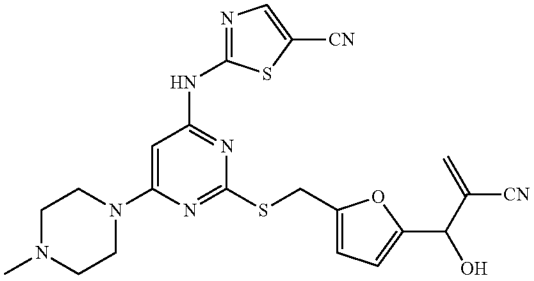

-continued
II-20
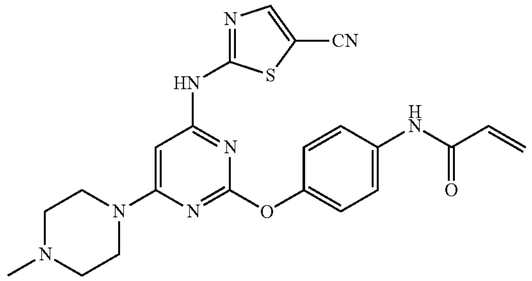
II-21
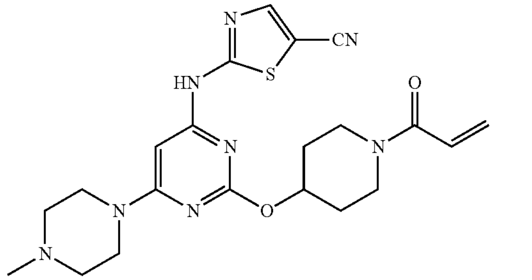
II-22
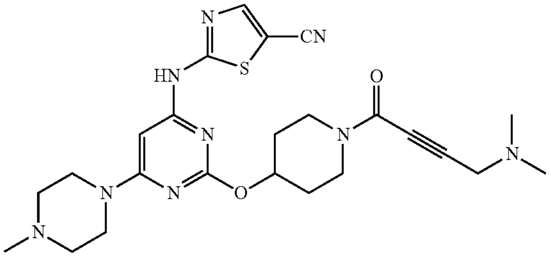
II-23
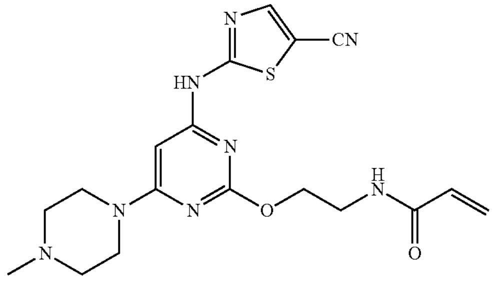
II-24
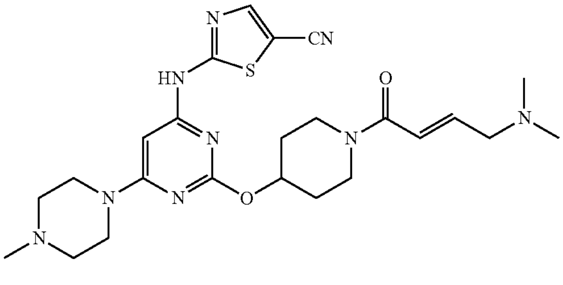
-continued
II-25
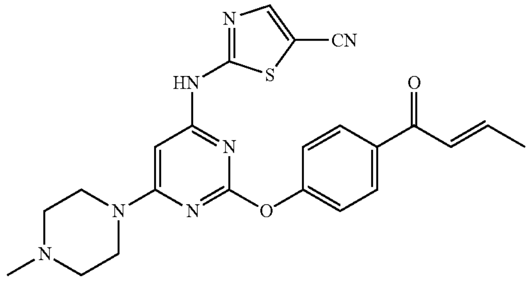
II-26
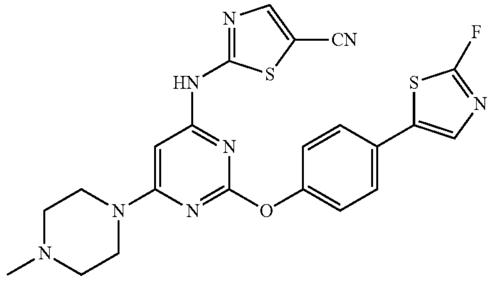
II-27
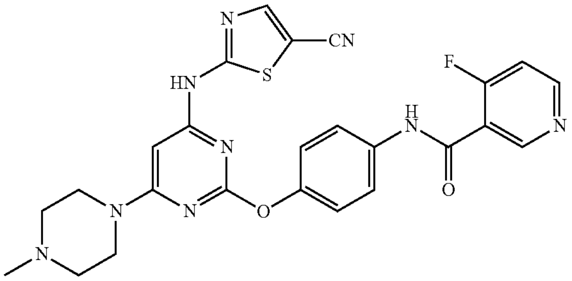
II-28
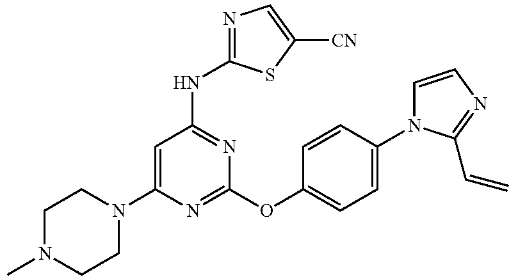
II-29
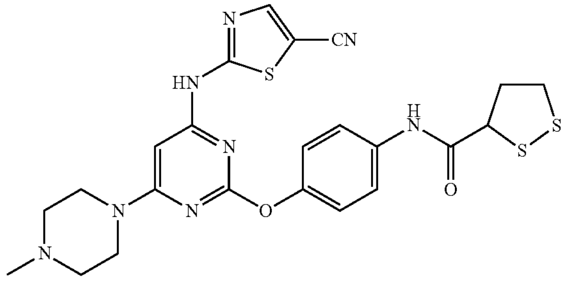

-continued
II-30
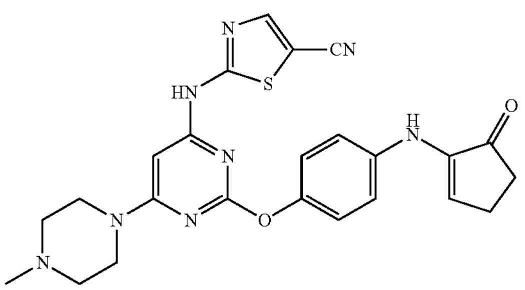
II-31
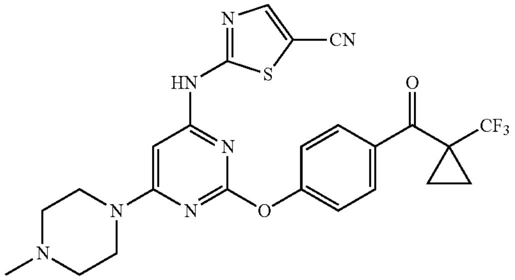
II-32
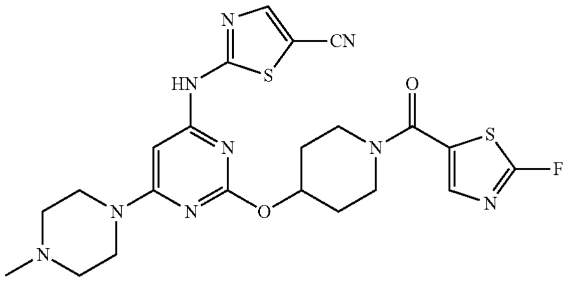
II-33
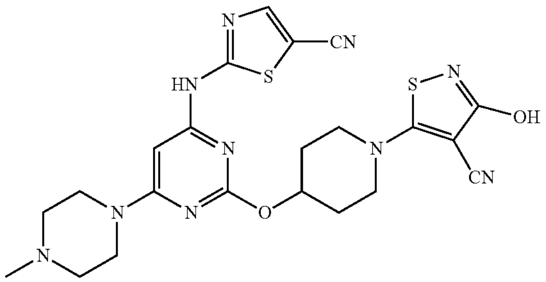
II-34
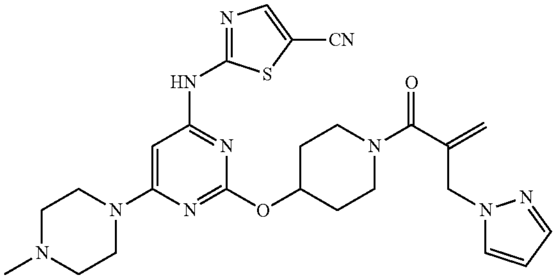
-continued
II-35
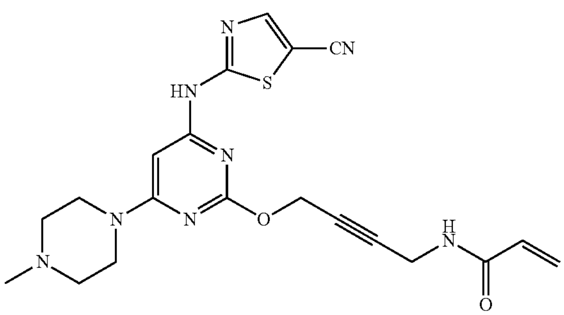
II-36
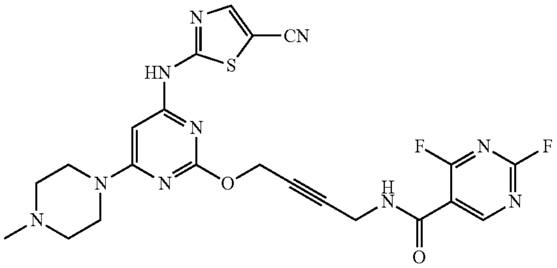
II-37
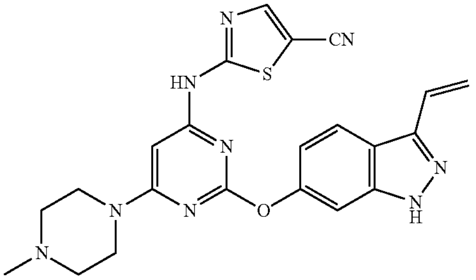
II-38
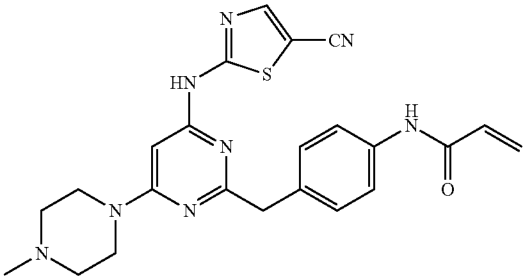
II-39
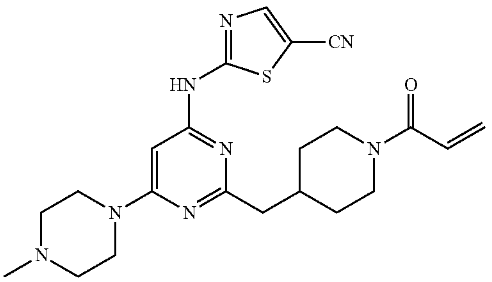

-continued
II-40
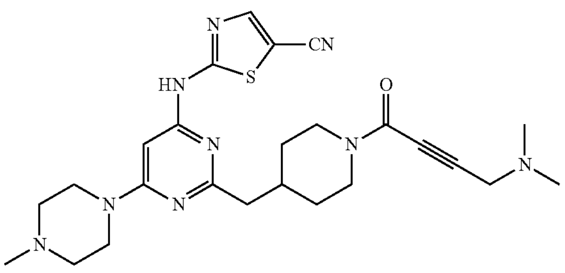
II-41
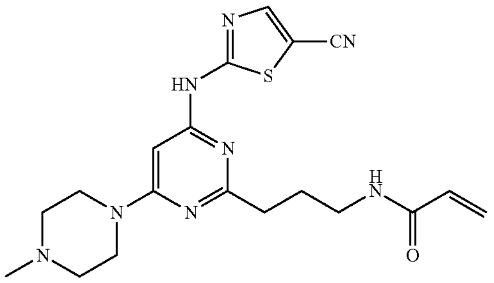
II-42
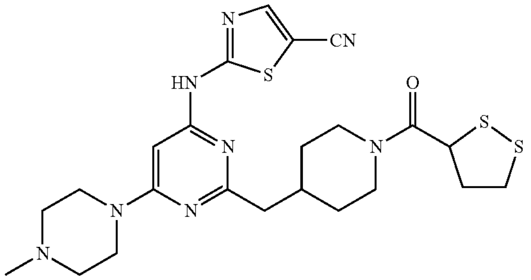
II-43
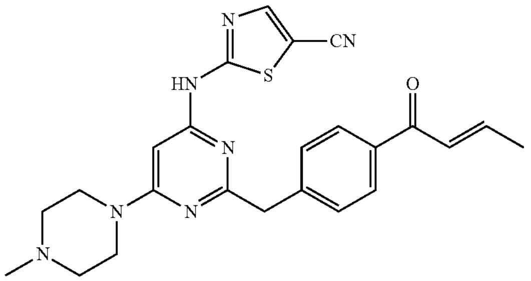
II-44
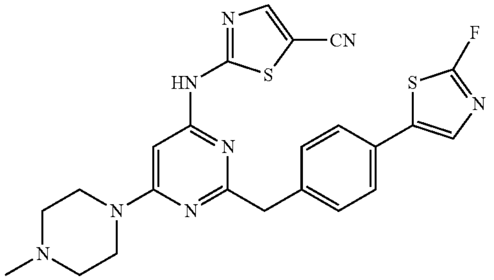
-continued
II-45
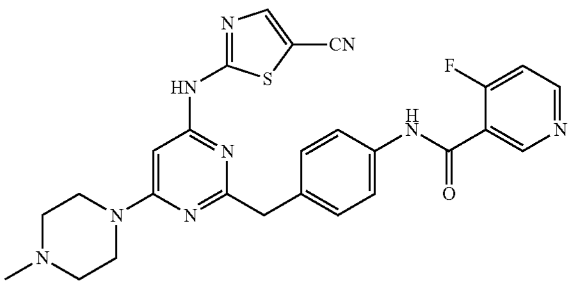
II-46
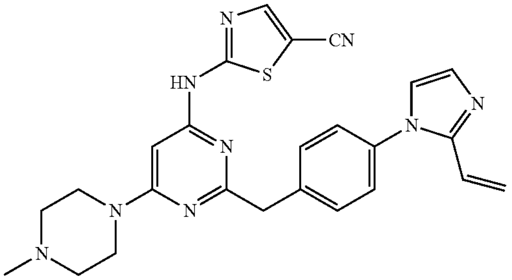
II-47
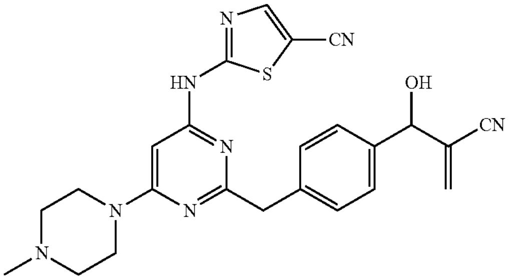
II-48
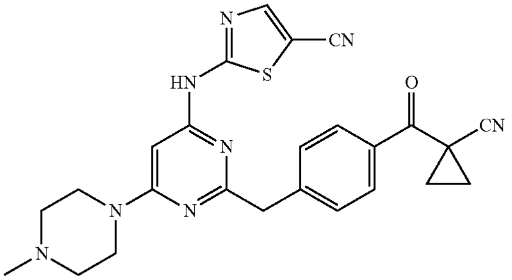
II-49
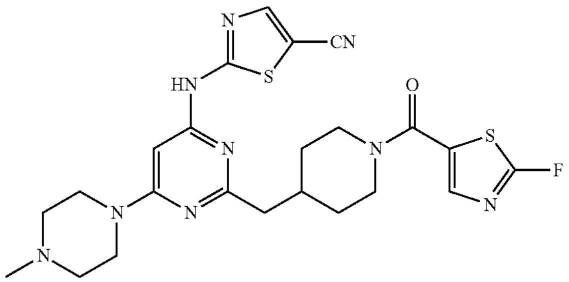

-continued
II-50
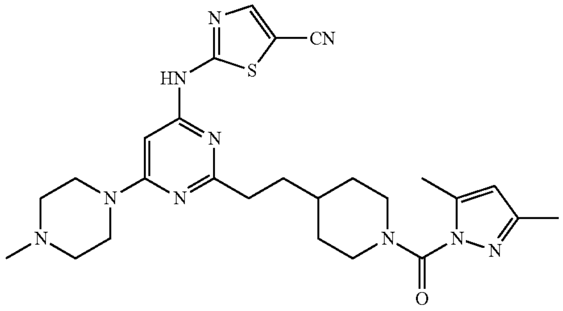
II-51
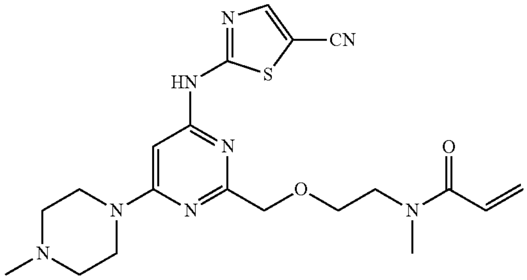
II-52
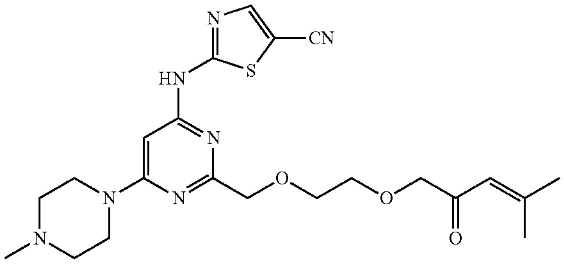
II-53
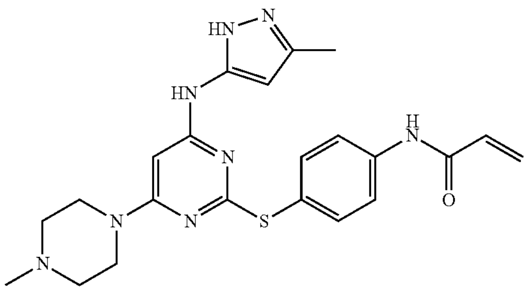
II-54
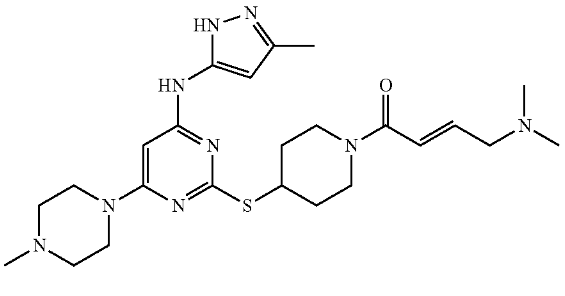
-continued
II-55
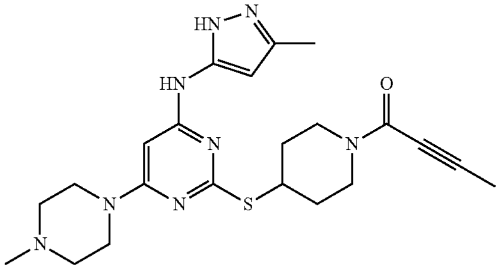
II-56
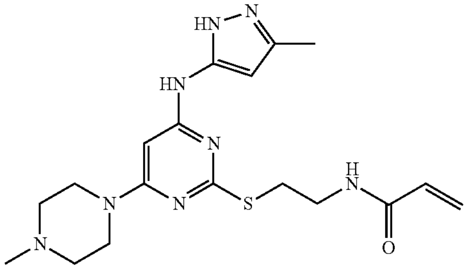
II-57
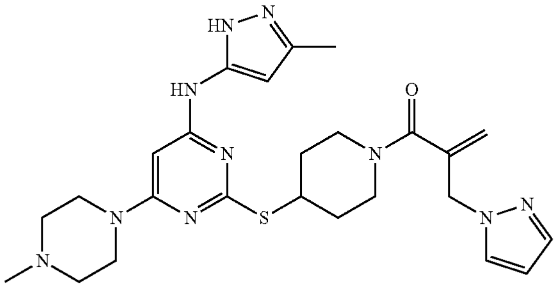
II-58
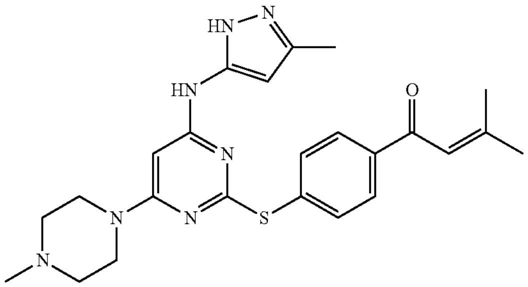
II-59
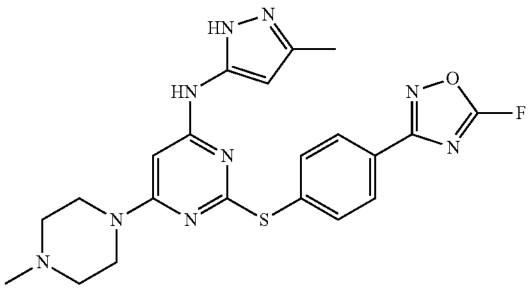

-continued
II-60
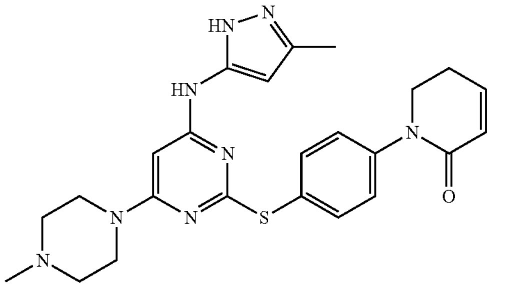
II-61
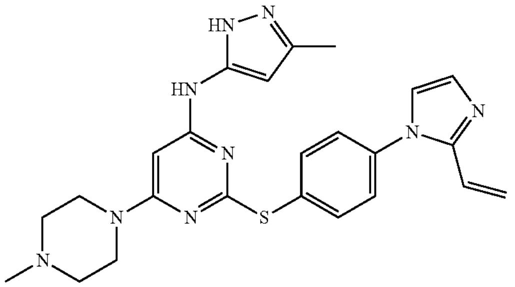
II-62
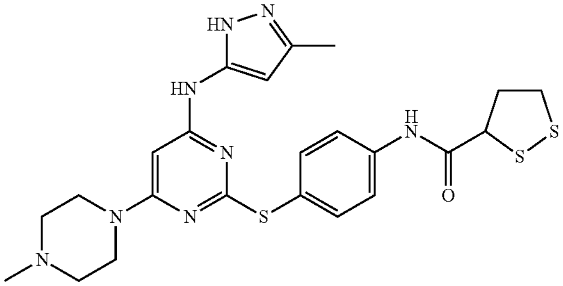
II-63
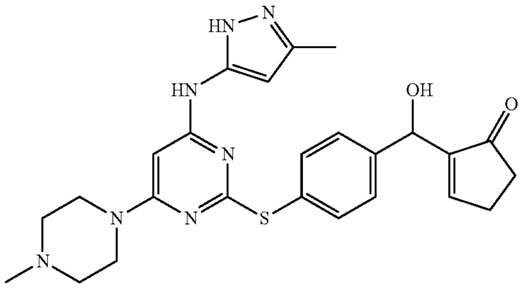
II-64
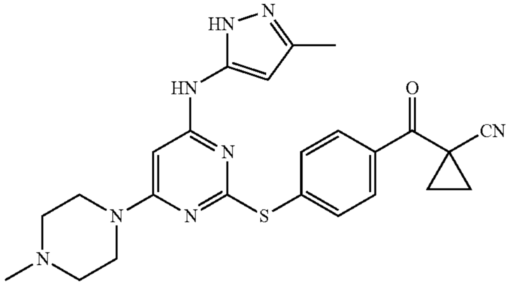
-continued
II-65
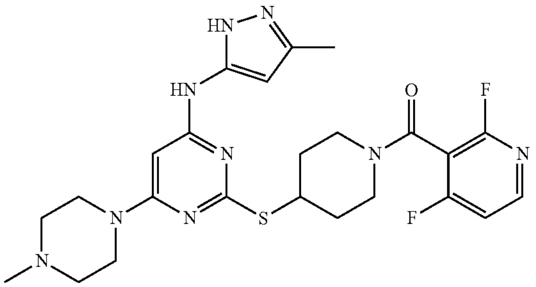
II-66
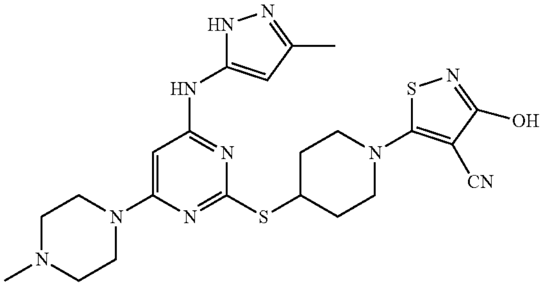
II-67
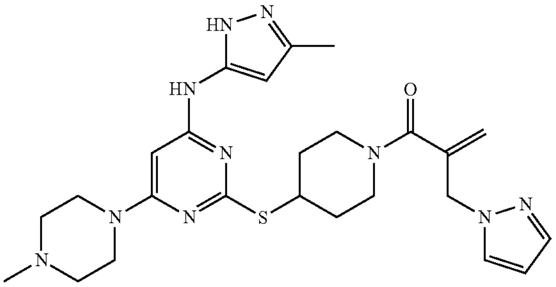
II-68
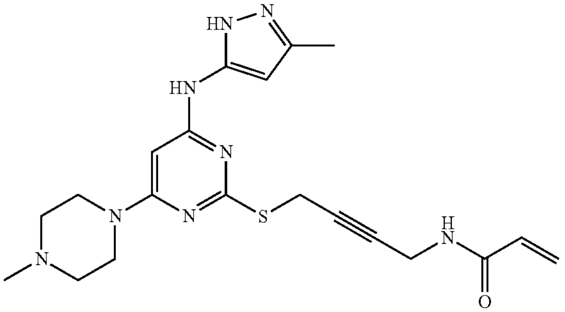
II-69
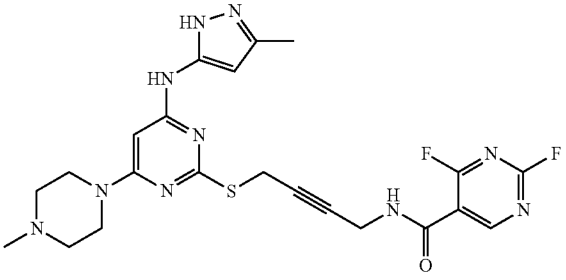

-continued
II-70
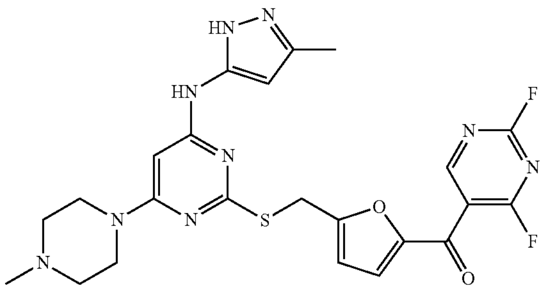
II-71
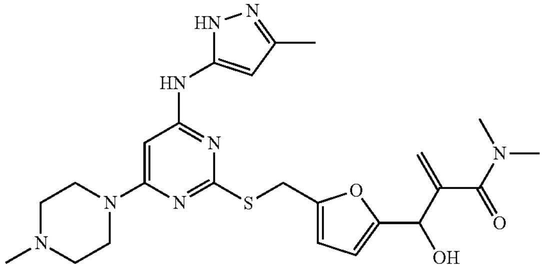
II-72
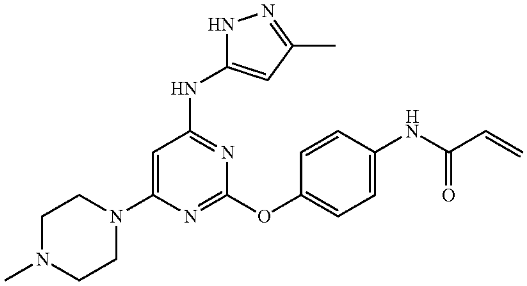
II-73
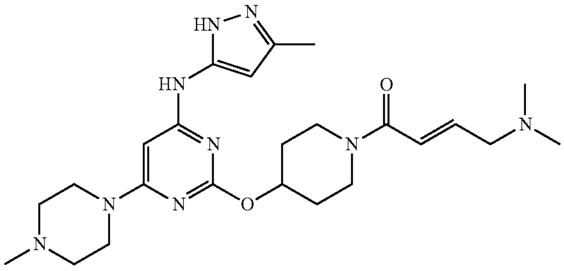
II-74
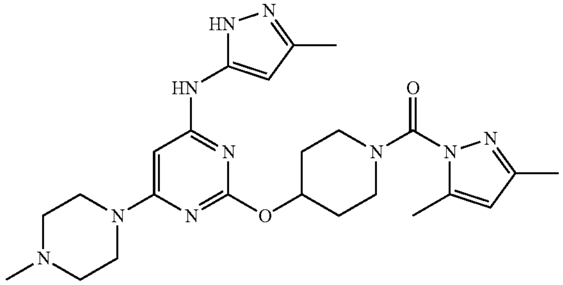
-continued
II-75
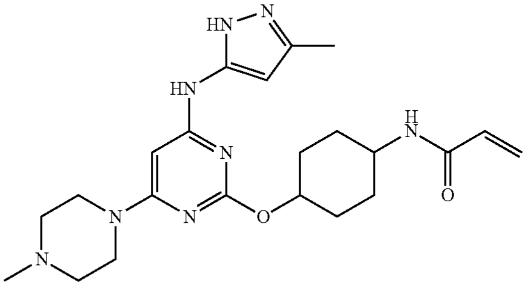
II-76
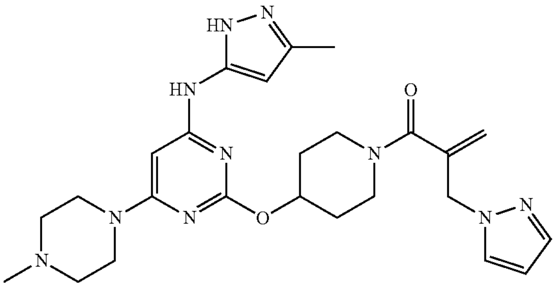
II-77
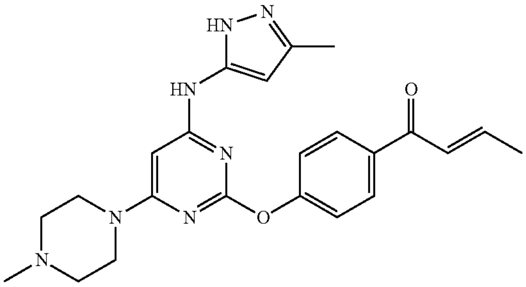
II-78
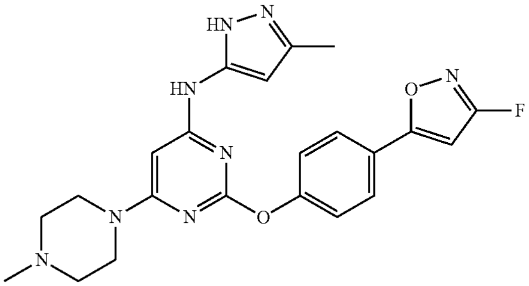
II-79
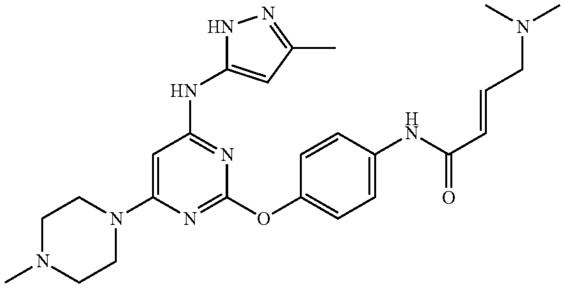

-continued
II-80
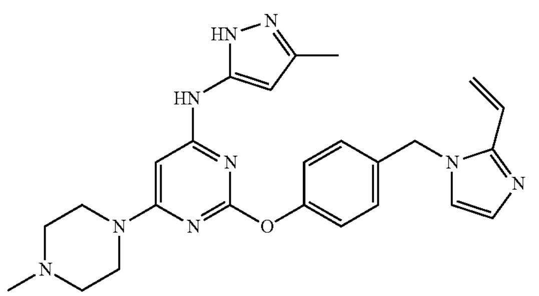
II-81
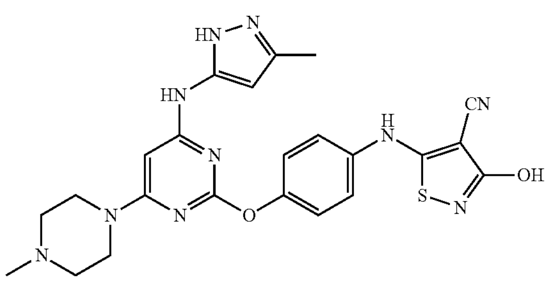
II-82
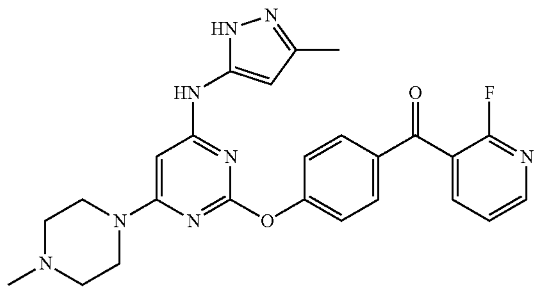
II-83
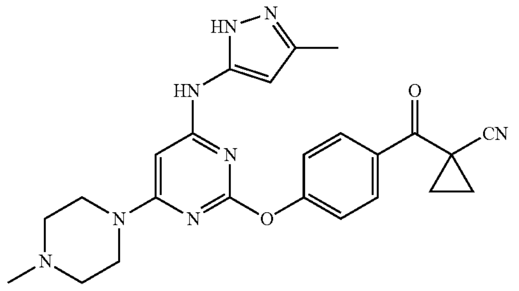
II-84
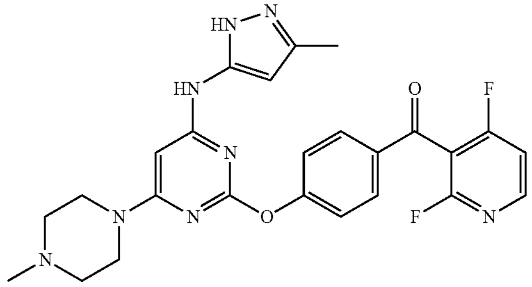
-continued
II-85
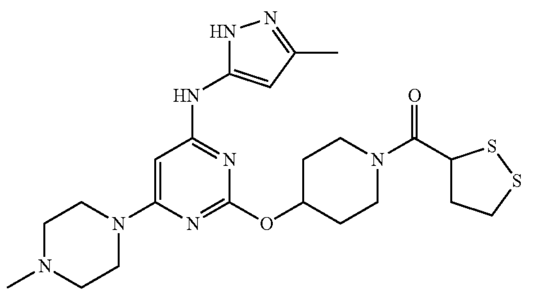
II-86
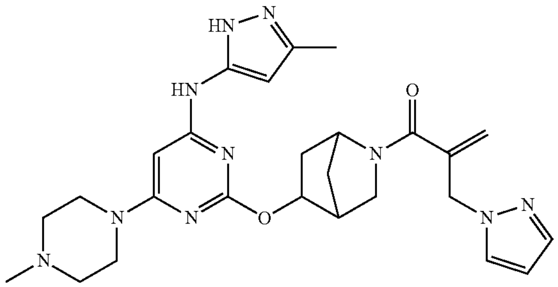
II-87
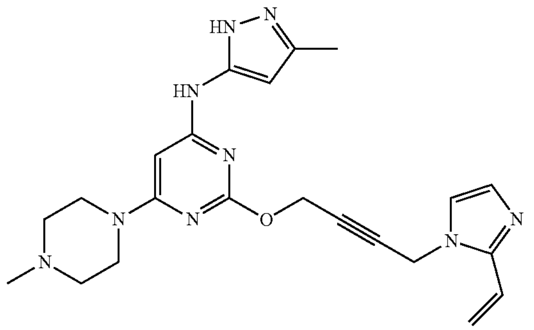
II-88
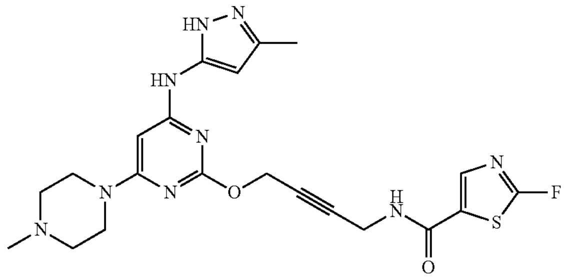
II-89
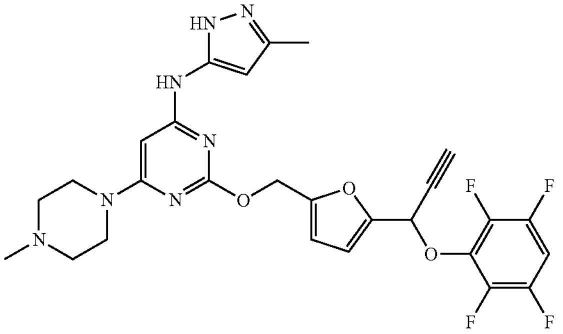

-continued
II-90
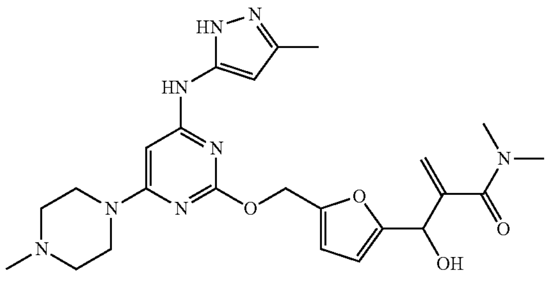
II-91
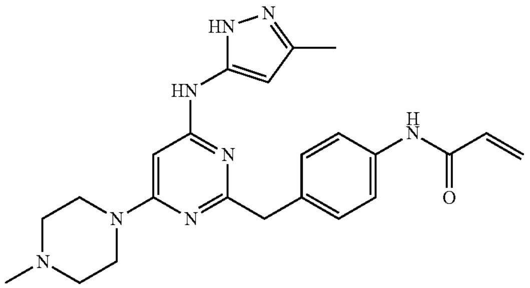
II-92
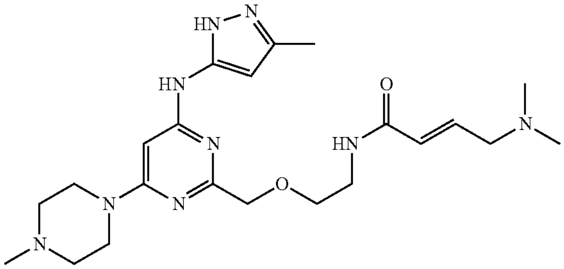
II-93
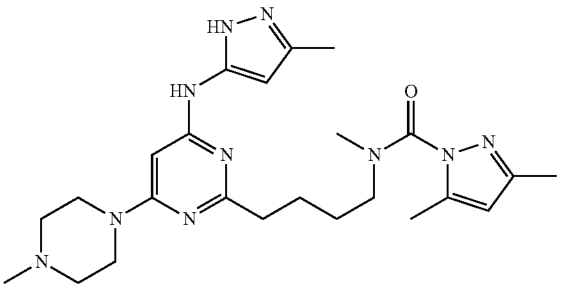
II-94
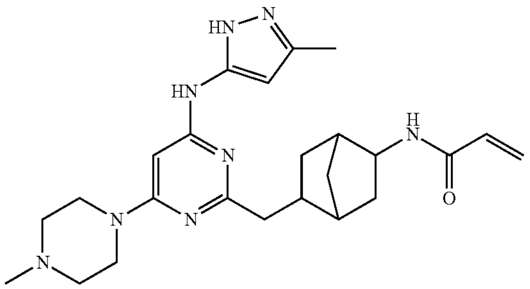
-continued
II-95
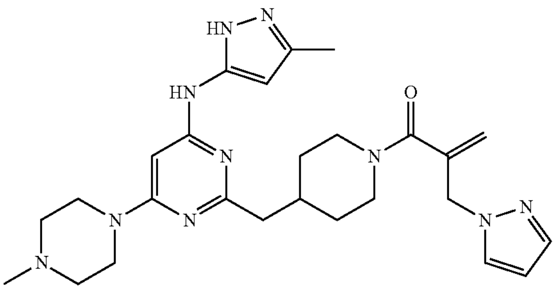
II-96
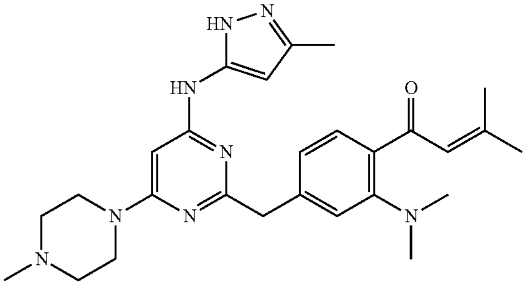
II-97
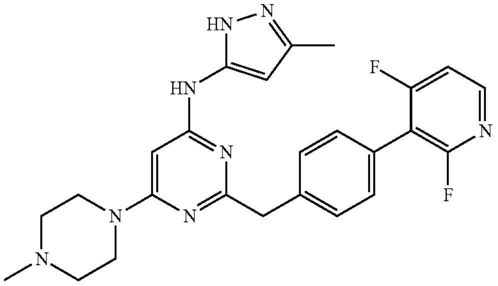
II-98
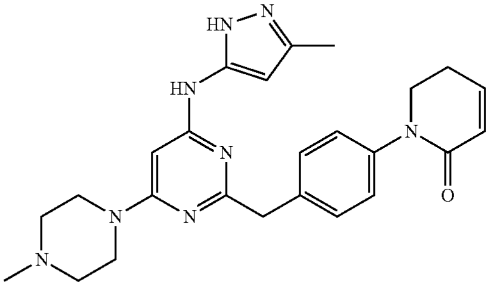
II-99
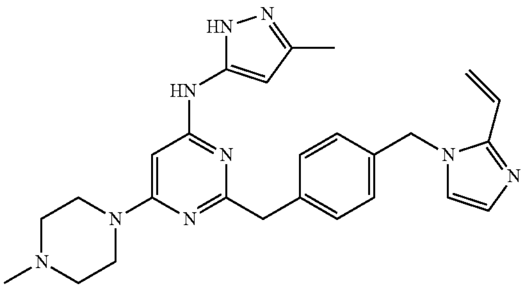

-continued
II-100
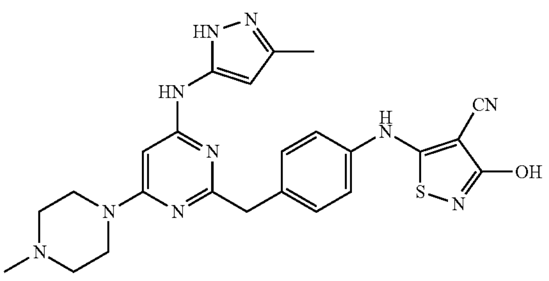
II-101
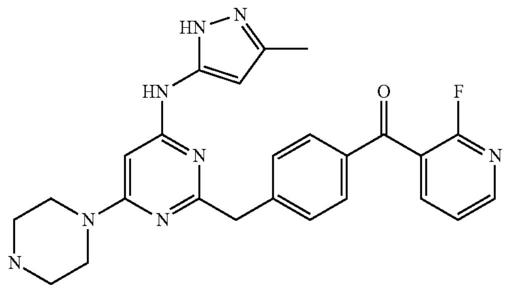
II-102
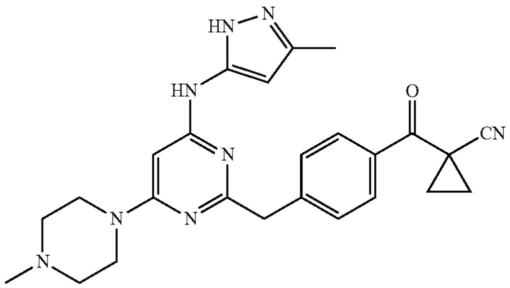
II-103
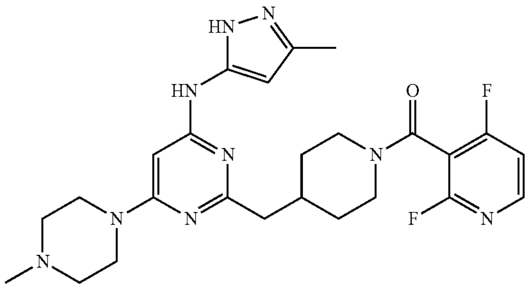
II-104
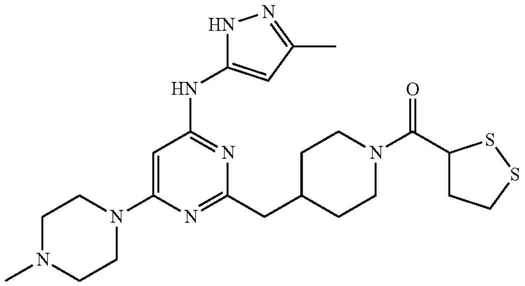
-continued
II-105
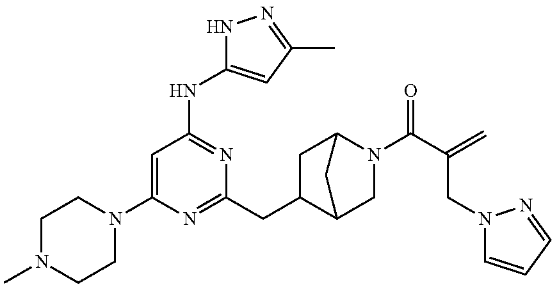
II-106
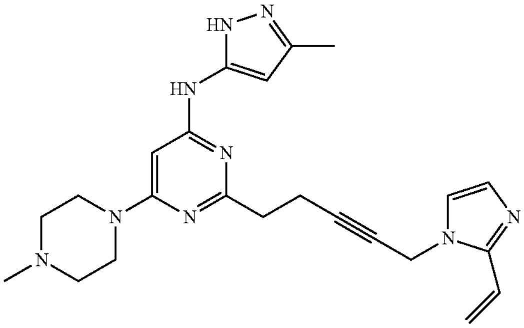
II-107
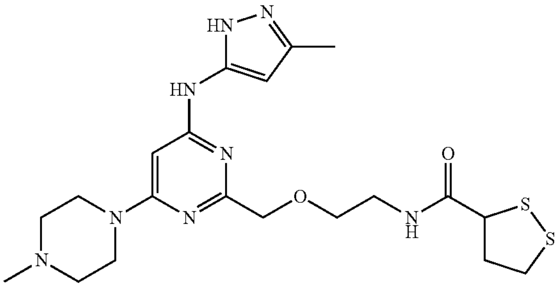
II-108
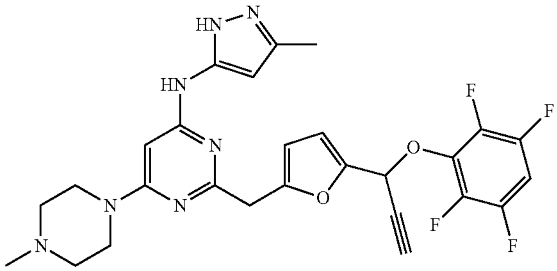
II-109
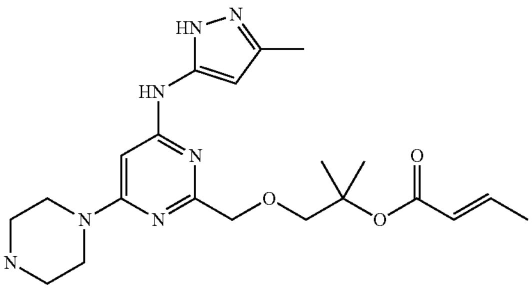

-continued
II-110
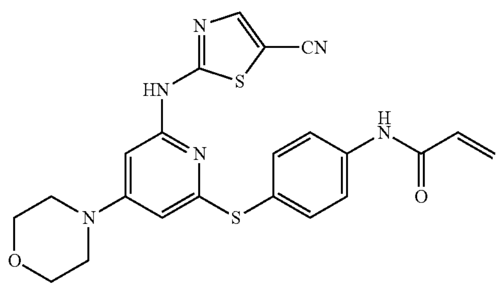
II-111
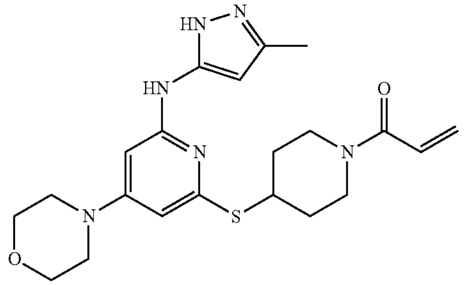
II-112
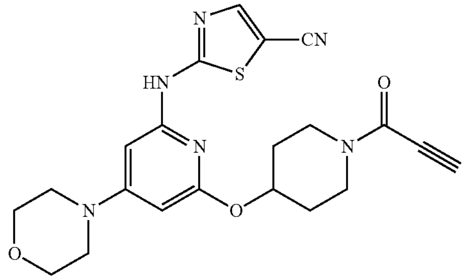
II-113
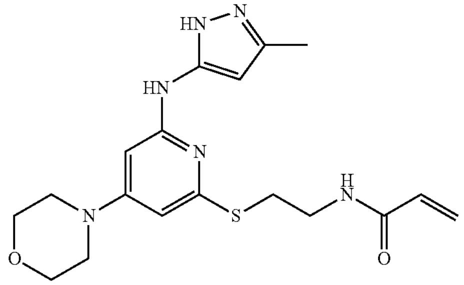
II-114
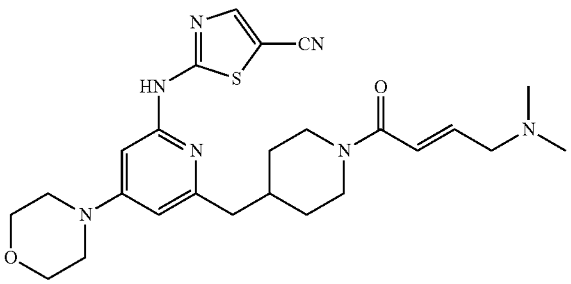
-continued
II-115
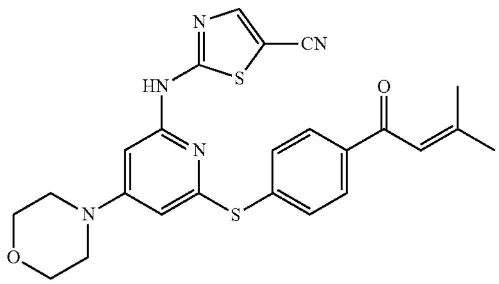
II-116
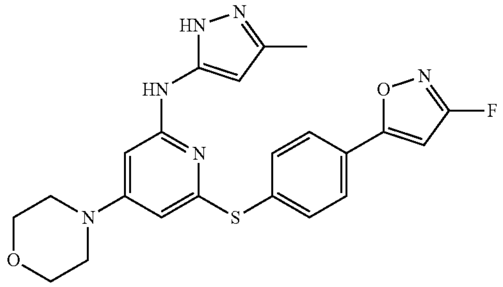
II-117
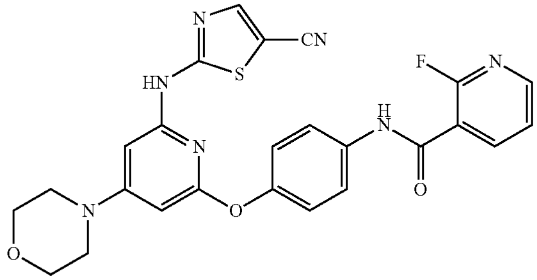
II-118
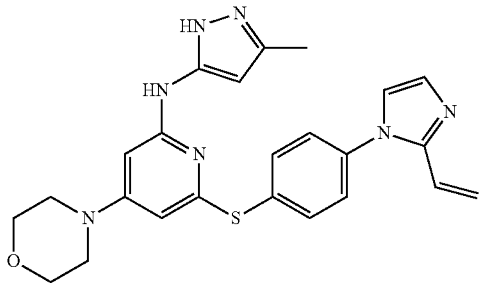
II-119
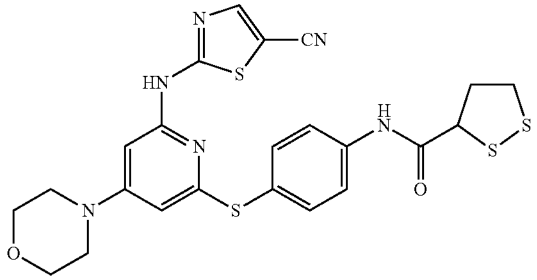

-continued
II-120
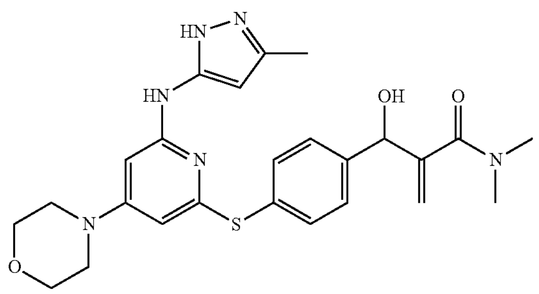
II-121
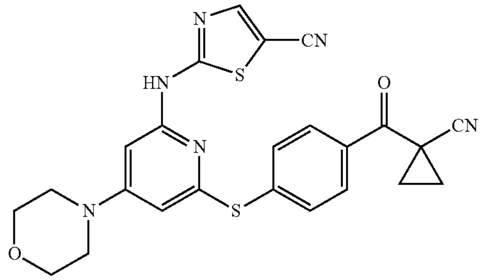
II-122
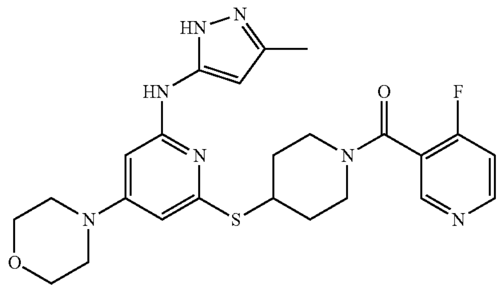
II-123
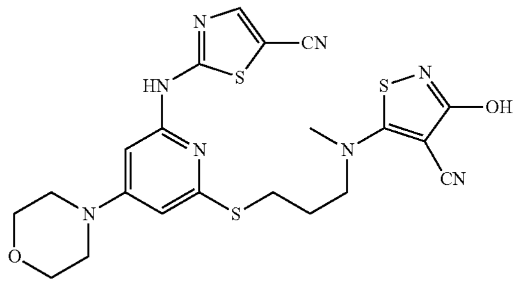
II-124
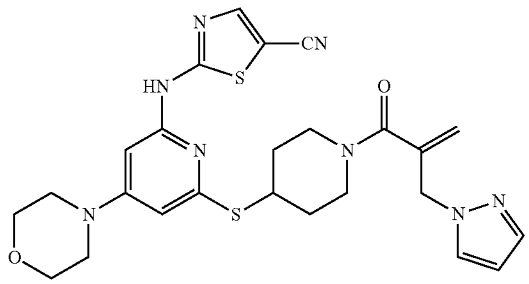
-continued
II-125
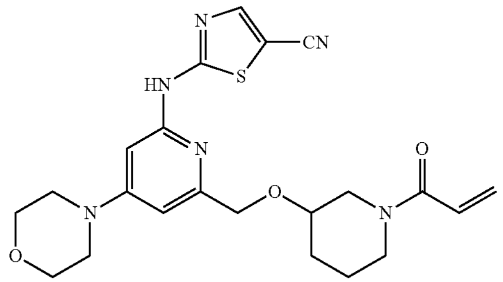
II-126
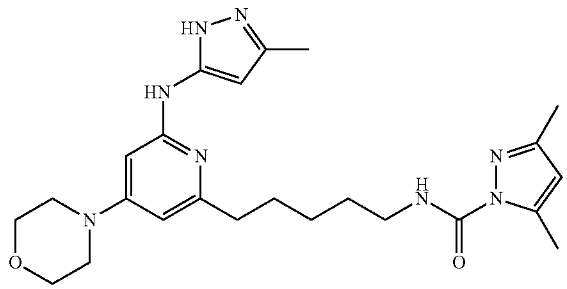
II-127
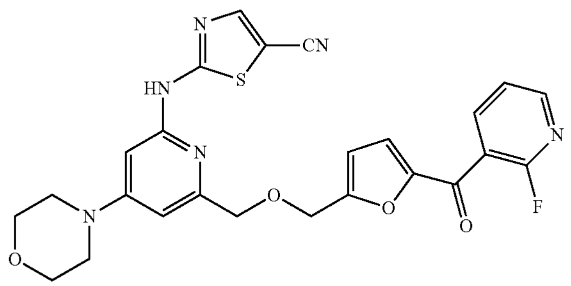
II-128
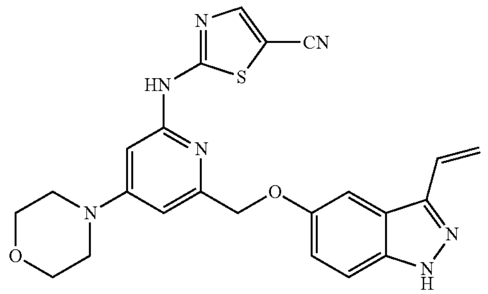
D. PLK Inhibitors
In some aspects the invention is a compound of Formula III
III
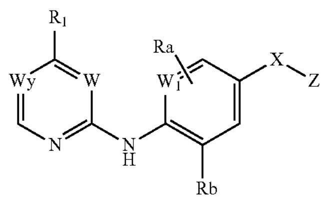
or a pharmaceutically acceptable salt thereof, wherein
Ra and Rb are independently selected from hydrogen, R, OR, halogen, —$CF_3$, —CN, —C≡C—R, —NRxRy, or —C(O)NRxRz;

each R, Rx and Ry is independently hydrogen, lower alkyl, lower haloalkyl, or lower cycloalkyl;

each Rz is independently hydrogen, aliphatic, or aryl;

X a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(═S)—, —C(═NR)—, —N═N—, or —C(═$N_2$)—;

Z is hydrogen, lower alkyl or a 5 or 6 membered saturated, partially unsaturated or aromatic ring that contains 0-3 heteroatoms selected from N, S and O, and contains 0-3 substituents selected from the group consisting of oxo, lower alkyl, —O-lower alkyl, a halogen, and —$CF_3$;

W and $W_1$ are independently N or CH;

Wy is N or C—Rc

Rc is R, OR, halogen, —$CF_3$, —CN, —C≡C—R, —NRxRy, —C(O)Rx or —C(O)NRxRz;

$R_1$ is -L-Y;

or Rc and $R_1$ taken together with the atoms to which they are bonded form a 5 or 6 membered partially unsaturated or aromatic ring that contains 0-3 heteroatoms selected from N, S and O, and is substituted with -L-Y and up to two other substituents selected from the group consisting of oxo, lower alkyl, —O-lower alkyl, a halogen, and —CF3.

The group -L-Y is as described herein in the detailed description of warheads.

In some embodiments, Wy is N—Rc, W is CH and $W_1$ is N.

In some embodiments, Wy is N—Rc, and Rc and $R_1$ are taken together to form

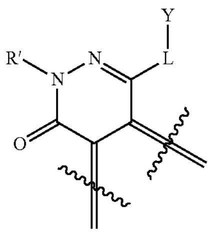

or

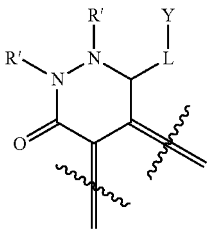

wherein R' is hydrogen, lower alkyl or a 3-10 membered monocyclic or bicyclic, saturated, partially unsaturated, or aryl ring having 0-3 heteroatoms independently selected from nitrogen, oxygen, and sulfur.

In any embodiments of the compounds of formula III, Z can be

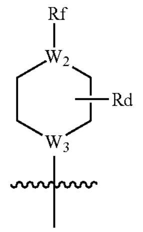

wherein $W_2$ and $W_3$ are independently CH or N, and Rf and Rd are independently hydrogen; R, OR, halogen, —$CF_3$, —CN, —C≡C—R, —NRxRy, —C(O)Rx or —C(O)NRxRz.

In certain embodiments, $R_1$ is characterized in that the -L-Y moiety is capable of covalently binding to a Cys4 residue in a protein kinase selected from PLK1 (Cys 67), PLK2 (Cys 96) and PLK3 (Cys 76), thereby irreversibly inhibiting the enzyme. In particular embodiments, R1 is characterized in that the -L-Y moiety is capable of covalently binding to Cys96 of PLK1, thereby irreversibly inhibiting the enzyme.

Exemplary PLK Inhibitors

III-1

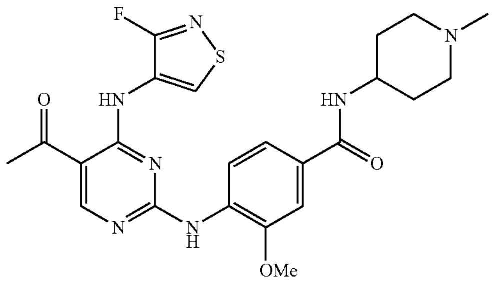

III-2

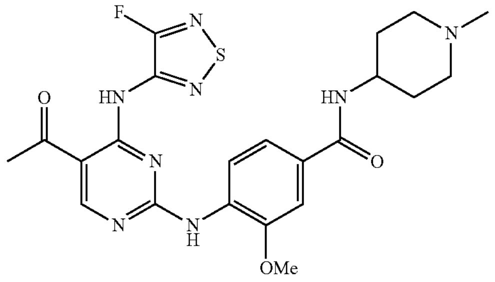

III-3

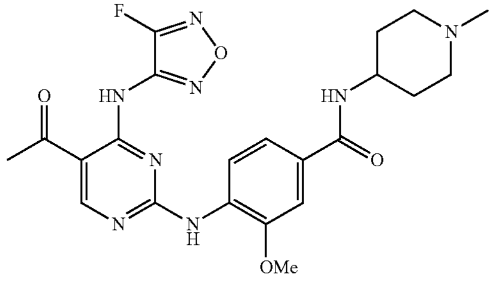

III-4

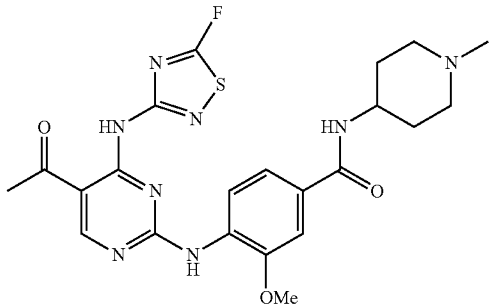

-continued
III-5
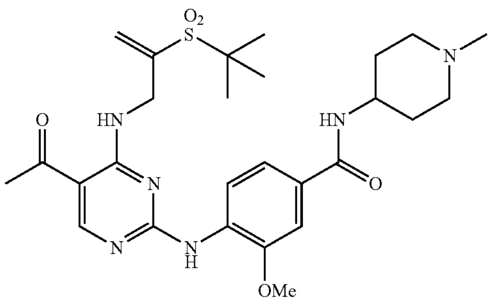
III-6
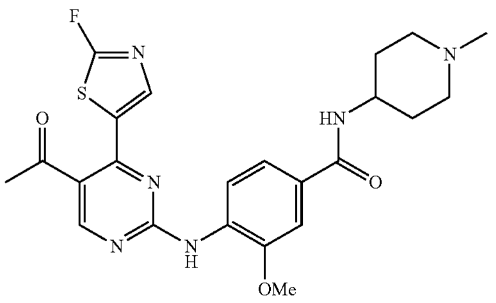
III-7
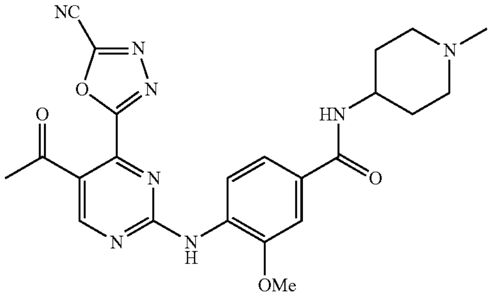
III-8
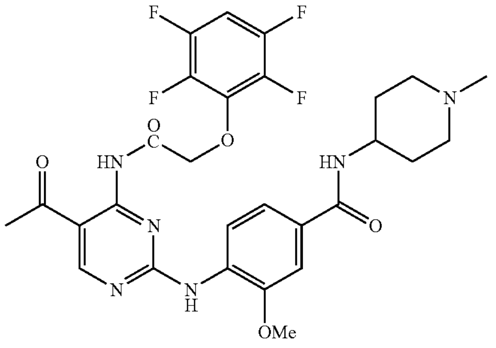
-continued
III-9
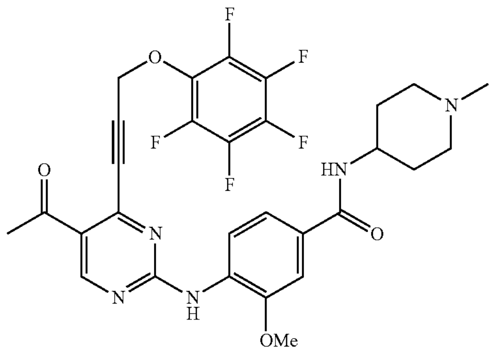
III-10
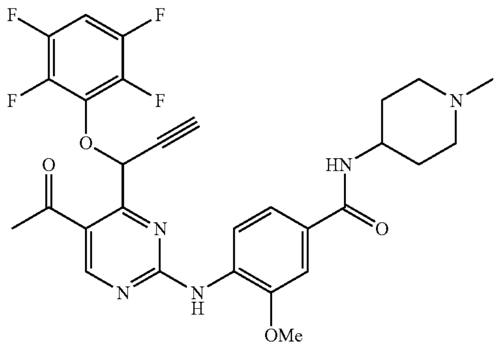
III-11
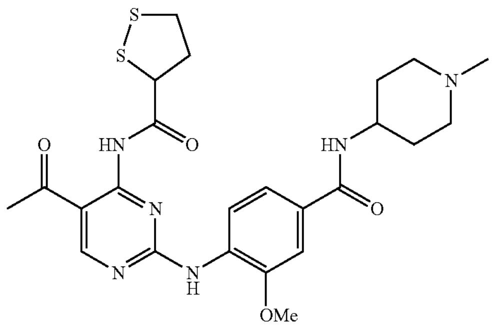
III-12
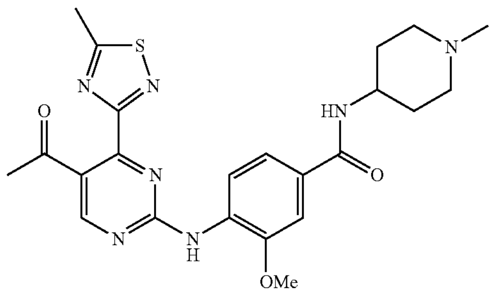

-continued
III-13
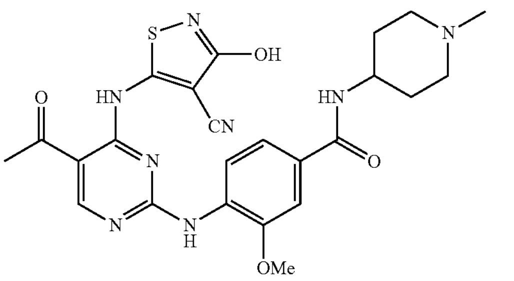
III-14
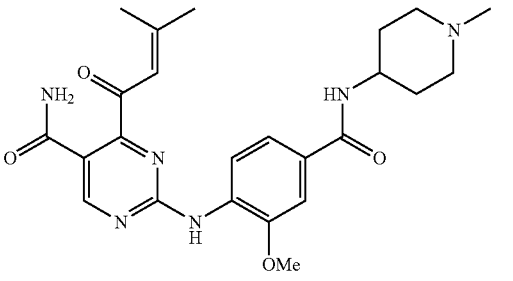
III-15
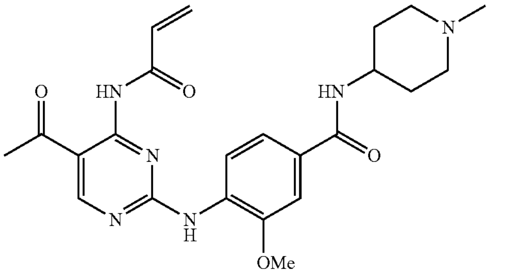
III-16
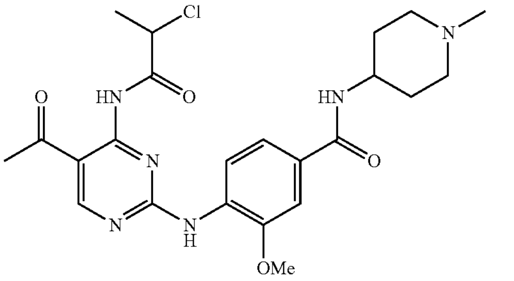
III-17
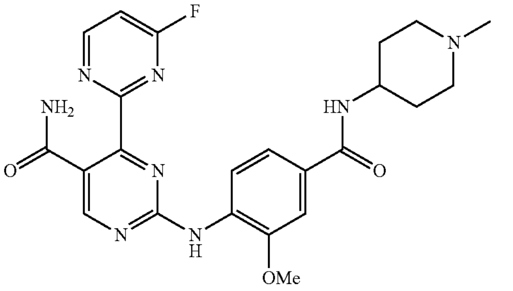
-continued
III-18
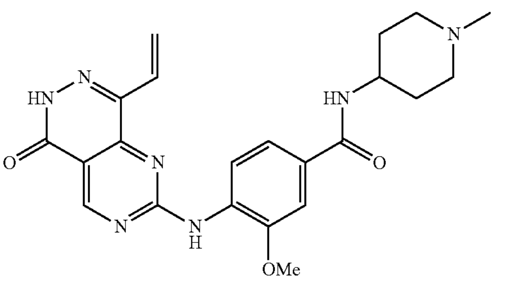
III-19
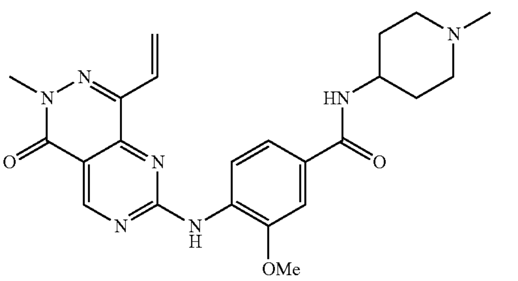
III-20
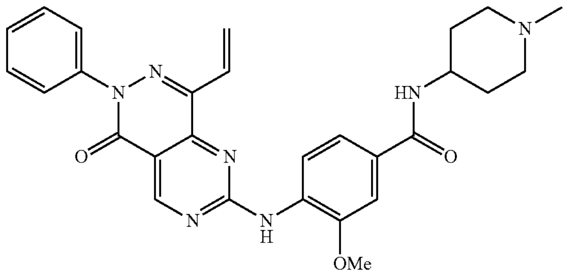
III-21
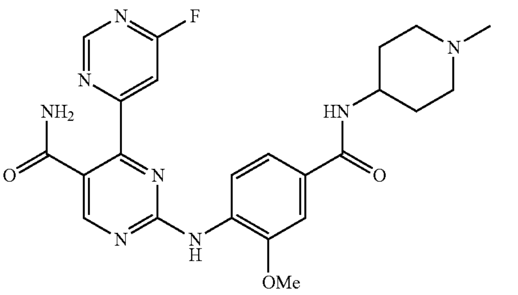
III-22
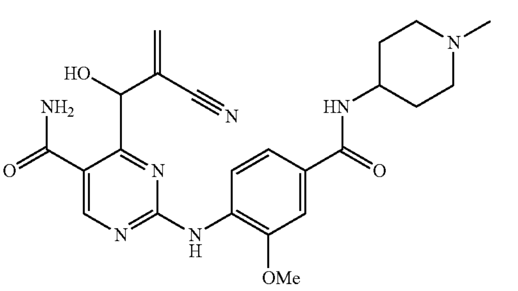

-continued
III-23
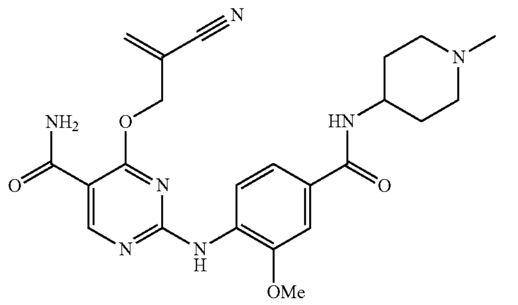
III-24
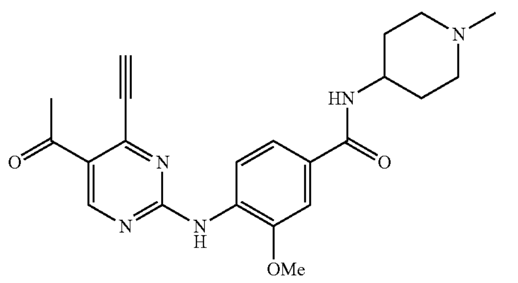
III-25
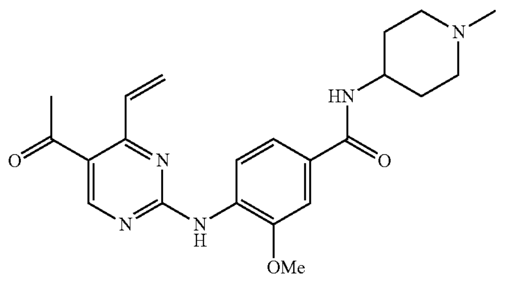
III-26
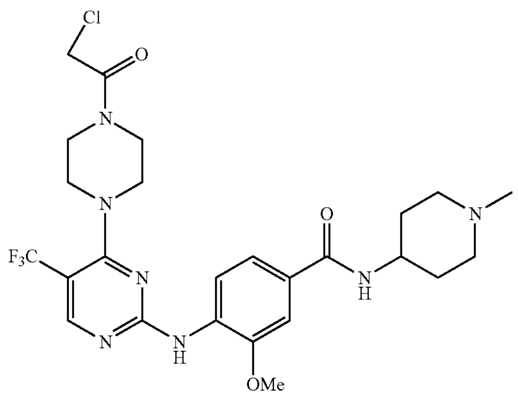
-continued
III-27
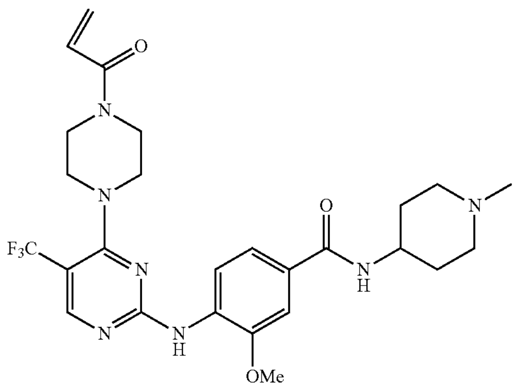
III-28
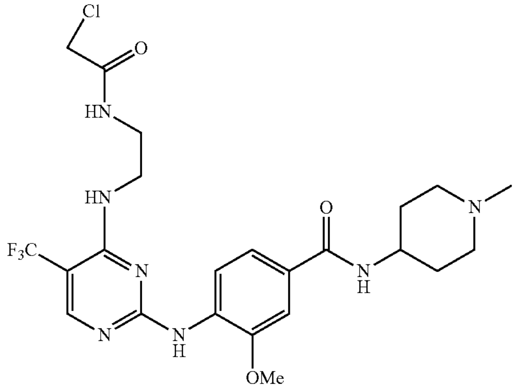
III-29
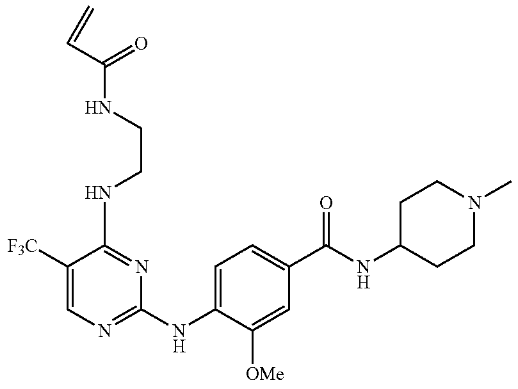
E. FAK Inhibitors
In another aspect, the invention is a compound of formula IV:
IV
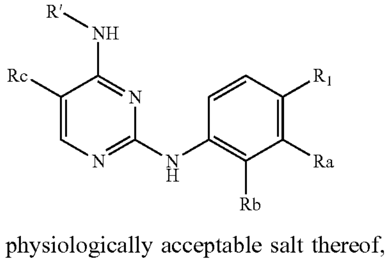
or a physiologically acceptable salt thereof, wherein
Ra, Rb and Rc are independently selected from R, OR, halogen, —$CF_3$, —CN, —C≡C—R, —NRxRy, or —C(O)NRxRz;

each R, Rx and Ry is independently hydrogen, lower alkyl, lower haloalkyl, or lower cycloalkyl;

each Rz is independently hydrogen, aliphatic, or aryl;

R' is

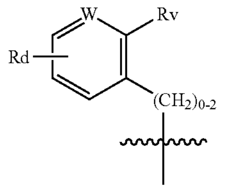

W is CH or N;

Rd is hydrogen, lower alkyl, —O-lower alkyl, —$CF_3$, or a halogen;

Rv is —C(O)NRxRy, —N(Rx)C(O)Rz; —$S(O)_2$NRxRy, or —N(Rx)$S(O)_2$Rz;

$R_1$ is -T-L-Y; or

Ra and $R_1$ taken together with the intervening carbon atoms to which they are bonded form a 5 or 6 membered partially unsaturated or aromatic ring that contains 0-3 heteroatoms selected from N, S and O, and is substituted with -L-Y and up to two other substituents selected from the group consisting of oxo, lower alkyl, —O-lower alkyl, a halogen, and —CF3.

T is absent or a 3-10 membered monocyclic or bicyclic, saturated, partially unsaturated, or aryl ring having 0-3 heteroatoms independently selected from nitrogen, oxygen and sulfur, and wherein said ring is optionally substituted with 1-4 $R^e$ groups;

each $R^e$ is independently selected from -Q-Z, OH, oxo, $NO_2$, halogen, CN, a suitable leaving group, or a $C_{1-6}$ aliphatic optionally substituted with oxo, halogen, $NO_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

The group -L-Y is as described herein in the detailed description of the warheads.

In some embodiments, Ra and $R_1$ are taken together to form

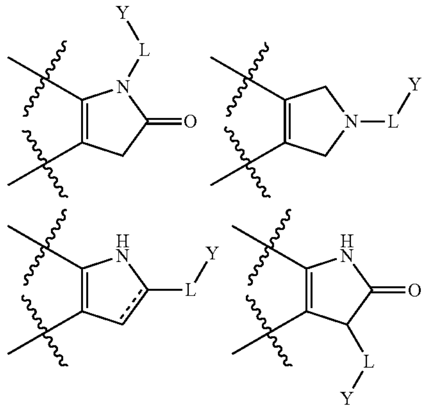

-continued

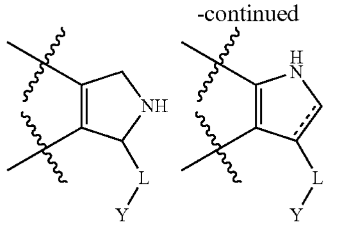

In some embodiments the FAK inhibitor a compound of formula IVa:

IVa

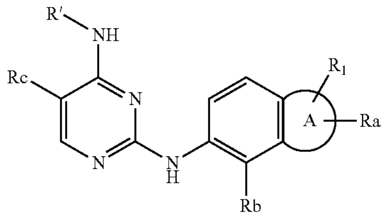

or a physiologically acceptable salt thereof, wherein

Ring A is a 5 or 6 membered partially unsaturated or aromatic ring that contains 0-3 heteroatoms selected from N, S and O, and is substituted with -L-Y and up to two other substituents selected from the group consisting of oxo, lower alkyl, —O-lower alkyl, a halogen, and —CF3;

Ra, Rb, Rc, $R_1$ and R' are as described for formula IV.

In other embodiments, the FAK inhibitor is a compound of formula IVb:

IVb

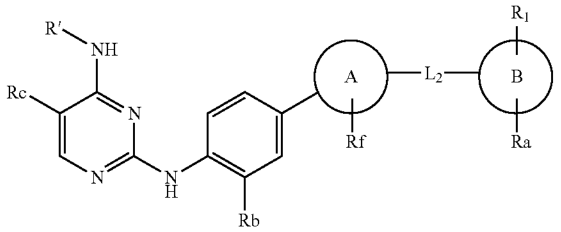

or a physiologically acceptable salt thereof, wherein

Rf is selected from R, OR, halogen, —$CF_3$, —CN, —C≡C—R, —NRxRy, or —C(O)NRxRz;

each R, Rx and Ry is independently hydrogen, lower alkyl, lower haloalkyl, or lower cycloalkyl;

each Rz is independently hydrogen, aliphatic, or aryl;

Ring A and Ring B are independently a 5 or 6 membered saturated, partially unsaturated or aromatic ring that contains 0-3 heteroatoms selected from N, S and O;

$L_2$ is a absent, a covalent bond, a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(═S)—, —C(═NR)—, —N═N—, or —C(═$N_2$)—. When $L_2$ is absent, Ring A and Ring B are fused or joined through a Spiro atom.

Ra, Rb, Rc, and R' are as described for formula IV.

$R_1$ is -L-Y; and -L-Y is as described herein in the detailed description of the warheads.

In some embodiments, Rings A and B are independently piperidine, tetrahydropyran, tetrahydrothiopyran, piperazine, dioxane, dithiane, morpholine, pyrrolidine, tetrahydrofuran, tetrahydrothiophene, benzene, pyridine, pyrrole, thiophene.
Exemplary FAK Inhibitors
IV-1
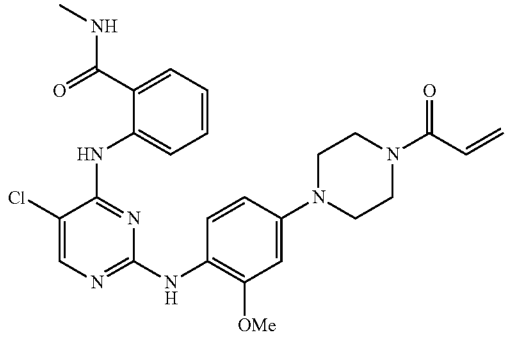
IV-2
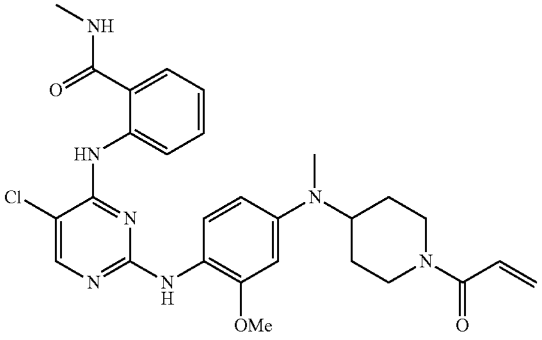
IV-3
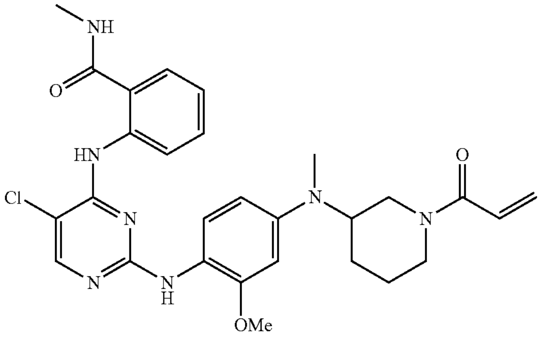
IV-4
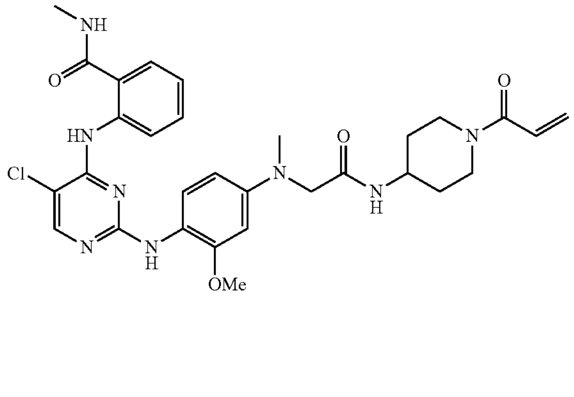
-continued
IV-5
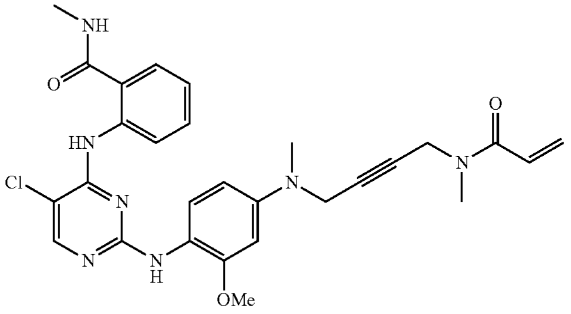
IV-6
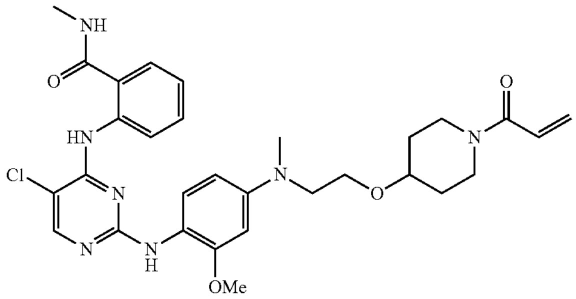
IV-7
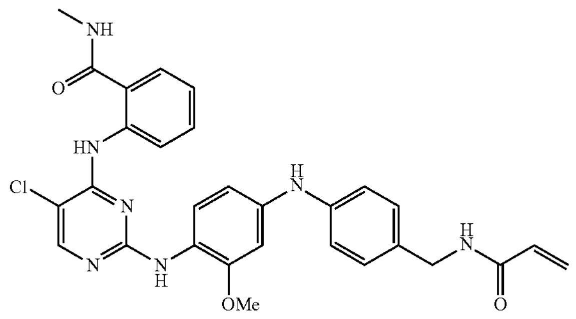
IV-8
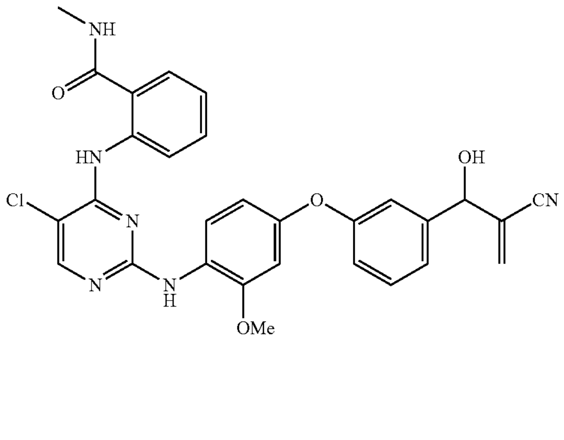

-continued
IV-9
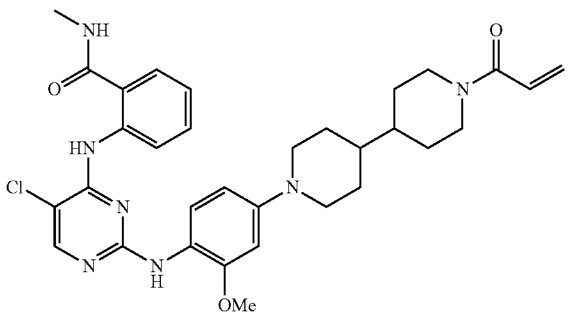
IV-10
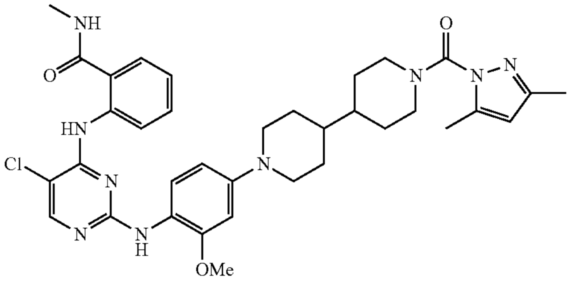
IV-11
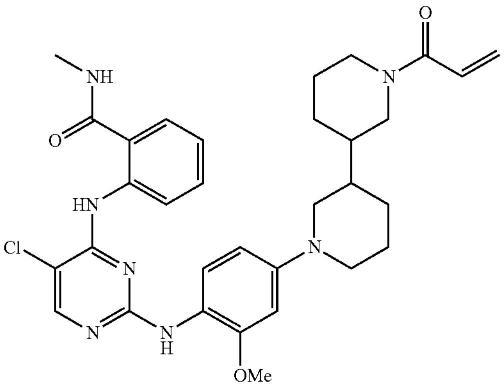
IV-12
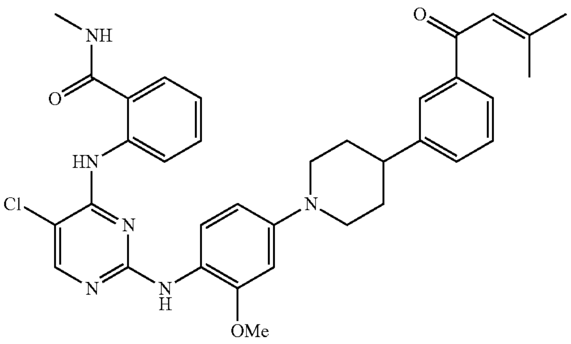
-continued
IV-13
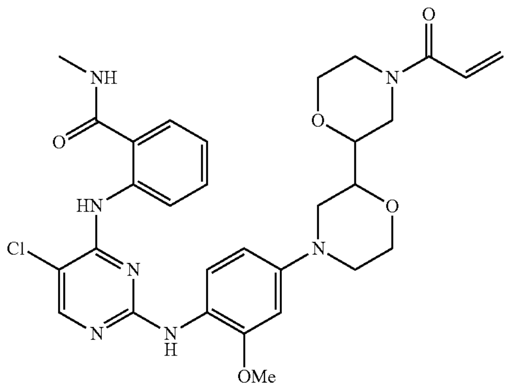
IV-14
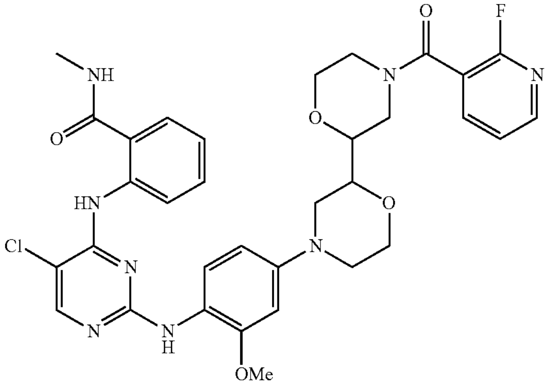
IV-15
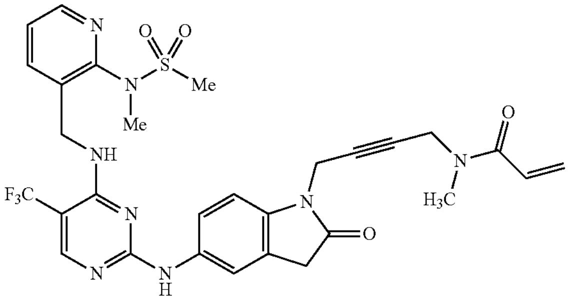
IV-16
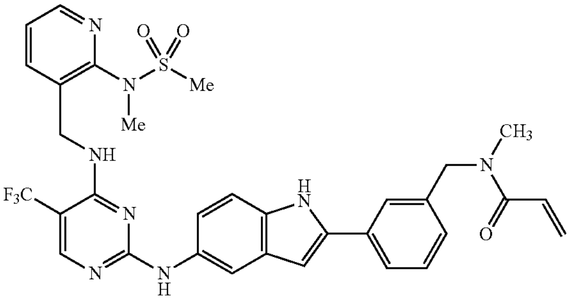

-continued
IV-17
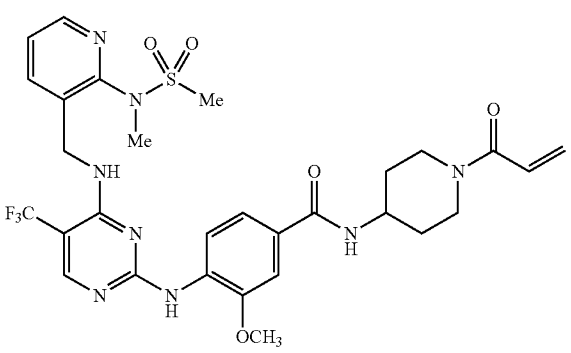
IV-18
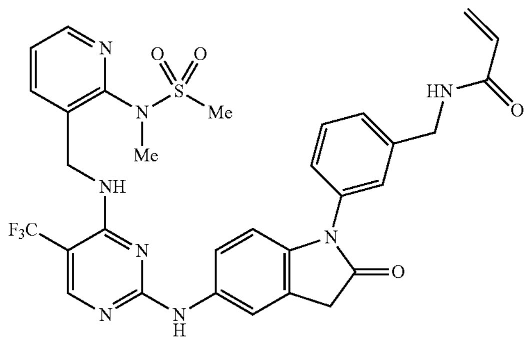
IV-19
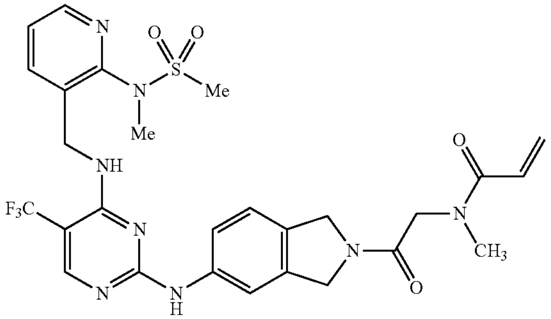
IV-20
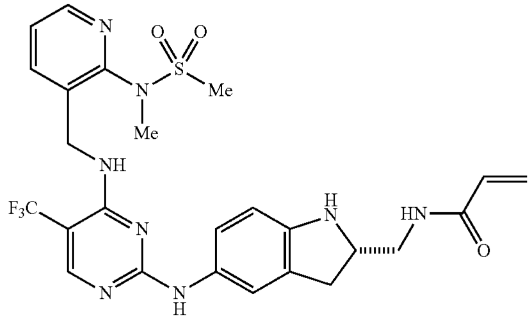
-continued
IV-21
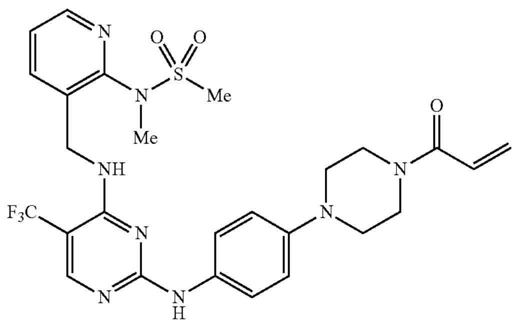
IV-22
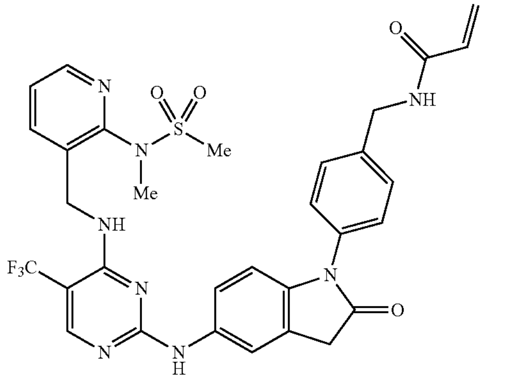
IV-23
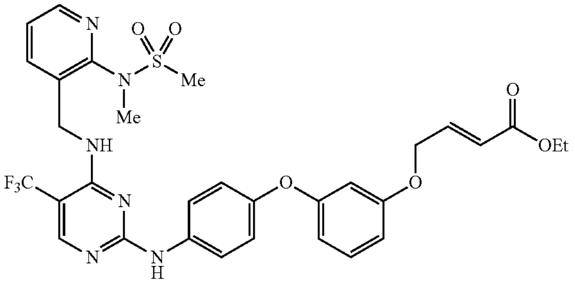
IV-24
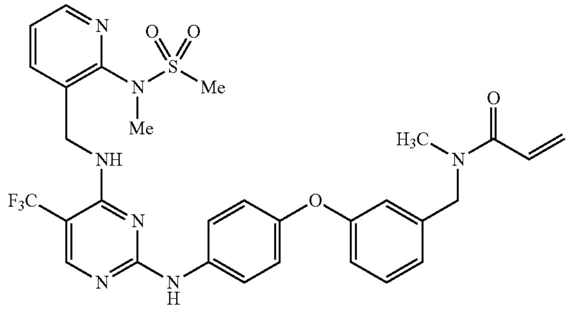

IV-25
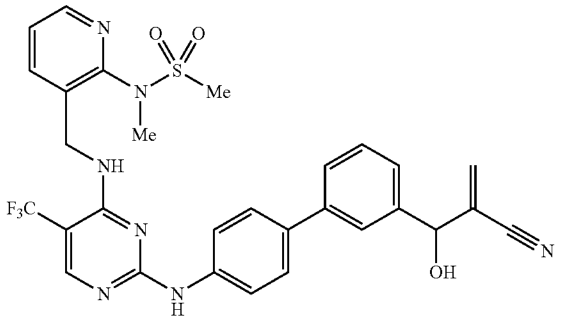
IV-26
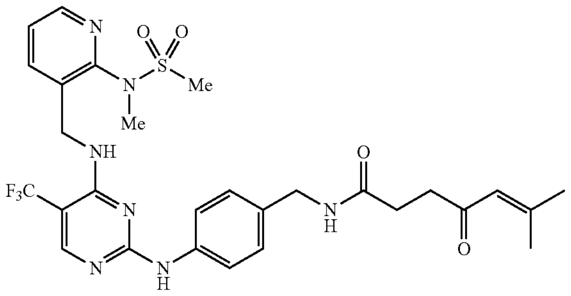
IV-27
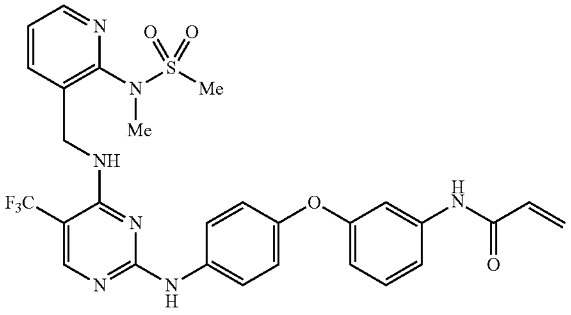
IV-28
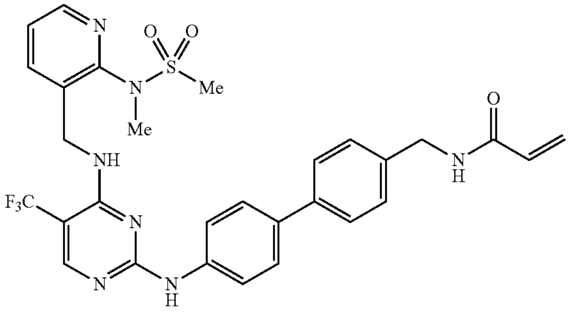
IV-29
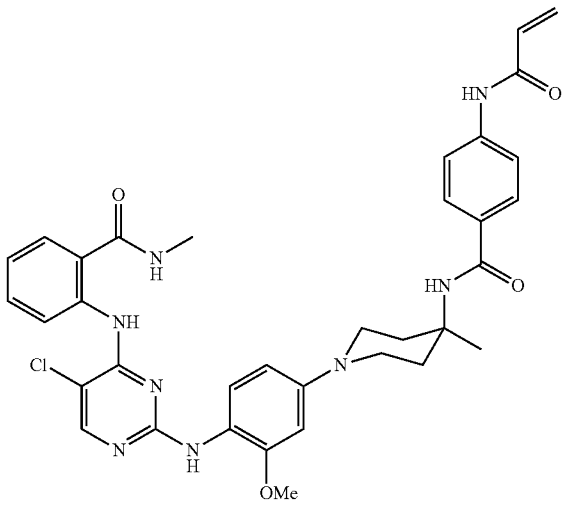
IV-30
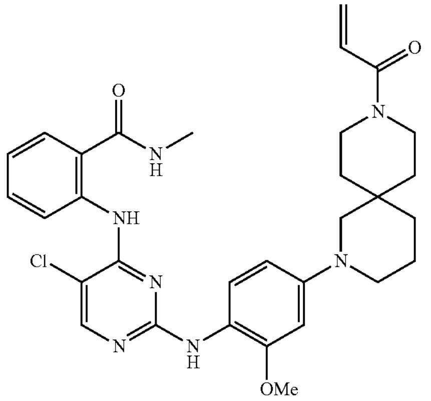
IV-31
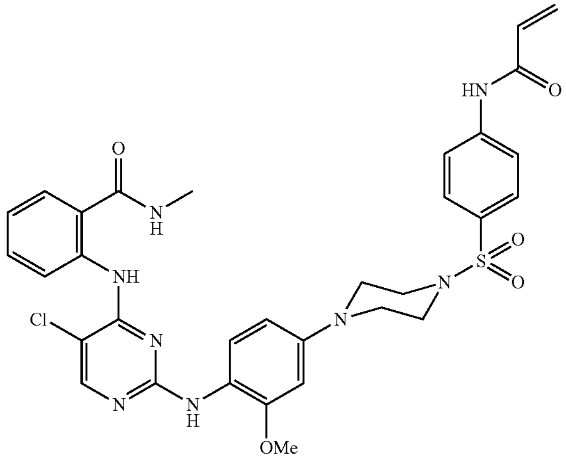

F. JAK3 Inhibitors

In another aspect, the invention is a compound of formula V

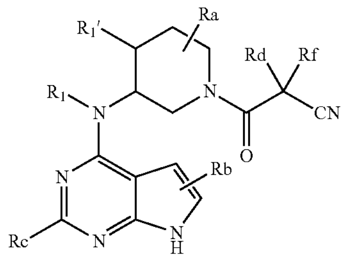

V or a physiologically acceptable salt thereof, wherein

Ra, Rb, Rc, Rd, and Rf are independently selected from R, OR, halogen and $-CF_3$;

each R is independently hydrogen, $C_1$-$C_6$ alkyl, $C_1$-$C_6$ alkenyl, $C_1$-$C_6$ alkynl, or lower haloalkyl;

$R_1$ or $R_{1'}$ is -L-Y, with the proviso that when $R_1$ is -L-Y, $R_{1'}$ is hydrogen or lower alkyl, and when $R_{1'}$ is -L-Y, $R_1$ is hydrogen or lower alkyl.

The group -L-Y is as described herein in the detailed description of the warheads.

In some embodiments, Ra, Rb, Rc, Rd and Rf are each hydrogen. In particular embodiments $R_1$ is -L-Y.

In certain embodiments, $R_1$ is characterized in that the -L-Y moiety is capable of covalently binding to a Cys909 in JAK3, thereby irreversibly inhibiting the enzyme.

Exemplary JAK-3 Inhibitors

V-1

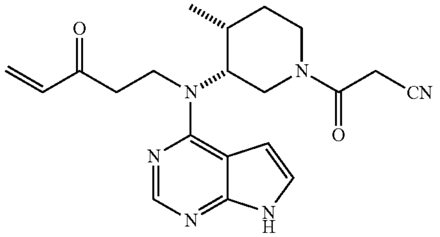

V-2

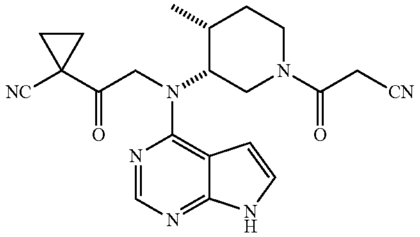

V-3

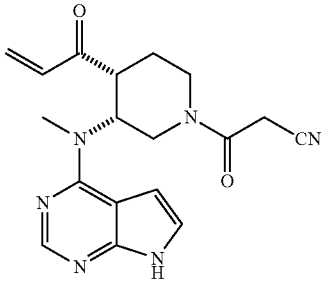

-continued

V-4

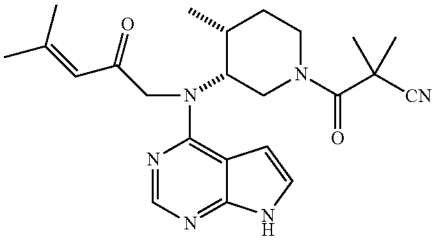

V-5

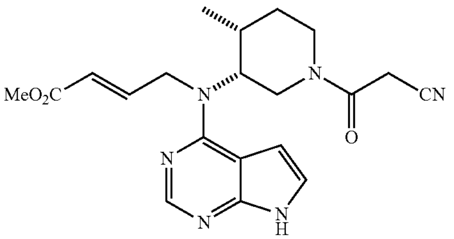

V-6

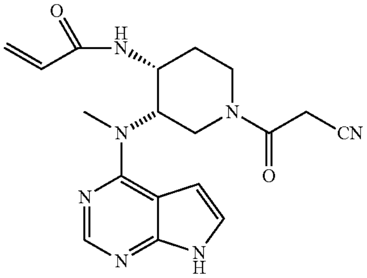

V-7

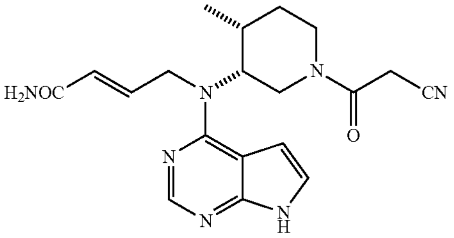

V-8

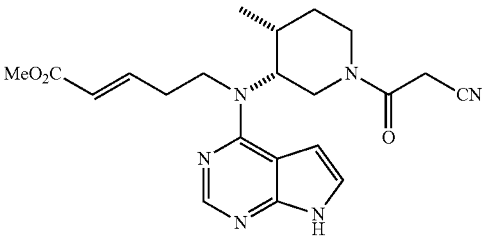

V-9

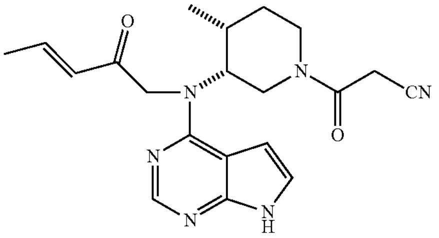

-continued

V-10

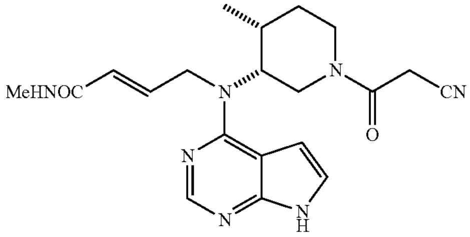

V-11

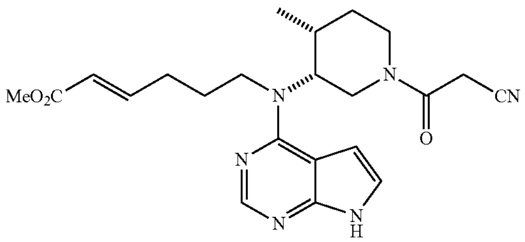

V-12

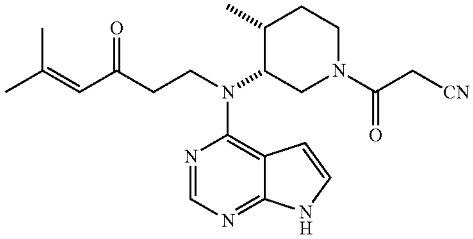

V-13

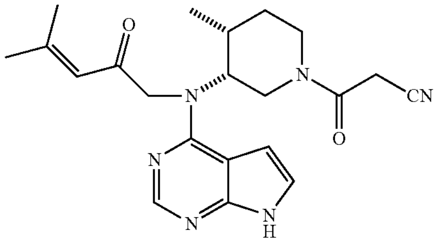

G. JNK Inhibitors

1. Formula VI

In other aspects, the invention is a compound of Formula VI

VI

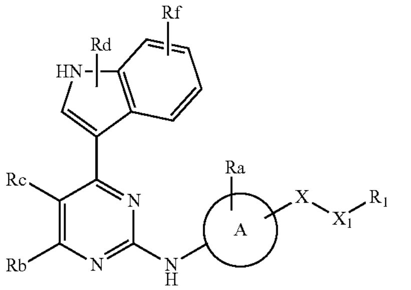

or a physiologically acceptable salt thereof, wherein

Ra, Rb, Rc, Rd and Rf are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

Ring A is a 3-10 membered monocyclic or bicyclic, saturated, partially unsaturated, or aryl ring containing 0-3 heteroatoms independently selected from the group consisting of nitrogen, oxygen, and sulfur;

X is a bond or a bivalent $C_1$-$C_6$ saturated or unsaturated, straight or branched hydrocarbon chain wherein optionally one, two or three methylene units of the hydrocarbon chain are independently replaced by —NR—, —O—, —C(O)—, —OC(O)—, —C(O)O—, —S—, —SO—, —$SO_2$—, —C(═S)—, —C(═NR)—, —N═N—, or —C(═$N_2$)—;

$X_1$ is a bond or is a bivalent 3-10 membered monocyclic or bicyclic, saturated, partially unsaturated, or aryl ring containing 0-3 heteroatoms independently selected from the group consisting of nitrogen, oxygen, and sulfur;

$R_1$ is -L-Y. The group -L-Y is as described herein in the detailed description of the warheads.

In some embodiments, $X_1$ is a bivalent six member ring wherein R1 is bonded para to the ring atom that is bonded to X. In particular examples of this embodiment, $X_1$ is

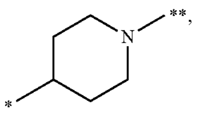

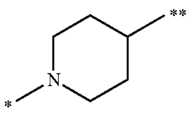 or

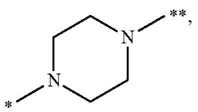

Wherein * indicates the point of attachment to X and ** indicates the point of attachment to $R_1$.

In some embodiments, X and $X_1$ are both a bond and Ring A is

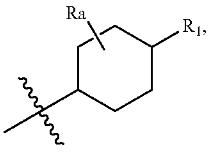

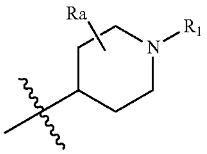 or

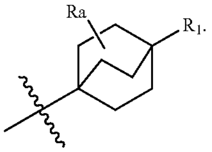

In certain embodiments, $R_1$ is characterized in that the -L-Y moiety is capable of covalently binding to a Cys5 residue in a protein kinase selected from JNK1 (Cys 116), JNK2 (Cys 116), and JNK3 (Cys 154), thereby irreversibly inhibiting the enzyme. In particular embodiments, $R_1$ is characterized in that the -L-Y moiety is capable of covalently binding to Cys 116 of JNK1, thereby irreversibly inhibiting the enzyme.

Exemplary JNK Inhibitors of Formula VI
VI-1
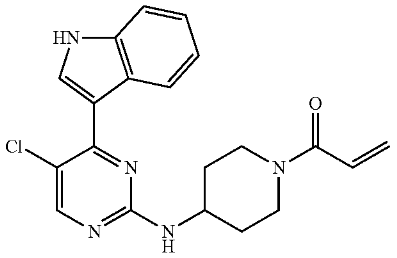
VI-2
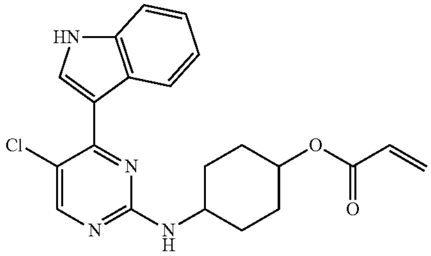
VI-3
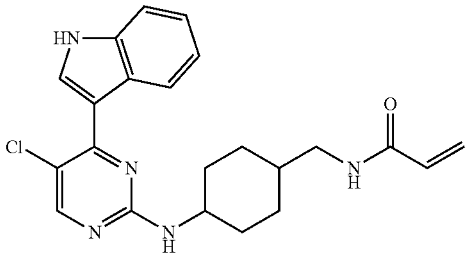
VI-4
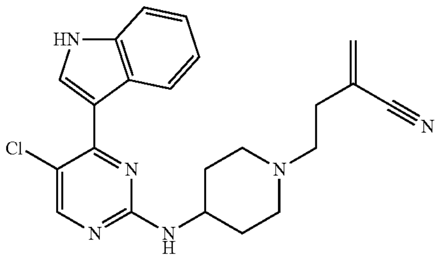
VI-5
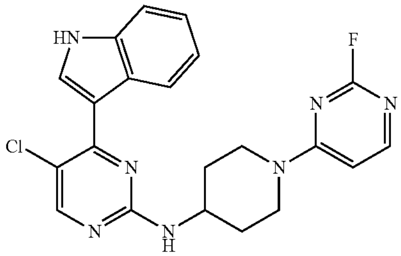
VI-6
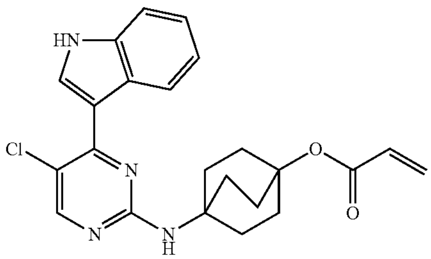
-continued
VI-7
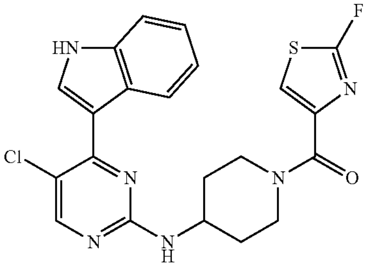
VI-8
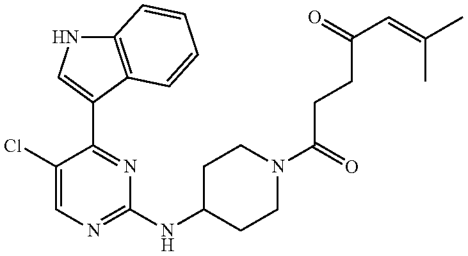
VI-9
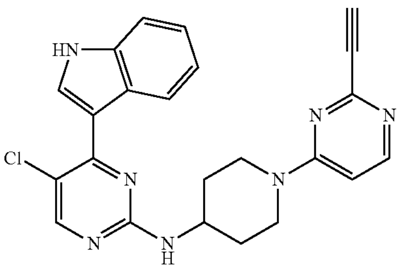
VI-10
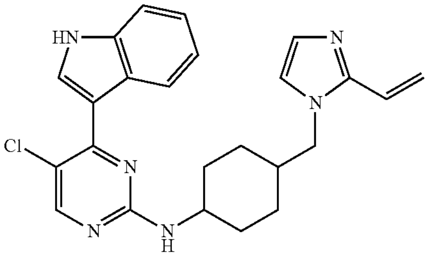
VI-11
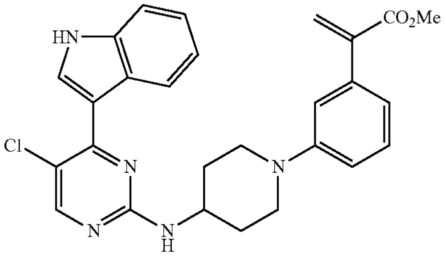
VI-12
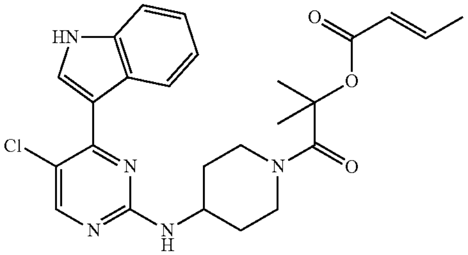

-continued
VI-13
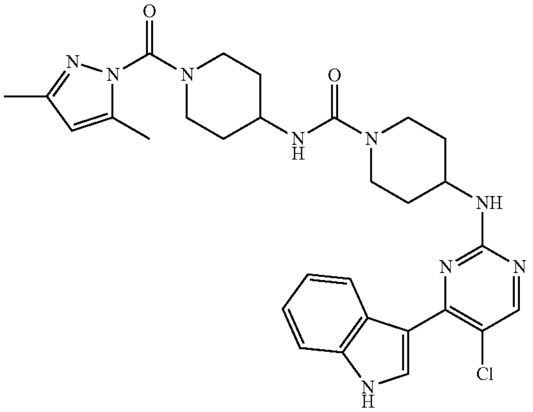
VI-14
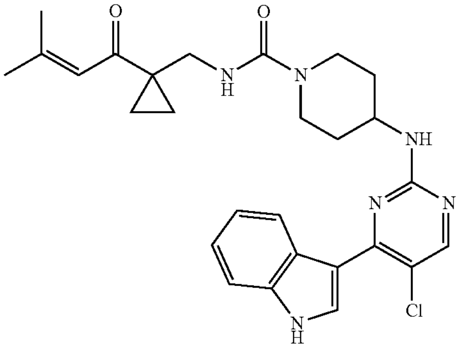
VI-15
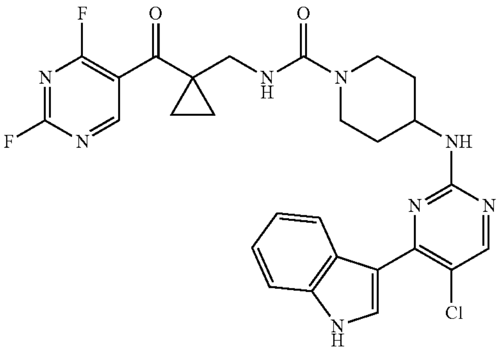
VI-16
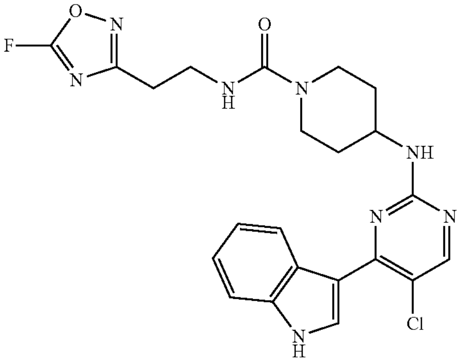
-continued
VI-17
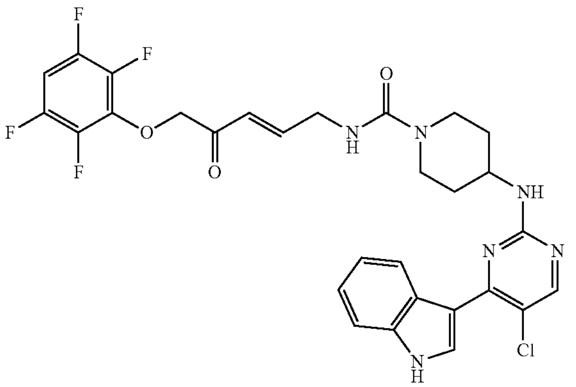
VI-18
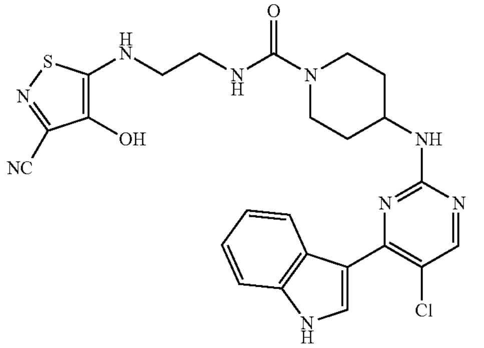
VI-19
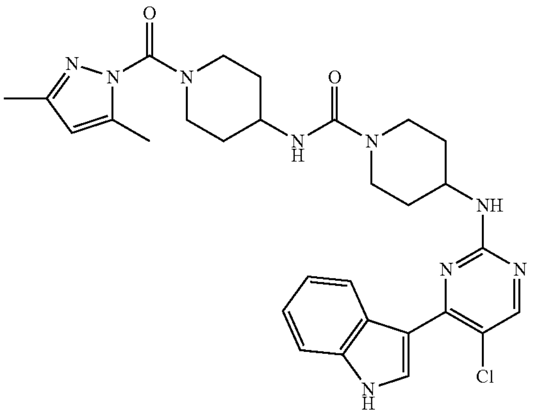
VI-20
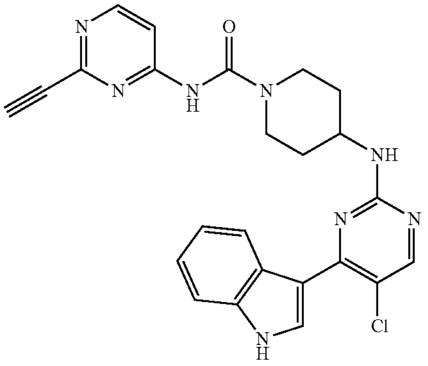

-continued

VI-21

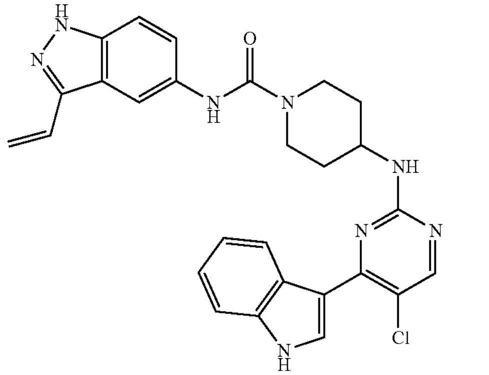

VI-22

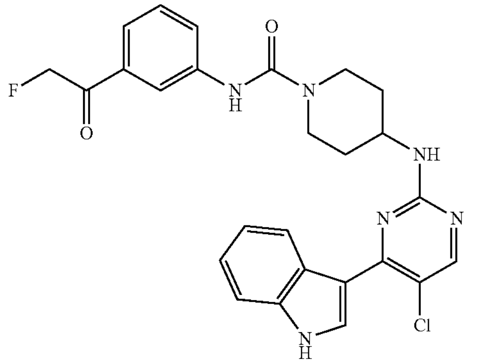

2. Formula VII

In another aspect, the invention is a compound of formula VII

VII

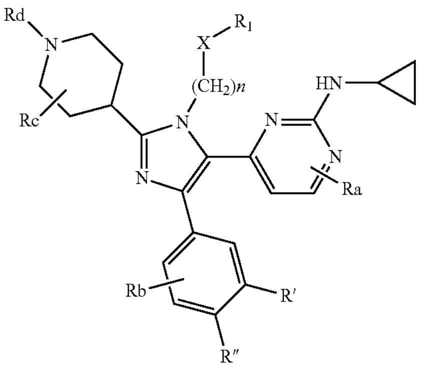

or a pharmaceutically acceptable salt thereof, wherein n is one, two, or three;

Ra, Rb, Rc and Rd are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

R' and R" are independently hydrogen or halogen;

X is a bond, or is selected from the group consisting of

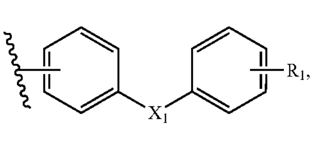

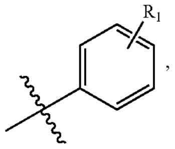

-continued

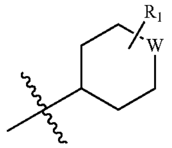

and

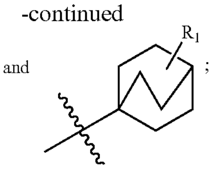

;

$X_1$ is O, NH or S;

W is $CH_2$ or NH;

$R_1$ is -L-Y. The group -L-Y is as described herein in the detailed description of the warheads.

In some embodiments, Ra, Rb and Rc are hydrogen, Rd is methyl, and X is

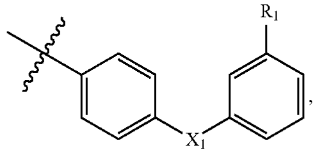

,

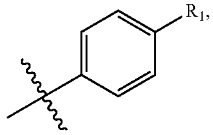

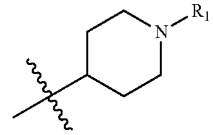

or

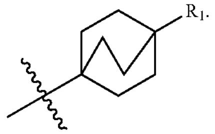

In certain embodiments, $R_1$ is characterized in that the -L-Y moiety is capable of covalently binding to a Cys5 residue in a protein kinase selected from JNK1 (Cys 116), JNK2 (Cys 116), and JNK3 (Cys 154), thereby irreversibly inhibiting the enzyme. In particular embodiments, $R_1$ is characterized in that the -L-Y moiety is capable of covalently binding to Cys 116 of JNK1, thereby irreversibly inhibiting the enzyme.

Exemplary JNK Inhibitors of Formula VII

VII-1

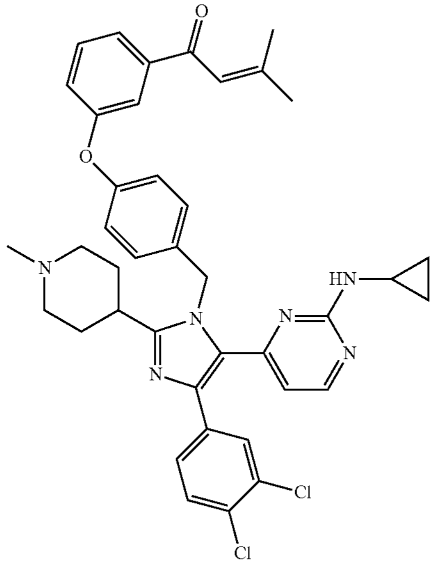

-continued
VII-2
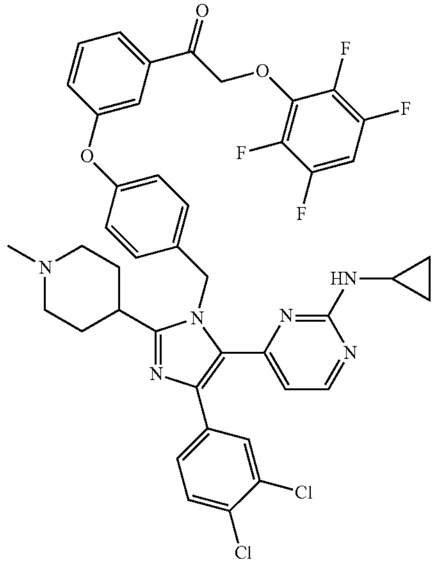
VII-3
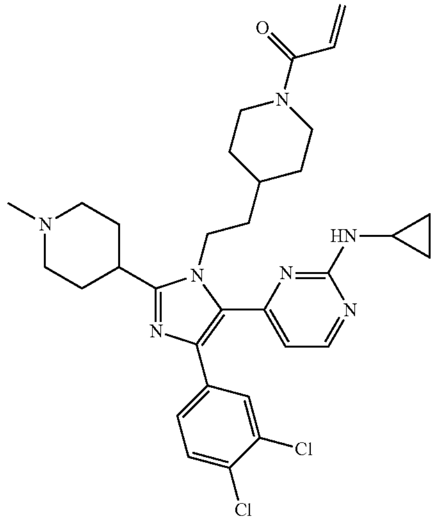
VII-4
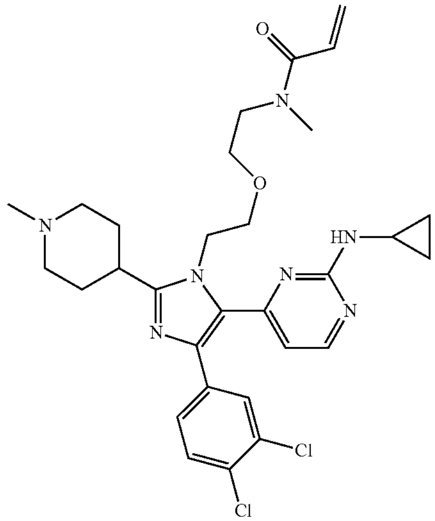
-continued
VII-5
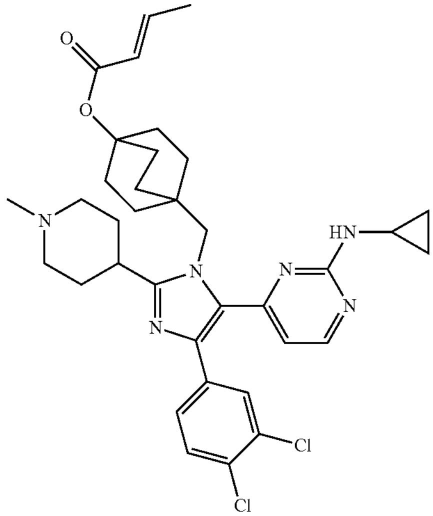
VII-6
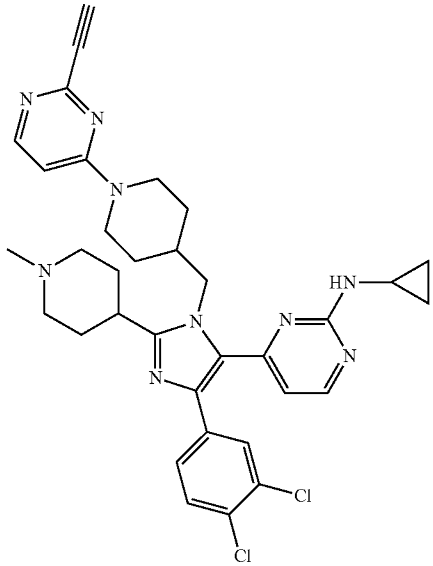
VII-7
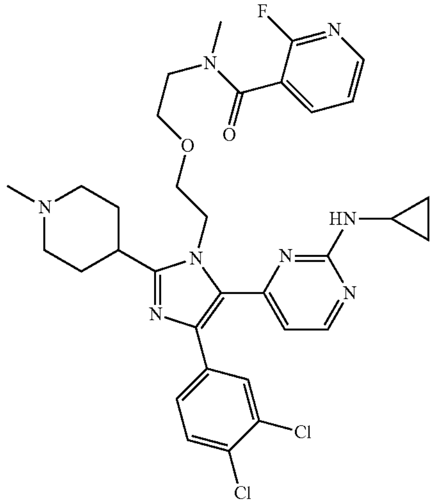

-continued
VII-8
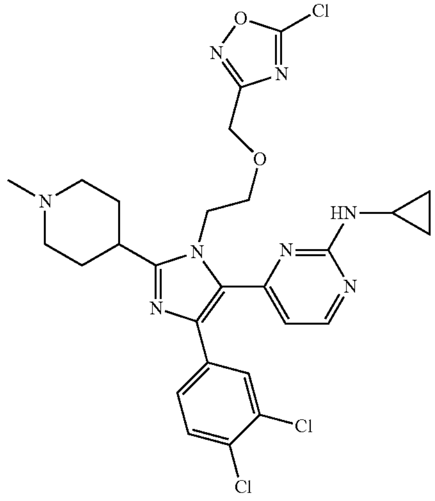
VII-9
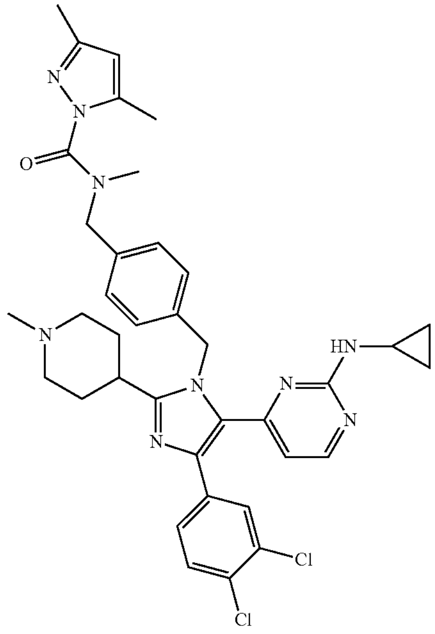
VII-10
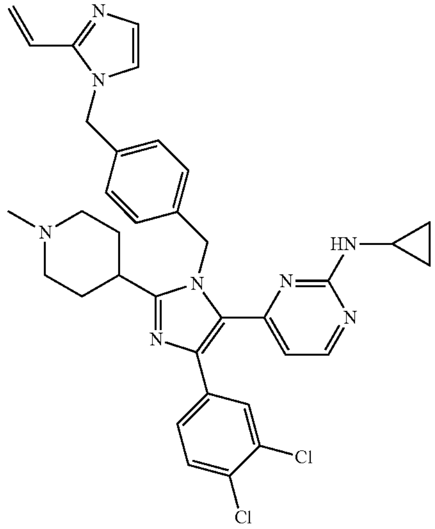
-continued
VII-11
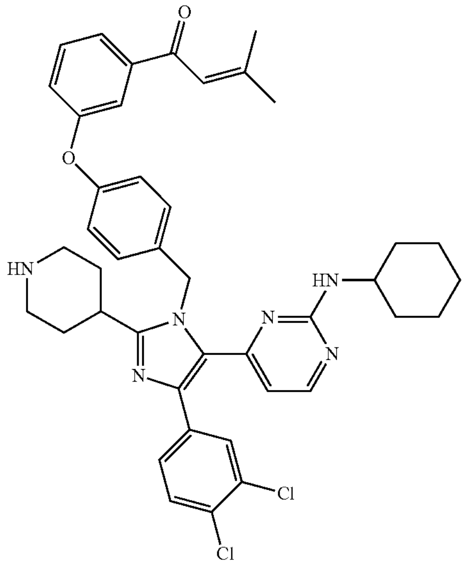
VII-12
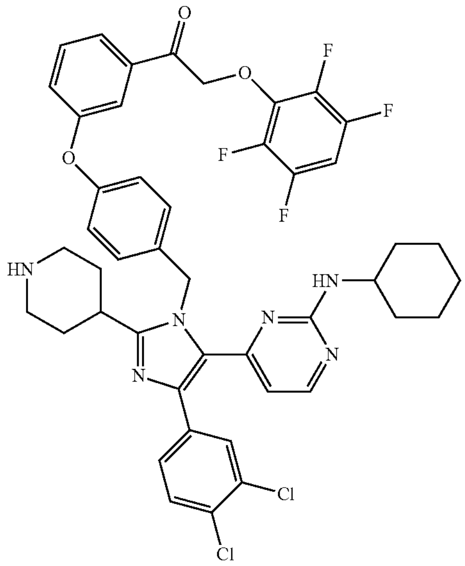
VII-13
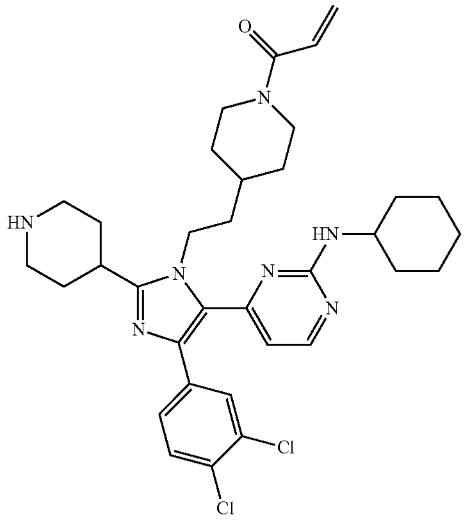

-continued
VII-14
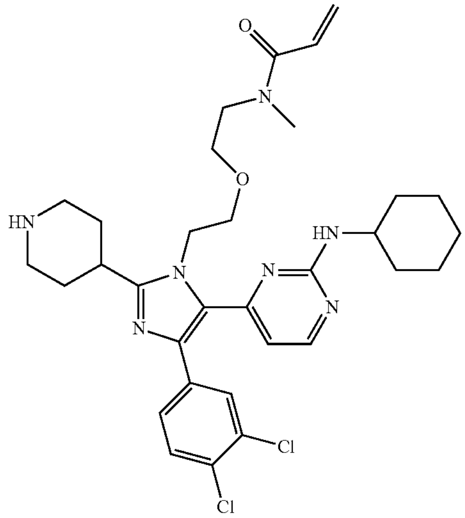
VII-15
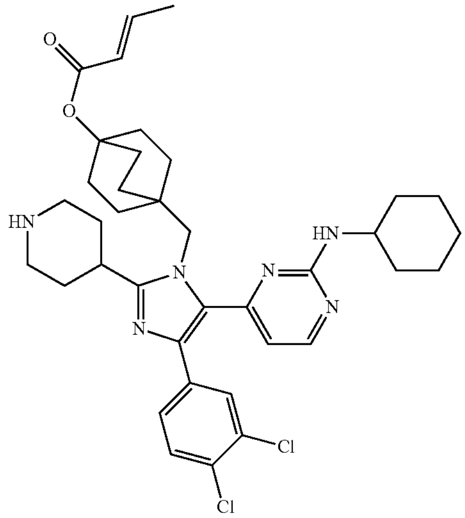
VII-16
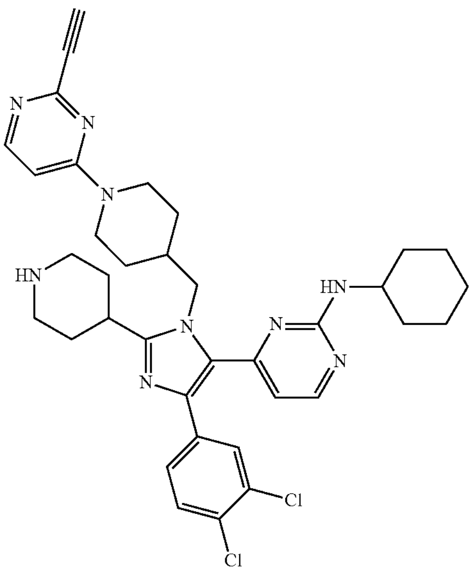
-continued
VII-17
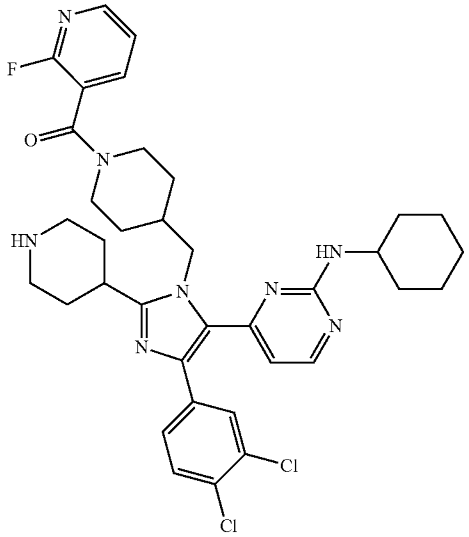
VII-18
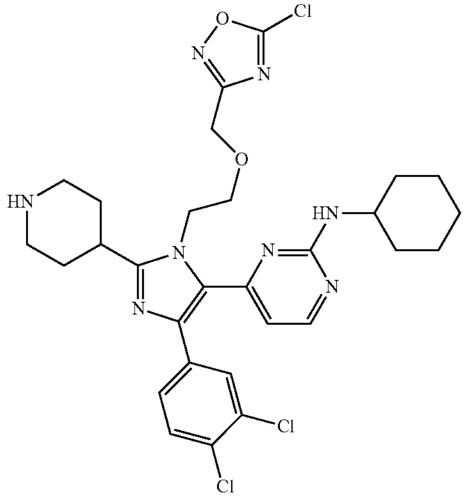
VII-19
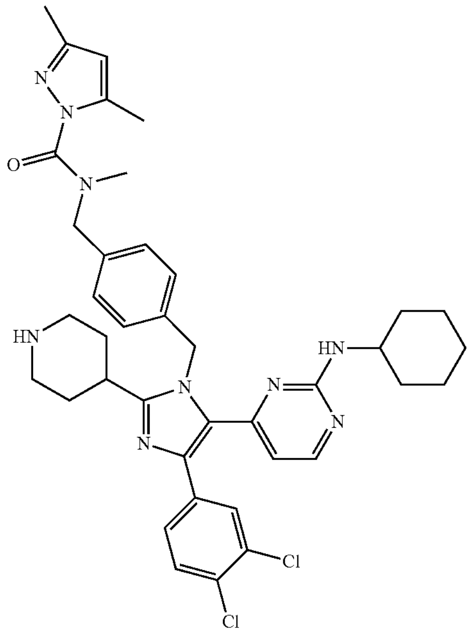

-continued

VII-20

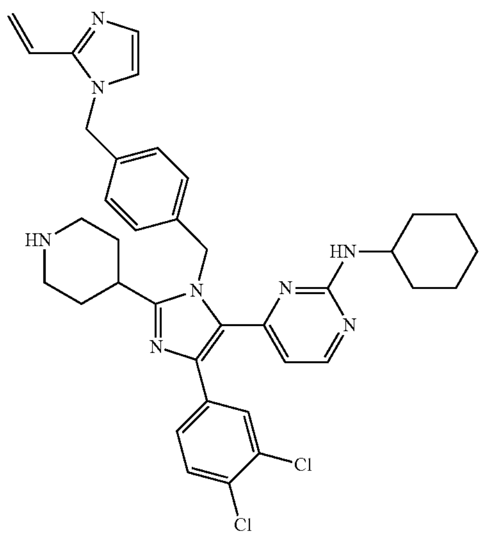

3. Formula VIII

In another aspect, the invention is a compound of formula VIII

VIII

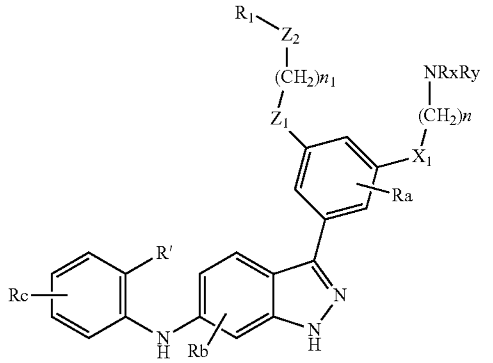

or a pharmaceutically acceptable salt thereof, wherein n and $n_1$ are independently zero, one, two, three or four;

Ra, Rb, and Rc are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

R' is halogen;

$X_1$ and $Z_1$ are independently —N(Ry)-C(O)—, —C(O)—N(Ry)-;

$Z_2$ is a bond or a 4 to 10 membered monocyclic or bicyclic, saturated, partially unsaturated or aryl ring having 0-3 heteroatoms independently selected from nitrogen, oxygen and sulfur;

$R_1$ is -L-Y. The group -L-Y is as described herein in the detailed description of the warheads.

In some embodiments, R' is chloro and Ra, Rb and Rc are each hydrogen.

In some embodiments, $X_1$ is —N(Ry)-C(O)—, n is three, and Ry and Rz are both methyl. In additional embodiments, $Z_1$ is —C(O)—N(Ry)-, $n_1$ is zero, and $Z_2$ is a 5 or 6 membered monocyclic saturated or aryl ring having 0-3 heteroatoms independently selected from nitrogen, oxygen and sulfur. In alternative embodiments, $Z_1$ is —C(O)—N(Ry)-, and $Z_2$ is a bond.

In certain embodiments, $R_1$ is characterized in that the -L-Y moiety is capable of covalently binding to a Cys5 residue in a protein kinase selected from JNK1 (Cys 116), JNK2 (Cys 116), and JNK3 (Cys 154), thereby irreversibly inhibiting the enzyme. In particular embodiments, $R_1$ is characterized in that the -L-Y moiety is capable of covalently binding to Cys 116 of JNK1, thereby irreversibly inhibiting the enzyme.

Exemplary INK Inhibitors of Formula VIII

VIII-1

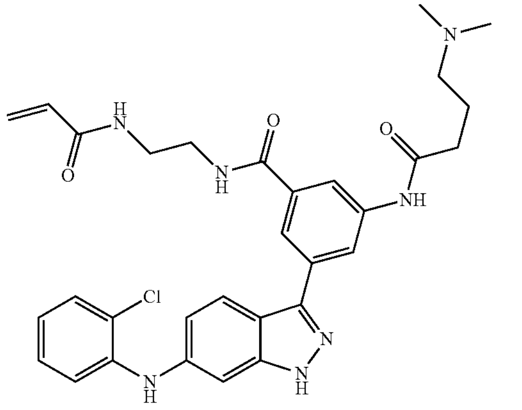

VIII-2

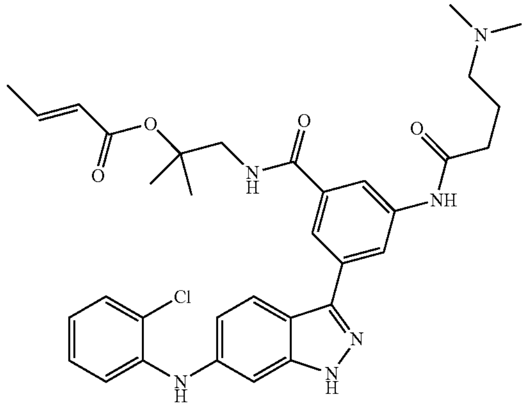

VIII-3

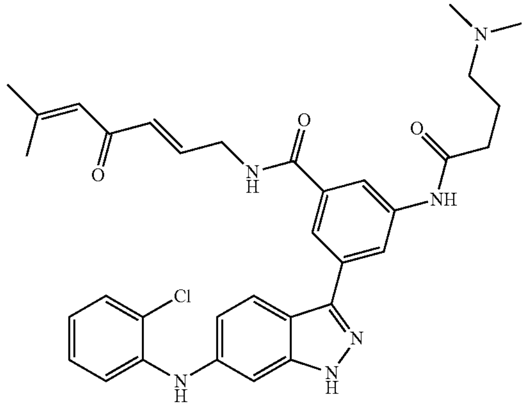

-continued
VIII-4
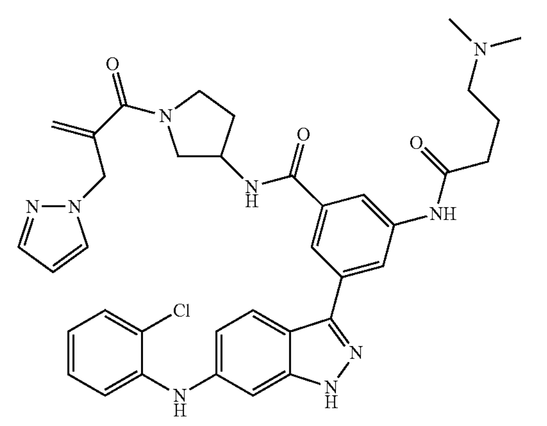
VIII-5
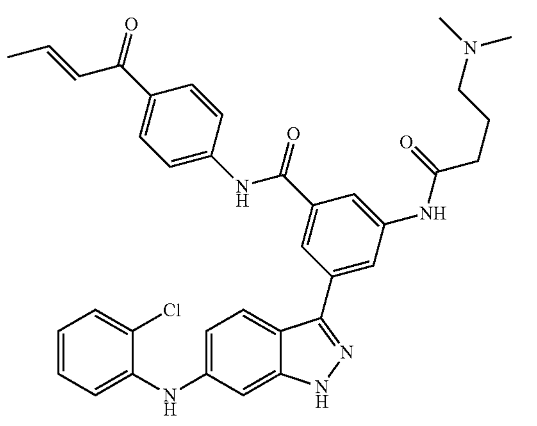
VIII-6
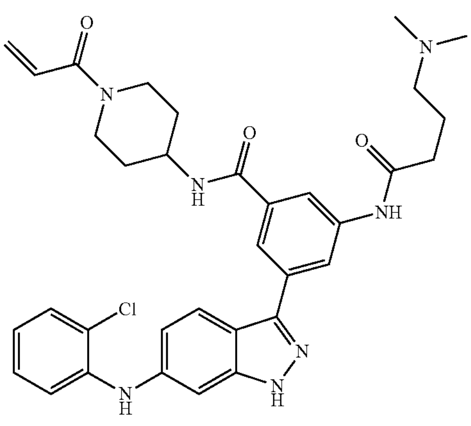
-continued
VIII-7
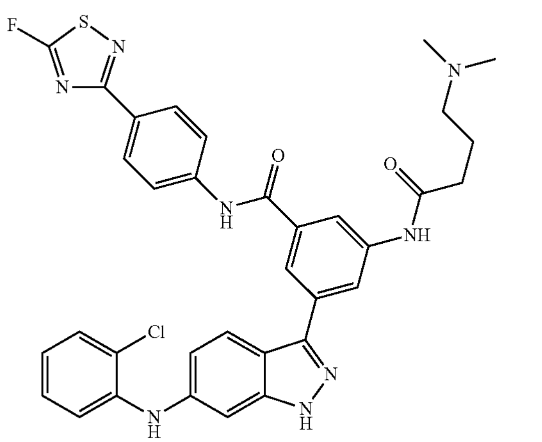
VIII-8
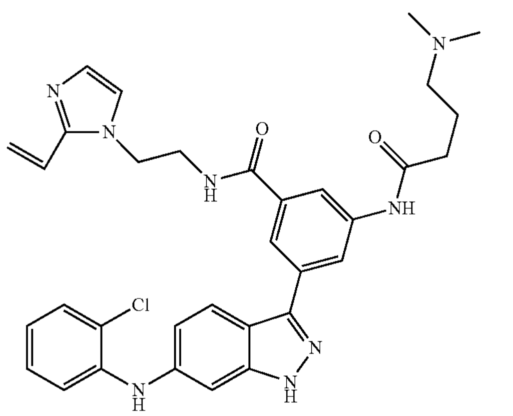
VIII-9
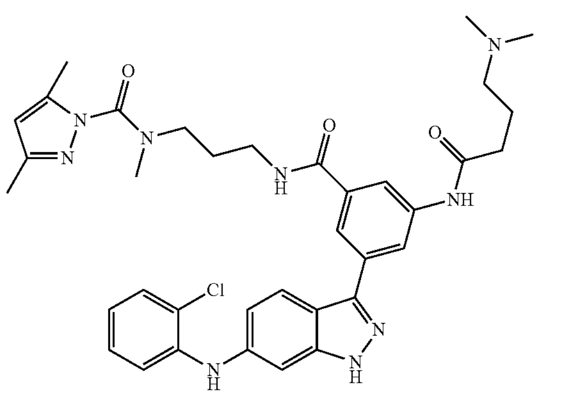
VIII-10
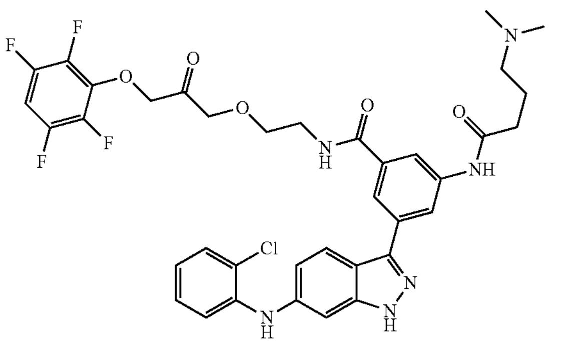

-continued

VIII-11

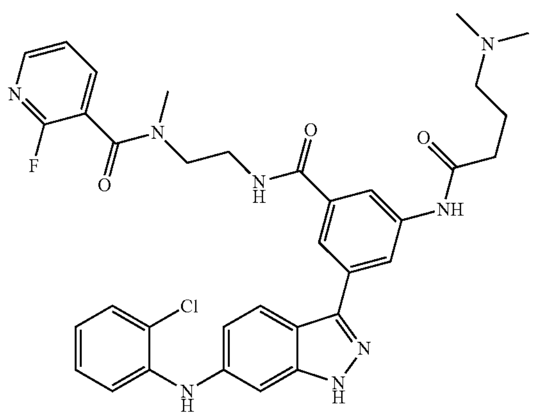

4. Formulas IX and IX-a

In another aspect, the invention is a compound of formula IX or X

IX

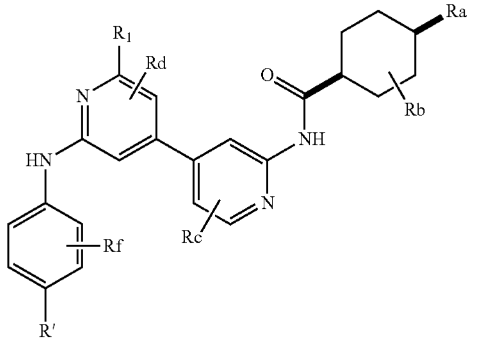

IX-a

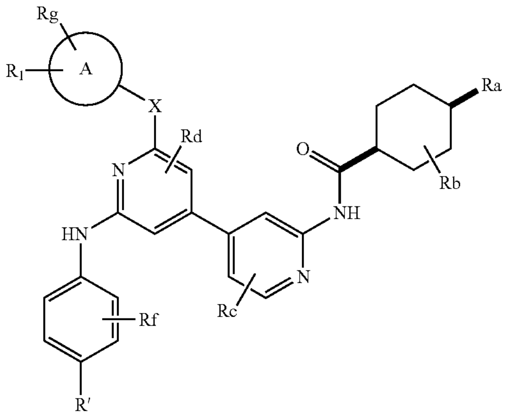

or a pharmaceutically acceptable salt thereof, where

Ra, Rb, Rc, Rd, Rf and Rg are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

R' is halogen;

X is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(=S)—, —C(=NR)—, —N=N—, or —C(=$N_2$)—;

Ring A is an 3-10 membered monocyclic or bicyclic, saturated, partially unsaturated, or aryl ring containing 0-3 heteroatoms independently selected from the group consisting of nitrogen, oxygen, and sulfur;

$R_1$ is -L-Y. The group -L-Y is as described herein in the detailed description of the warheads.

In some embodiments, the compound is of Formula IX, wherein R' is fluorine, Ra is methoxy, and Rb, Rc, Rd and Rf are each hydrogen.

In other embodiments, the compound is of Formula IX-a wherein R' is fluorine, Ra is methoxy, and Rb, Rc, Rd and Rf are each hydrogen, and Ring A is a six membered aromatic ring.

In certain embodiments, $R_1$ is characterized in that the -L-Y moiety is capable of covalently binding to a Cys5 residue in a protein kinase selected from JNK1 (Cys 116), JNK2 (Cys 116), and JNK3 (Cys 154), thereby irreversibly inhibiting the enzyme. In particular embodiments, $R_1$ is characterized in that the -L-Y moiety is capable of covalently binding to Cys 116 of JNK1, thereby irreversibly inhibiting the enzyme.

Exemplary JNK Inhibitors or Formula IX or IX-a

IX-1

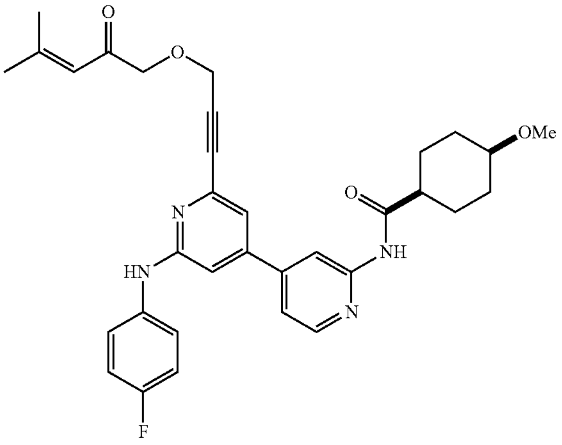

IX-2

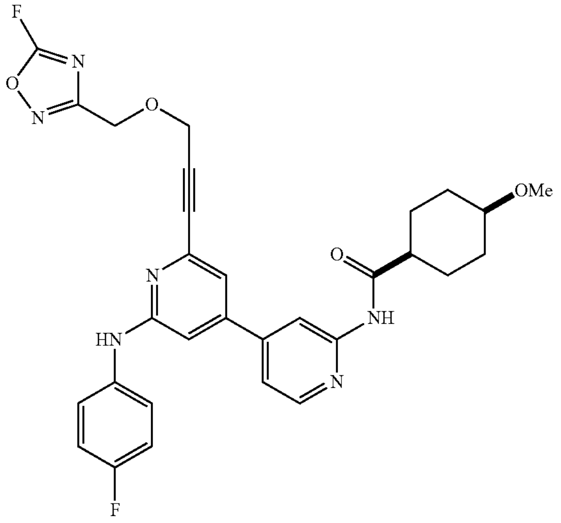

-continued
IX-3
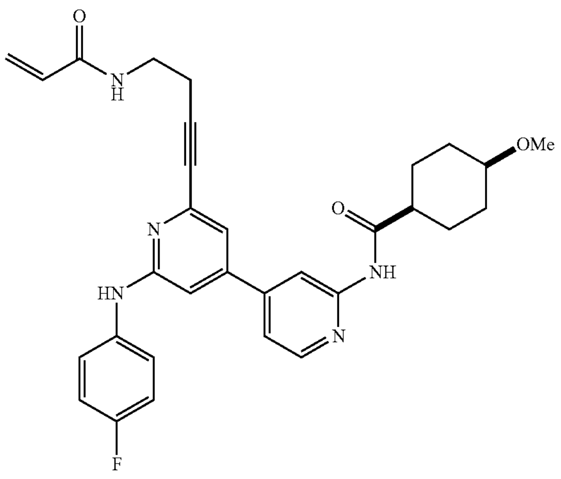
IX-4
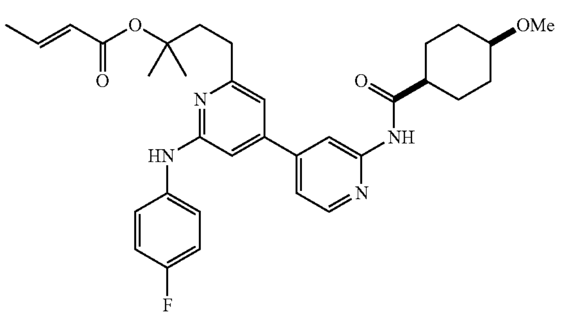
IX-5
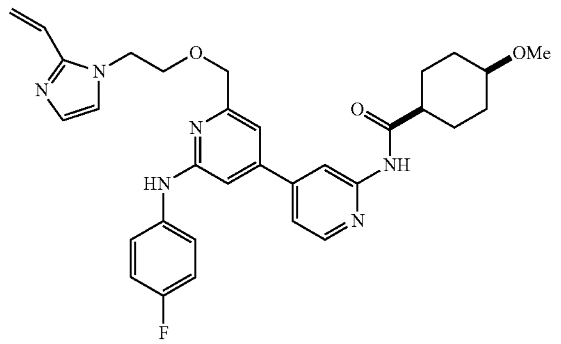
IX-6
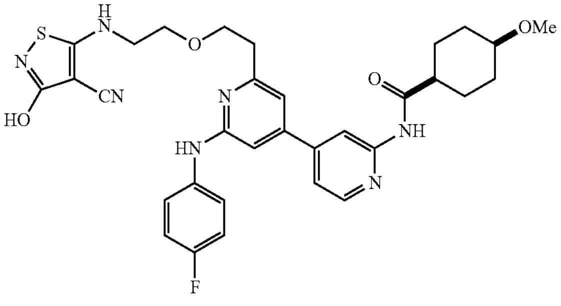
-continued
IX-7
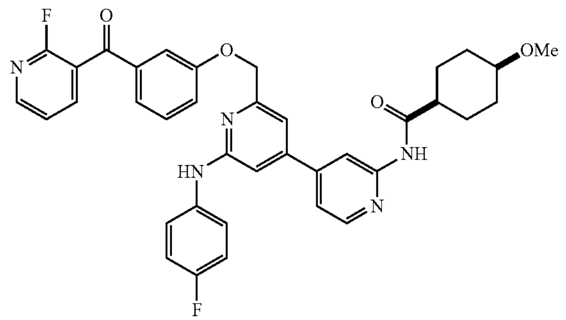
IX-8
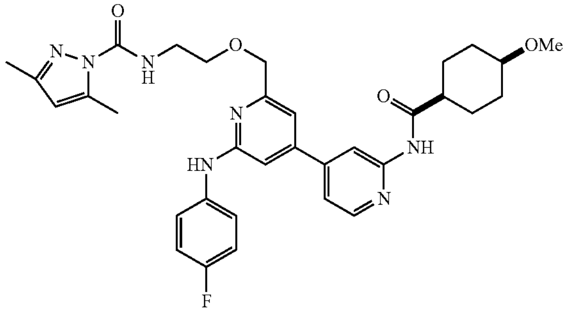
5. Formulas X and X-a
In another aspect, the invention is a compound of formula X or formula X-a
X
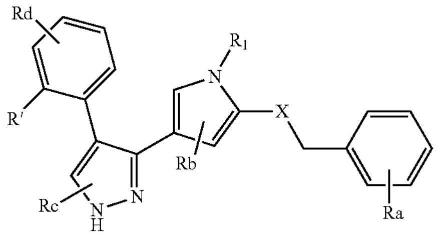
X-a
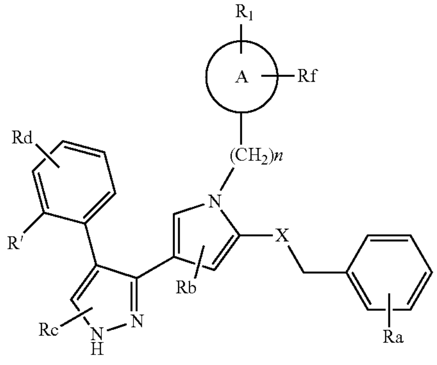
or a pharmaceutically acceptable salt thereof, wherein
n is one, two, or three;
Ra, Rb, Rc, Rd and Rf are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

R' is a halogen;

X is —C(O)NRx- or —NRx-C(O)—;

Ring A is a 4-10 membered monocyclic or bicyclic, saturated, partially unsaturated, or aryl ring containing 0-3 heteroatoms independently selected from the group consisting of nitrogen, oxygen, and sulfur;

$R_1$ is -L-Y. The group -L-Y is as described herein in the detailed description of the warheads.

In other embodiments, the compound is of Formula X wherein R1 is fluorine, and Ra, Rb, Rc, and Rd are each hydrogen.

In other embodiments, the compound is of Formula X-a wherein R' is fluorine, and Ra, Rb, Rc, and Rd are each hydrogen, and ring A is a six membered aromatic ring.

In certain embodiments, $R_1$ is characterized in that the -L-Y moiety is capable of covalently binding to a Cys5 residue in a protein kinase selected from JNK1 (Cys 116), JNK2 (Cys 116), and JNK3 (Cys 154), thereby irreversibly inhibiting the enzyme. In particular embodiments, $R_1$ is characterized in that the -L-Y moiety is capable of covalently binding to Cys 116 of JNK1, thereby irreversibly inhibiting the enzyme.

Exemplary JNK Inhibitors of Formulas X and X-a.

X-1

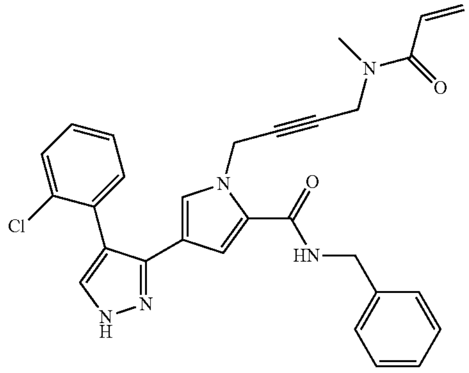

X-2

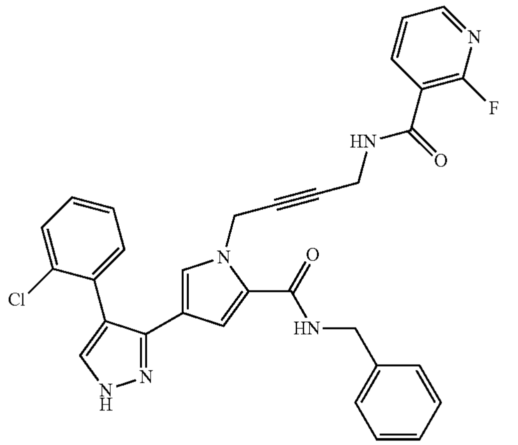

-continued

X-3

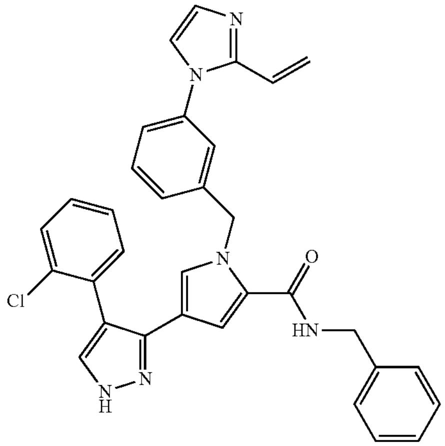

X-4

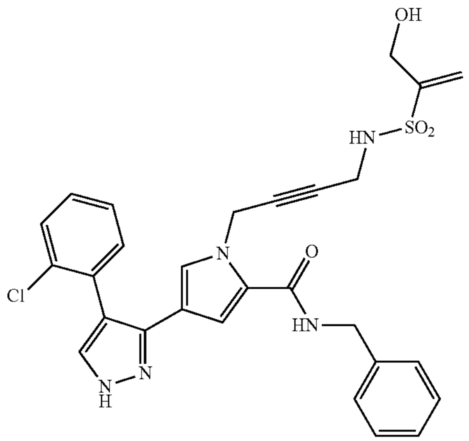

X-5

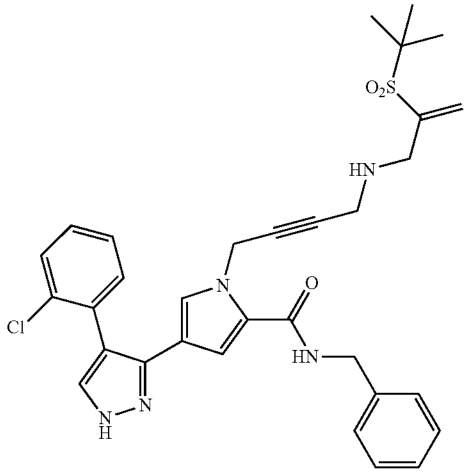

-continued

X-6

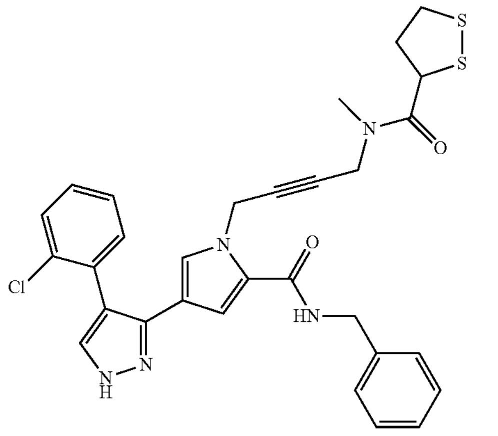

X-7

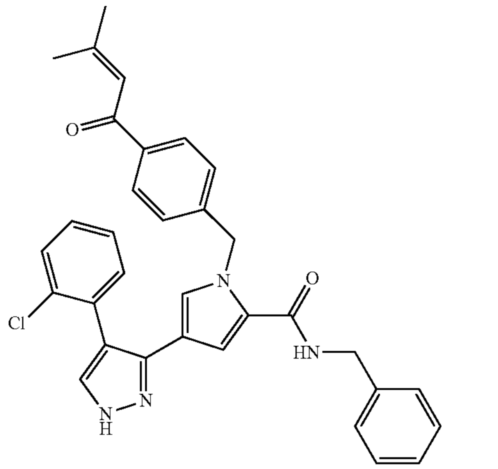

X-8

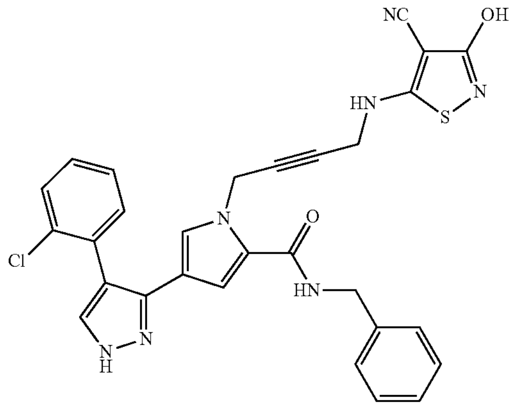

-continued

X-9

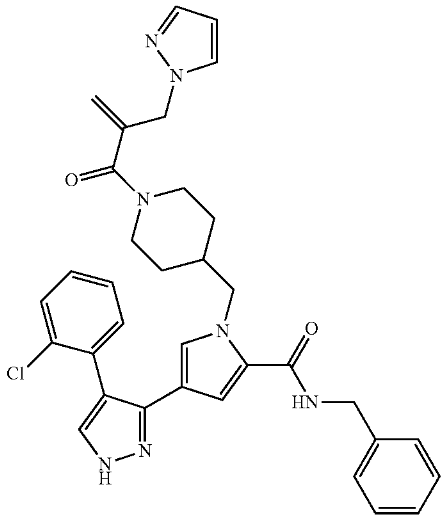

6. Formula XI

In another aspect, the invention is a compound of formula XI

XI

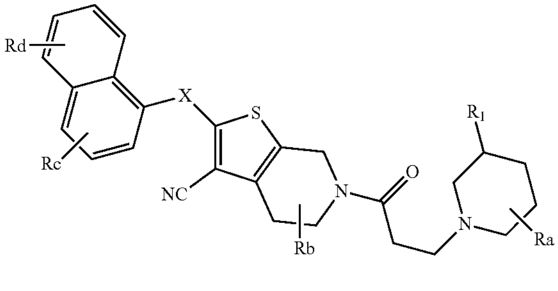

or a pharmaceutically acceptable salt thereof, wherein

Ra, Rb, Re and Rd are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

X is —C(O)NRx- or —NRx-C(O)—;

$R_1$ is -L-Y. The group -L-Y is as described herein in the detailed description of the warheads.

In some embodiments, X is —C(O)NRx, and Ra, Rb, Rc and Rd are hydrogen.

In certain embodiments, $R_1$ is characterized in that the -L-Y moiety is capable of covalently binding to a Cys5 residue in a protein kinase selected from JNK1 (Cys 116), JNK2 (Cys 116), and JNK3 (Cys 154), thereby irreversibly inhibiting the enzyme. In particular embodiments, $R_1$ is characterized in that the -L-Y moiety is capable of covalently binding to Cys 116 of JNK1, thereby irreversibly inhibiting the enzyme.

Exemplary JNK Inhibitors of Formula XI
XI-1
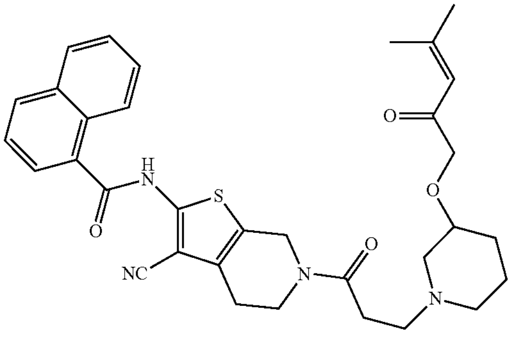
XI-2
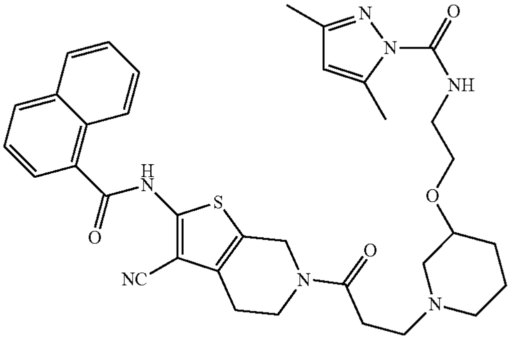
XI-3
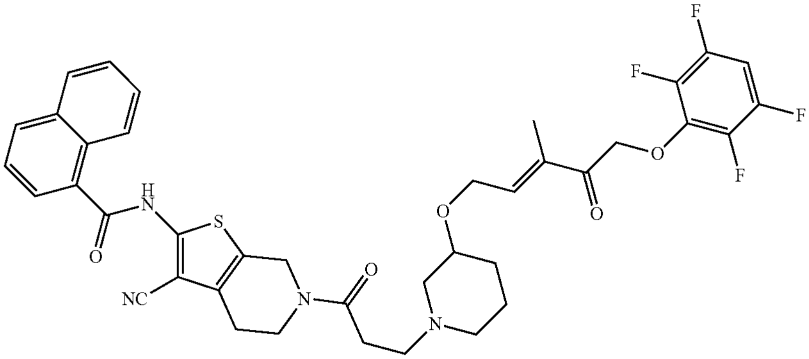
XI-4
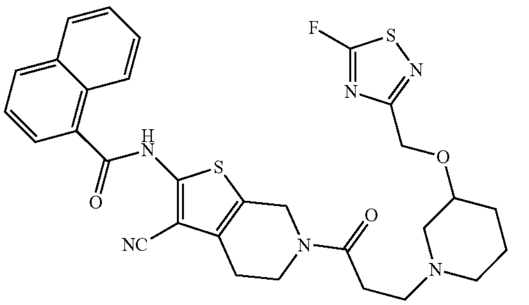
XI-5
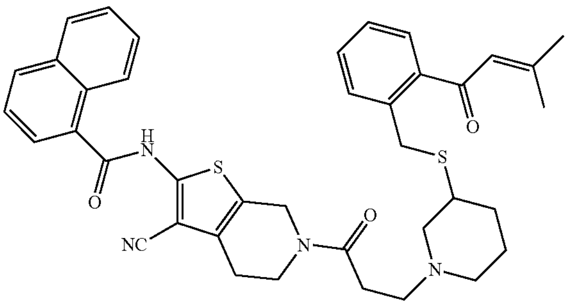
XI-6
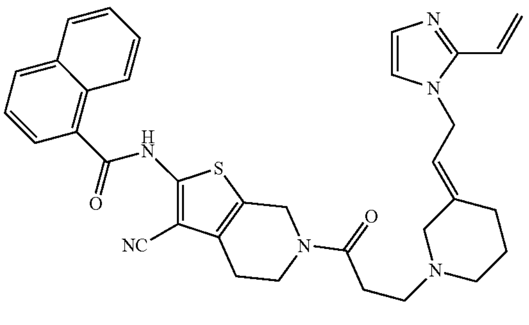
XI-7
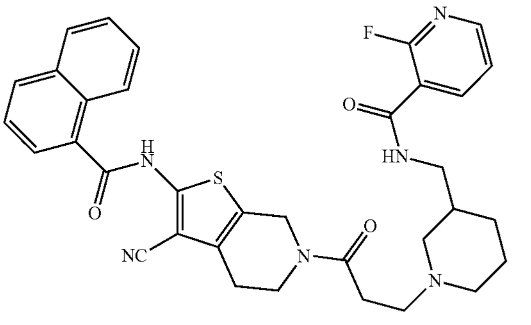

-continued

XI-8

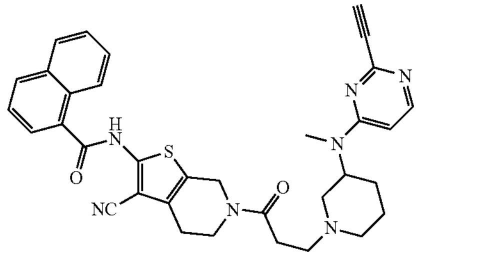

XI-9

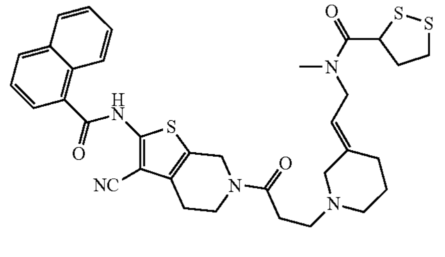

XI-10

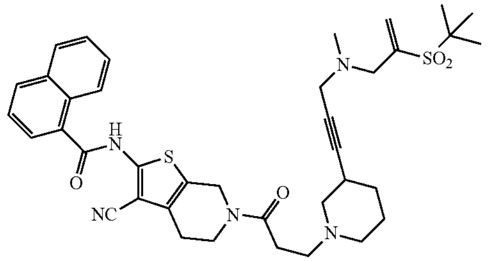

XI-11

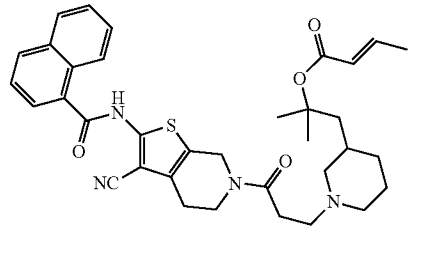

XI-12

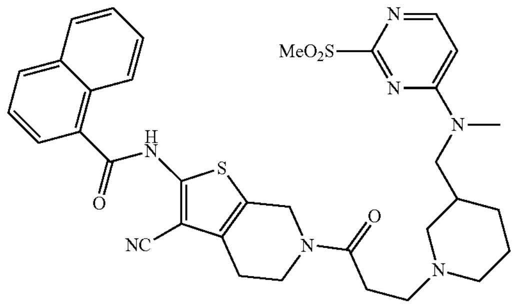

7. Formula XII and XII-a

In another aspect, the invention is a compound of formula XII or XII-a

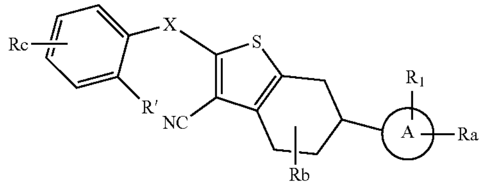

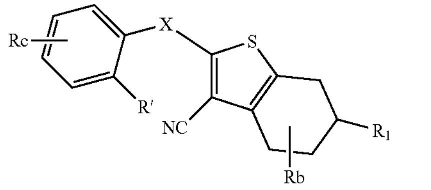

or a pharmaceutically acceptable salt thereof, wherein

Ra, Rb, and Rc are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

R' is a halogen;

X is —C(O)NRx- or —NRx-C(O)—;

Ring A is a 4-10 membered monocyclic or bicyclic, saturated, partially unsaturated, or aryl ring containing 0-3 heteroatoms independently selected from the group consisting of nitrogen, oxygen, and sulfur;

$R_1$ is -L-Y. The group -L-Y is as described herein in the detailed description of the warheads.

In some embodiments, the compound is of Formula XII and Ring A is

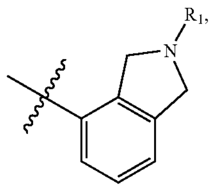

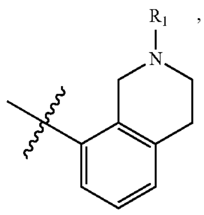

,

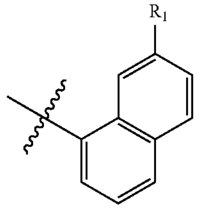

or

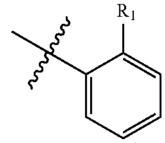

.

In additional examples of this embodiment, R' is fluoro, X is —C(O)NRx-, and Ra, Rb and Rc are hydrogen.

In other embodiments, the compound is of Formula XII-a, wherein R' is fluoro, X is —C(O)NRx-, and Rb and Rc are hydrogen.

In certain embodiments, $R_1$ is characterized in that the -L-Y moiety is capable of covalently binding to a Cys5 residue in a protein kinase selected from JNK1 (Cys 116), JNK2 (Cys 116), and JNK3 (Cys 154), thereby irreversibly inhibiting the enzyme. In particular embodiments, $R_1$ is characterized in that the -L-Y moiety is capable of covalently binding to Cys 116 of JNK1, thereby irreversibly inhibiting the enzyme.

Exemplary JNK Inhibitors of Formula XII and XII-a

XII-1

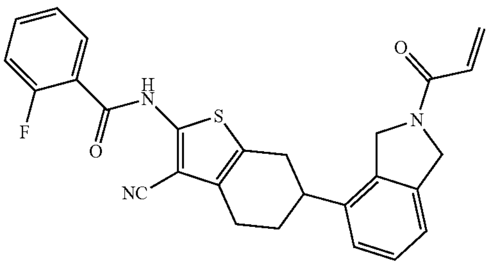

XII-2

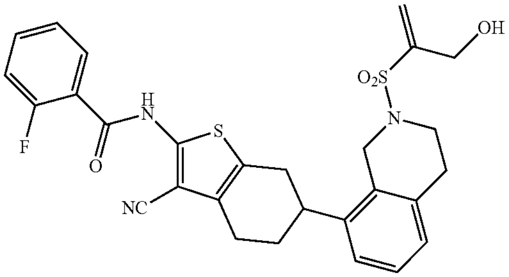

XII-3

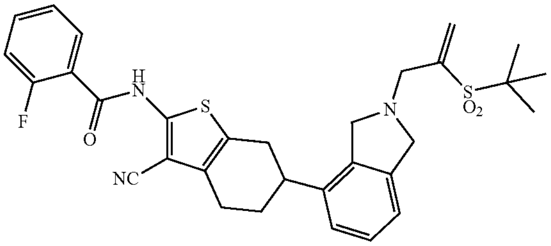

XII-4

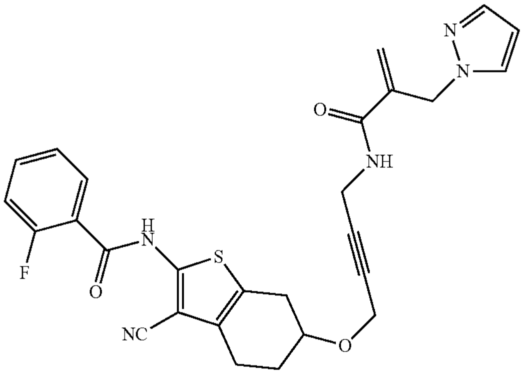

-continued

XII-5

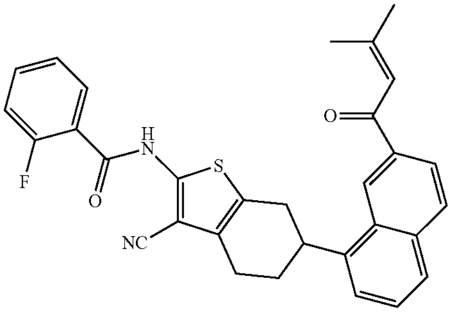

XII-6

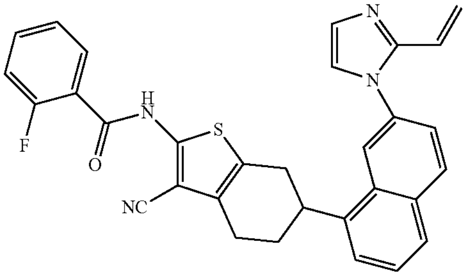

XII-7

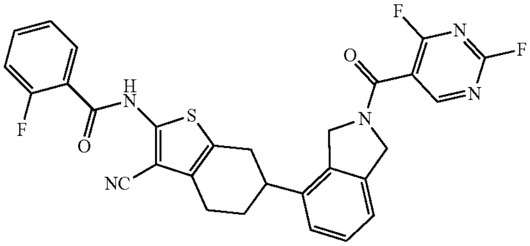

XII-8

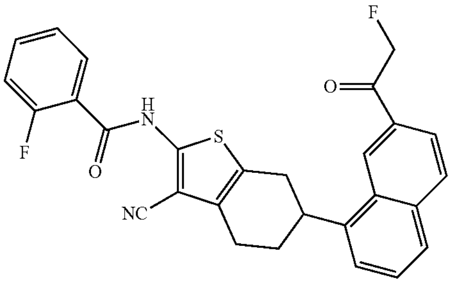

XII-9

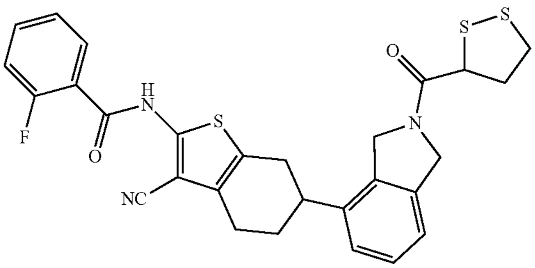

-continued

XII-10

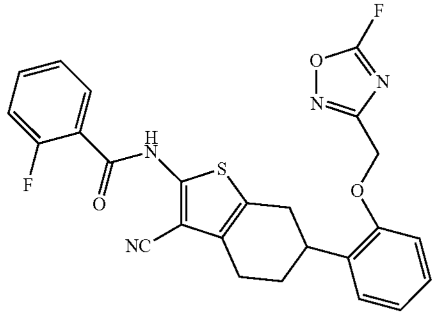

XII-11

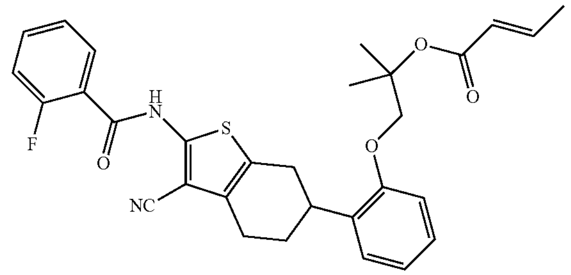

XII-12

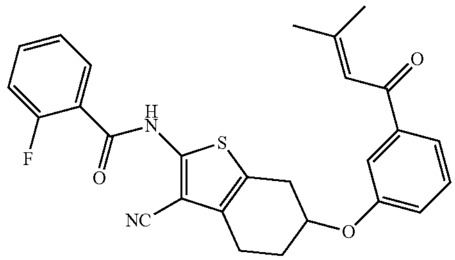

H. RON Inhibitors

1. Formulas XIII-a and XIII-b

In another aspect the invention is a compound of formula XIII-a or XIII-b

XIII-a

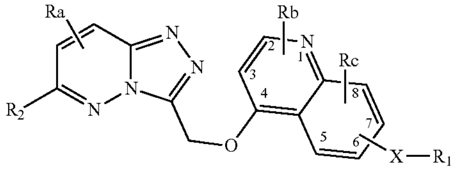

XIII-b

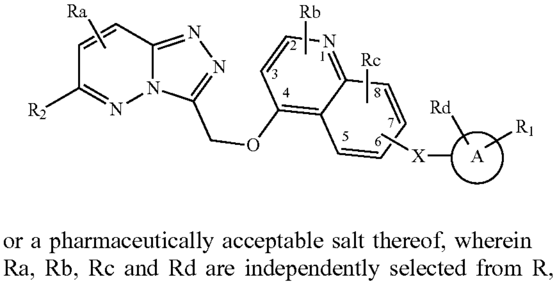

or a pharmaceutically acceptable salt thereof, wherein

Ra, Rb, Rc and Rd are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

$R_2$ is hydrogen optionally substituted aryl, or optionally substituted heteroaryl;

X is a bond or a bivalent $C_1$-$C_6$ saturated or unsaturated, straight or branched hydrocarbon chain wherein optionally one, two or three methylene units of the hydrocarbon chain are independently replaced by —NR—, —O—, —C(O)—, —OC(O)—, —C(O)O—, —S—, —SO—, —$SO_2$—, —C(═S)—, —C(═NR)—, —N═N—, or —C(═$N_2$)—;

Ring A is a 4-10 membered monocyclic or bicyclic, saturated, partially unsaturated, or aryl ring containing 0-3 heteroatoms independently selected from the group consisting of nitrogen, oxygen, and sulfur;

$R_1$ is -L-Y. The group -L-Y is as described herein in the detailed description of the warheads.

Preferably in the compounds of formula XIII-a or formula XIII-b, the moiety that contains X and $R_1$ is bonded to the 6, 7 or 8 position of the quinoline ring system, as shown in formulas XIII-a and XIII-b. More preferable the moiety that contains X and $R_1$ is bonded to the 7 position of the quinoline ring system such that the compound is of formula XIII-c or XIII-d.

XIII-c

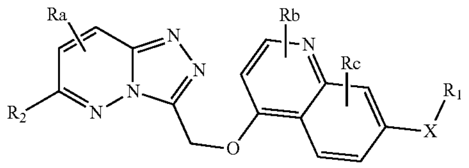

XIII-d

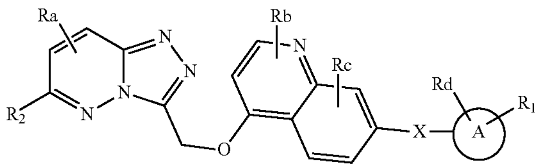

In some embodiments of compounds of formula XIII-a, XIII-b, XIII-c or XIII-d, X is a bond, —O—, —NH—, —S—, —O—$CH_2$—C≡C—, —NH—$CH_2$—C≡C— or —S—$CH_2$—C≡C—.

In some embodiments compounds of formula XIII-a, XIII-b, XIII-c or XIII-d, $R_2$ is phenyl or phenyl substituted with Rf, wherein Rf is selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl.

In some embodiments, the compound is of Formula XIII-d wherein X is —O— and ring A is selected from

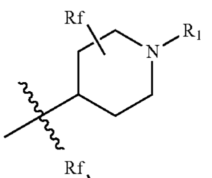

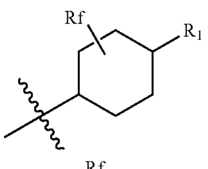

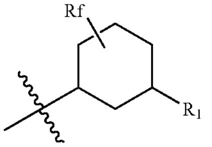

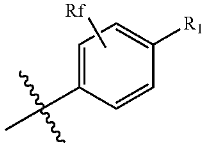

-continued
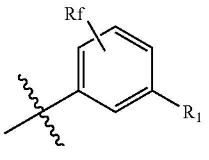 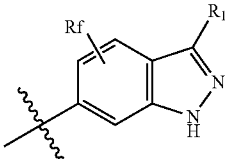
In certain embodiments, $R_1$ is characterized in that the -L-Y moiety is capable of covalently binding to a Cys11 residue of RON (Cys 1165), thereby irreversibly inhibiting the enzyme
Exemplary Ron Inhibitors of Formula XIII-a and XIII-b.
XIII-1
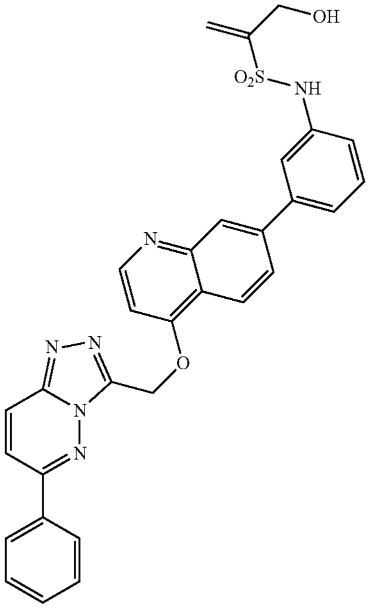
XIII-2
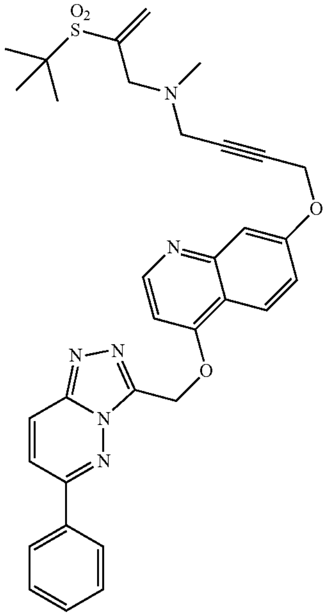
-continued
XIII-3
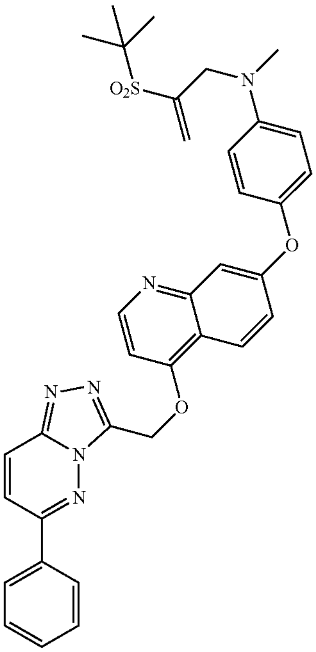
XIII-4
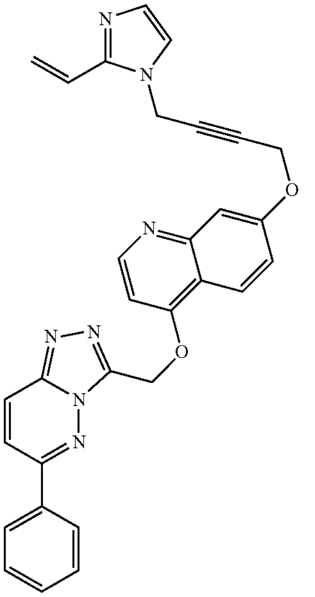

-continued
XIII-5
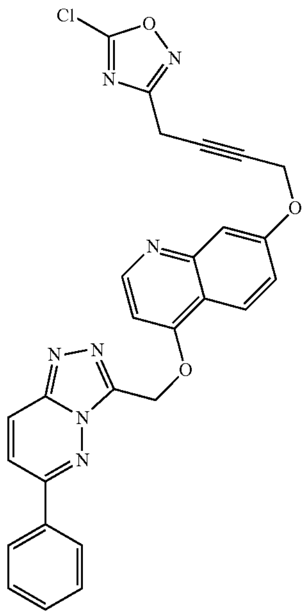
XIII-6
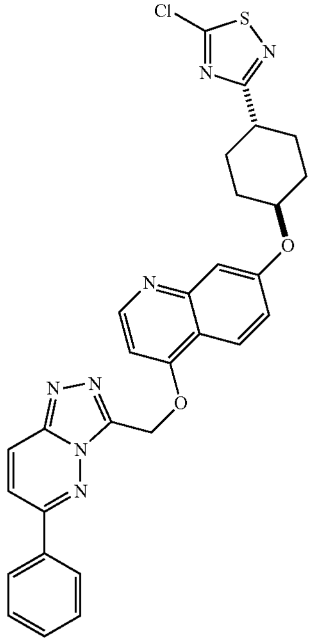
-continued
XIII-7
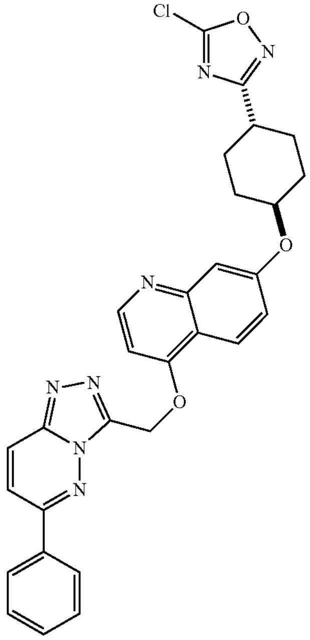
XIII-8
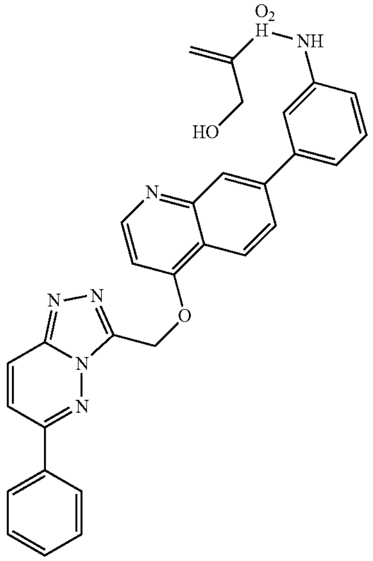

-continued
XIII-9
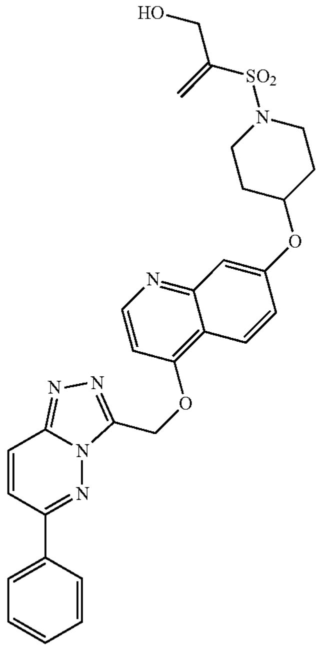
XIII-10
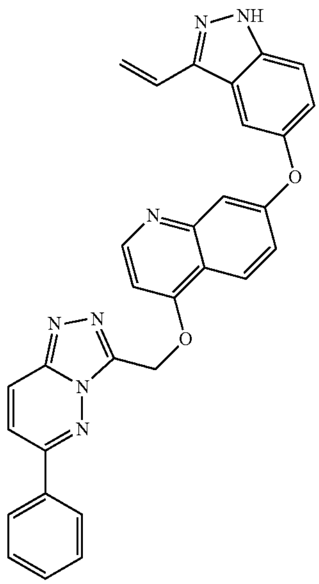
-continued
XIII-11
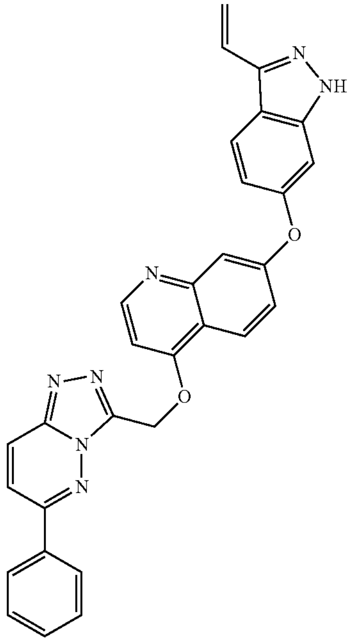
XIII-12
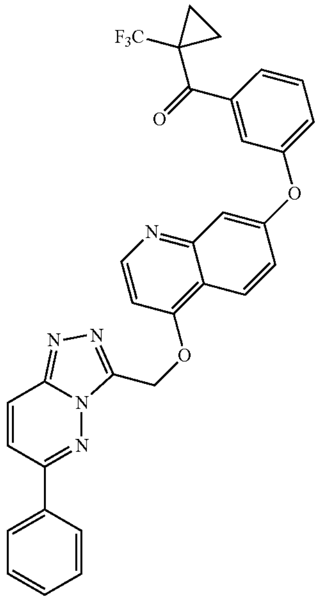

XIII-13
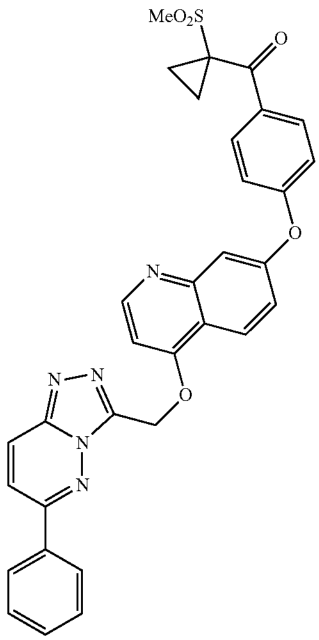
XIII-15
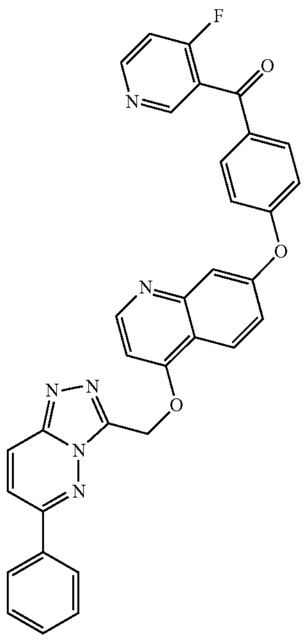
XIII-14
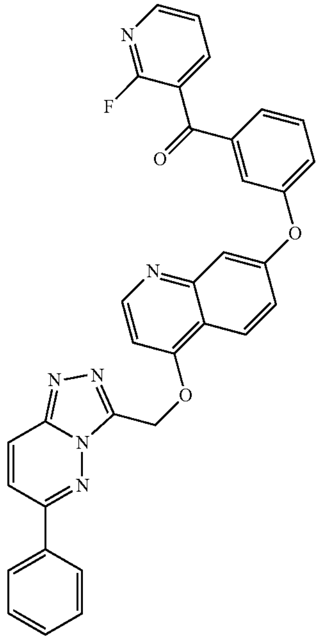
XIII-16
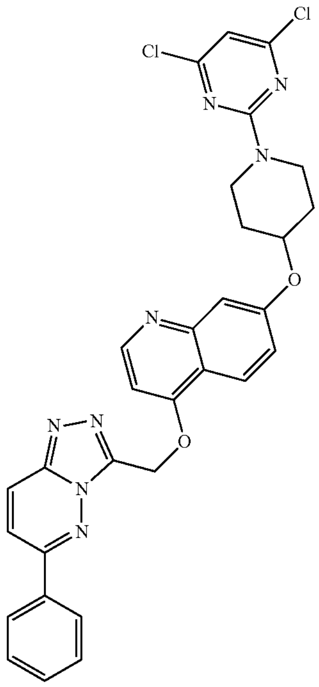

-continued
XIII-17
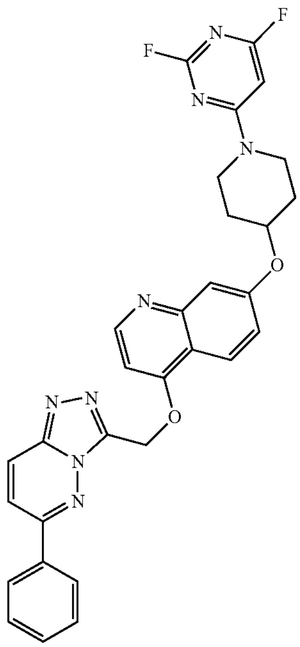
XIII-18
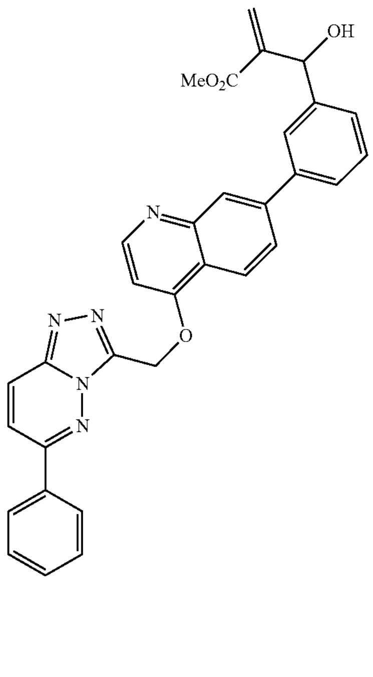
-continued
XIII-19
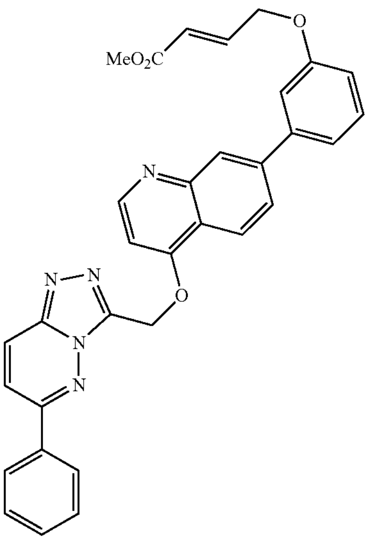
XIII-20
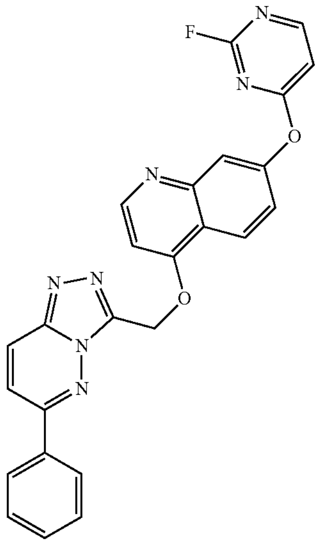
XIII-21
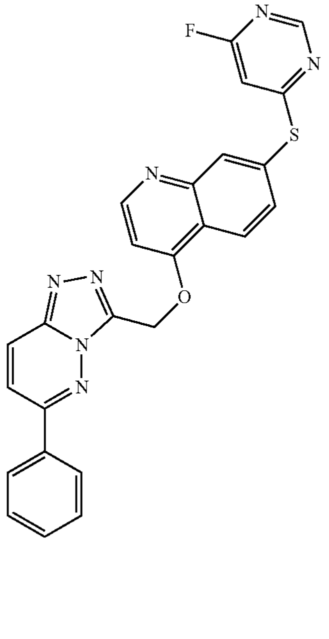

-continued
XIII-22
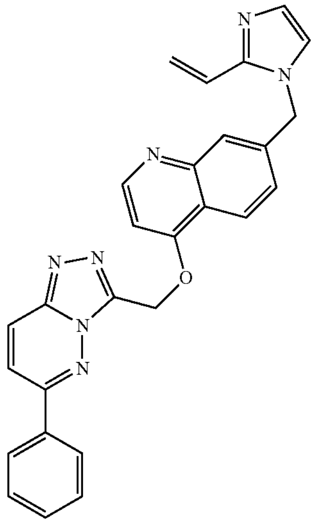
XIII-23
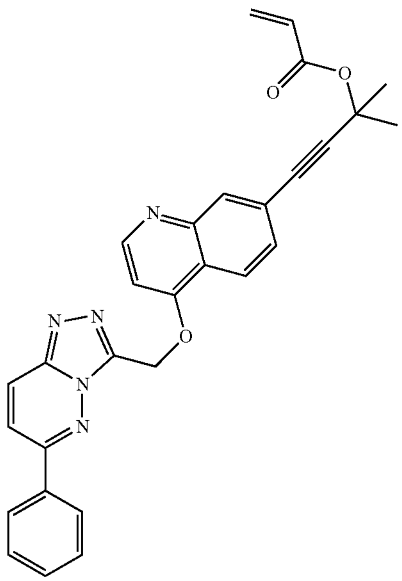
-continued
XIII-24
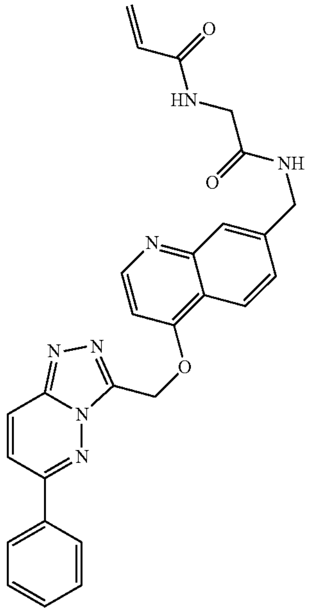
XIII-25
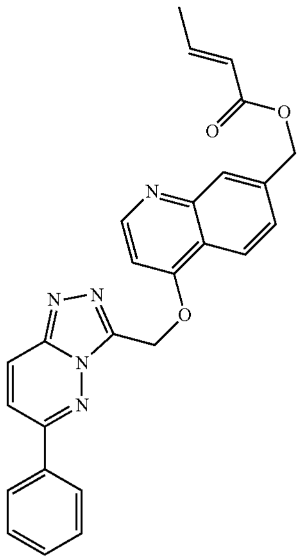

XIII-26
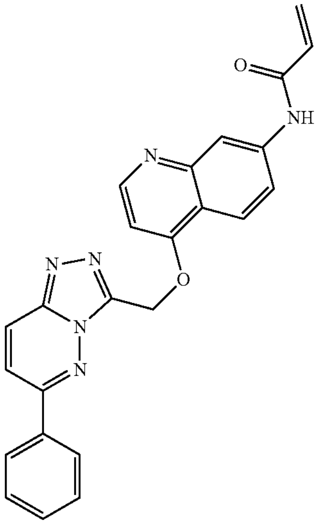
XIII-27
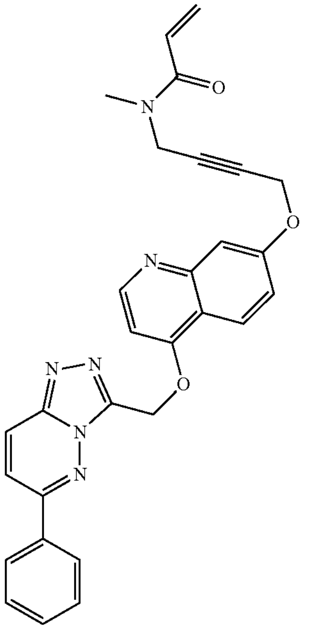
XIII-28
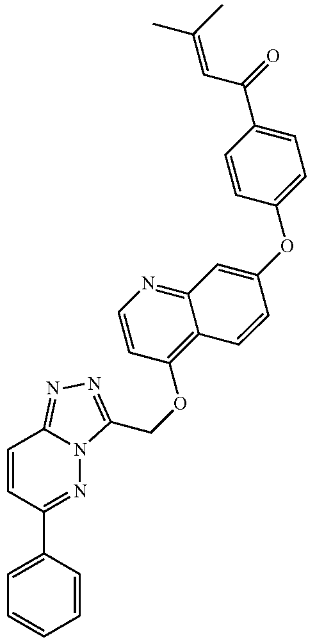
XIII-29
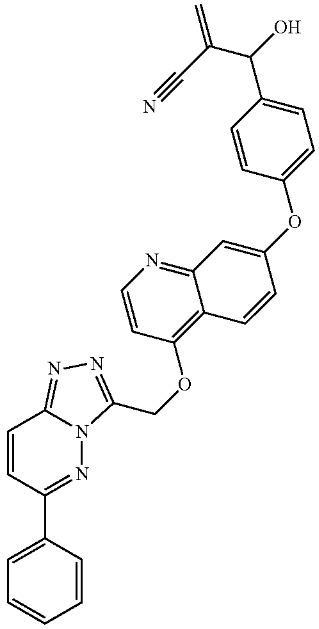

-continued

XIII-30

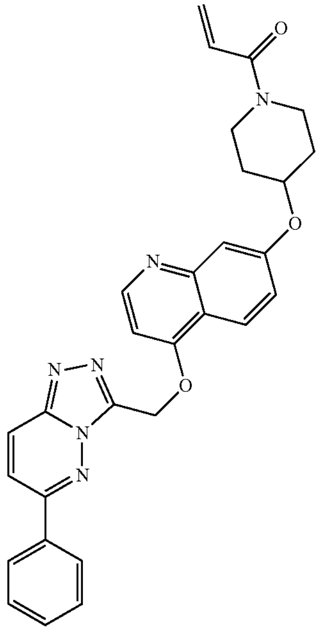

2. Formula XIV

In other aspects, the invention is a compound of formula XIV

XIV

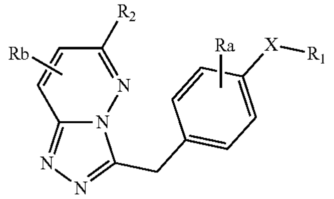

or a pharmaceutically acceptable salt thereof, wherein

Ra, and Rb are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

$R_2$ is hydrogen, optionally substituted aryl, or optionally substituted heteroaryl;

X is a bond or a bivalent $C_1$-$C_6$ saturated or unsaturated, straight or branched hydrocarbon chain wherein optionally one, two or three methylene units of the hydrocarbon chain are independently replaced by —NR—, —O—, —C(O)—, —OC(O)—, —C(O)O—, —S—, —SO—, —$SO_2$—, —C(═S)—, —C(═NR)—, —N═N—, or —C(═$N_2$)—;

$R_1$ is -L-Y. The group -L-Y is as described herein in the detailed description of the warheads.

In some embodiments, Ra and Rb are both hydrogen, and $R_2$ is phenyl or phenyl substituted with Rc, wherein Rc is selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl. In particular embodiments, $R_2$ is phenyl.

In some embodiments, X is —O—$CH_2$—$CH_2$—O—, —O—$(CH_2)_3$—, or —O—$(CH_2)_2$—$C(CH_3)_2$—

In certain embodiments, $R_1$ is characterized in that the -L-Y moiety is capable of covalently binding to a Cys11 residue of RON (Cys 1165), thereby irreversibly inhibiting the enzyme.

Exemplary RON Inhibitors of Formula XIV

XIV-1

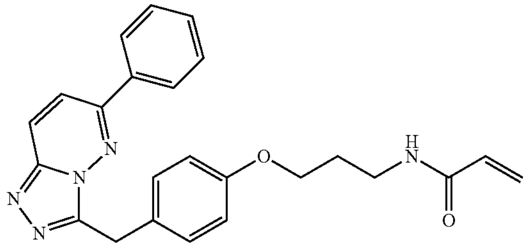

XIV-2

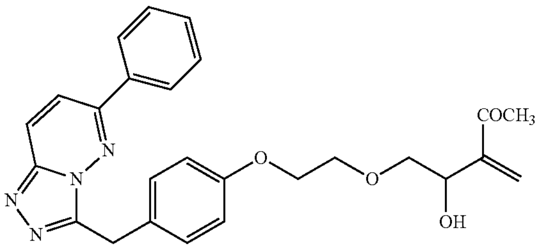

XIV-3

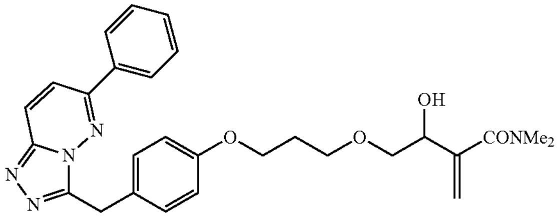

XIV-4

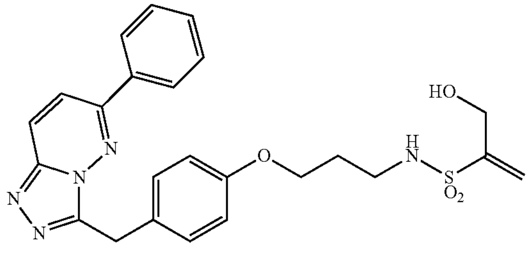

XIV-5

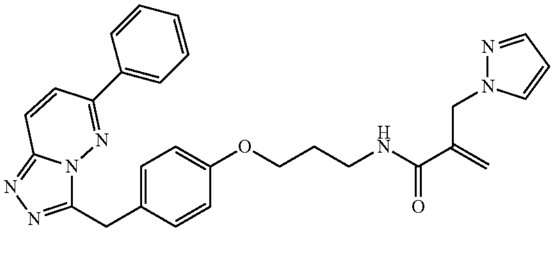

-continued

XIV-6

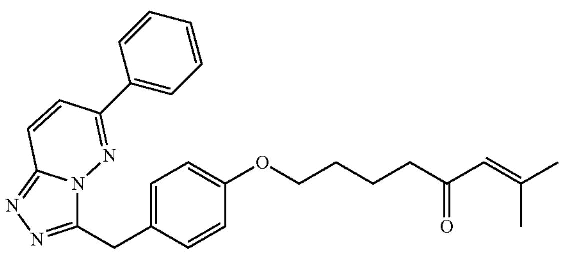

XIV-7

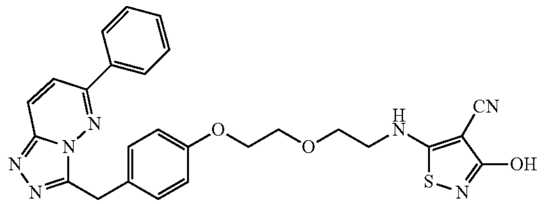

XIV-8

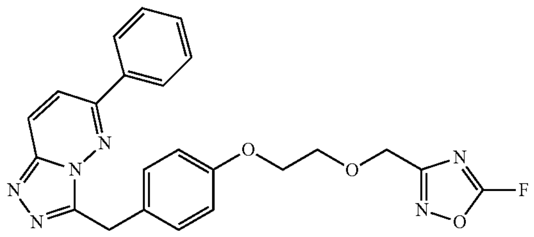

XIV-9

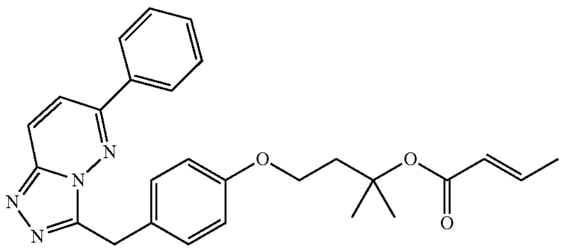

XIV-10

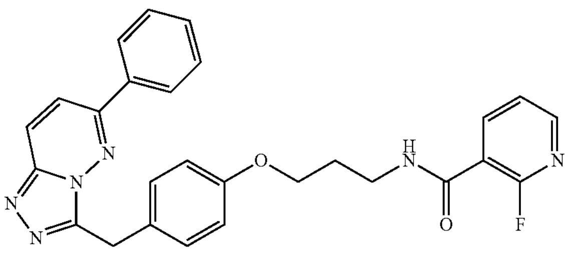

XIV-11

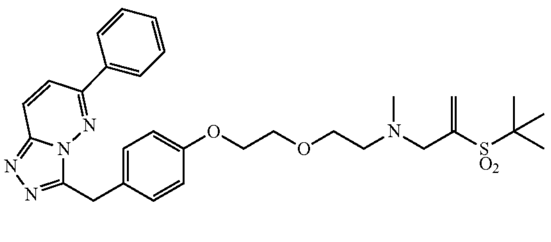

-continued

XIV-12

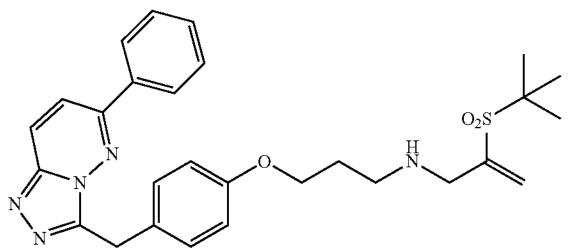

XIV-13

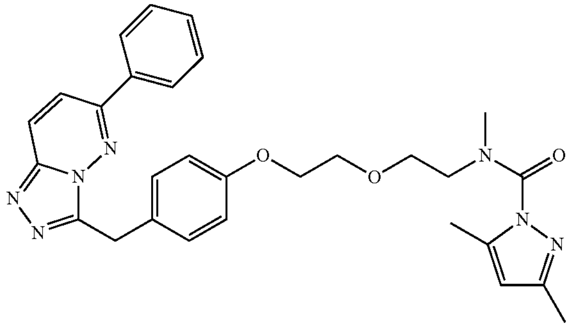

3. Formula XV

In other aspects, the invention is a compound of formula XV

XV

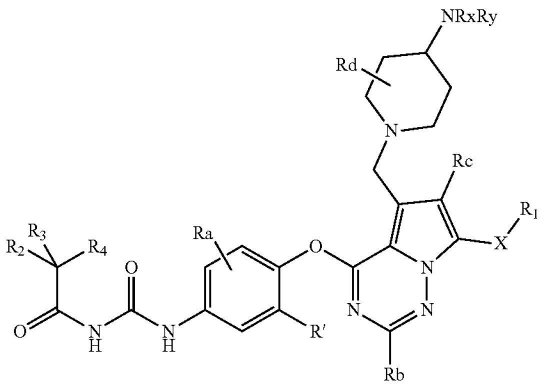

or a pharmaceutically acceptable salt thereof, wherein

Ra, Rb, Rc and Rd are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

$R_2$ is hydrogen optionally substituted aryl, or optionally substituted heteroaryl;

$R_3$ and $R_4$ are independently R, OR, —OH, or halogen;

R' is halogen;

X is a bond or a bivalent $C_1$-$C_6$ saturated or unsaturated, straight or branched hydrocarbon chain wherein optionally one, two or three methylene units of the hydrocarbon chain are independently replaced by —NR—, —O—, —C(O)—, —OC(O)—, —C(O)O—, —S—, —SO—, —$SO_2$—, —C(═S)—, —C(═NR)—, —N═N—, or —C(═$N_2$)—;

$R_1$ is -L-Y. The group -L-Y is as described herein in the detailed description of the warheads.

In some embodiments, $R_2$ is phenyl or phenyl substituted with Rf, R" or Rf and R", wherein Rf is selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

R" is halogen. For example, in some embodiments $R_2$ is p-halophenyl, such as p-fluorophenyl, p-chlorophenyl, p-bromophenyl or p-iodophenyl.

In some embodiments Ra, Rb, Rc and Rd are each hydrogen, and R" is fluoro.

In some embodiments $R_3$ and $R_4$ are each hydrogen.

In certain embodiments, $R_1$ is characterized in that the -L-Y moiety is capable of covalently binding to a Cys11 residue of RON (Cys1165), thereby irreversibly inhibiting the enzyme.

Exemplary Ron Inhibitors of Formula XV

XV-1

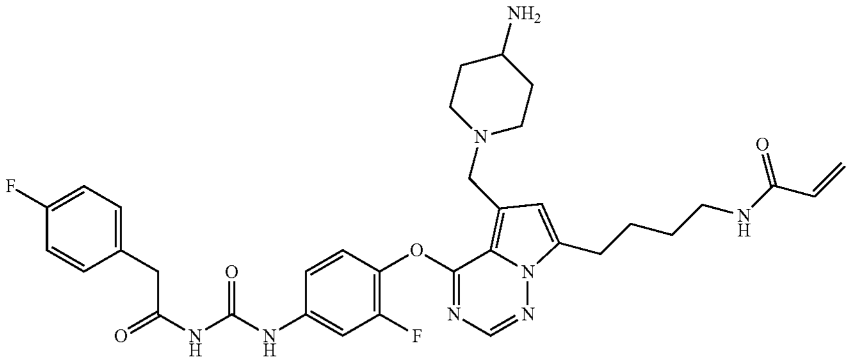

XV-2

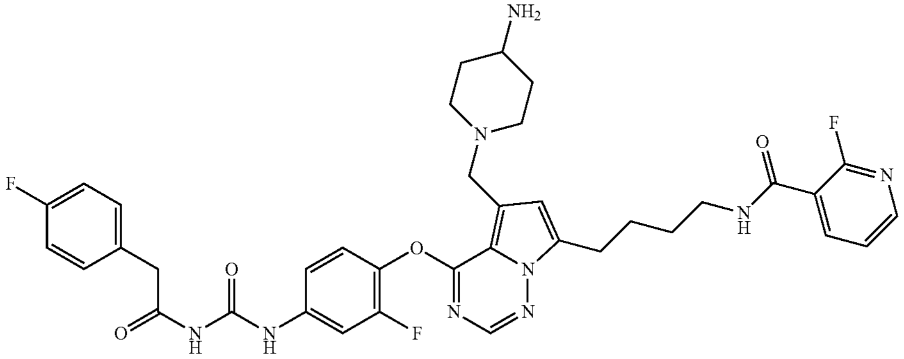

XV-3

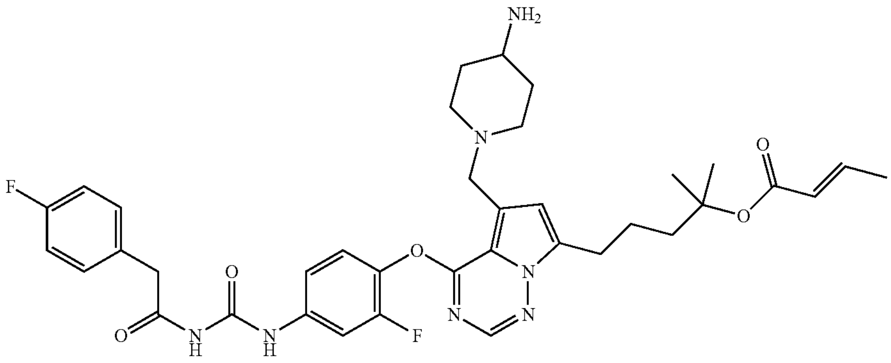

-continued
XV-4
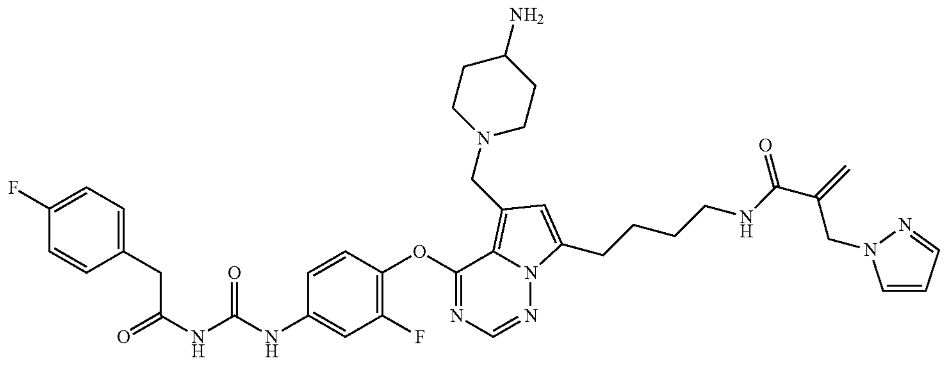
XV-5
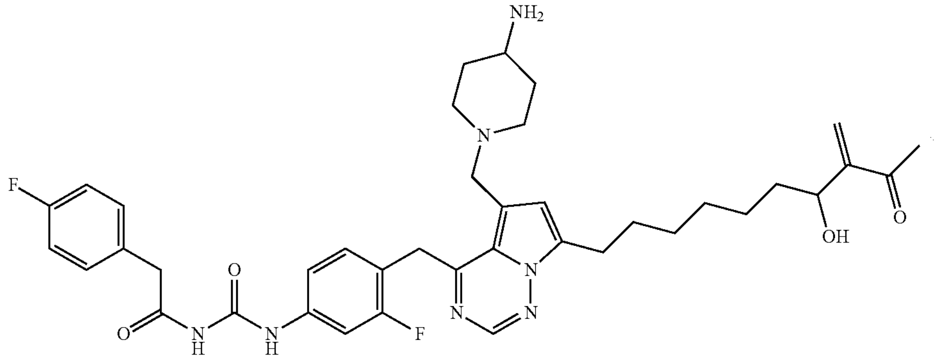
XV-6
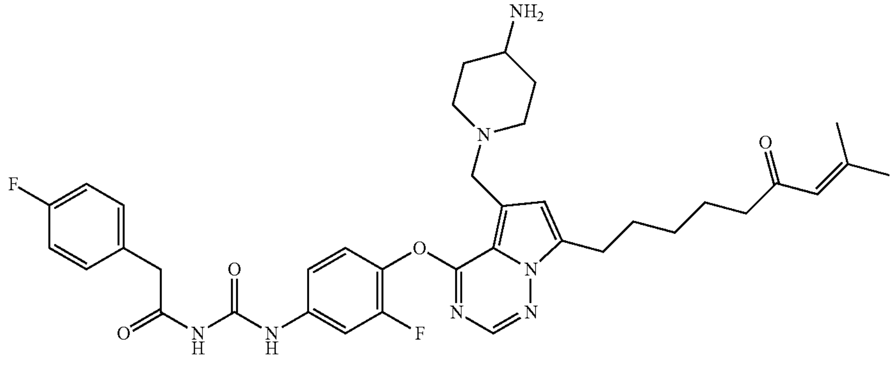
XV-7
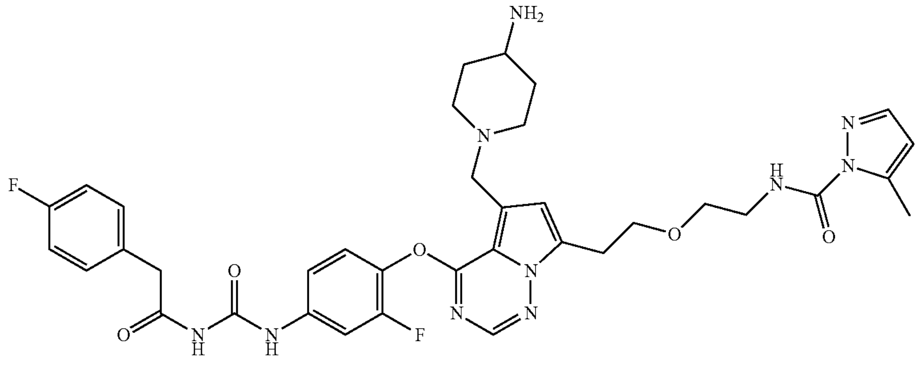

-continued
XV-8
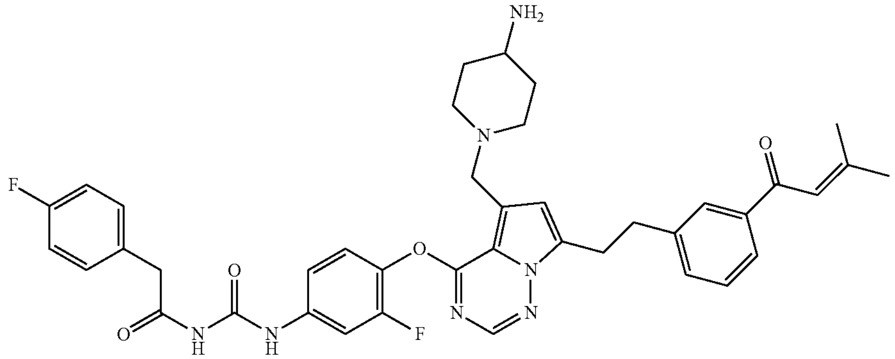
XV-9
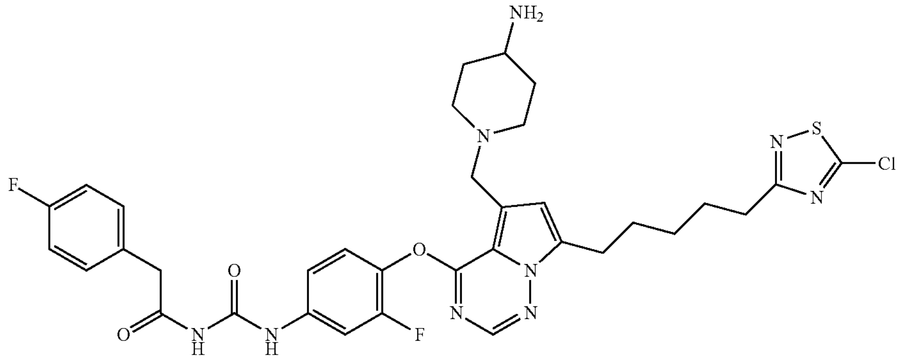
XV-10
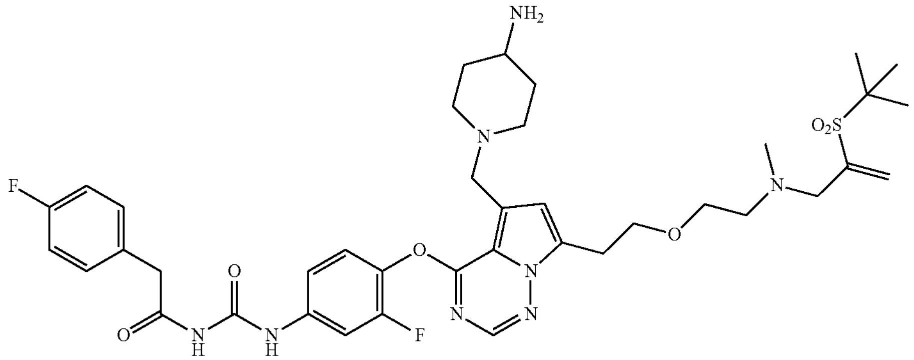
XV-11
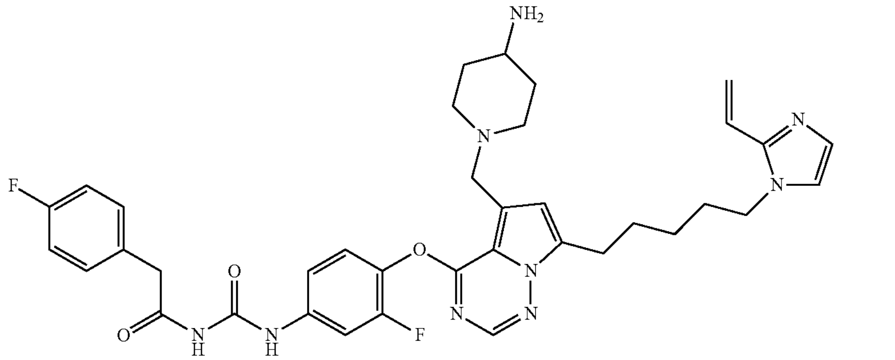
R = $CH_3$, OMe, $NMe_2$ 4. Formula XVI In other aspects, the invention is a compound of formula XVI

XVI

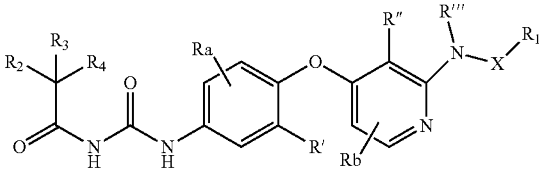

XVI-a

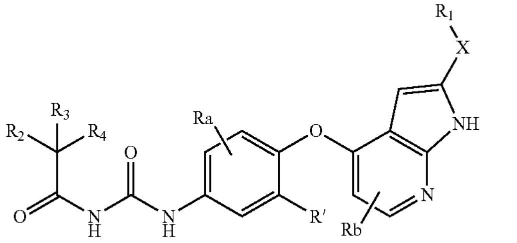

or a pharmaceutically acceptable salt thereof, wherein

Ra and Rb are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

$R_2$ is hydrogen optionally substituted aryl, or optionally substituted heteroaryl;

$R_3$ and $R_4$ are independently hydrogen, R, OR, —OH, or halogen;

R' is halogen;

R" and R'" are independently selected from R, OR, halogen, —$CF_3$, —CN, —C≡C—R, —NRxRy, and —C(O)NHRz, X is a bond or a bivalent $C_1$-$C_6$ saturated or unsaturated, straight or branched hydrocarbon chain wherein optionally one, two or three methylene units of the hydrocarbon chain are independently replaced by —NR—, —O—, —C(O)—, —OC(O)—, —C(O)O—, —S—, —SO—, —$SO_2$—, —C(=S)—, —C(=NR)—, —N=N—, or —C(=$N_2$)—;

$R_1$ is -L-Y. The group -L-Y is as described herein in the detailed description of the warheads.

In some embodiments, $R_2$ is phenyl or phenyl substituted with Re, substituted with R"" or substituted with Rc and R"", wherein Re is selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

R"" is halogen. For example, in some embodiments $R_2$ is p-halophenyl, such as p-fluorophenyl, p-chlorophenyl, p-bromophenyl or p-iodophenyl.

In some embodiments Ra and Rb are each hydrogen, and R' is fluoro.

In some embodiments $R_3$ and $R_4$ are each hydrogen.

In particular embodiments, the compound is of formula XV1-b or XVI-c

XVI-b

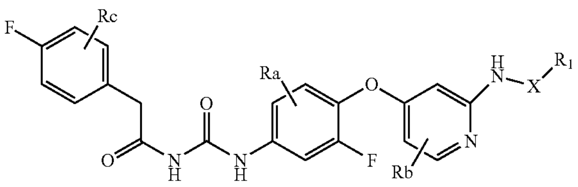

XVI-c

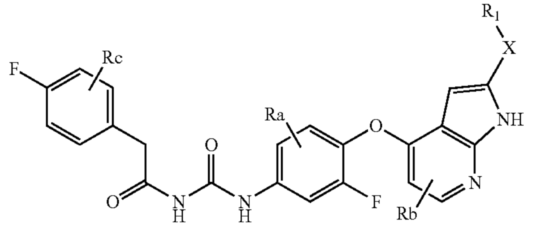

wherein Ra, Rb, Rc, X and $R_1$ are as defined in Formula XVI. In some embodiments, Ra, Rb, and Rc are each hydrogen.

In certain embodiments, $R_1$ is characterized in that the -L-Y moiety is capable of covalently binding to a Cys11 residue of RON (Cys 1165), thereby irreversibly inhibiting the enzyme.

Exemplary Ron Inhibitors of Formula XVI.

XVI-1

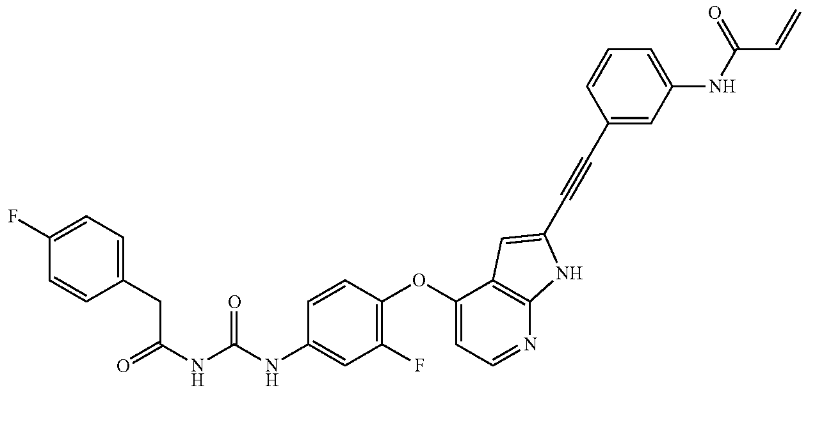

-continued
XVI-2
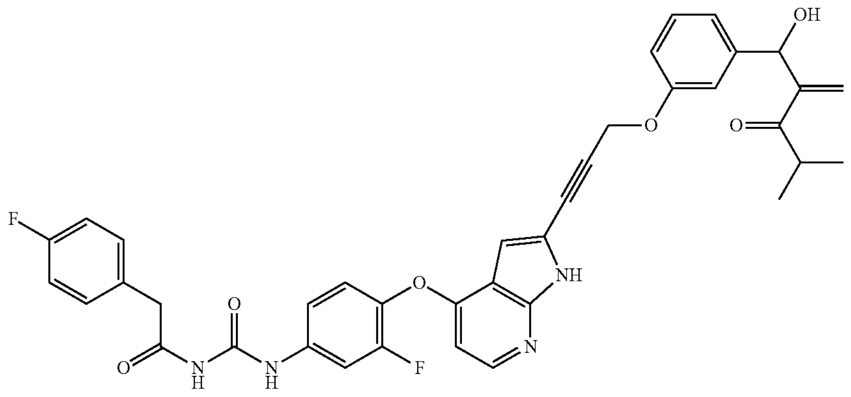
XVI-3
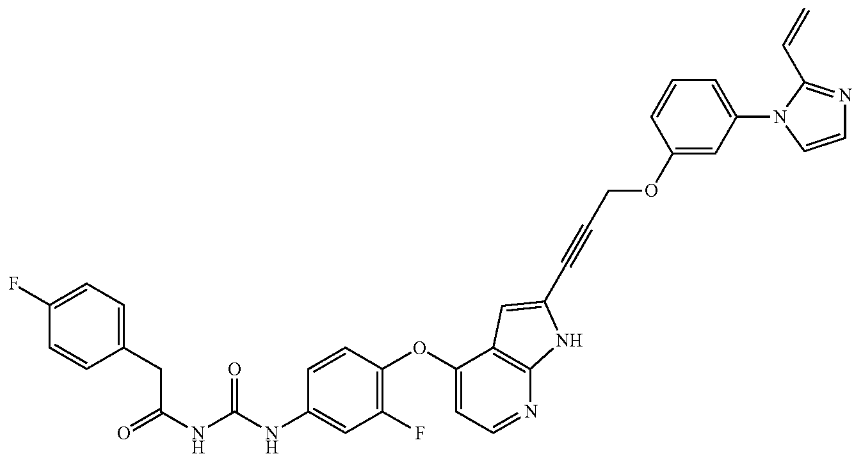
XVI-4
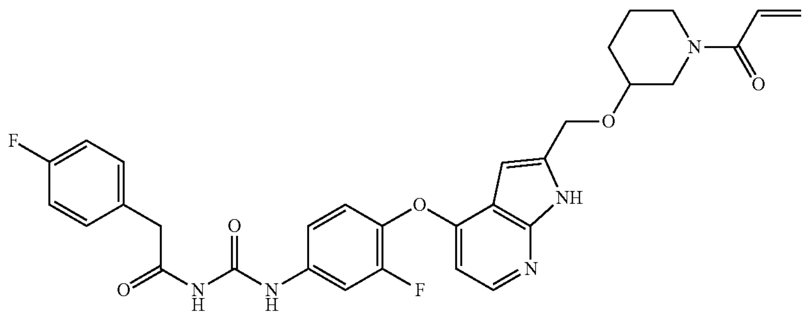
XVI-5
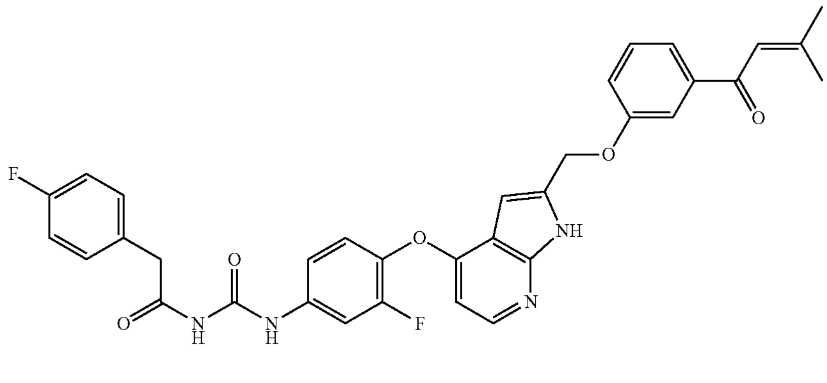

-continued
XVI-6
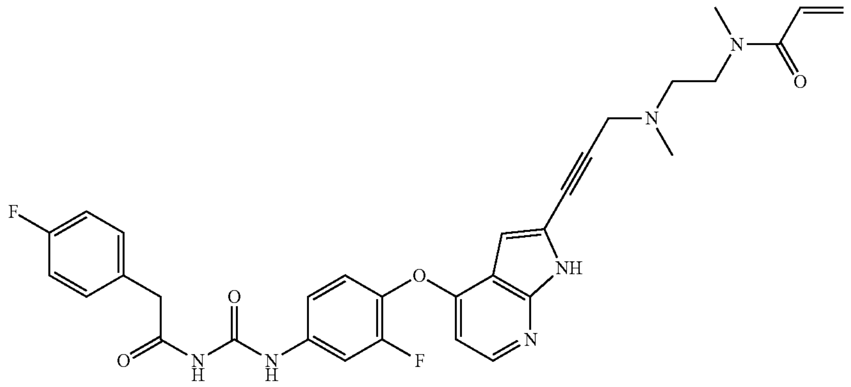
XVI-7
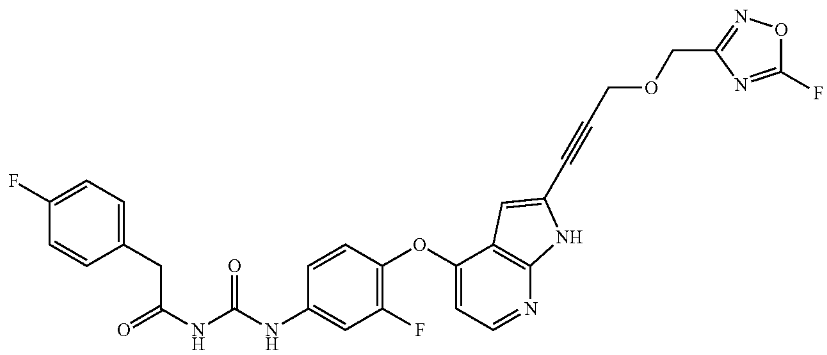
XVI-8
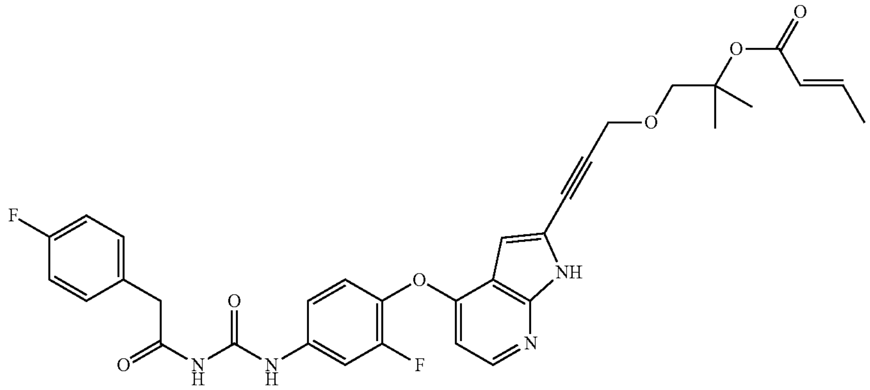
XVI-9
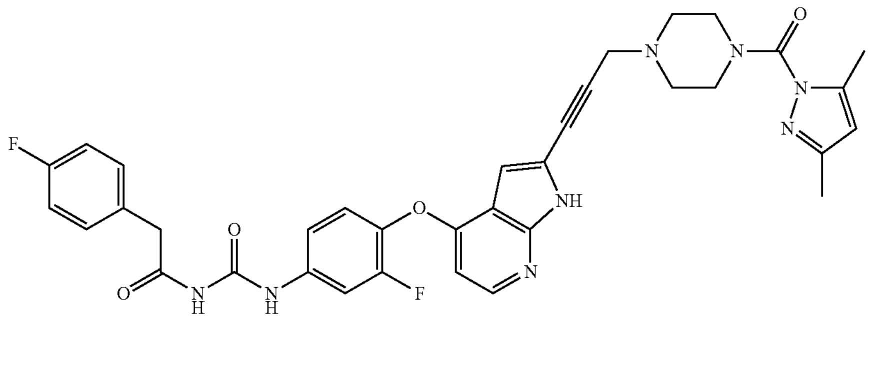

-continued
XVI-10
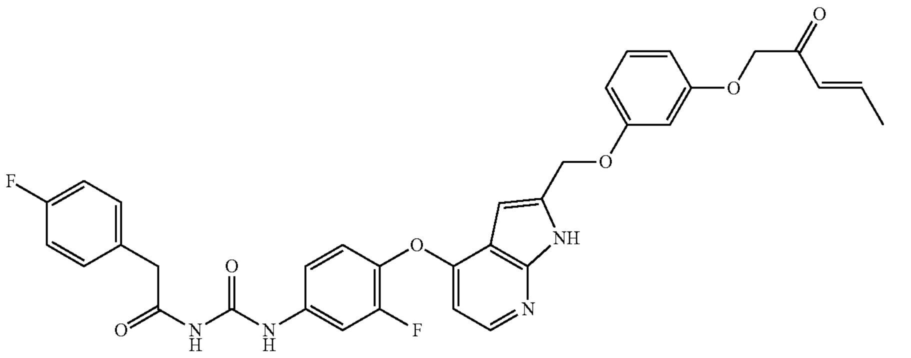
XVI-11
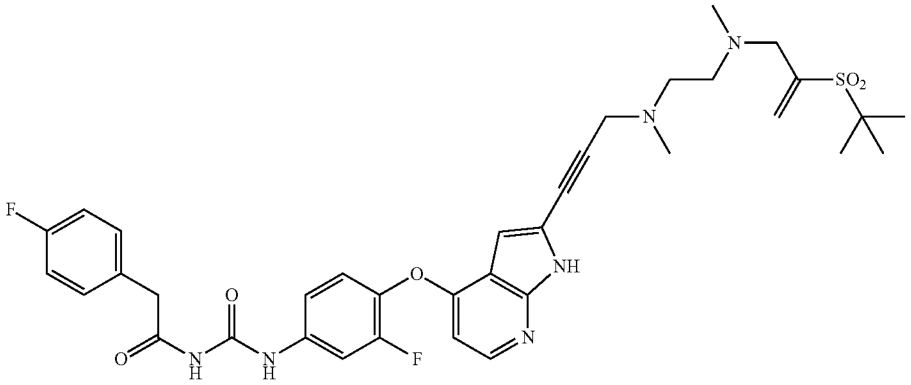
XVI-12
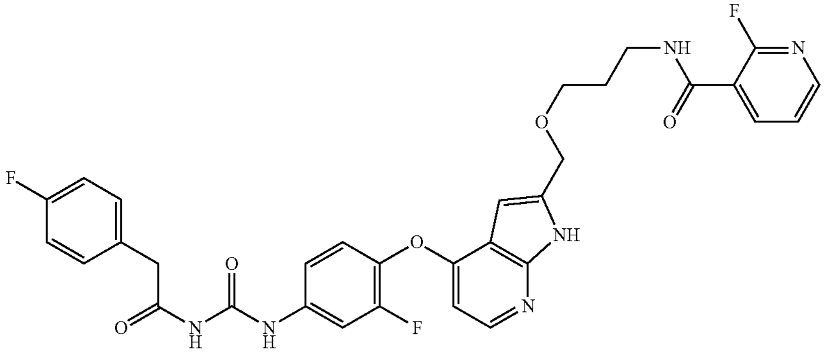
XVI-13
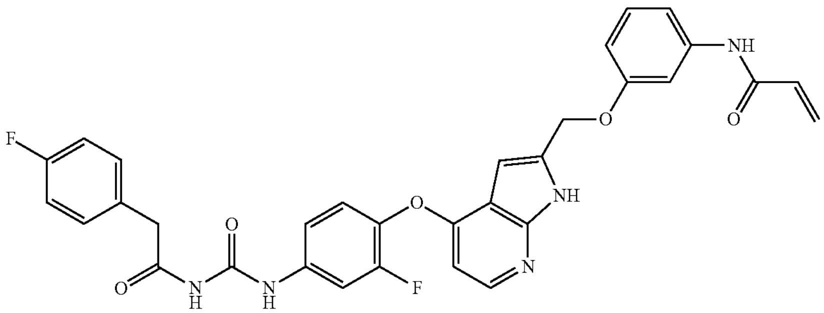
XVI-14
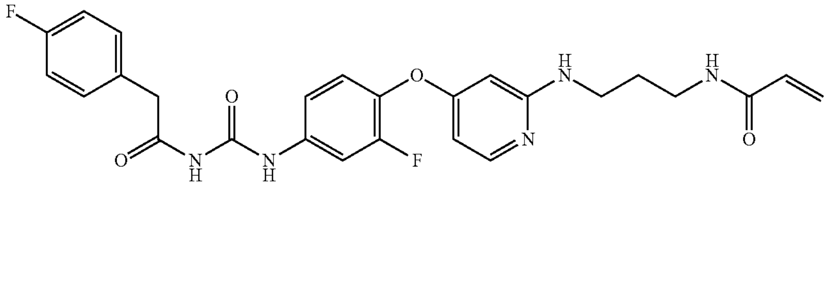

-continued
XVI-15
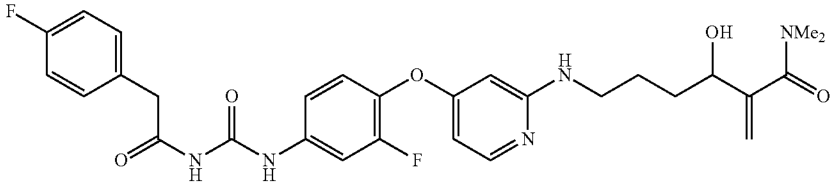
XVI-16
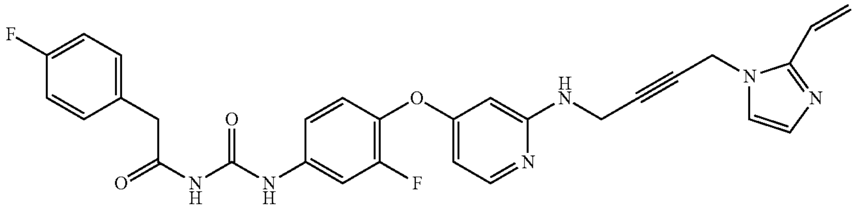
XVI-17
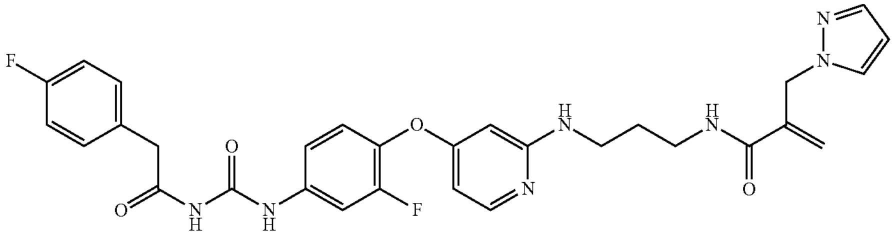
XVI-18
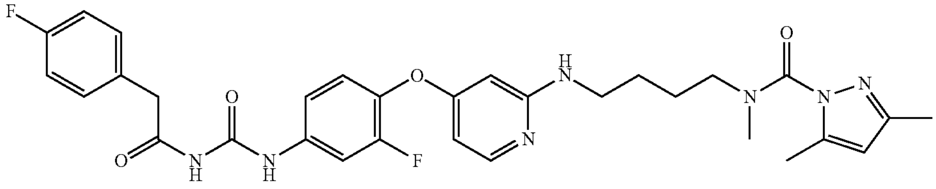
XVI-19
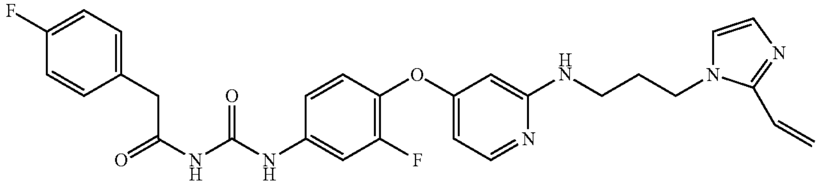
XVI-20
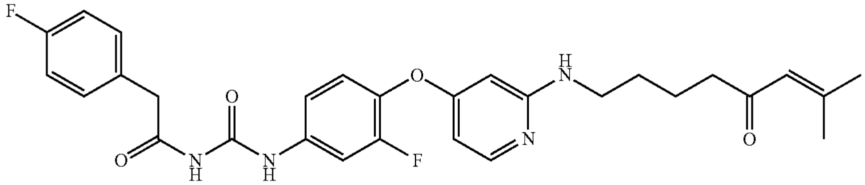
XVI-21
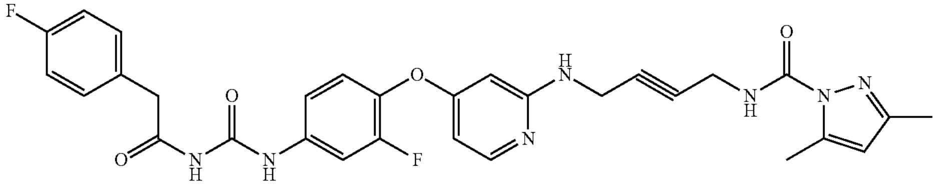
XVI-22
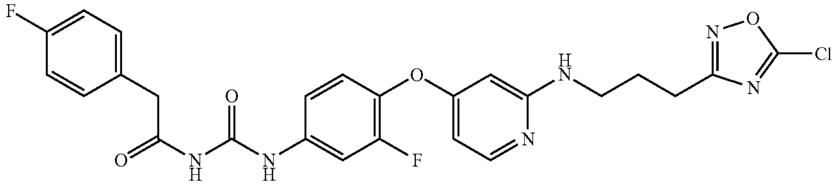

-continued
XVI-23
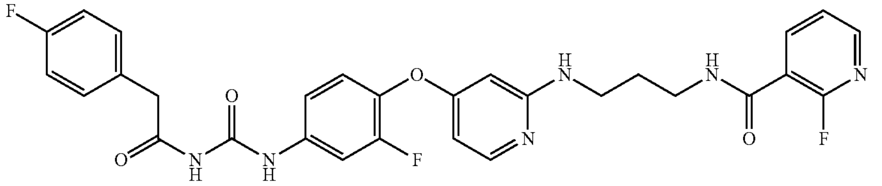
XVI-24
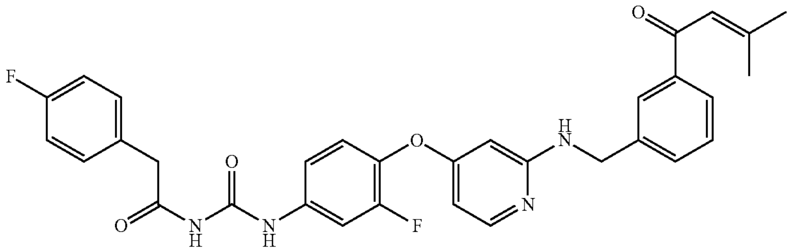
XVI-25
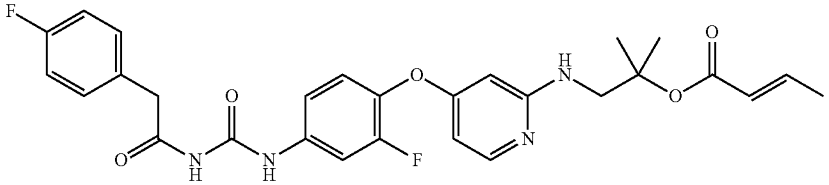
XVI-26
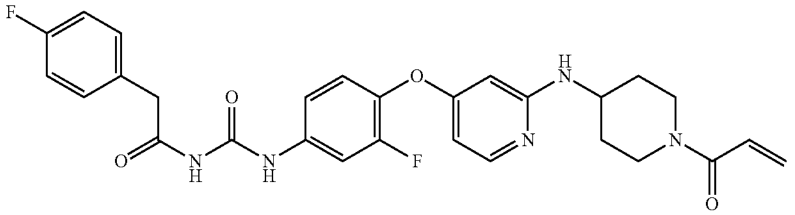
XVI-27
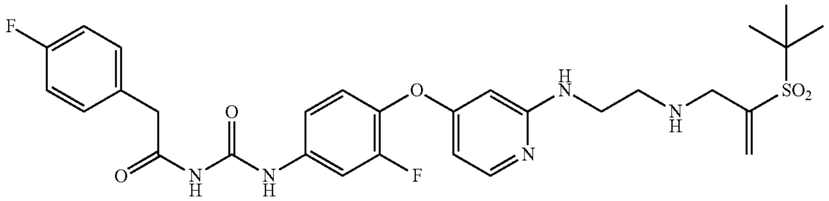
XVI-28
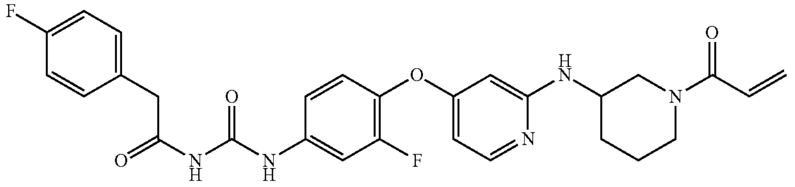
XVI-29
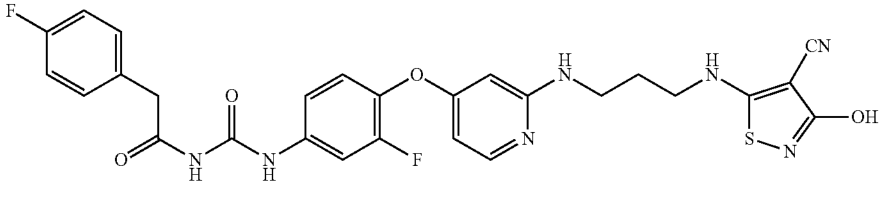

5. Formula XVII

In other aspects, the invention is a compound of formula XVII

XVII

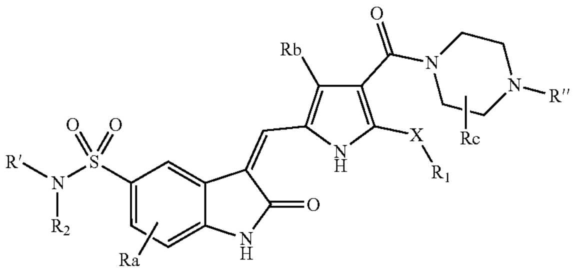

or a pharmaceutically acceptable salt thereof, wherein

Ra, Rb, and Rc are independently selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

$R_2$ is hydrogen, lower alkyl, lower haloalkyl, lower cycloalkyl, optionally substituted aryl, or optionally substituted heteroaryl;

R' and R" are independently hydrogen or lower alkyl;

X is a bond or a bivalent $C_1$-$C_6$ saturated or unsaturated, straight or branched hydrocarbon chain wherein optionally one, two or three methylene units of the hydrocarbon chain are independently replaced by —NR—, —O—, —C(O)—, —OC(O)—, —C(O)O—, —S—, —SO—, —$SO_2$—, —C(═S)—, —C(═NR)—, —N═N—, or —C(═$N_2$)—;

$R_1$ is -L-Y. The group -L-Y is as described herein in the detailed description of the warheads.

In some embodiments, $R_2$ is phenyl or phenyl substituted with Rd, Rd and R''' or R''', wherein Rd is selected from R, OR, halogen, —$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

R''' is halogen. For example, in some embodiments, R2 is m-halophenyl, such as m-chlorophenyl, m-fluorophenyl, m-bromophenyl or m-iodophenyl.

In some embodiments, R' and R" are both methyl.

In some embodiments, Ra, Rb and Rc are each hydrogen.

In certain embodiments, $R_1$ is characterized in that the -L-Y moiety is capable of covalently binding to a Cys11 residue of RON (Cys 1165), thereby irreversibly inhibiting the enzyme.

Exemplary Ron Inhibitors of Formula XVII

XVII-1

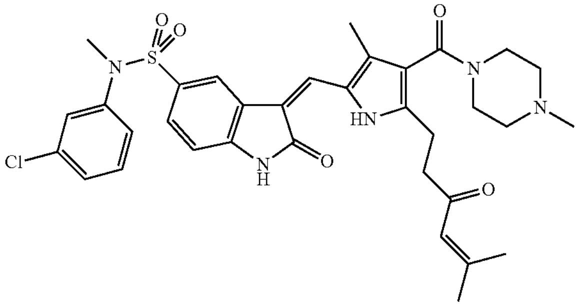

-continued

XVII-2

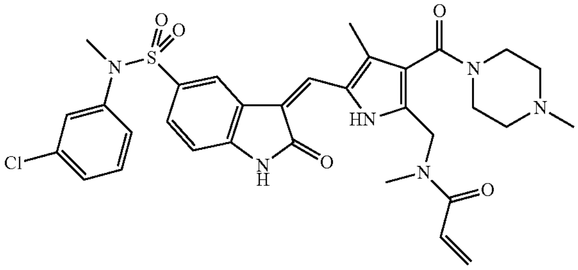

XVII-3

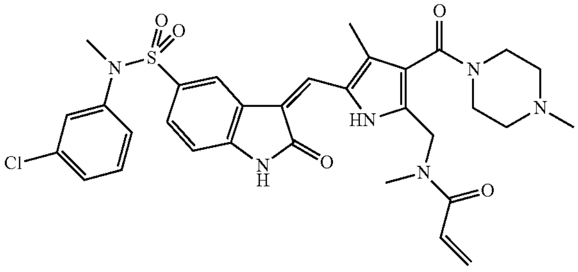

XVII-4

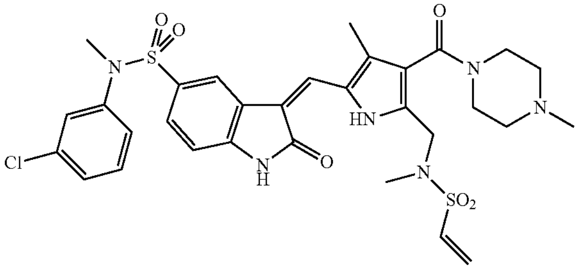

XVII-5

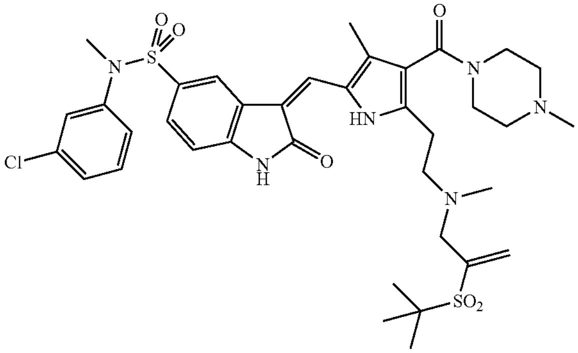

XVII-6

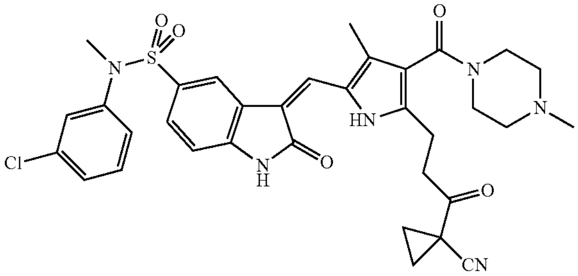

-continued

XVII-7

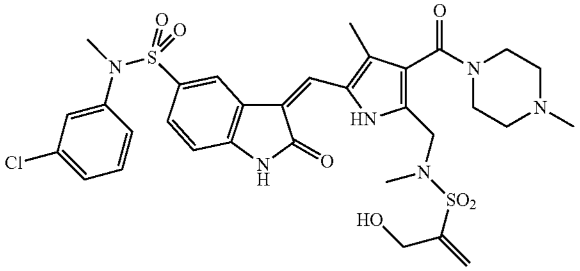

XVII-8

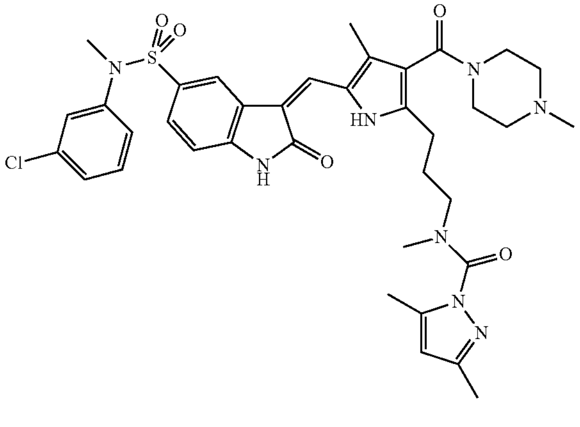

XVII-9

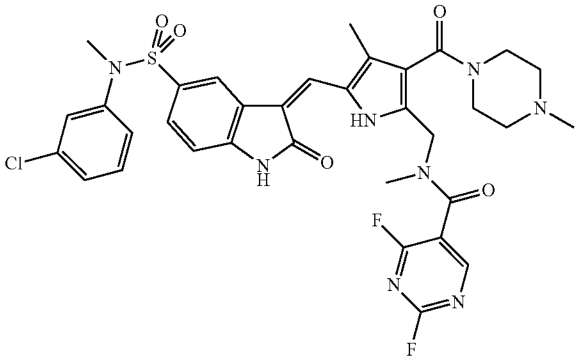

I. C-KIT, PDGFR, CSF1R, FLT3, KDR Inhibitors

1. Formula XVIII

In other aspects, the invention is a compound of formula XVIII

XVIII

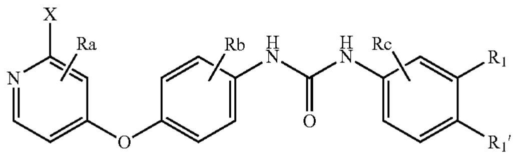

or a pharmaceutically acceptable salt thereof, wherein

Ra, Rb, and Rc are independently selected from hydrogen, R, OR, halogen, —$CF_3$, —O—CF3, —CN, —C≡C—R, —NRxRy, —C(O)NHRz, and a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R;

each R, Rx and Ry is independently hydrogen, lower alkyl, lower haloalkyl, or lower cycloalkyl;

each Rz is independently hydrogen, aliphatic, or aryl;

X is —C(O)—NRxRy-, or —NRxRy-C(O)—Rz;

$R_1$ or $R_{1'}$ is -L-Y; with the proviso that when $R_1$ is -L-Y, $R_{1'}$ is selected from hydrogen, R, OR, halogen, —$CF_3$, —CN, —C≡C—R, —NRxRy, —C(O)NHRz, and a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R; and when $R_{1'}$ is -L-Y, $R_1$ is selected from hydrogen, R, OR, halogen, —$CF_3$, —CN, —C≡C—R, —NRxRy, —C(O)NHRz, and a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R.

The group -L-Y is as described herein in the detailed description of the warheads.

In some embodiments $R_1$ is -L-Y.

In preferred embodiments, $R_{1'}$ is -L-Y, and $R_1$ is $CF_3$.

In some embodiments, Ra, Rb and Rc are each hydrogen.

In some embodiments X is —C(O)—NRxRy, Rx is hydrogen and Ry is methyl.

In certain embodiments, $R_1$ or $R_{1'}$ is characterized in that the -L-Y moiety is capable of covalently binding to a Cys1 residue of C-KIT, PDGFR, CSF1R, FLT3, and/or KDR, thereby irreversibly inhibiting the enzyme.

Exemplary Inhibitors of Formula XVIII

XVIII-1

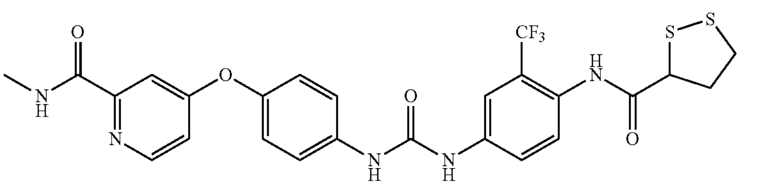

XVIII-2

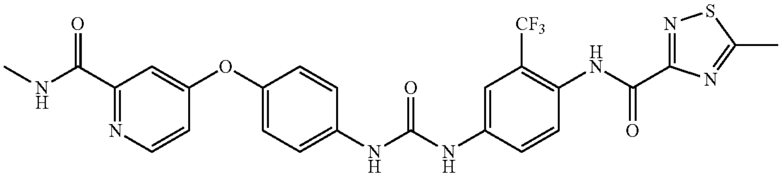

-continued
XVIII-3
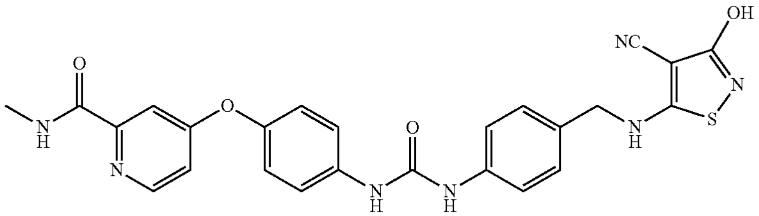
XVIII-4
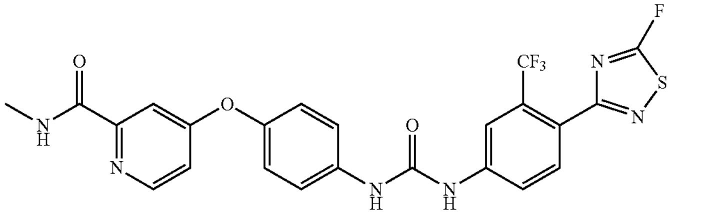
XVIII-5
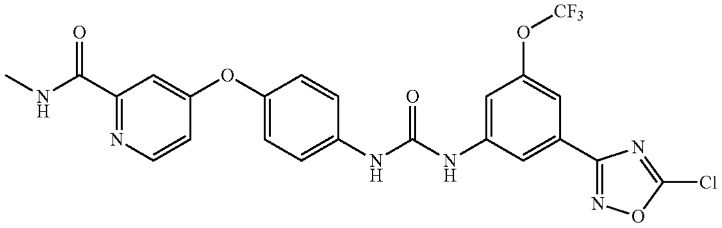
XVIII-6
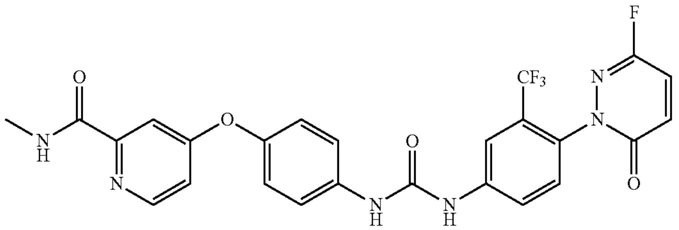
XVIII-7
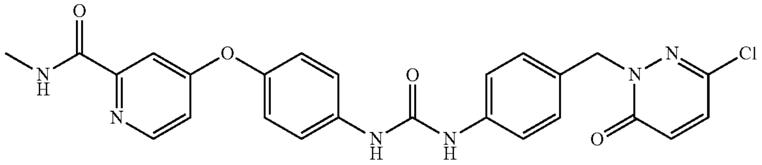
XVIII-8
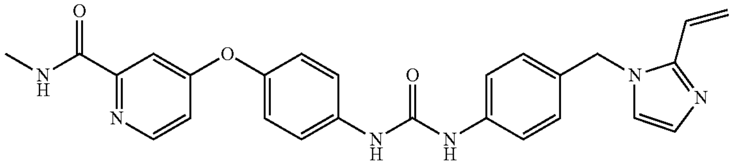
XVIII-9
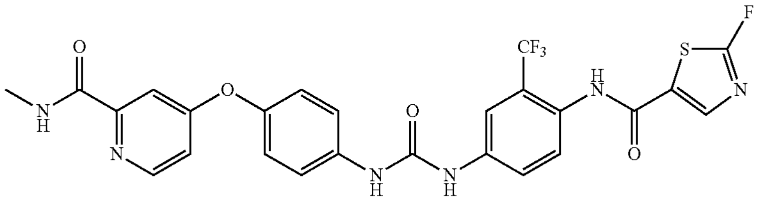

-continued
XVIII-10
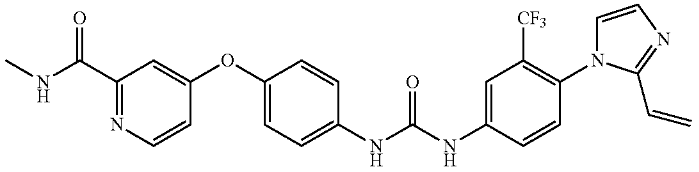
XVIII-11
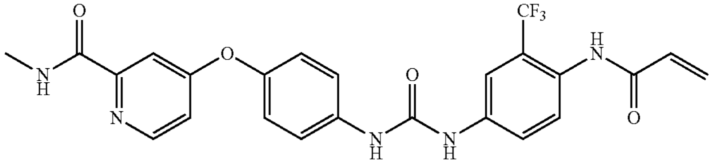
XVIII-12
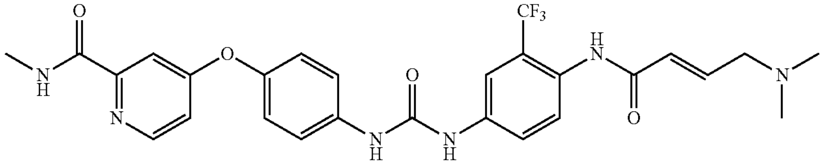
XVIII-13
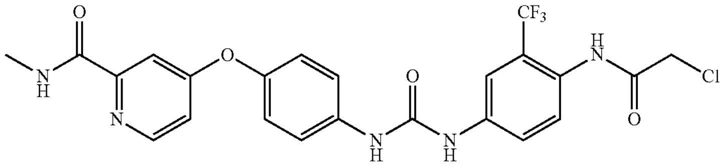
XVIII-14
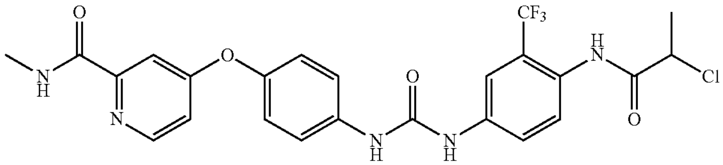
XVIII-15
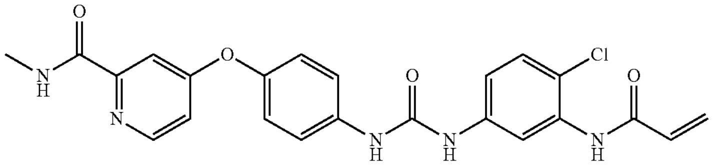
XVIII-16
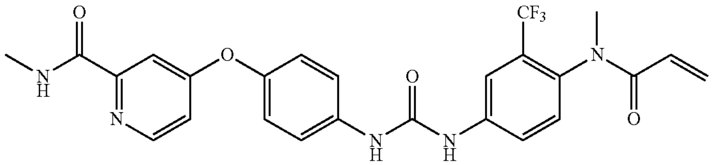
XVIII-17
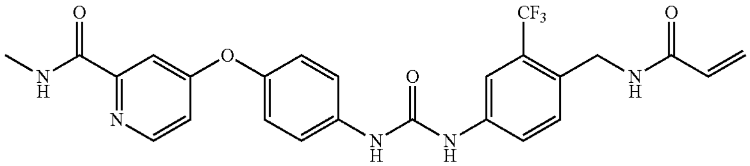
XVIII-18
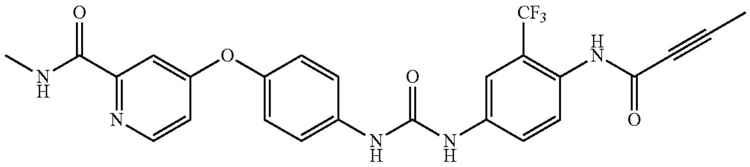

-continued
XVIII-19
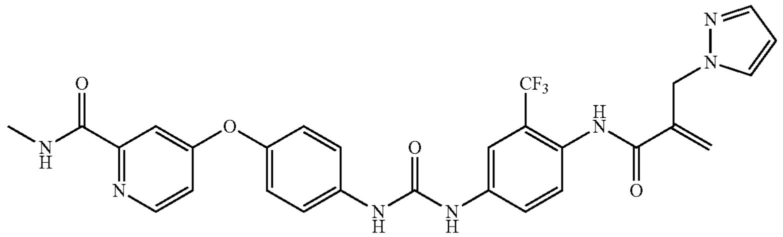
XVIII-20
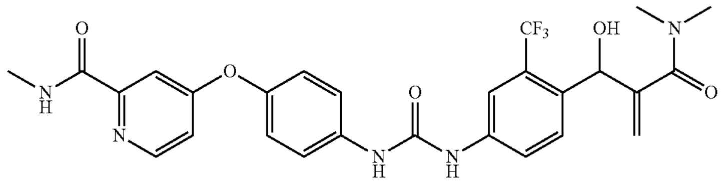
XVIII-21
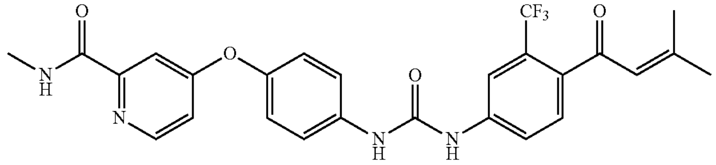
XVIII-22
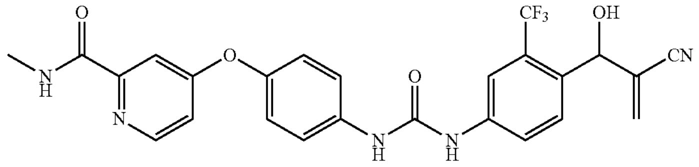
XVIII-23
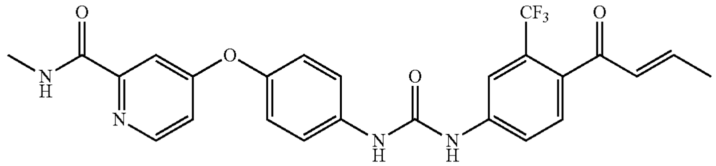
XVIII-24
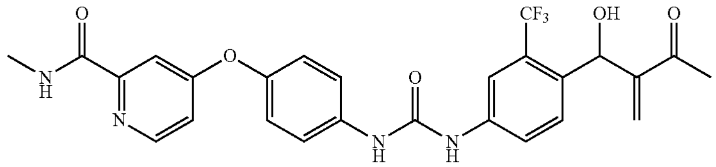
XVIII-25
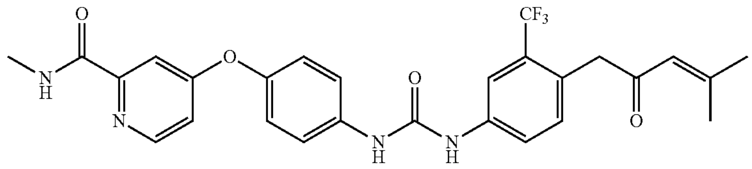
XVIII-26
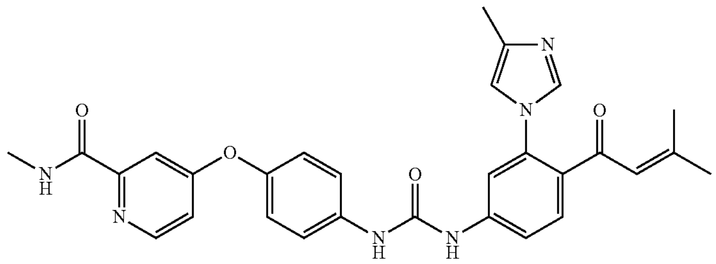

-continued
XVIII-27
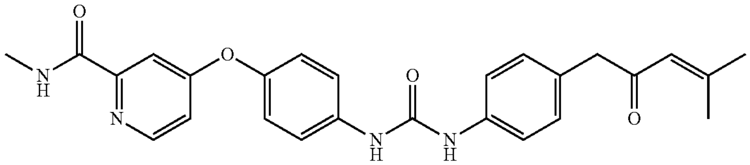
XVIII-28
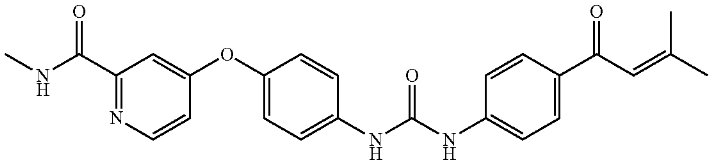
XVIII-29
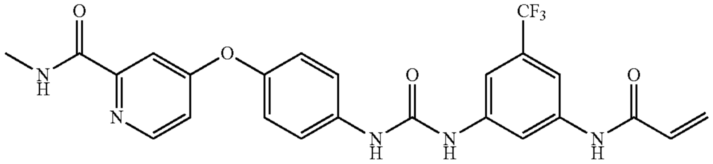
XVIII-30
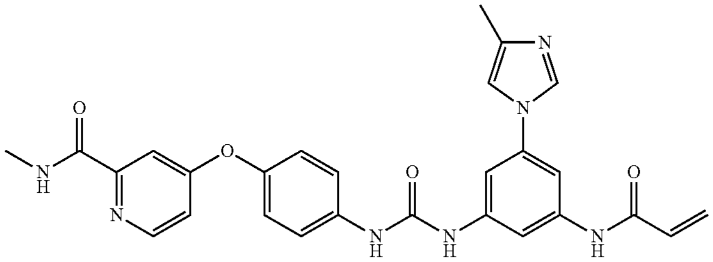
XVIII-31
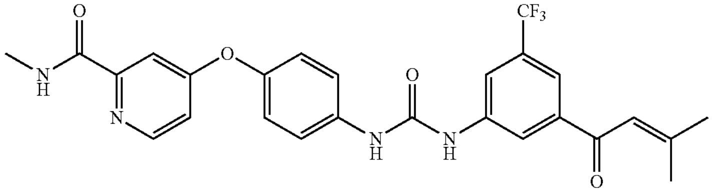
XVIII-32
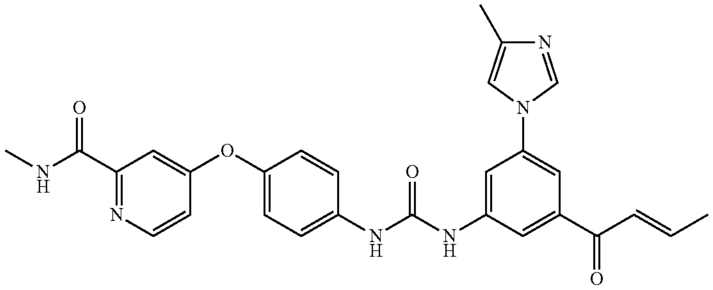
XVIII-33
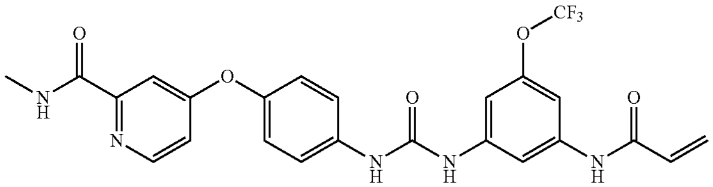

-continued
XVIII-34
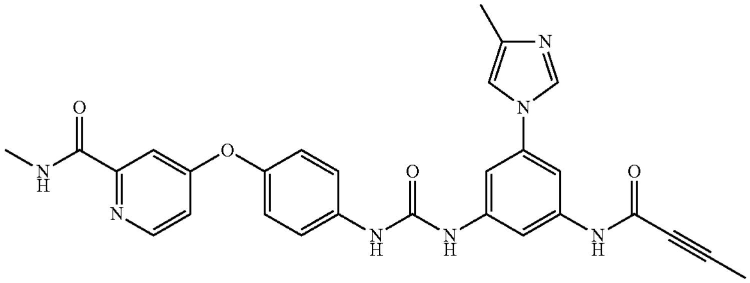
XVIII-35
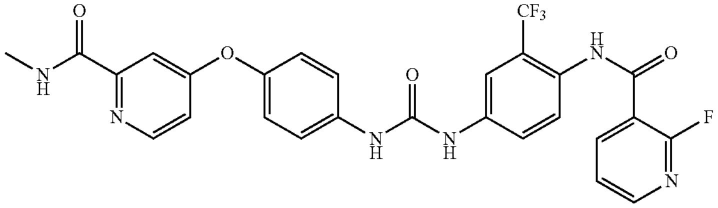
XVIII-36
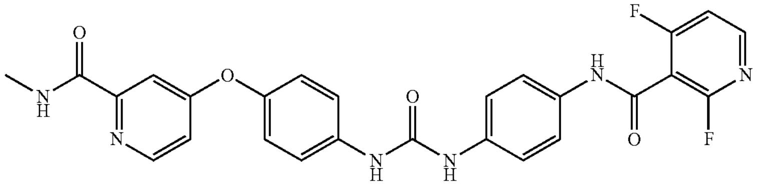
XVIII-37
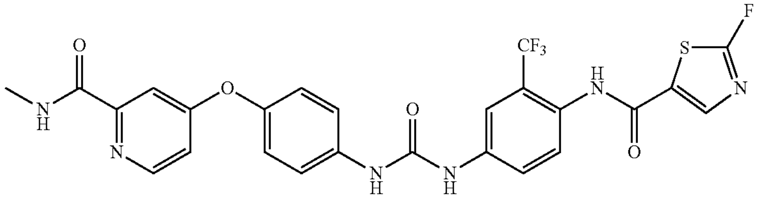
XVIII-38
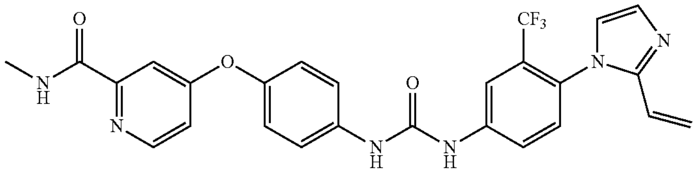
XVIII-39
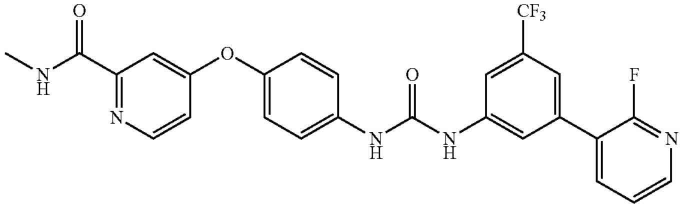
XVIII-40
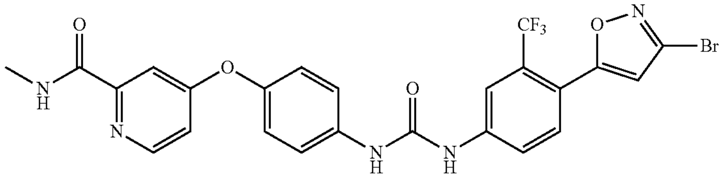

-continued

XVIII-41

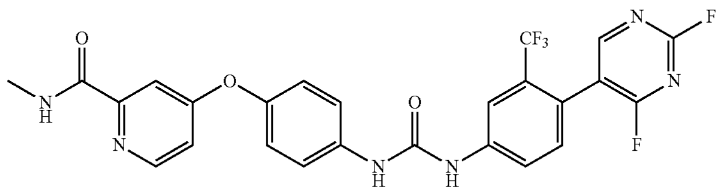

XVIII-42

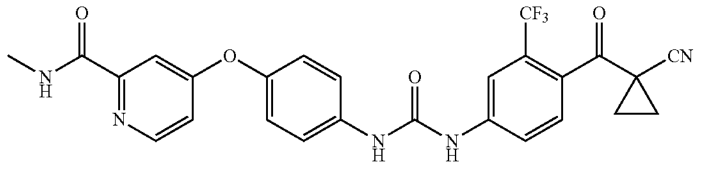

XVIII-43

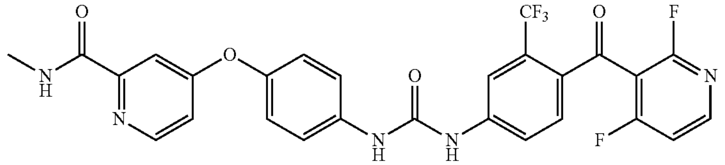

XVIII-44

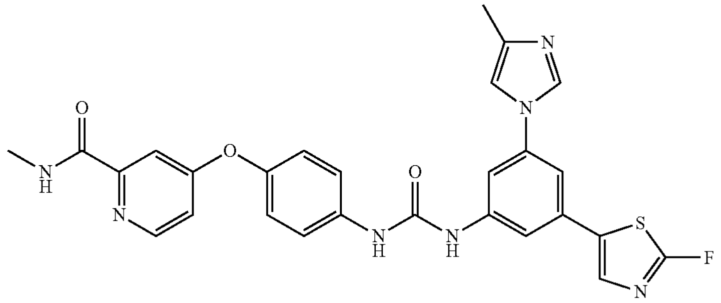

XVIII-45

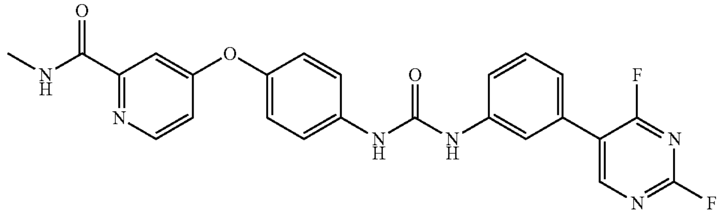

XVIII-46

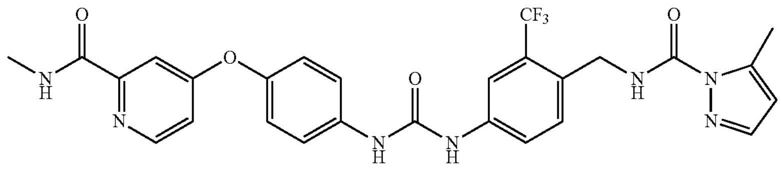

J. c-KIT, PDGFR Inhibitors

1. Formula XIX

In other aspects, the invention is a compound of formula XIX

XIX

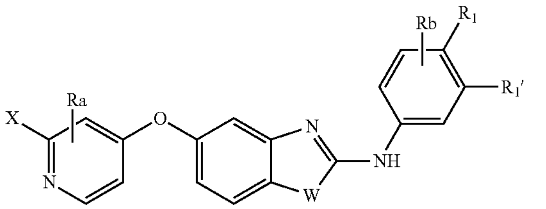

or a pharmaceutically acceptable salt thereof, wherein

Ra and Rb are independently selected from hydrogen, R, OR, halogen, —$CF_3$, —O—CF3, —CN, —C≡C—R, —NRxRy, —C(O)NHRz, and a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R;

each R, Rx and Ry is independently hydrogen, lower alkyl, lower haloalkyl, or lower cycloalkyl;

each Rz is independently hydrogen, aliphatic, or aryl;

X is —C(O)—NRxRy or —NRx-C(O)—Rz;

W is O, NH or N—Rc;

Rc is hydrogen, lower alkyl, lower haloalkyl, or lower cycloalkyl;

$R_1$ or $R_{1'}$ is -L-Y; with the proviso that when R1 is -L-Y, $R_{1'}$ is selected from hydrogen, R, OR, halogen, —$CF_3$, —CN, —C≡C—R, —NRxRy, —C(O)NHRz, and a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R; and when $R_{1'}$ is -L-Y, $R_1$ is selected from hydrogen, R, OR, halogen, —$CF_3$, —CN, —C≡C—R, —NRxRy, —C(O)NHRz and a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R.

The group -L-Y is as described herein in the detailed description of the warheads.

In certain embodiments, the compound is of formula XIX-a, XIX-b or XIX-c

XIX-a

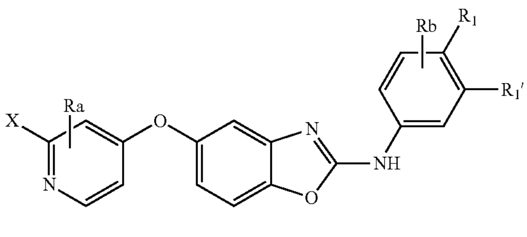

-continued

XIX-b

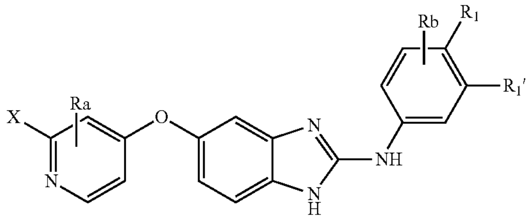

XIX-c

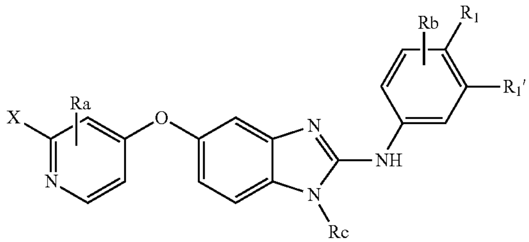

Wherein X, Ra, Rb, Rc, $R_1$ and $R_{1'}$ are as defined in formula XIX. Preferably, in the compounds of formula XIX-a, XIX-b and XIX-c, X is —C(O)—NRxRy, wherein Rx is hydrogen and Ry is methyl.

In some embodiments of compounds of formula XIX-a or XIX-b, Ra and Rb are each hydrogen. In some embodiments of formula XIX-c, Ra and Rb are each hydrogen and Rc is methyl.

In certain embodiments, $R_1$ or $R_{1'}$ is characterized in that the -L-Y moiety is capable of covalently binding to a Cys 1 residue of c-KIT and/or PDGFR, thereby irreversibly inhibiting the enzyme.

Exemplary Compounds of Formula XIX

XIX-1

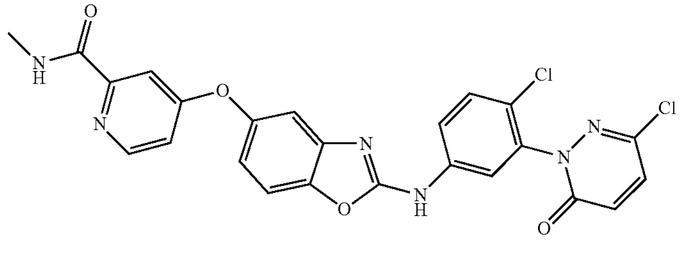

XIX-2

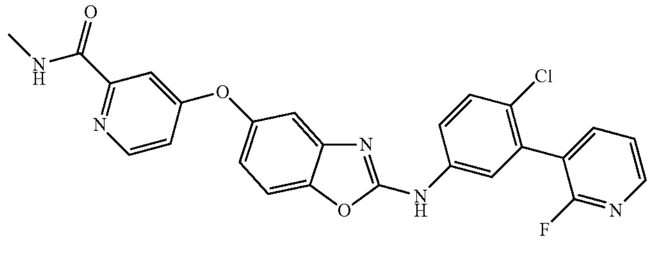

XIX-3

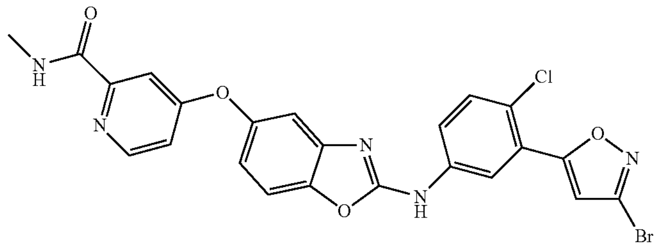

-continued
XIX-4
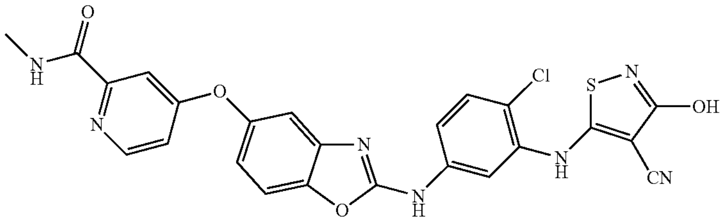
XIX-5
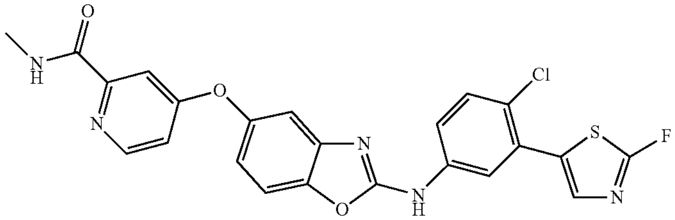
XIX-6
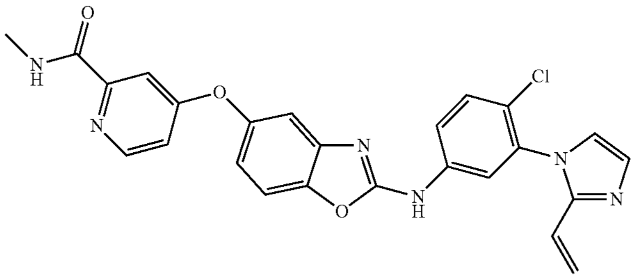
XIX-7
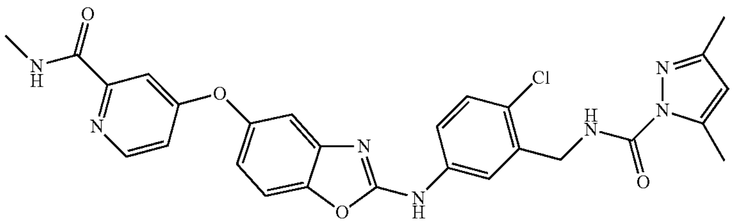
XIX-8
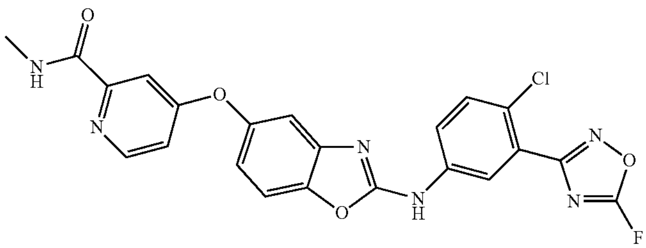
XIX-9
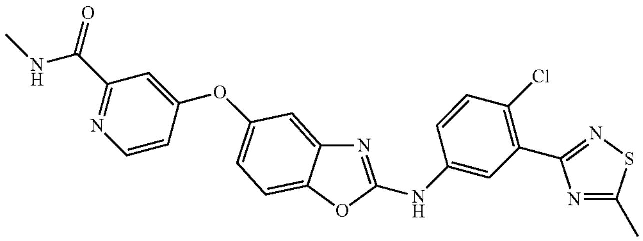

-continued
XIX-10
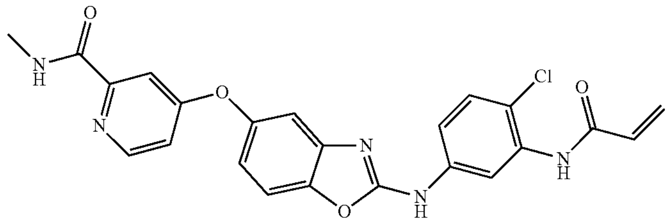
XIX-11
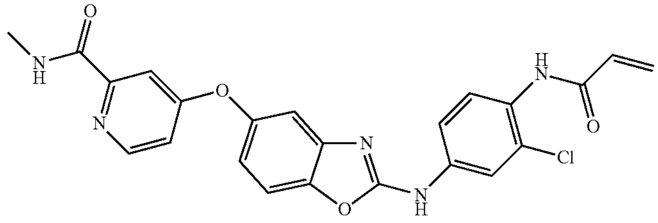
XIX-12
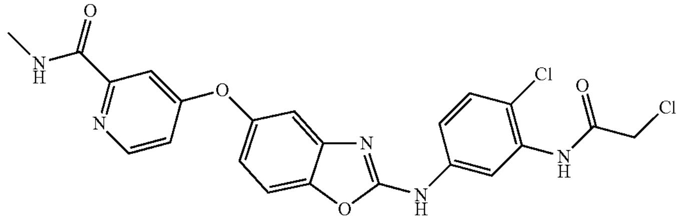
XIX-13
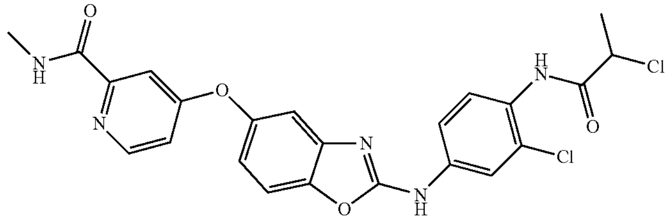
XIX-14
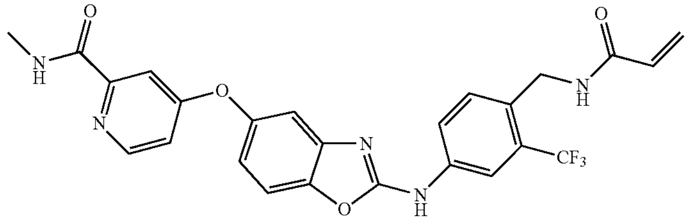
XIX-15
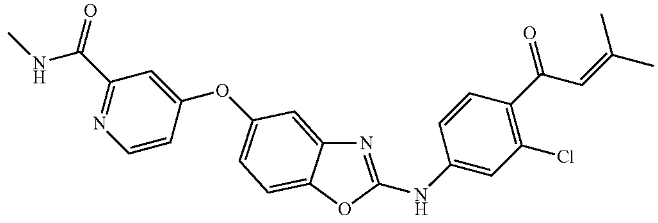

-continued
XIX-16
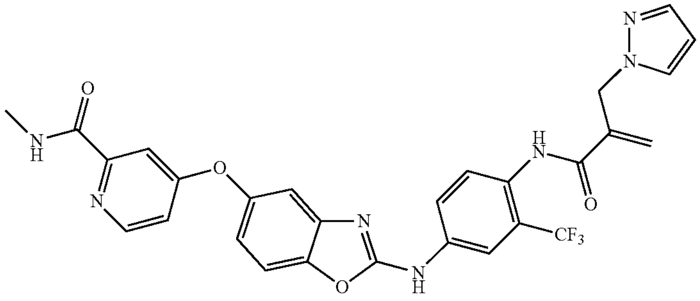
XIX-17
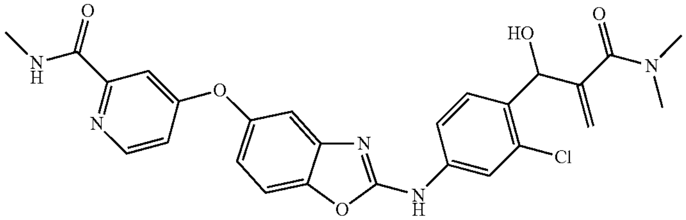
XIX-18
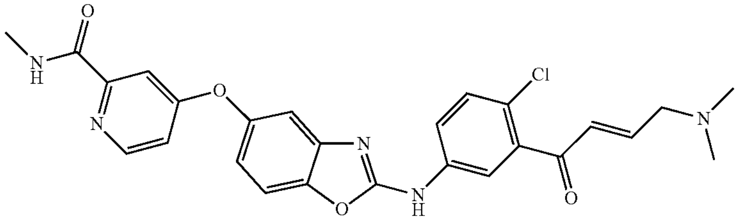
XIX-19
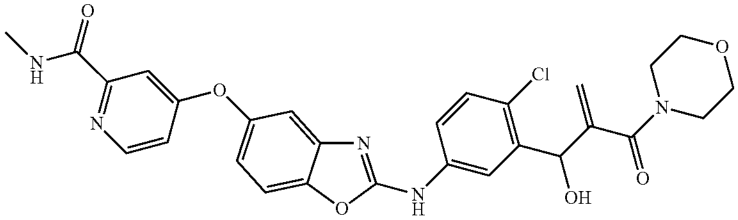
XIX-20
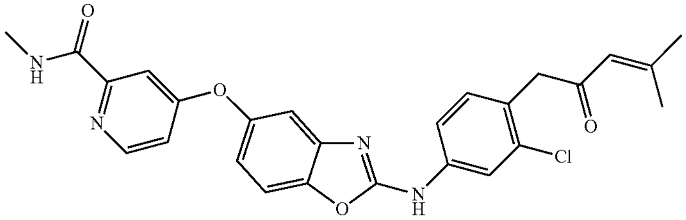
XIX-21
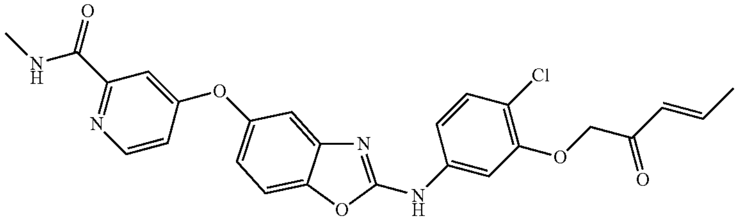

-continued
XIX-22
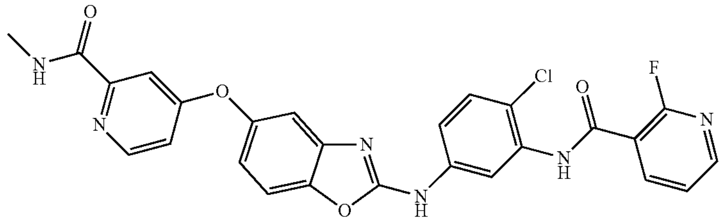
XIX-23
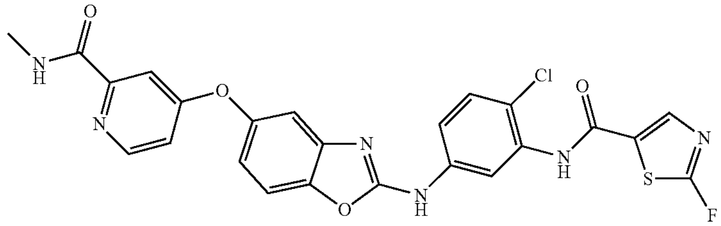
XIX-24
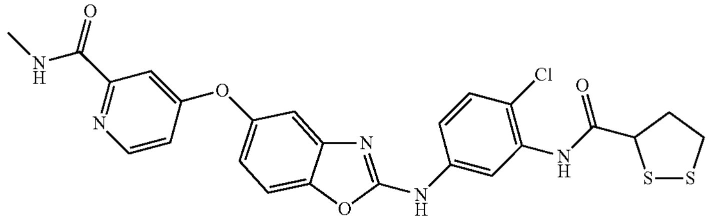
XIX-25
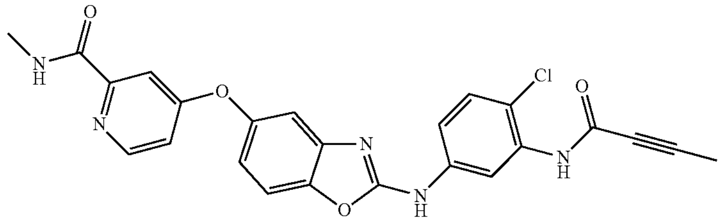
XIX-26
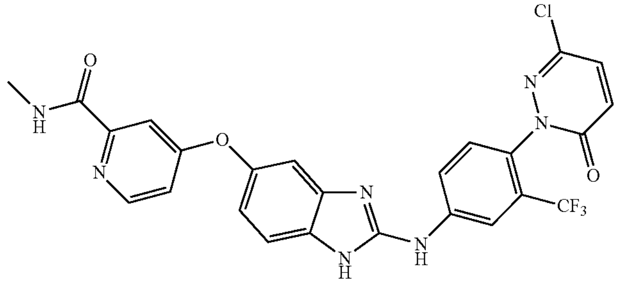
XIX-27
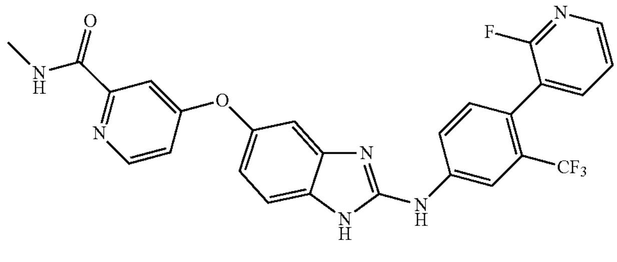

-continued
XIX-28
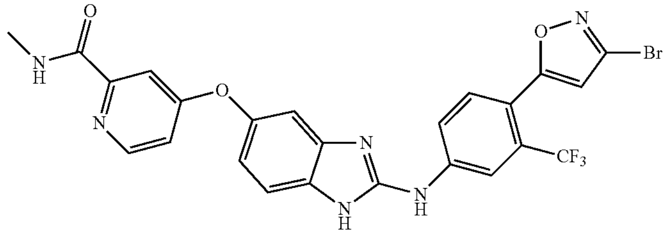
XIX-29
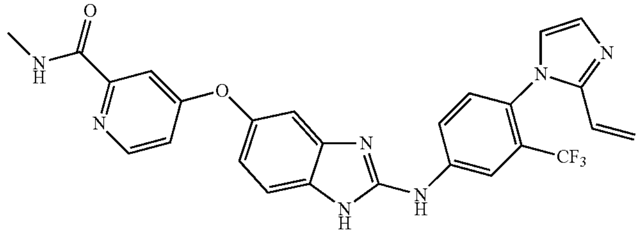
XIX-30
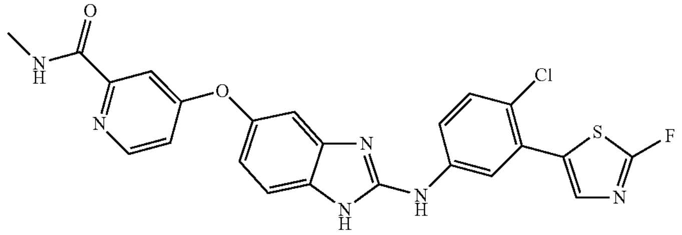
XIX-31
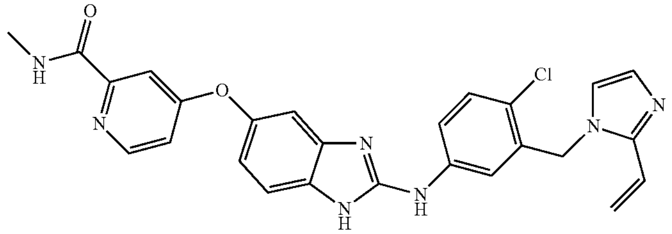
XIX-32
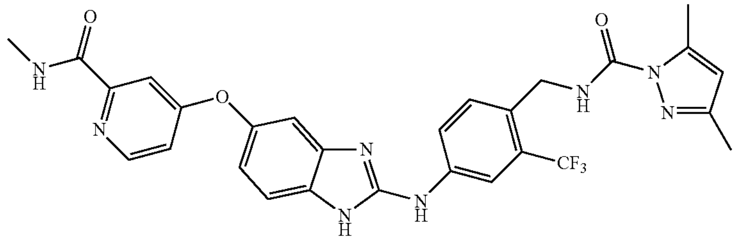
XIX-33
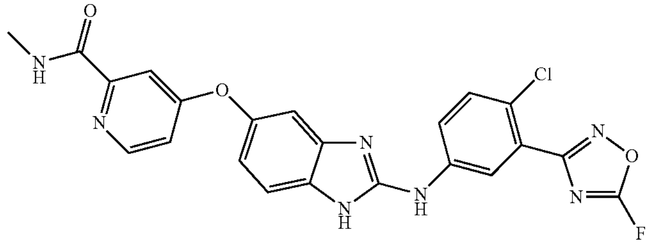

-continued
XIX-34
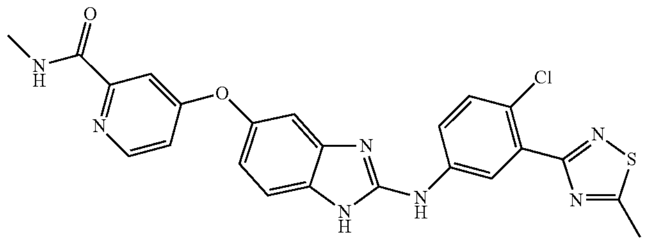
XIX-35
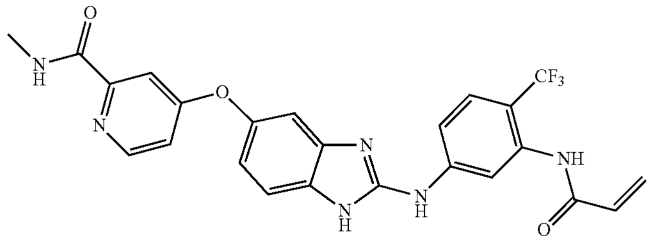
XIX-36
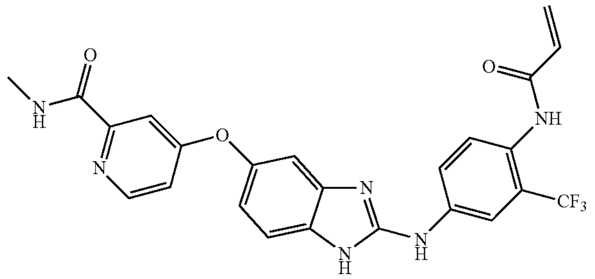
XIX-37
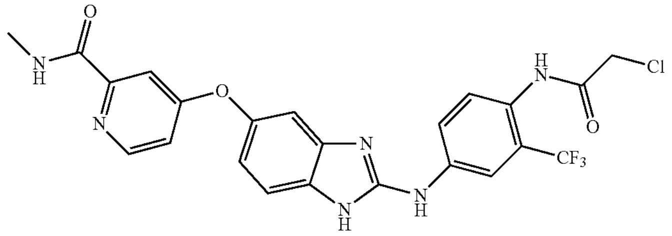
XIX-38
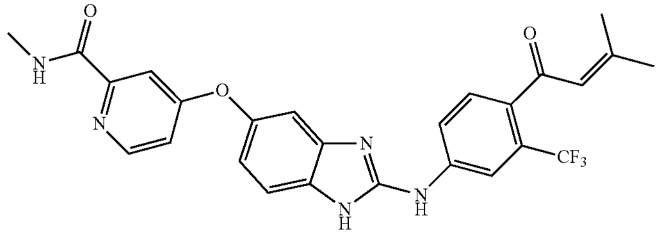
XIX-39
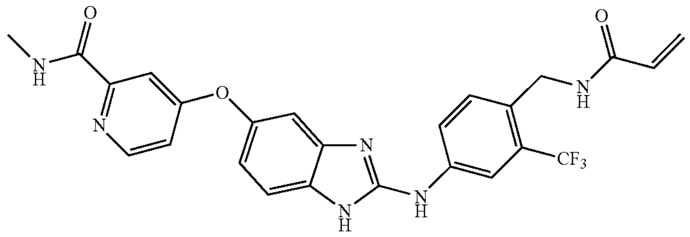

-continued
XIX-40
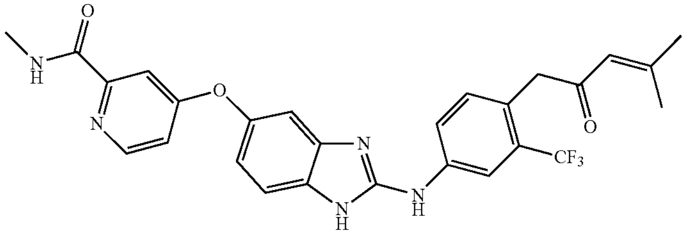
XIX-41
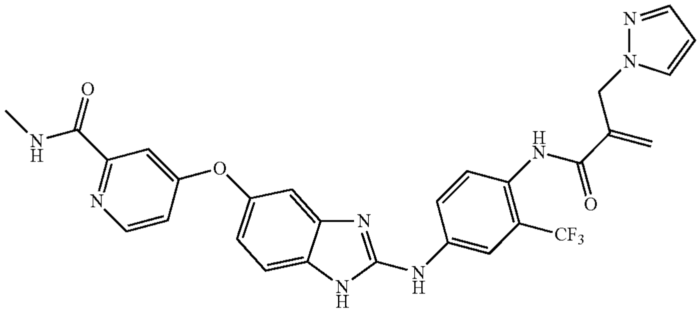
XIX-42
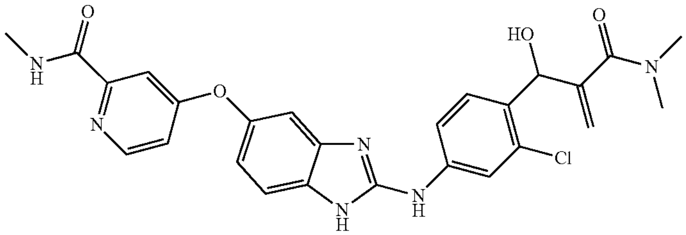
XIX-43
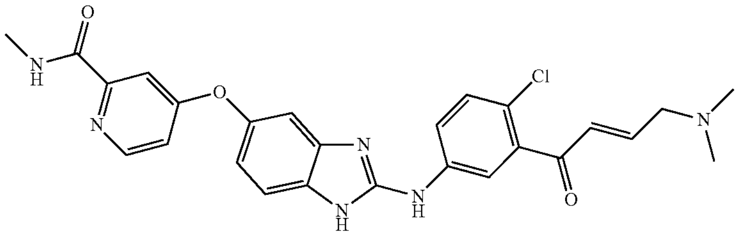
XIX-44
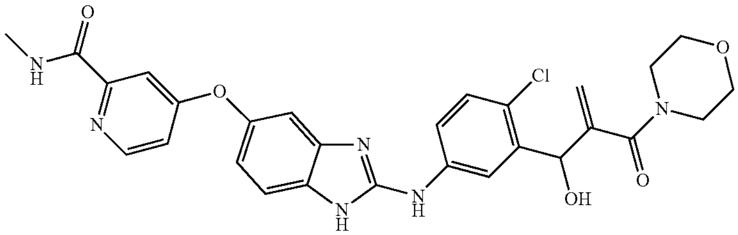
XIX-45
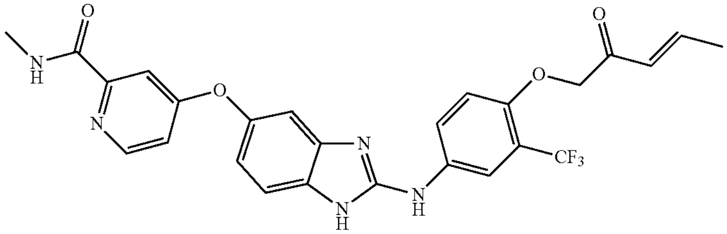

-continued
XIX-46
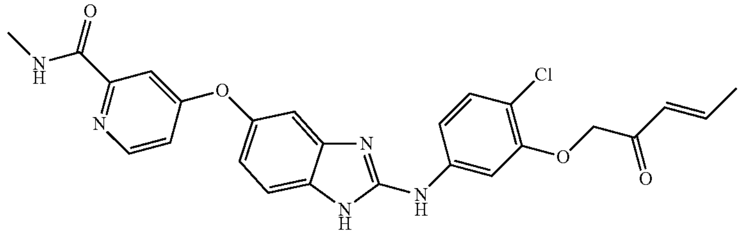
XIX-47
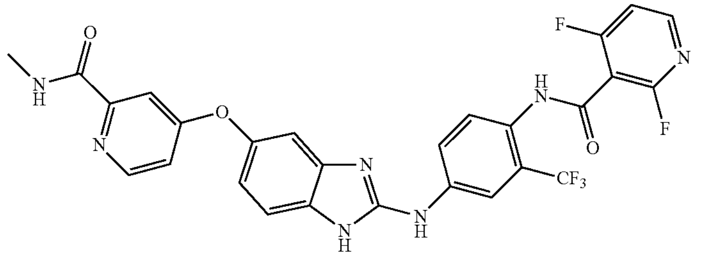
XIX-48
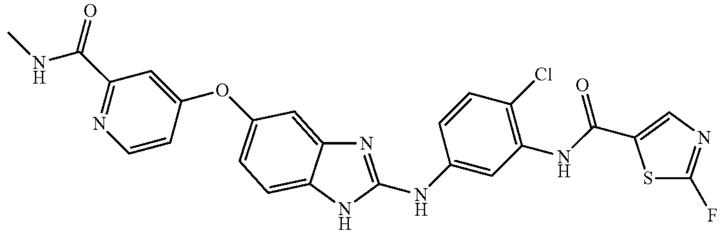
XIX-49
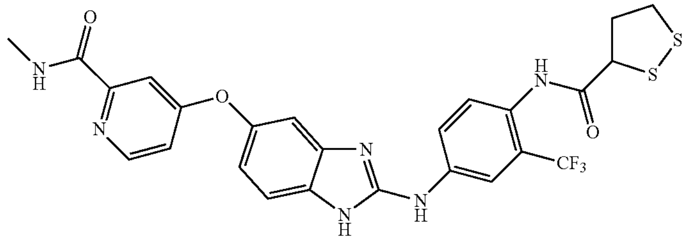
XIX-50
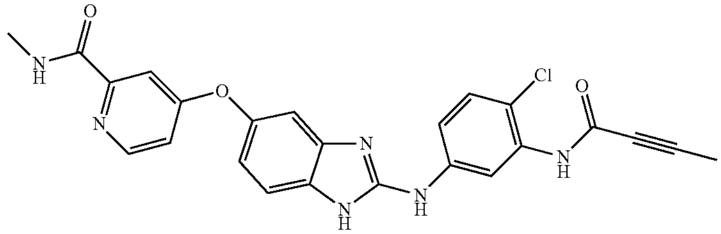
XIX-51
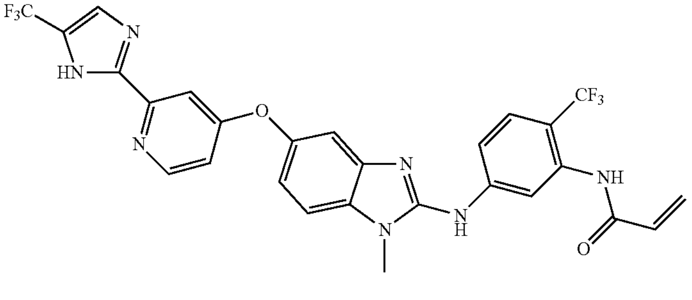

-continued
XIX-52
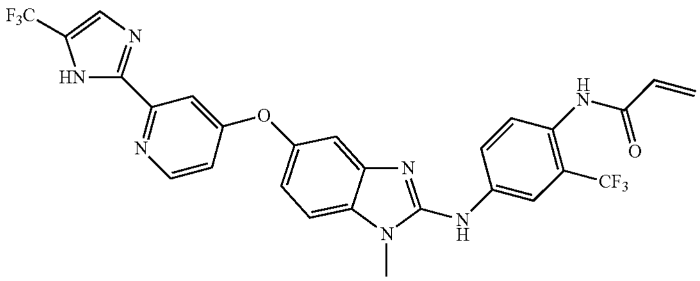
XIX-53
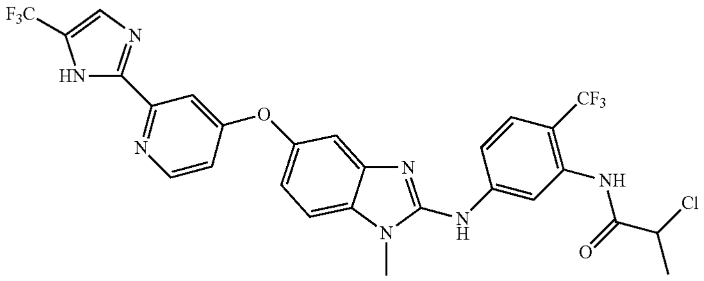
XIX-54
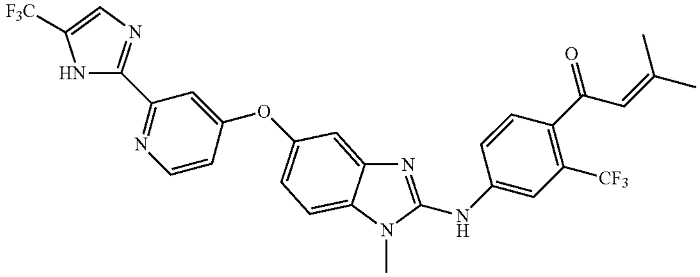
XIX-55
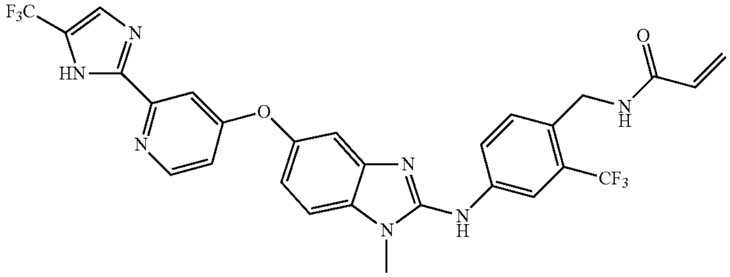
XIX-56
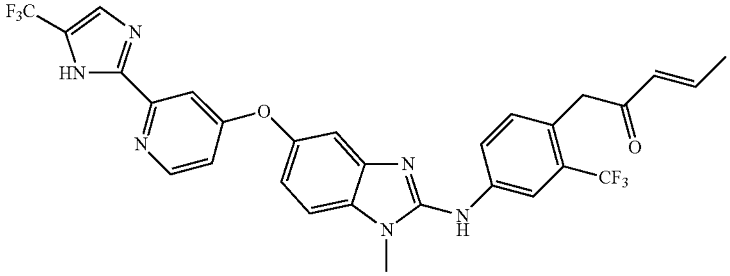

-continued
XIX-57
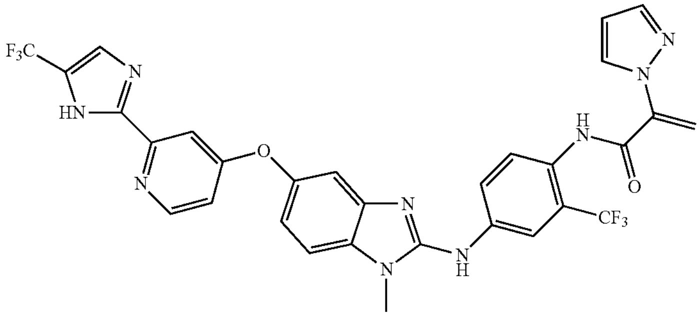
XIX-58
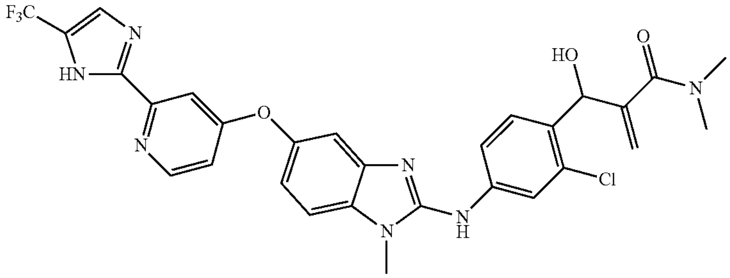
XIX-59
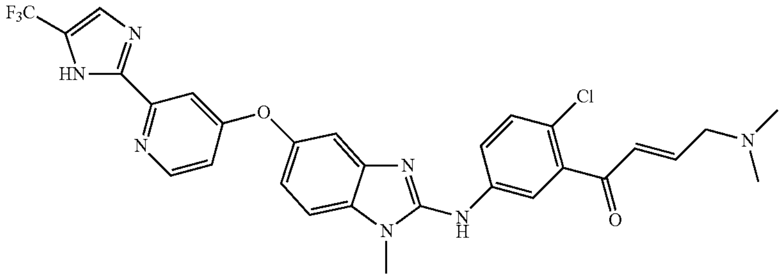
XIX-60
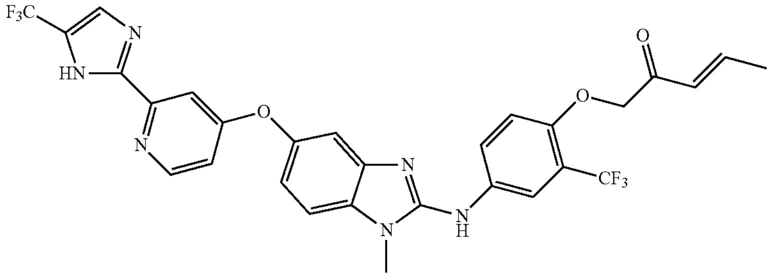
XIX-61
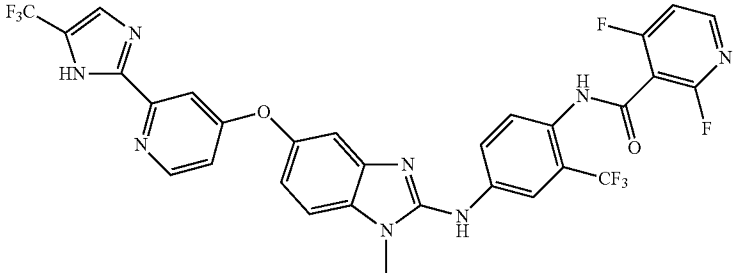

-continued
XIX-62
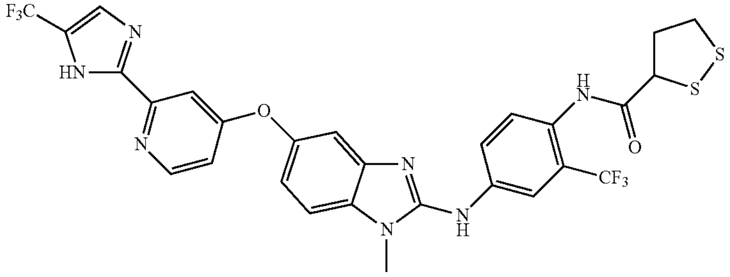
XIX-63
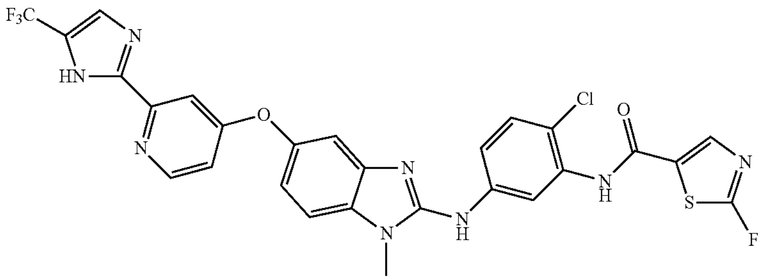
XIX-64
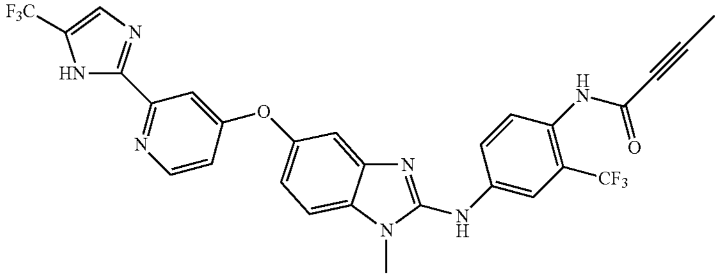
XIX-65
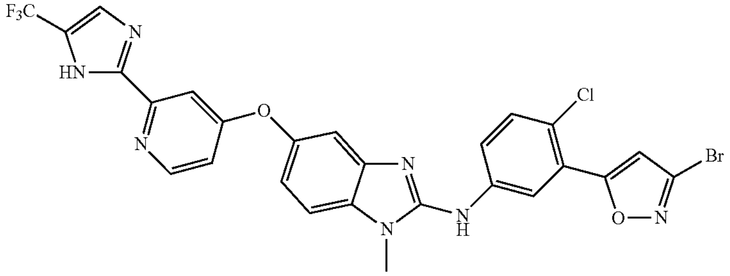
XIX-66
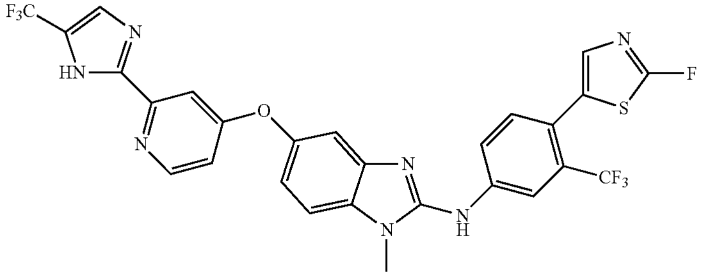

2. Formula XX

In other aspects, the invention is a compound of formula XX

XX

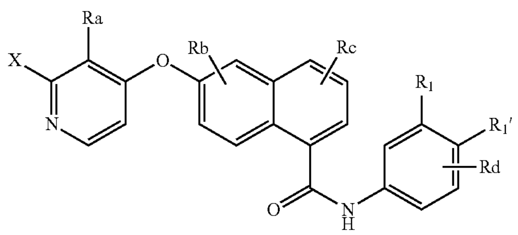

or a pharmaceutically acceptable salt thereof, wherein

Ra, Rb, Rc and Rd are independently selected from hydrogen, R, OR, halogen, —$CF_3$, —O—$CF_3$, —CN, —C≡C—R, —NRxRy, —C(O)NHRz and a 3-10 membered monocyclic or bicyclic, saturated, partially unsaturated, or aryl ring having 0-3 heteroatoms independently selected from nitrogen, oxygen, or sulfur, and wherein said ring is optionally substituted with 1-4 substituents selected from lower alkyl, lower haloalkyl, lower cycloalkyl, lower alkoxy, lower haloalkoxy, lower cycloalkoxy, —$CF_3$, —O—$CF_3$, —CN, —C≡C—R, —NRxRy, and —C(O)NHRz;

each R, Rx and Ry is independently hydrogen, lower alkyl, lower haloalkyl, or lower cycloalkyl;

each Rz is independently hydrogen, aliphatic, or aryl;

X is —C(O)—NRxRy or —NRx-C(O)—Rz;

Or Ra and X taken together with the atoms to which they are bonded form a benzo ring that is optionally substituted one or more of Rf, Rf1, Rf2 and Rf3;

Rf, Rf1, Rf2 and Rf3 are independently selected from lower alkyl, lower haloalkyl, lower cycloalkyl, lower alkoxy, lower haloalkoxy, lower cycloalkoxy, —$CF_3$, —O—$CF_3$, —CN, —C≡C—R, —NRxRy, and —C(O)NHRz;

$R_1$ or $R_{1'}$ is -L-Y; with the proviso that when $R_1$ is -L-Y, $R_{1'}$ is selected from hydrogen, R, OR, halogen, —$CF_3$, —CN, —C≡C—R, —NRxRy, —C(O)NHRz and a 3-10 membered monocyclic or bicyclic, saturated, partially unsaturated, or aryl ring having 0-3 heteroatoms independently selected from nitrogen, oxygen, or sulfur, and wherein said ring is optionally substituted with 1-4 R, and when $R_{1'}$ is -L-Y, $R_1$ is selected from hydrogen, R, OR, halogen, —$CF_3$, —CN, —C≡C—R, —NRxRy, —C(O)NHRz and a 3-10 membered monocyclic or bicyclic, saturated, partially unsaturated, or aryl ring having 0-3 heteroatoms independently selected from nitrogen, oxygen, or sulfur, and wherein said ring is optionally substituted with 1-4 R.

The group -L-Y is as described herein in the detailed description of the warheads.

In some embodiments, X is —C(O)NRxRy, Rx is hydrogen and Ry is methyl.

In some embodiments, Ra, Rb, Rc and Rd are each hydrogen.

In some embodiments $R_1$ is -L-Y and R1' is CF3, or R1 is $CF_3$ and $R_{1'}$ is -L-Y.

In some embodiments X and Ra are taken together with the atoms to which they are bonded to form a substituted benzo ring, and the compound has the formula XX-a

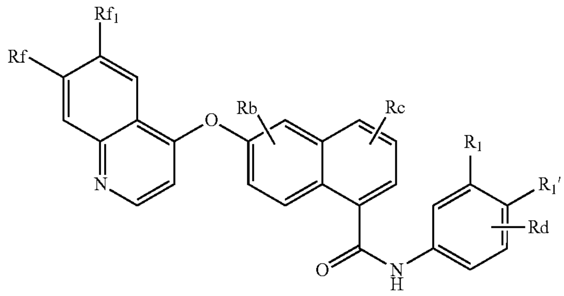

Wherein Rf, Rf1, Rb, Rc, Rd, $R_1$ and $R_{1'}$ are as described in Formula XX.

In some embodiments of formula XX-a, Rf and Rf1 are both methoxy. In other embodiments, Rb, Rc and Rd are each hydrogen. In some embodiments, R1 is -L-Y and $R_{1'}$ is $CF_3$, or $R_1$ is $CF_3$ and $R_{1'}$ is -L-Y.

In certain embodiments, $R_1$ is characterized in that the -L-Y moiety is capable of covalently binding to a Cys1 residue of c-KIT and/or PDGF, thereby irreversibly inhibiting the enzyme.

Exemplary Compounds of Formula XX

XX-1

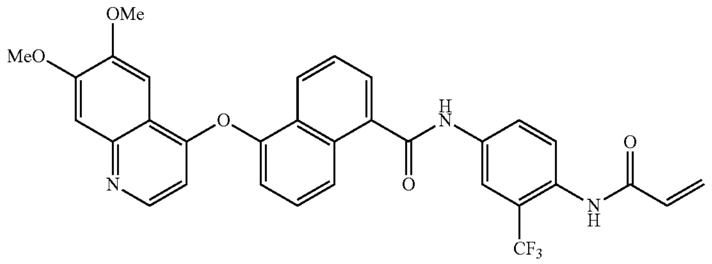

XX-2

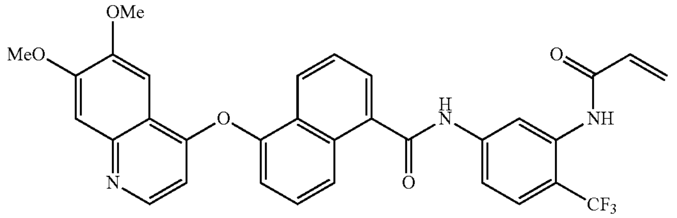

-continued
XX-3
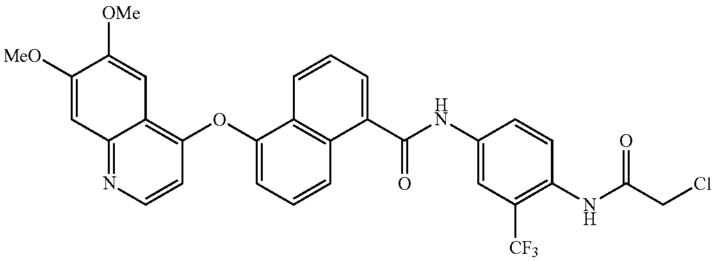
XX-4
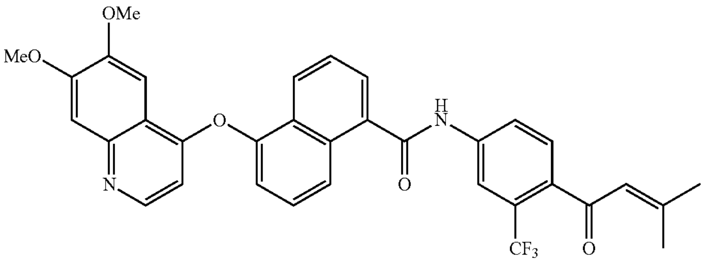
XX-5
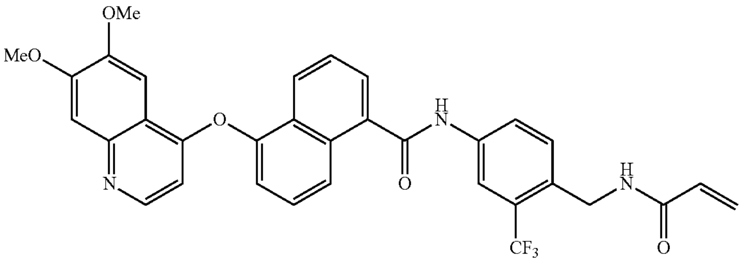
XX-6
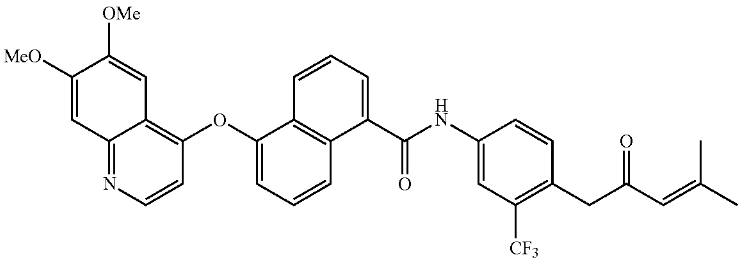
XX-7
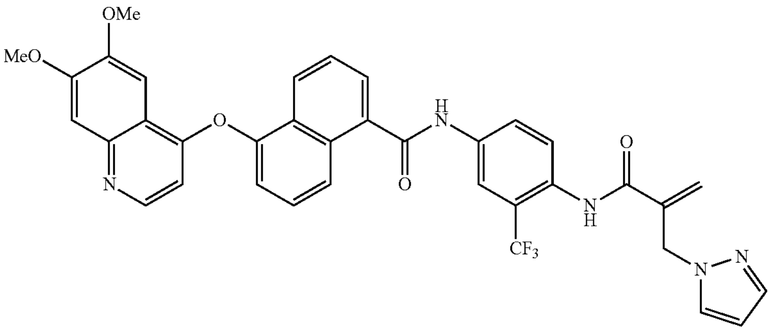

-continued
XX-8
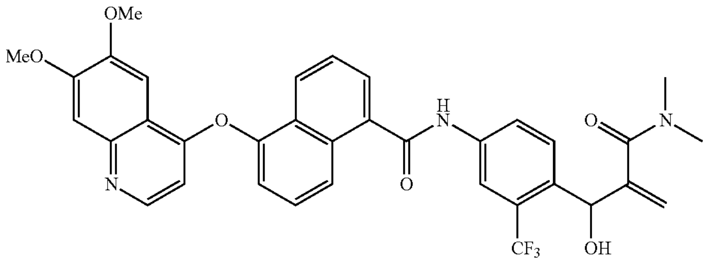
XX-9
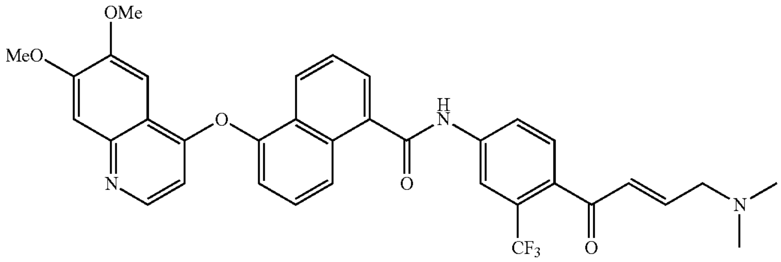
XX-10
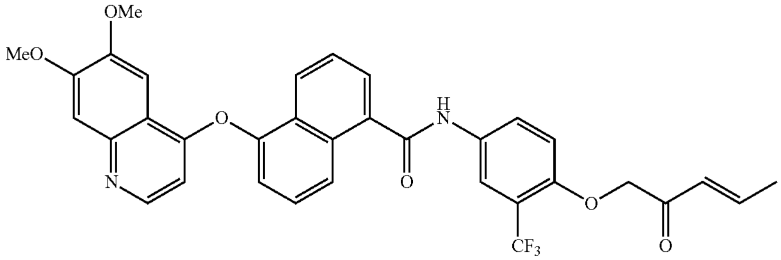
XX-11
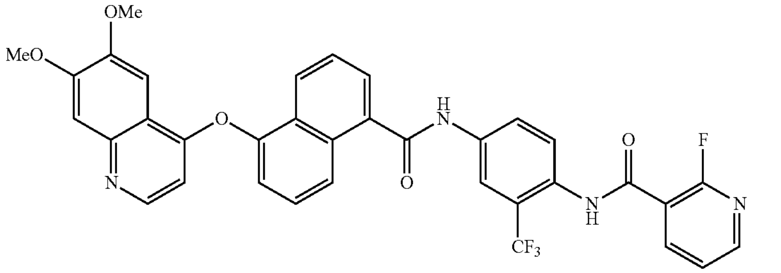
XX-12
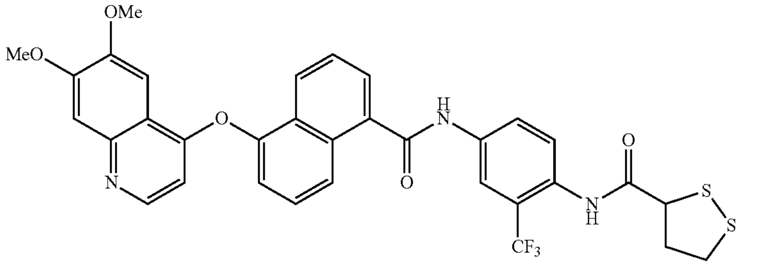
XX-13
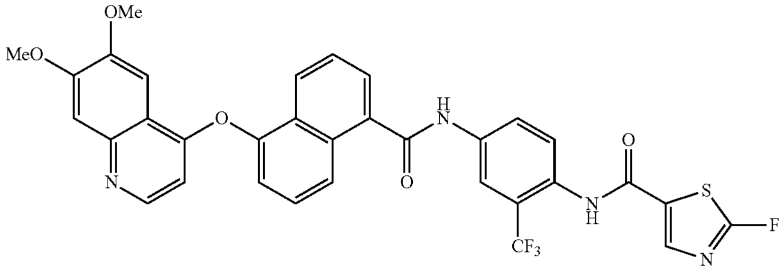

-continued
XX-14
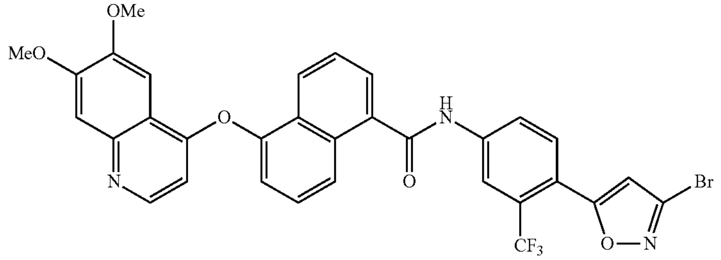
XX-15
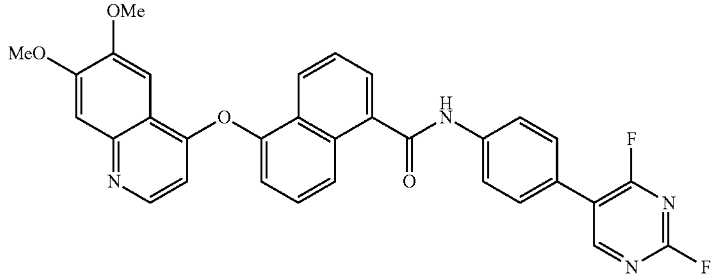
XX-16
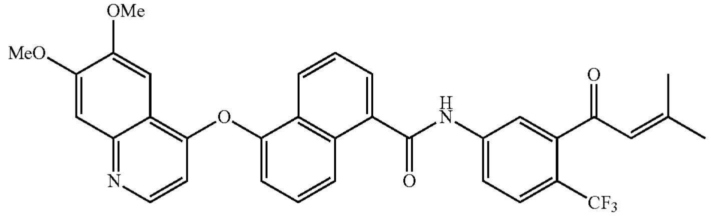
XX-17
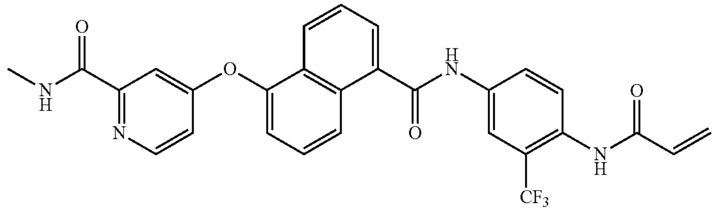
XX-18
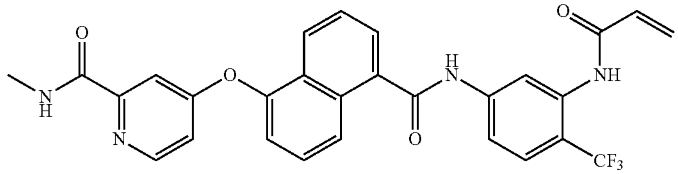
XX-19
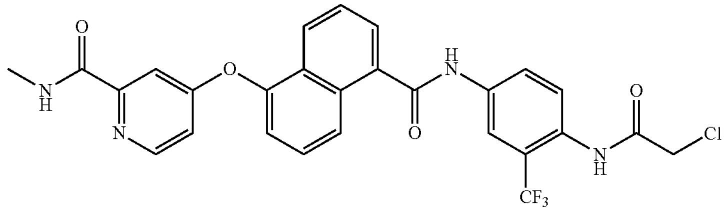
XX-20
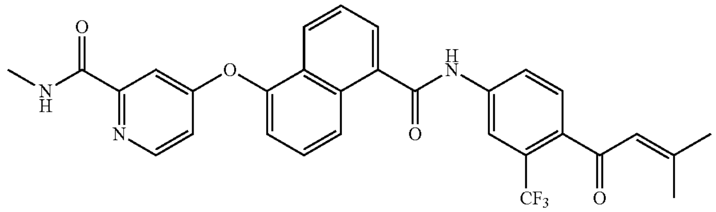

-continued
XX-21
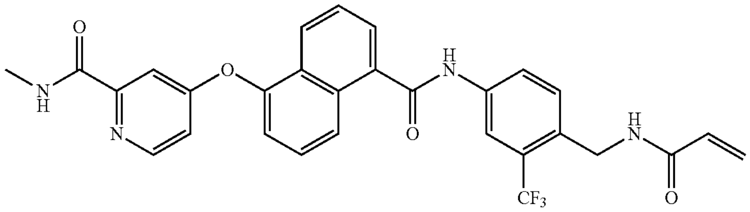
XX-22
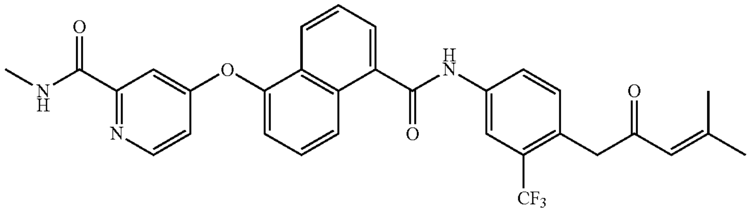
XX-23
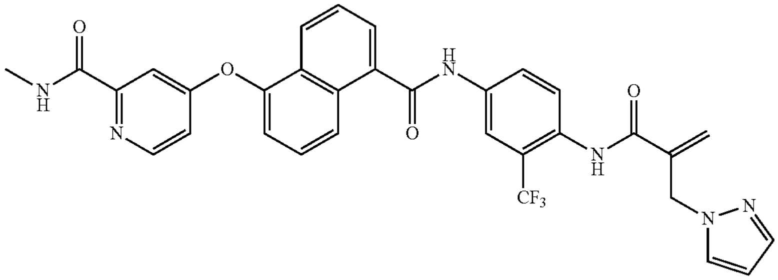
XX-24
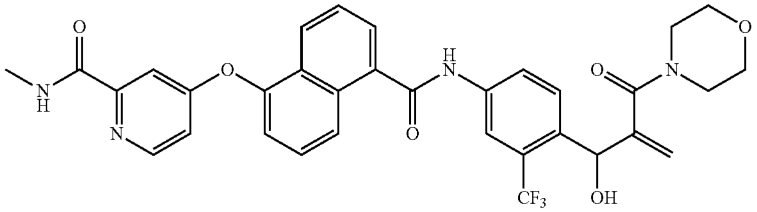
XX-25
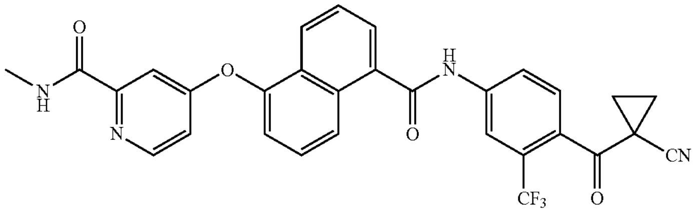
XX-26
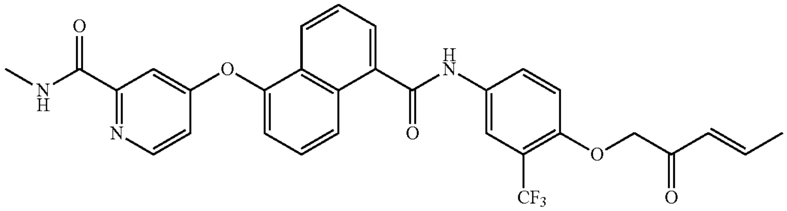
XX-27
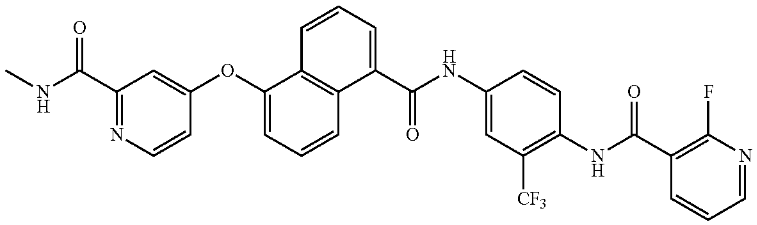

-continued

XX-28

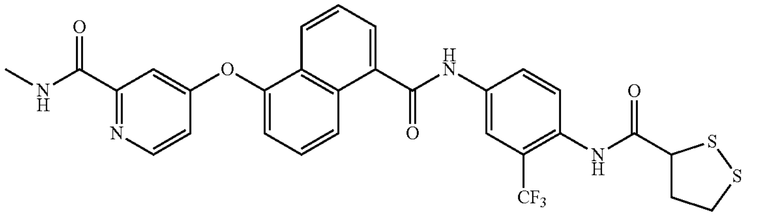

XX-29

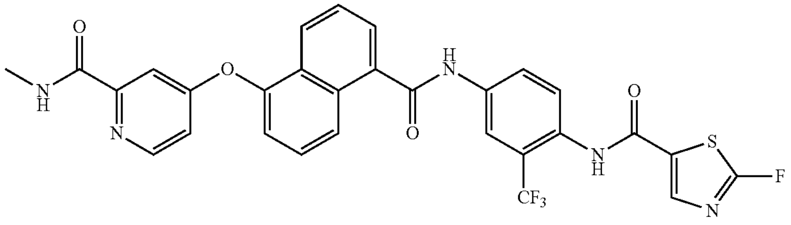

XX-30

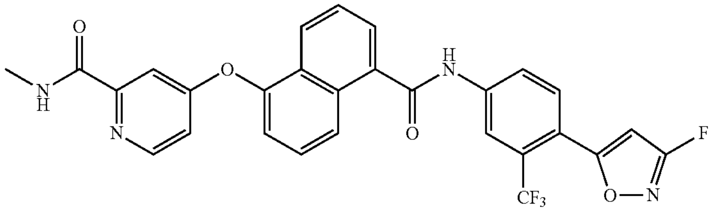

XX-31

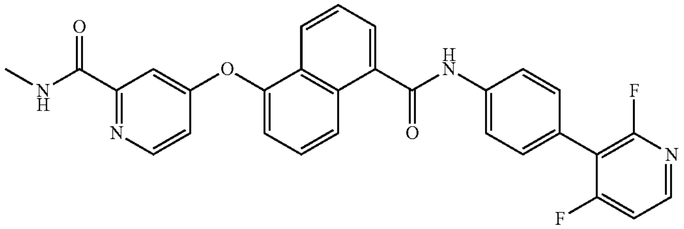

XX-32

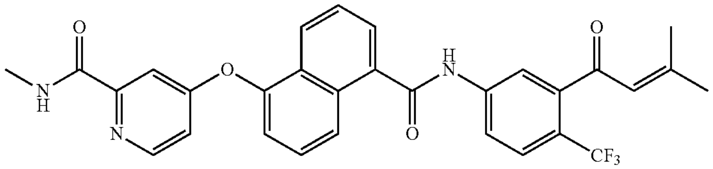

4. Uses, Formulation and Administration

A. Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a target protein kinase, particularly at least one of ZAP70, FLT3, PLK, FAK, JAK3, JNK, RON or a mutant thereof, in a biological sample or in a patient. In certain embodiments, the amount of compound in compositions of this invention is such that is effective to measurably inhibit at least one of ZAP70, FLT3, PLK, FAK, JAK3, JNK, RON, or a mutant thereof, in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term “inhibitorily active metabolite or residue thereof” means that a metabolite or residue thereof is also an inhibitor of at least one of ZAP70, FLT3, PLK, FAK, JAK3, JNK, RON, or a mutant thereof.

Compositions of the present invention may be administered orally, parenterally, by inhalation spray, topically, rectally, nasally, buccally, vaginally or via an implanted reservoir. The term “parenteral” as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer’s solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

B. Uses of Compounds and Pharmaceutically Acceptable Compositions

Compounds and compositions described herein are generally useful for the inhibition of protein kinase activity of one or more enzymes. The compounds can also be used to form conjugates as described herein, that can be used, for example, as biomarkers to assess efficacy of therapy using the irreversible inhibitor. The compounds can also be used as imaging agents, for example medical imaging. Compounds that contain a detectable moiety or label can bind the target protein kinase and be used to detect the presence or location of the formed conjugate. Suitable detectable moieties and labels are described herein.

Drug resistance is emerging as a significant challenge for targeted therapies. For example, drug resistance has been reported for Gleevec® and Iressa®, as well as several other kinase inhibitors in development. In addition, drug resistance has been reported for the cKit and PDGFR receptors. It has been reported that irreversible inhibitors may be effective against drug resistant forms of protein kinases (Kwak, E. L., R. Sordella, et al. (2005). "Irreversible inhibitors of the EGF receptor may circumvent acquired resistance to gefitinib." *PNAS* 102(21): 7665-7670.) Without wishing to be bound by any particular theory, it is believed that compounds of the present invention may be effective inhibitors of drug resistant forms of protein kinases.

As used herein, the term "clinical drug resistance" refers to the loss of susceptibility of a drug target to drug treatment as a consequence of mutations in the drug target.

As used herein, the term "resistance" refers to changes in the wild-type nucleic acid sequence coding a target protein, and/or the protein sequence of the target, which changes decrease or abolish the inhibitory effect of the inhibitor on the target protein.

Examples of kinases that are inhibited by the compounds and compositions described herein and against which the methods described herein are useful include ZAP70, FLT3, PLK, FAK, JAK3, JNK, RON, or a mutant thereof.

The activity of a compound utilized in this invention as an inhibitor of a target kinase, in particular ZAP70, FLT3, PLK, FAK, JAK3, JNK, RON or a mutant thereof, may be assayed in vitro, in vivo or in a cell line. In vitro assays include assays that determine inhibition of either the phosphorylation activity and/or the subsequent functional consequences, or ATPase activity of activated target kinase, or a mutant thereof. Alternate in vitro assays quantitate the ability of the inhibitor to bind to target kinase, e.g., ZAP70, FLT3, PLK, FAK, JAK3, JNK, RON. Inhibitor binding may be measured by radiolabelling the inhibitor prior to binding, isolating the inhibitor/target kinase complex and determining the amount of radiolabel bound. Alternatively, inhibitor binding may be determined by running a competition experiment where new inhibitors are incubated with target kinase bound to known radioligands. Detailed conditions for assaying a compound utilized in this invention as an inhibitor of certain kinases, or a mutant thereof, are set forth in the Examples below.

Protein kinases are a class of enzymes that catalyze the transfer of a phosphate group from ATP or GTP to an acceptor amino acid residue (e.g., tyrosine, serine, theonine) residue located on a protein substrate. Receptor kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of one or more of target kinase, e.g., ZAP70, FLT3, PLK, FAK, JAK3, JNK, RON and are therefore useful for treating one or more disorders associated with activity of one of more of the target kinases. Thus, in certain embodiments, the present invention provides a method for treating an ZAP70-mediated, FLT3-mediated, PLK-mediated, FAK-mediated, JAK3-mediate, JNK-mediated, or RON-mediated disorder comprising the step of administering to a patient in need thereof a compound of the present invention, or pharmaceutically acceptable composition thereof.

As used herein, the terms "ZAP70-mediated," "FLT3-mediated," "PLK-mediated," "FAK-mediated," "JAK3-mediate," "JNK-mediated," or "RON-mediated" disorders or conditions as used herein means any disease or other deleterious condition in which one or more of ZAP70, FLT3, PLK, FAK, JAK3, JNK, or RON, or a mutant thereof, are known to play a role. Accordingly, another embodiment of the present invention relates to treating or lessening the severity of one or more diseases in which one or more of ZAP70, FLT3, PLK, FAK, JAK3, JNK, and/or RON or a mutant thereof, are known to play a role. Specifically, the present invention relates to a method of treating or lessening the severity of a disease or condition selected from a proliferative disorder, wherein said method comprises administering to a patient in need thereof a compound or composition according to the present invention.

In some embodiments, the present invention provides a method for treating or lessening the severity of one or more disorders selected from a cancer. In some embodiments, the cancer is associated with a solid tumor. In certain embodiments, the cancer is breast cancer, glioblastoma, lung cancer, cancer of the head and neck, colorectal cancer, bladder cancer, or non-small cell lung cancer. In some embodiments, the present invention provides a method for treating or lessening the severity of one or more disorders selected from squamous cell carcinoma, salivary gland carcinoma, ovarian carcinoma, or pancreatic cancer. In other embodiments, the cancer is associated with a soluble tumor, such as a leukemia, lymphoma or myeloma.

In some embodiments, the present invention provides a method for treating or lessening the severity of one or more immunological or hypersensitivity disorders, such as asthma, allergy, transplant rejection, graft versus host disease, and autoimmune diseases such as rheumatoid arthritis, amyotrophic lateral sclerosis, and multiple sclerosis, as well as in solid and hematologic malignancies such as leukemias, lymphomas, and myelomas, wherein said method comprises administering to a patient in need thereof a composition according to the present invention.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated."

For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

C Inhibition of Angiogenesis

The invention relates to formulations, and methods for inhibiting angiogenesis. The method comprise topical, and preferably local, application of an irreversible inhibitor of an angiogenesis target. Angiogenesis refers to the growth of new blood vessels, and is an important contributor to a number of pathological conditions. For example, the role of angiogenesis is promoting and supporting the growth and viability of solid tumors is well documented. Angiogenesis also contributes to other pathological conditions, such as psoriasis and asthma, and pathological conditions of the eye, such as the wet form of age-related macular degeneration (AMD), diabetic retinopathy, diabetic macular edema, and retinopathy of prematurity.

Irreversible inhibitors provide advantages for inhibiting the activity of pro-angiogenic proteins to inhibit angiogenesis, for example to treat eye disease associated with ocular angiogenesis. Irreversible inhibitors produce sustained inhibition of a target protein. Once protein activity is inhibited it is only regained through the production of new target protein. Therefore, a short exposure to irreversible inhibitor can produce lasting effects without the need to maintain a saturating dose of a reversible inhibitor for a prolonged period, which can contribute to toxicity and side effects and is difficult to achieve and sustain via topical application.

The invention provide a method for treating angiogenesis comprising administering an irreversible inhibitors of one or more angiogenesis target proteins topically to the area where angiogenesis is to be inhibited. The invention provide a method for treating ocular angiogenesis comprising administering an irreversible inhibitors of one or more angiogenesis target proteins topically to the eye of a subject in need thereof. Suitable angiogenesis target proteins include any proteins that are involved in the growth of new blood vessels. Many kinases and non-kinases are known to play a role in angiogenesis. Examples of angiogenesis targets that are kinases include, VEGF Receptor 2/KDR, PDGFR (e.g., PDGFRA, PDGFRB), SRC, FAK, PI3K, MEK, FGFR (e.g., FGFR1, FGFR2, FGFR3, FGFR4), PLK (e.g., PLK-1, PLK-2, PLK-3) and Eph receptors. Non-kinase angiogenesis targets include methionine aminopeptide-2 and Hsp90. In this aspect of the invention, the irreversible inhibitor can form a covalent bond with a cysteine residue or with any other suitable residue.

An irreversible inhibitor that inhibits an angiogenesis target can be administered together with another therapeutic agent, such as an anti-VEGF agent or another irreversible inhibitor that inhibits a different angiogenesis target. This approach can provide additive or synergistic effects. When two or more agents are administered they are administered to provide substantial overlap of therapeutic effect, but need not be administered concurrently. For example, anti-VEGF agents, such as ranibizumab a Fab fragment of an antibody that binds VEGFA, are administered via intraocular injection about every 4 to 6 weeks. In combination therapy using ranibizumab and an irreversible inhibitor of an angiogenesis target, ranibuzumab can be administered by injection once every 4 to 6 weeks, and the irreversible inhibitor can be administered topically, for example, once a day.

In one embodiment, an irreversible inhibitor that inhibits more than one angiogenesis target is administered. Using this approach, superior therapy can be achieved using a single therapeutic agent. This can produce advantages for formulating the agent for topical administration by reducing the number of components and variables that must be considered in developing and testing the safety, efficacy and stability of the formulation. For example, an irreversible inhibitor that irreversibly inhibits KDR and PDGFR can be administered.

The irreversible inhibitor is formulated for topical administration. For example, the irreversible inhibitor can be formulated for delivery topical delivery to the lung (e.g., as an aerosol, such as a dry powder or liquid formulation) to treat asthma, as a cream, ointment, lotion or the like for topical application to the skin to treat psoriasis, or as an ocular formulation for topical application to the eye to treat an ocular disease. Such a formulation will contain an irreversible inhibitor and an pharmaceutically acceptable carrier. Additional components, such as preservatives, and agents to increase viscosity of the formulation such as natural or synthetic polymers may also be present. The ocular formulation can be in any suitable form, such as a liquid, an ointment, a hydrogel or a powder.

An effective amount of the irreversible inhibitor is administered topically, for example to the eye, lung or skin. An effective amount for topical delivery is an amount sufficient to have the desired effect, such as an amount sufficient to substantially inhibit the activity of the angiogenesis target, an amount to inhibit formation of new blood vessels, or an amount sufficient to slow or prevent disease progression.

In one aspect, the invention is a method of treating an angiogenesis-related ocular disease comprising topically administering to the eye of a subject in need thereof an effective amount of an irreversible inhibitor of an angiogenesis target. The irreversible inhibitor can be an irreversible inhibitor of one or more proteins selected from the group consisting of VEGF Receptor 2/KDR, PDGFR (e.g., PDGFRA, PDGFRB), SRC, FAK, PI3K, MEK, FGFR (e.g., FGFR1, FGFR2, FGFR3, FGFR4), PLK (e.g., PLK-1, PLK-2, PLK-3), Eph receptors, methionine aminopeptide-2 and Hsp90. In particular embodiments, the subject that is treated is afflicted with wet age-related macular degeneration, diabetic retinopathy, diabetic macular edema, and retinopathy of prematurity. In particular embodiments, an irreversible inhibitor of KDR and an irreversible inhibitor of PDGFR are administered. In another particular embodiment, a single irreversible inhibitor that inhibits KDR and PDGFR is administered.

In one aspect, the invention is a method of treating a psoriasis comprising topically administering to a subject in need thereof an effective amount of an irreversible inhibitor of an angiogenesis target. The irreversible inhibitor can be an irreversible inhibitor of one or more proteins selected from the group consisting of VEGF Receptor 2/KDR, PDGFR (e.g., PDGFRA, PDGFRB), SRC, FAK, PI3K, MEK, FGFR (e.g., FGFR1, FGFR2, FGFR3, FGFR4), PLK (e.g., PLK-1, PLK-2, PLK-3), Eph receptors, methionine aminopeptide-2 and Hsp90. In particular embodiments, the irreversible inhibitor is topically administered to the skin. In particular embodiments, an irreversible inhibitor of KDR and an irreversible inhibitor of PDGFR are administered. In another particular embodiment, a single irreversible inhibitor that inhibits KDR and PDGFR is administered.

In one aspect, the invention is a method of treating a asthma comprising topically administering to a subject in need thereof an effective amount of an irreversible inhibitor of an angiogenesis target. The irreversible inhibitor can be an irreversible inhibitor of one or more proteins selected from the group consisting of VEGF Receptor 2/KDR, PDGFR (e.g., PDGFRA, PDGFRB), SRC, FAK, PI3K, MEK, FGFR (e.g., FGFR1, FGFR2, FGFR3, FGFR4), PLK (e.g., PLK-1, PLK-2, PLK-3), Eph receptors, methionine aminopeptide-2 and Hsp90. In particular embodiments, the irreversible inhibitor is topically administered to the lung, for example as an aerosol. In particular embodiments, an irreversible inhibitor of KDR and an irreversible inhibitor of PDGFR are administered. In another particular embodiment, a single irreversible inhibitor that inhibits KDR and PDGFR is administered.

EXEMPLIFICATION

Example 1

N-(4-(4-(5-Cyanothiazol-2-ylamino)-6-(4-methylpiperazin-1-yl)pyrimidin-2-ylthio)phenyl)acrylamide II-1

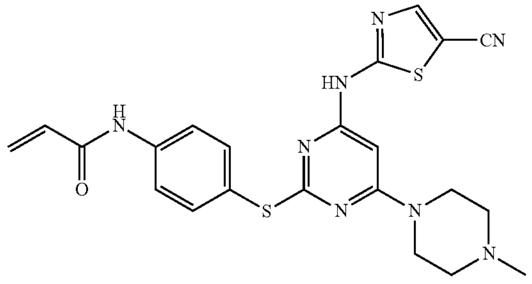 [SMILES: C=CC(=O)Nc1ccc(Sc2nc(Nc3ncc(C#N)s3)cc(N3CCN(C)CC3)n2)cc1]

2-(6-Chloro-2-methylthiopyrimidin-4-ylamino)thiazole-5-carbonitrile

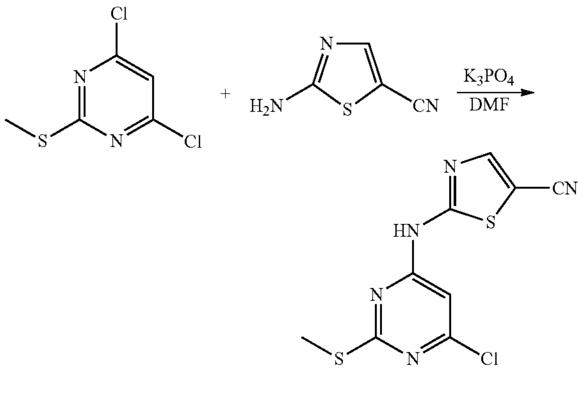

4,6-Dichloro-2-methylthiopyrimidine (3.00 g, 15.4 mmol) and 2-amino-thiazole-5-carbonitrile (1.92 g, 15.4 mmol) were dissolved in N,N-dimethylformamide (40 mL). Potassium phosphate tribasic was added to the reaction mixture and heated at 100° C. for 5 h. The solvent was removed in vacuo at 65° C. The residue was dissolved in water (50 mL). The pH was adjusted to 4-5 with concentrated HCl. The resulting solid was isolated, washed with water and diethyl ether and then vacuum dried to give the title compound, a brick red solid (2.397 g, 55% yield).

2-(6-Chloro-2-methanesulfonyl-pyrimidin-4-ylamino) thiazole-5-carbonitrile

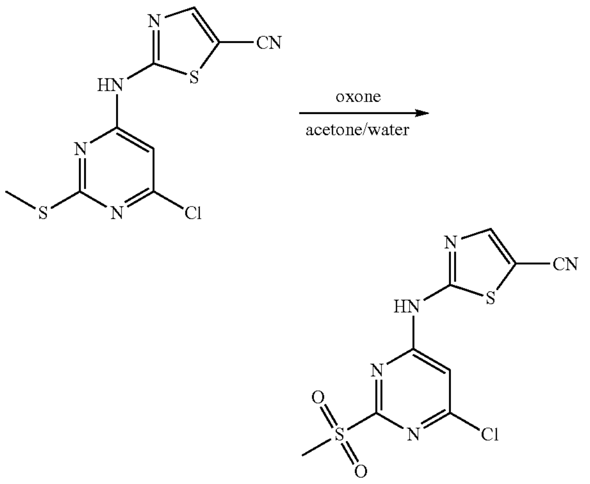

A slurry of oxone (15.5 g, 25.3 mmol) in water (30 mL) was added to 2-(6-Chloro-2-methylthiopyrimidin-4-ylamino)thiazole-5-carbonitrile (2.39 g, 8.42 mmol) in acetone (100 mL). The mixture was heated to 55° C. for 2 h. The warm mixture was filtered. Acetone was removed from the filtrate in vacuo and the resulting orange solid filtered, washed with water and dried in vacuo. The solid was placed on the top of a column of silica gel and eluted with EtOAc. The title compound, an orange foam, was isolated from the EtOAc (1.56 g, 59% yield).

2-(2-(4-Aminophenylthio)-6-chloropyrimidin-4-ylamino)thiazole-5-carbonitrile

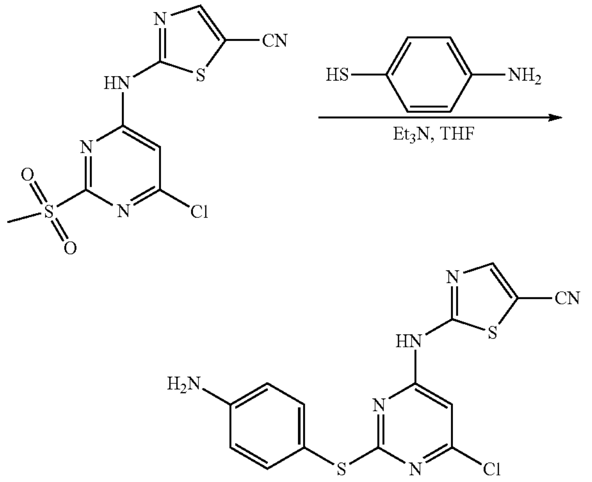

2-(2-Chloro-6-methanesulfonyl-pyrimidin-4-ylamino)-thiazole-5-carbonitrile (800 mg, 2.53 mmol) was dissolved in tetrahydrofuran (40 mL) and triethylamine (0.5 mL, 3.6 mmol). The solution was degassed with several cycles of vacuum and nitrogen flush. With the reaction was under $N_2$, 4-aminothiophenol (380 mg, 3.04 mol) was added in a solution of tetrahydrofuran (5 mL). The solution was stirred at room temperature, under $N_2$ for 2.5 h. The reaction volume was reduced to about 5 mL by evaporation in vacuo and the remaining solution applied to a dry silica gel column (40 g). The column was eluted with hexane:ethyl acetate 1:1 to give the title compound (351 mg, 38% yield).

2-(2-(4-Aminophenylthio)-6-(4-methylpiperazin-1-yl)pyrimidin-4-ylamino)thiazole-5-carbonitrile

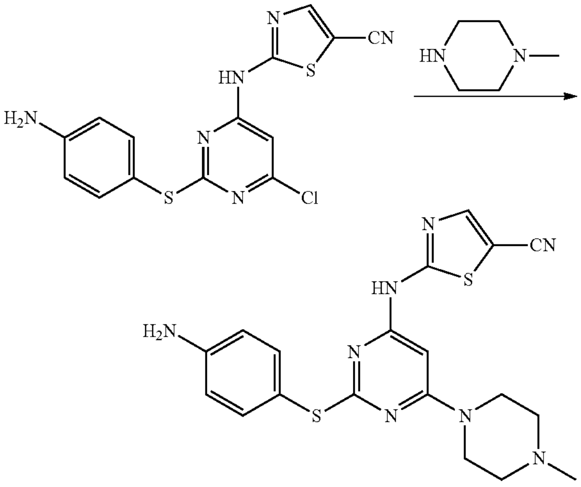

1-Methylpiperazine (2.7 mL, 24 mmol) was added to 2-(2-(4-aminophenylthio)-6-chloropyrimidin-4-ylamino) thiazole-5-carbonitrile (385 mg, 1.07 mmol). The mixture was heated at 100° C. for 3 h. Water (25 mL) was added to the cooled reaction and the resulting solid filtered. The solid was washed with water (2×10 mL), vacuum dried at 45° C. for 3 h to give the title compound (385 mg 85% yield).

N-(4-(4-(5-Cyanothiazol-2-ylamino)-6-(4-methyl-piperazin-1-yl)pyrimidin-2-ylthio)phenyl)acrylamide II-1

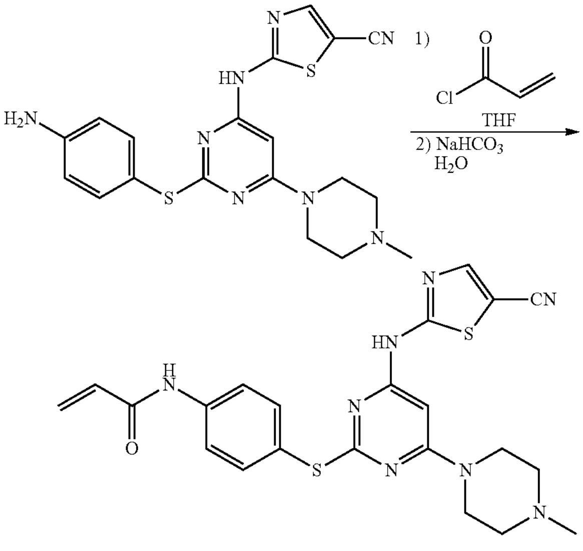

A suspension of 2-(2-(4-aminophenylthio)-6-(4-methyl-piperazin-1-yl)pyrimidin-4-ylamino)thiazole-5-carbonitrile (150 mg, 0.35 mmol) in tetrahydrofuran (6 mL) and triethylamine (0.5 mL, 1.4 mmol) and cooled in an ice bath under $N_2$. Acryloyl chloride (0.034 mL, 0.42 mmol) was added. After 20 min the reaction was warmed to room temperature. The reaction was followed by HPLC. After 2.5 h additional acryloyl chloride (0.010 mL, 0.11 mmol) was added. After 6 hr the solvent was evaporated to give yellow solid. The solid was triturated with water (2×2 mL) and then vacuum dried at room temperature for 2 h. Flash Chromatography on silica gel, eluting with chloroform:MeOH:ammonia 17:3:0.1 gave the title compound (10.3 mg, 6% yield): MS (ES+) 479 (M+H, 100%); 1H NMR (DMSO-$d_6$, 300 MHz) δ (ppm): 12.0 (broad s, 1H), 10.35 (s, 1H), 8.07 (s, 1H), 7.84 (d, 2H, J=3.9 Hz), 7.58 (d, 2H, J=3.9 Hz), 6.44 (m, 1H), 6.40 (d, 1H, J=10 Hz) 5.89 (s, 1H), 5.73 (d, 1H, J=5.7 Hz), 3.47 (s, 3H), 2.34 (m, 4H), 2.20 (m, 4H).

Reversible Reference Compound 1

N-(4-(4-(5-Cyanothiazol-2-ylamino)-6-(4-methyl-piperazin-1-yl)pyrimidin-2-ylthio)phenyl)propionamide

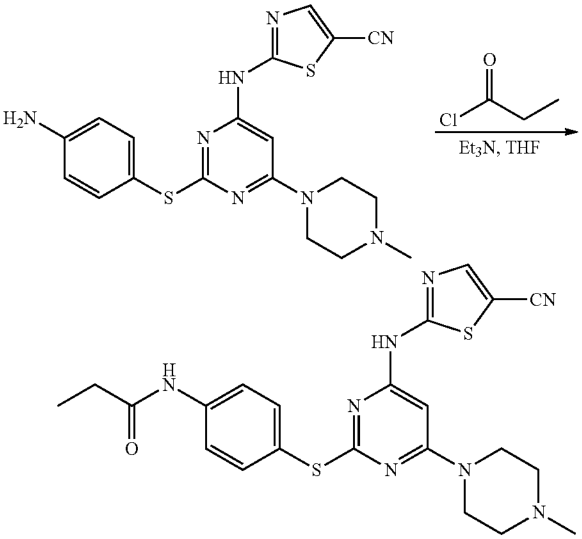

A suspension of 2-(2-(4-aminophenylthio)-6-(4-methyl-piperazin-1-yl) pyrimidin-4-ylamino)thiazole-5-carbonitrile (70 mg, 0.16 mmol) was suspended in tetrahydrofuran (6 mL) and triethylamine (0.1 mL, 0.7 mmol) and cooled in an ice bath under $N_2$. Propionyl chloride (0.017 mL, 0.19 mmol) in tetrahydrofuran (1 mL) was added. After 10 min the reaction was warmed to room temperature. After 50 minutes additional propionyl chloride (0.005 mL, 0.055 mmol) was added. After 2 h the solvent was evaporated to give an off-white solid. The solid was triturated with water (2×2 mL) and EtOAc (2×2 mL) and then vacuum dried at 45° C. for 16 h to give the title compound (56 mg, 78% yield): MS (ES+) 503 (M+Na, 25%), 481 (M+H, 100%); 1H NMR (DMSO-$d_6$, 300 MHz) δ (ppm): 12.0 (s, 1H), 10.07 (s, 1H), 8.08 (s, 1H), 7.77 (d, 2H, J=3.7 Hz), 7.54 (d, 2H, J=3.7 Hz), 5.92 (s, 1H), 3.54 (s, 3H), 2.48 (m, 4H), 2.34 (m, 4H), 1.07 (m, 3H, J=1.5 Hz).

Example 2

2-(2-(1-Acryloylpiperidin-4-ylthio)-6-(4-methylpiperazin-1-yl)pyrimidin-4-ylamino)thiazole-5-carbonitrile II-2

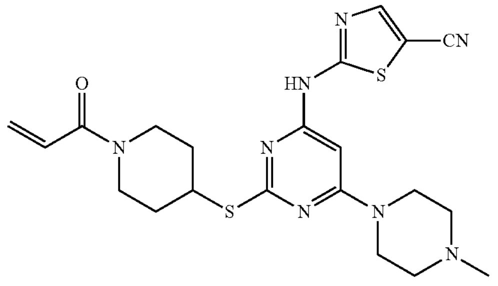 [SMILES: C=CC(=O)N1CCC(Sc2nc(Nc3ncc(C#N)s3)cc(N3CCN(C)CC3)n2)CC1]

Tert-butyl 4-(4-chloro-6-(5-cyanothiazol-2-ylamino)pyrimidin-2-ylthio)piperidine-1-carboxylate

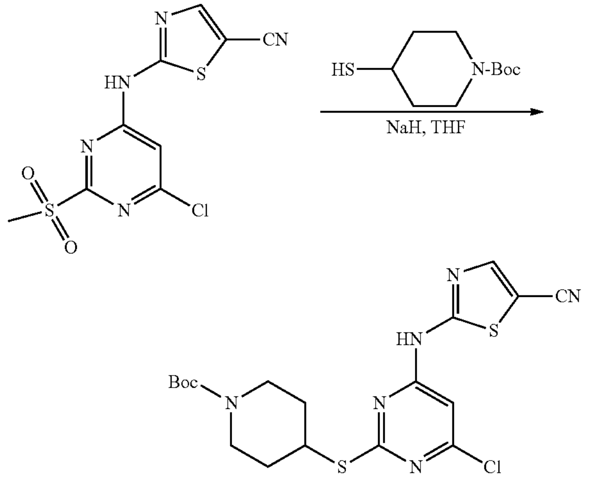

A stirred solution of 4-mercapto-piperidine-1-carboxylic acid, tert-butyl ester (482 mg, 2.22 mmol, (prepared as described in WO2007/030366, pg. 136) in anhydrous THF (20 ml) under nitrogen was treated with sodium hydride (60% dispersion, 189 mg, 4.72 mmol). After 15 minutes, 2-(6-chloro-2-methanesulfonyl-pyrimidin-4-ylamino) thiazole-5-carbonitrile (700 mg, 2.22 mmol) was added in one portion and the reaction mixture was stirred at ambient temperature for 18 hours. The excess reagent was quenched with water and the organic solvent was removed in vacuo. The residue was partitioned between water and ethyl acetate and the organic layer was dried ($MgSO_4$), was filtered and was concentrated in vacuo. The crude product was eluted through a flash column (silica gel 60, 230-400 mesh, 3:2 hexanes EtOAc) to give the title compound, an orange, amorphous solid, 250 mg (25%). MS ($ES^+$): $(M+Na)^+$=475; $^1$H-NMR (DMSO-$d_6$): δ 12.82 (br s, 1H), 8.38 (s, 1H), 6.79 (s, 1H), 4.02 (m, 1H), 3.80 (m, 4H), 1.98-2.08 (m, 2H), 1.55 (m, 2H), 1.39 (s, 9H).

Tert-butyl 4-(4-(5-cyanothiazol-2-ylamino)-6-(4-methylpiperazin-1-yl)pyrimidin-2-ylthio)piperidine-1-carboxylate

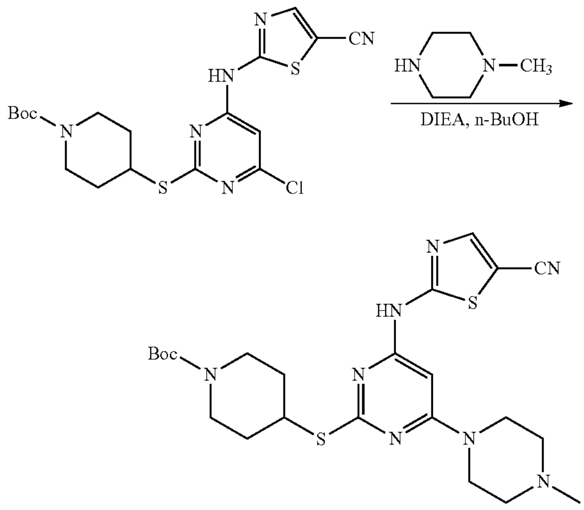

A mixture of tert-butyl 4-(4-chloro-6-(5-cyanothiazol-2-ylamino)pyrimidin-2-ylthio)piperidine-1-carboxylate (250 mg, 0.55 mmol), N-methylpiperazine (0.187 ml, 1.66 mmol) and N,N-diisopropylethyl-amine (0.289 ml, 1.66 mmol) in n-butanol (7 ml) was heated at 120° C. for 1.5 hours. The reaction mixture was concentrated and the residue was slurried with water. The product obtained was filtered off and washed with water and acetone to give 225 mg (79%) of the title compound. MS ($ES^+$): $(M+1)^+$=517, $(M+Na)^+$=539; $^1$H-NMR (DMSO-$d_6$): □12.00 (br s, 1H), 8.25 (s, 1H), 5.93 (s, 1H), 3.92 (m, 1H), 3.83 (m, 2H), 3.50 (m, 4H), 3.04 (m, 2H), 2.36 (m, 4H), 2.20 (s, 3H), 2.06 (m, 2H), 1.52 (m, 2H), 1.40 (s, 9H).

2-(2-(Piperidin-4-ylthio)-6-(4-methylpiperazin-1-yl)pyrimidin-4-ylamino)thiazole-5-carbonitrile

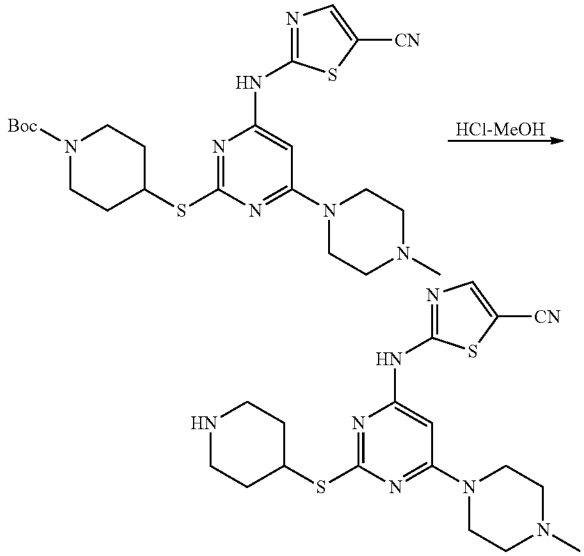

A mixture of tert-butyl 4-(4-(5-cyanothiazol-2-ylamino)-6-(4-methylpiperazin-1-yl)pyrimidin-2-ylthio)piperidine-1-carboxylate (292 mg, 0.57 mmol) in 3.0 N HCl solution in methanol (8 mL) was stirred under ambient temperature for 19 hours. The reaction mixture was concentrated and the residue was swirled in saturated aqueous sodium bicarbonate solution for a few minutes. The light beige, amorphous solid was washed with water upon collection and dried in vacuo at 40-50° C. to give 187 mg (79%) of the title compound. MS ($ES^+$) $(M+1)^+$=417.

2-(2-(1-Acryloylpiperidin-4-ylthio)-6-(4-methylpiperazin-1-yl)pyrimidin-4-ylamino)thiazole-5-carbonitrile II-2

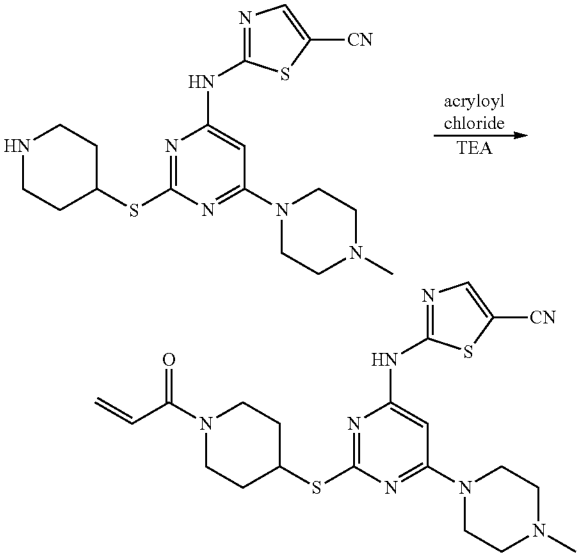

To a solution of 2-(2-(piperidin-4-ylthio)-6-(4-methylpiperazin-1-yl)pyrimidin-4-ylamino)thiazole-5-carbonitrile (225 mg) in anhydrous THF (2 ml) was added triethylamine (0.188 ml, 1.35 mmol) and acryloyl chloride (0.044 ml, 0.54 mmol). The reaction mixture was stirred at ambient temperature for 1 hour and was concentrated in vacuo. The residue was eluted through a flash column (silica gel 60, 230-400 mesh, 5% 2.0 M $NH_3$-methanolic solution in chloroform to 10% 2.0 M $NH_3$-methanolic solution in chloroform). The product was found to co-elute with triethylamine hydrochloride and this mixture was swirled in water for 12 hours at ambient temperature. The remaining insoluble solid was collected, was washed with water, and was dried in vacuo at 40-50° C. to give 21.5 mg (10%) of the title compound. MS ($ES^+$): $(M+1)^+$=471; $^1$H-NMR (DMSO-$d_6$): δ 12.00 (br s, 1H), 8.25 (s, 1H), 6.90 (m, 1H), 6.10 (d, 1H), 5.94 (s, 1H), 5.68 (d, 1H), 4.40 (m, 1H), 4.00 (m, 2H), 3.60 (m, 4H), 3.10 (m, 2H), 2.37 (m, 4H), 2.21 (s, 3H), 2.12 (m, 2H), 1.60 (m, 2H).

Example 3

(E)-2-(2-(1-(4-dimethylamino)but-2-enoyl)piperidin-4-ylthio)-6-(4-methylpiperazin-1-yl)pyrimidin-4-ylamino)thiazole-5-carbonitrile II-5

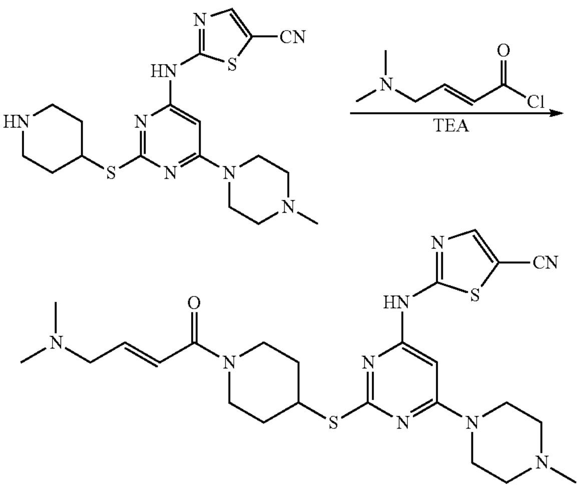

To a stirring suspension at 0° C. under $N_2$ of 4-dimethylamino-but-2-enoic acid, hydrochloride (0.322 g, 1.944 mmol) in 10 mL of THF containing 5 drops of DMF was added dropwise (via syringe) oxalyl chloride (0.18 mL, 2.063 mmol). Gas formation started immediately. The sample was stirred at 0° C. for ~30 min, room temperature for ~4 h, recooled to 0° C., then treated with dropwise addition of a suspension of 2-(2-(piperidin-4-ylthio)-6-(4-methylpiperazin-1-yl)pyrimidin-4-ylamino)thiazole-5-carbonitrile (0.405 g, 0.972 mmol) in 50 mL of THF followed by triethylamine (0.34 mL, 2.439 mmol). The ice-bath was removed and the sample was stirred at room temperature for ~2 h. The sample was concentrated then partitioned between EtOAc and sat. $NaHCO_3$ solution. The organic extract was washed with saturated aqueous NaCl solution, was dried ($MgSO_4$), was filtered, concentrated and was chromatographed (MPLC, silica gel, 200 mL of 10% MeOH in $CHCl_3$ then 1% concentrated ammonium hydroxide-10% methanol in $CHCl_3$ to give 0.201 g (39%) of the title compound, as off-white solid. $^1$H NMR (DMSO-$d_6$) δ 1.59 (m, 2H), 2.16-2.21 (m, 11H), 2.36-2.38 (m, 4H), 3.03 (m, 4H), 3.52 (m, 4H), 3.97-4.01 (m, 2H), 4.19-4.21 (m, 1H), 5.95 (b, 1H), 6.61 (m, 2H), 8.26 (s, 1H) and 12.0 (bs, 1H). MS (APCI) m/z 528 (M+1, 100%).

Example 4

2-(2-(1-but-2-ynoyl)piperidin-4-ylthio)-6-(4-methylpiperazin-1-yl)pyrimidin-4-ylamino)thiazole-5-carbonitrile II-3

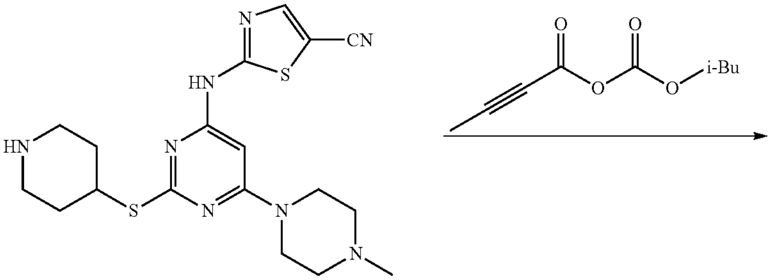

-continued

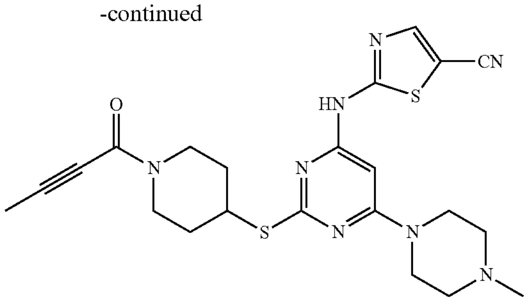

To a stirring solution at 0° C. under $N_2$ of 2-butynoic acid (0.63 g, 0.749 mmol) and triethylamine (0.104 mL, 0.746 mmol) in 5 mL of THF was added iso-butylchloroformate (0.097 mL, 0.748 mmol). The mixture was stirred at 0° C. for 15 min then a solution of 2-(2-(piperidin-4-ylthio)-6-(4-methylpiperazin-1-yl)pyrimidin-4-ylamino)thiazole-5-carbonitrile (0.250 g, 0.600 mmol) in 20 mL of THF was added dropwise. The sample was stirred at 0° C. for 1 h, then partitioned between EtOAc and sat. $NaHCO_3$ solution. The organic extract was washed with saturated aqueous NaCl solution, dried ($MgSO_4$), was filtered and was concentrated in vacuo. The residue was chromatographed (silica gel, 1% $NH_4OH$-10% MeOH in $CHCl_3$) to give 0.067 g (23%) of the title compound, as light yellow solid. $^1H$ NMR (DMSO-$d_6$) δ 1.35-1.66 (m, 2H), 2.03-2.21 (m, 7H), 2.38 (bs, 3H), 3.10 (m, 1H), 3.34-3.52 (m, which also contains the water peak, ~7H), 3.98 (bs, 1H), 4.08-4.16 (m, 2H), 5.95 (s, 1H), 8.26 (s, 1H) and 12.10 (bs, 1H). MS (APCI) m/z 483 (M+1, 100%).

Reversible Reference Compound 2

2-(2-(1-Propionylpiperidin-4-ylthio)-6-(4-methylpiperazin-1-yl)pyrimidin-4-ylamino)thiazole-5-carbonitrile

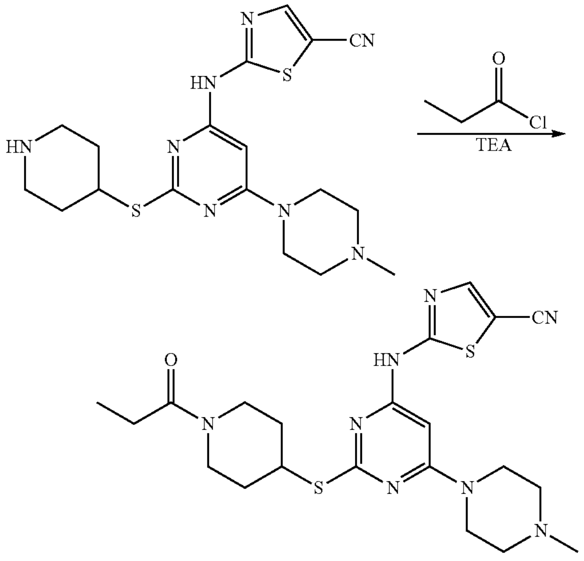

To a stirring suspension at 0° C. under $N_2$ of 2-(2-(piperidin-4-ylthio)-6-(4-methylpiperazin-1-yl)pyrimidin-4-ylamino)thiazole-5-carbonitrile (0.200 g, 0.480 mmol) and triethylamine (0.20 mL, 1.435 mmol) in 5 mL of THF was added propionyl chloride (0.05 mL, 0.576 mmol). The sample was stirred at 0° C. for 1 h, then partitioned between EtOAc and sat. $NaHCO_3$ solution. The organic extract was washed with saturated aqueous NaCl solution, dried ($MgSO_4$), filtered and concentrated. The residue was chromatographed (silica gel, 1% $NH_4OH$-10% MeOH in $CHCl_3$) to give 0.169 g (74%) of the title compound, as a light yellow solid. $^1H$ NMR (DMSO-$d_6$) δ 0.99 (m, 3H), 1.49-1.60 (m, 2H), 2.0-2.6 (m, which also contains DMSO, ~11H), 2.97 (m, 1H), 3.2-3.6 (m, which also contains water, ~5H), 3.81-4.19 (m, 3H), 5.95 (s, 1H), 8.26 (s, 1H) and 12.06 (bs, 1H). MS (APCI) m/z 473 (M+1, 100%).

Example 5

N-(2-(4-(5-cyanothiazol-2-ylamino)-6-(4-methylpiperazin-1-yl)pyrimidin-2-ylthio)ethyl)acrylamide II-4

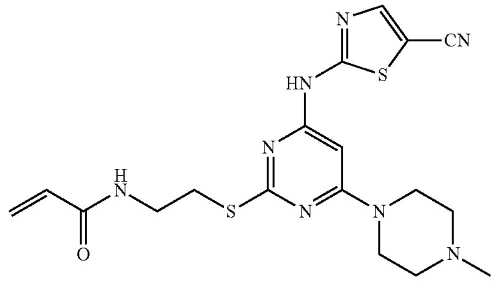 [SMILES: C=CC(=O)NCCSc1nc(Nc2ncc(C#N)s2)cc(N2CCN(C)CC2)n1]

Tert-butyl 2-(4-chloro-6-(5-cyanothiazol-2-ylamino)pyrimidin-2-ylthio)ethylcarbamate

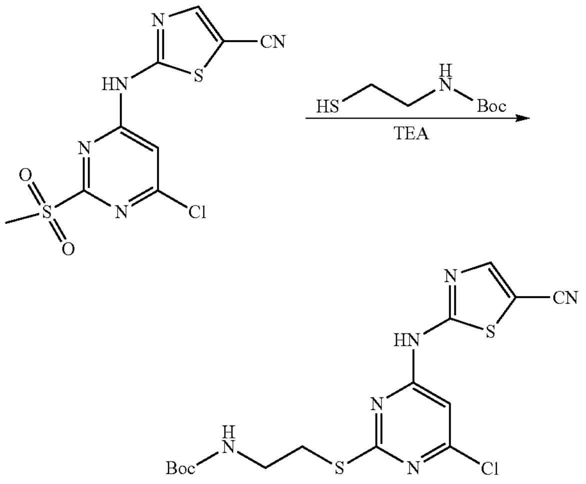

To a stirring solution at room temperature under $N_2$ of 2-(6-chloro-2-methanesulfonylpyrimidin-4-ylamino)thiazole-5-carbonitrile (2.80 g, 8.87 mmol) and triethylamine (3.1 mL, 22.24 mmol) in 50 ml of THF was added dropwise a solution of Boc-cysteamine (2.00 g, 11.28 mmol) in 10 mL of THF. The reaction was stirred for 4 h, concentrated, then partitioned between EtOAc and sat. NaHCO3 solution. The organic extract was washed with saturated aqueous NaCl solution, dried ($MgSO_4$), filtered and concentrated to a brown oil and solid. The sample was suspended into 30 mL of EtOAc, stirred at room temperature for 30 min and filtered. The solid was washed with cold EtOAc and vacuum dried to give 1.44 g (39%) of the title compound as tan solid. MS (APCI) m/z 435/437 (M+23, 100/43%), 413/415 (M+1, 10/4%) and 357/359 (M−55, 20/8%). TLC ($SiO_2$, 50% EtOAc in hexanes), a single component at $R_f$ 0.37.

Tert-butyl 2-(4-(5-cyanothiazol-2-ylamino)-6-(4-methylpiperazin-1-yl)pyrimidin-2-ylthio)ethylcarbamate

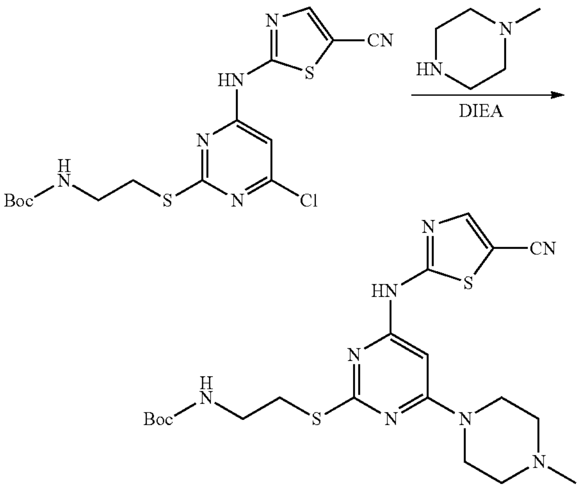

A mixture of tert-butyl 2-(4-chloro-6-(5-cyanothiazol-2-ylamino)pyrimidin-2-ylthio)ethylcarbamate (1.44 g, 3.48 mmol), 1-methylpiperazine (0.48 mL, 4.32 mmol) and diisopropylethylamine (1.30 mL, 7.46 mmol) in 20 mL of EtOH in a sealed vial was heated at 80° C. for 24 h. The sample was cooled and was filtered. The solid was washed with cold EtOH and vacuum dried to give 1.16 g (70%) of the title compound as off-white solid. MS (APCI) m/z 477 (M+1, 100%). TLC ($SiO_2$, 10% MeOH in $CHCl_3$), a single component at $R_f$ 0.28.

2-(4-(5-Cyanothiazol-2-ylamino)-6-(4-methylpiperazin-1-yl)pyrimidin-2-ylthio)ethylamine

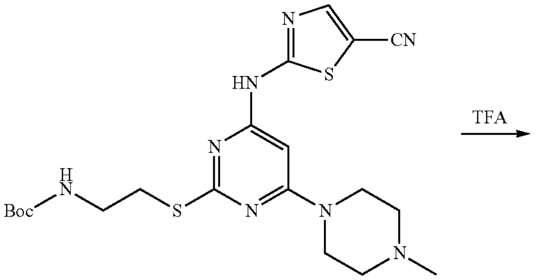

-continued

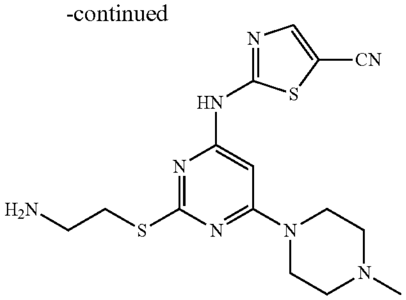

A stirring suspension at room temperature under $N_2$ of tert-butyl 2-(4-(5-cyanothiazol-2-ylamino)-6-(4-methylpiperazin-1-yl)pyrimidin-2-ylthio)ethylcarbamate (1.13 g, 2.37 mmol) in 20 mL of $CH_2Cl_2$ was treated with 20 mL of trifluoroacetic acid. Upon addition, all solid went into solution. The solution was stirred at room temperature for 2 h then concentrated in vacuo to a dark brown oil. Basification of the residue with sat. $NaHCO_3$ solution produced a solid. The sample was stirred at room temperature for ~2 h, filtered, washed with water, and vacuum dried to give 0.913 g (>100%) of the title compound as light brown solid.

N-(2-(4-(5-cyanothiazol-2-ylamino)-6-(4-methylpiperazin-1-yl)pyrimidin-2-ylthio)ethyl)acrylamide II-4

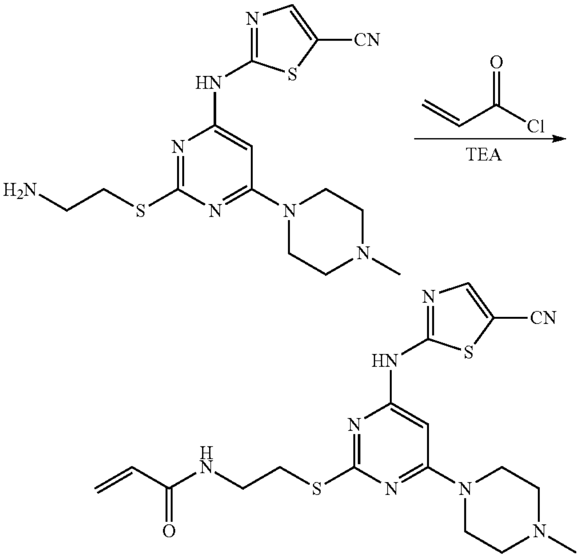

To a stirring suspension at 0° C. under $N_2$ of 2-(4-(5-cyanothiazol-2-ylamino)-6-(4-methylpiperazin-1-yl)pyrimidin-2-ylthio)ethylamine (0.473 g, 1.256 mmol) and triethylamine (0.35 mL, 2.51 mmol) in 25 mL of THF was added acryloyl chloride (0.13 mL, 1.60 mmol). The sample was allowed to slowly warm to room temperature overnight then partitioned between EtOAc and 1 N NaOH solution. The organic extract was washed with saturated aqueous NaCl solution, dried ($MgSO_4$), filtered, concentrated, and chromatographed (silica gel, 1% concentrated $NH_4OH$-10% MeOH in $CHCl_3$) to give the title compound as an off-white solid. $^1H$ NMR (DMSO-$d_6$) δ 2.12-2.61 (m, which also contains DMSO, ~7H), 3.16-3.67 (m, which also contains water, ~8H), 5.59-5.61 (m, 1H), 5.95 (s, 1H), 6.11 (m, 1H), 6.19-6.21 (m, 2H), 8.24 9s, 1H) and 8.37 (bs, 1H). MS (APCI) m/z 431 (M+1, 100%).

Example 6

N-(4-(4-(3-Methyl-1H-pyrazol-5-ylamino)-6-(4-methylpiperazin-1-yl)pyrimidin-2ylthio)phenyl)acrylamide II-53

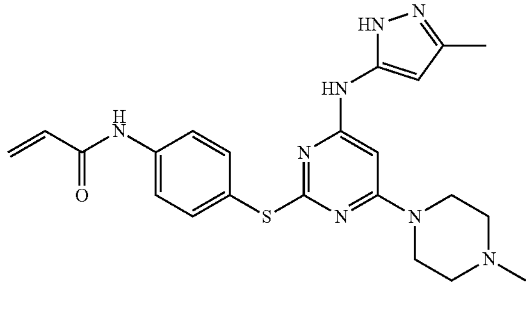 [SMILES: C=CC(=O)Nc1ccc(Sc2nc(Nc3cc(C)n[nH]3)cc(N3CCN(C)CC3)n2)cc1]

4,6-dichloro-2-methylsulfonyl pyrimidine

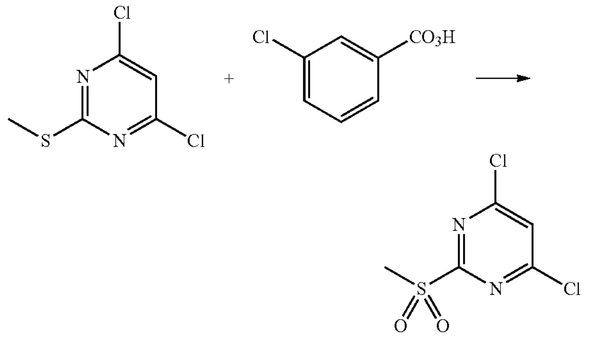

4,6-Dichloro-2-(methylthio)pyridine (24 g, 0.123 mol) was dissolved in 500 ml of $CH_2Cl_2$, under stirring and ice bath. Meta-chloroperoxybenzoic acid (about 0.29 mol) was added slowly in a period of 40 min. The reaction mixture was stirred for 4 h, was diluted with $CH_2Cl_2$, and was then treated with 50% $Na_2S_2O_3$/$NaHCO_3$ solution. The organic phase was washed with saturated aqueous NaCl, was dried over $MgSO_4$, and was then filtered. Removal of solvent under vacuum yielded about 24 g of the title compound as a light purple colored solid.

Tert-Butyl N-(4-mercaptophenyl)carbamate

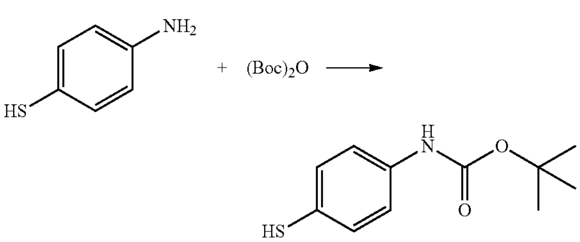

4-Aminothiophenol (25 g, 0.2 mol) was dissolved in 250 ml of EtOAc. The solution was cooled with an ice bath and di-t-butyldicarbonate (48 g, 0.22 mol) was added dropwise with stirring. After stirring for 1 h, saturated $NaHCO_3$ in water (200 ml) was added. The reaction mixture was stirred for overnight. The organic phase was washed with water, saturated aqueous NaCl solution, was dried over $MgSO_4$, and was then filtered. Removal of organic solvent under vacuum yielded about 68 g of yellow oil, which was treated with hexane to yield about 50 g of the title compound as a yellow solid.

Tert-butyl 4-(4,6-dichloropyrimidin-2-ylthio)phenylcarbamate

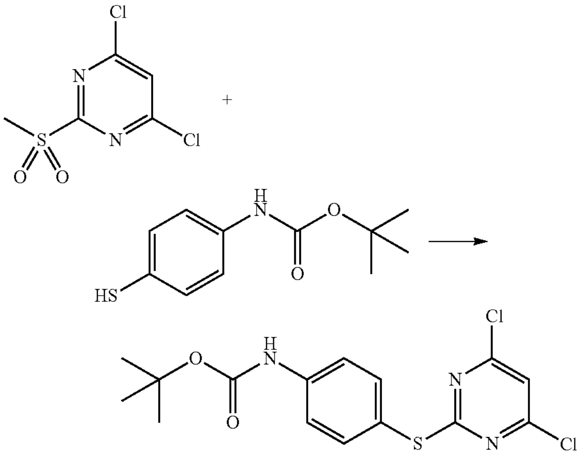

A mixture of tert-butyl N-(4-mercaptophenyl)carbamate (5 g, 0.022 mol) and 4,6-dichloro-2-methylsulfonylpyrimidine (5 g, 0.026 mol) in 150 ml of t-BuOH was heated at reflux for 1 h and then NaOAc (0.5 g) was added. The reaction was heated at reflux for an additional 14 h. Solvent was removed under vacuum and the residue was dissolved in ethyl acetate. The organic phase was washed successively with $K_2CO_3$ solution and saturated aqueous NaCl, was dried over $MgSO_4$, and was then filtered. Removal of the solvent yielded about 5 g of the title compound as yellow solid.

Tert-butyl 4-(4-chloro-6-(3-methyl-1H-pyrazol-5-ylamino)pyrimidin-2-ylthio)phenylcarbamate

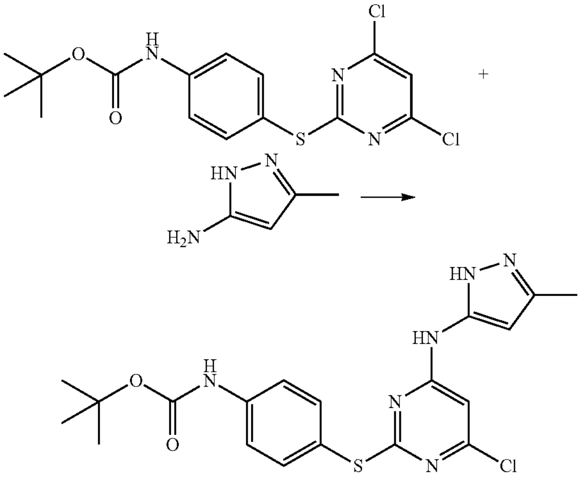

A solution of tert-butyl 4(4,6-dichloropyrimidin-2-ylthio) phenylcarbamate (100 mg, 0.27 mmol), 3-methyl-5-amino-1H-pyrazol (28.7 mg, 0.3 mmol), diisopropylethylamine (41.87 mg), and NaI (48.6 mg, 0.324 mmol) in 1 ml of DMF was heated at 85° C. for 4 h. Following cooling and dilution with 20 mL of ethyl acetate, the organic phase was washed successively with water and saturated aqueous NaCl, was dried over MgSO4, and was then filtered. Removal of solvent in vacuum yielded about 120 mg of crude product, which was purified by silica gel (30% EtOAc/hexanes) to yield 64 mg of the title compound.

Tert-butyl 4-(4-(3-methyl-1H-pyrazol-5-ylamino)-6-(4-methylpiperazin-1-yl)pyrimidin-2-ylthio)phenylcarbamate

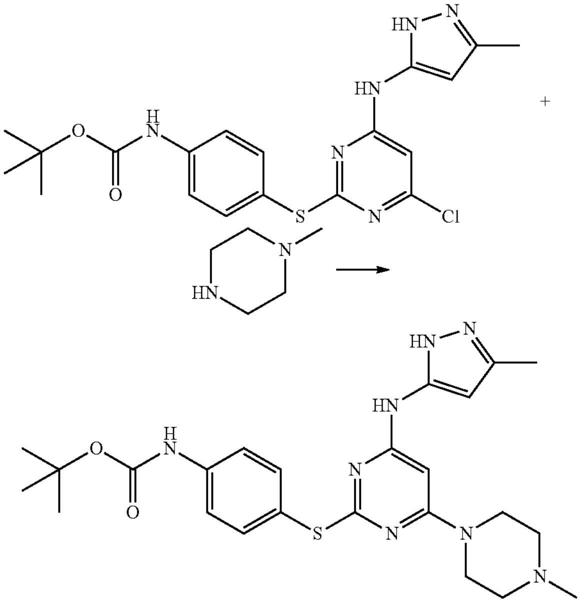

A mixture of tert-butyl 4-(4-chloro-6-(3-methyl-1H-pyrazol-5-ylamino)pyrimidin-2-ylthio)phenylcarbamate (61 mg, 0.14 mmol) and 1 ml of methylpiperazine was heated at 110° C. for 2 h. The reaction mixture was diluted with 20 mL ethyl acetate. The organic phase was washed with water, was dried over MgSO4, and was then filtered. Removal of solvent in vacuum yielded about 68.2 mg of crude product as light brown solid, which was purified by silica gel (30% EtOAc/hexanes) to give 49.5 mg of the title compound. MS ($M+H^+$): 497.36.

2-(4-Aminophenylthio)-N-(3-methyl-1H-pyrazol-5-ylamino)-6-(4-methylpiperazin-1-yl)pyrimidin-4-amine

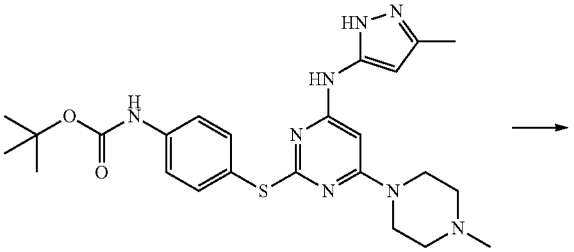

-continued

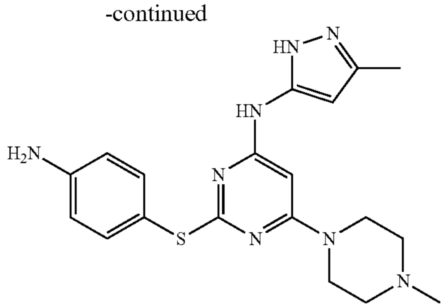

A solution of tert-butyl 4-(4-(3-methyl-1H-pyrazol-5-ylamino)-6-(4-methylpiperazin-1-yl)pyrimidin-2-ylthio) phenylcarbamate (44.5 mg) in 5 ml of MeOH was treated with 2 ml of 5N HCl. When TLC was showed that no starting material remained, the reaction mixture was diluted with ethyl acetate. The organic phase was washed with $NaHCO_3$, and saturated aqueous NaCl, was dried over $MgSO_4$, and was then filtered. Removal of solvent in vacuum gave about 32.1 mg of the title compound. $^1$H NMR (300 MHz, DMSO-$d_6$): δ 11.68 (s, 1H), 9.65 (s, 1H), 9.25 (s, 1H), 7.60 (d, 2H), 7.45 (d, 2H), 6.00 (s, 1H), 5.43 (s, 1H), 2.38 (m, 4H), 2.20 (m, 2H), 2.05 (m, 2H), 1.52 (s, 6H), MS ($M+H^+$): 397.18.

N-(4-(4-(3-Methyl-1H-pyrazol-5-ylamino)-6-(4-methylpiperazin-1-yl)pyrimidin-2ylthio)phenyl)acrylamide II-53

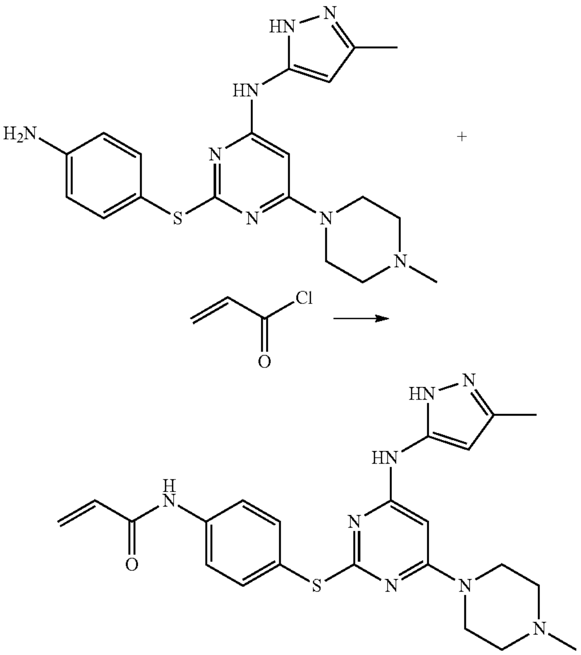

Acryloyl chloride (6.85 mL, 7.33 mg, 0.081 mmol) was added to a solution of 2-(4-aminophenylthio)-N-(3-methyl-1H-pyrazol-5-yl)-6-(4-methylpiperazin-1-yl)pyrimidin-4-amine (32.1 mg, 0.081 mmol) in 3 ml of $CH_2Cl_2$ at 0° C. After 30 min the reaction mixture was diluted with ethyl acetate. The organic phase was washed with NaHCO3 solution, saturated aqueous NaCl solution, was dried over MgSO4, and was then filtered. Removal of solvent yielded the crude product, which was purified by silica gel to give 20 mg of the product. MS ($M+H^+$): 451.36.

Example 7

4-(4-(3-(4-Acrylamido-3-(trifluoromethyl)phenyl)ureido)phenoxy)-N-methylpicolinamide XVIII-11

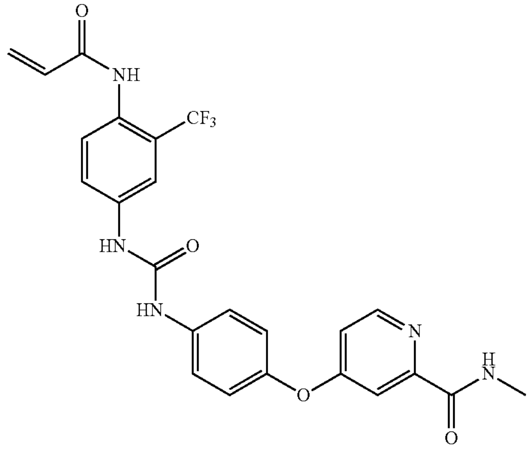 [SMILES: C=CC(=O)Nc1ccc(NC(=O)Nc2ccc(Oc3ccnc(C(=O)NC)c3)cc2)cc1C(F)(F)F]

C,C'-Bis-tert-butyl N-4-amino-2-trifluoromethylphenyl)iminodicarbonate

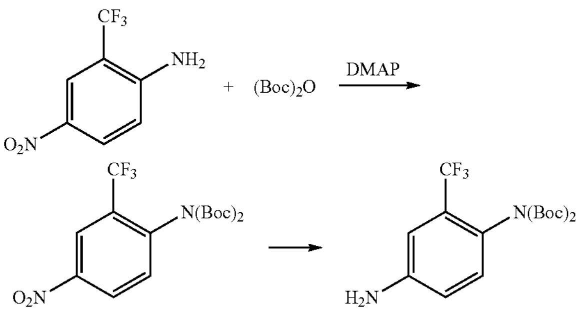

To a stirred solution of 4-nitro-2-trifluoromethylaniline (4.12 g, 20 mmol) in 1,4-dioxane (50 mL) was added 4-DMAP (1.22 g, 10 mmol) and Boc anhydride (13.13 g, 50 mmol) at room temperature. The reaction mixture was heated at 110° C. for 2 h. The reaction mixture was cooled, concentrated under reduced pressure and the residue was dissolved in EtOAc (25 mL). It was washed with 10% citric acid solution (5 mL), water (5 mL) and saturated aqueous NaCl (2 mL). Drying over $Na_2SO_4$ followed by concentration under reduced pressure offered a residue which was purified by column chromatography ($SiO_2$, 60-120, pet ether/ethyl acetate, 6/4) to give 5.3 g (13 mmol) of the bis-Boc intermediate as faint yellow solid. This material was dissolved in 50 mL methanol. To this solution under nitrogen atmosphere was added acetic acid (3 mL) followed by iron powder (1.71 g, 19.4 g-atom). The reaction mixture was heated at 70° C. for 2 h, was cooled to room temperature and was filtered through a Celite® bed. The filtrate was concentrated under reduced pressure and the residue was diluted with EtOAc (30 mL). It was washed with water (2 mL) and saturated aqueous NaCl (2 mL) and dried over $Na_2SO_4$. Concentration under reduced pressure gave a residue, which was further purified by column chromatography ($SiO_2$, 60-120, pet ether/ethyl acetate, 6/4) to give 3.19 g of the title compound as an off-white solid.

4-(4-(3-(4-amino-3-(trifluoromethyl)phenyl)ureido)phenoxy)-N-methylpicolinamide

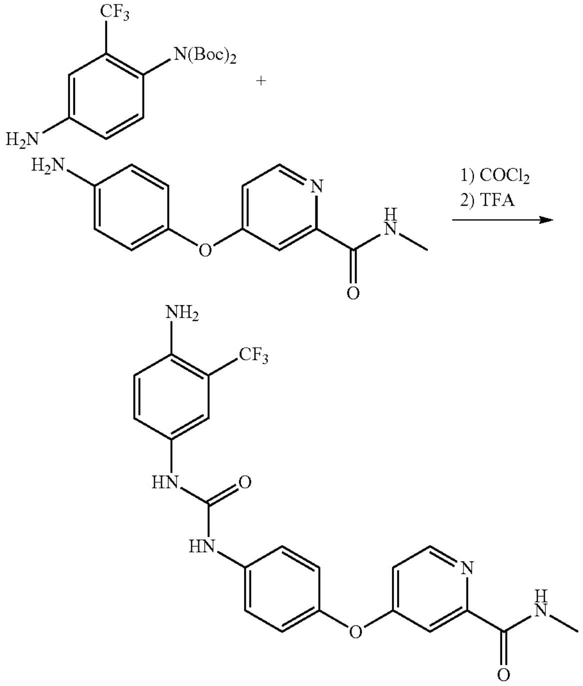

To a stirred solution of C,C'-bis-tert-butyl N-4-amino-2-trifluoromethylphenyl)iminodicarbonate (0.5 g, 1.32 mmol) and $Et_3N$ (0.6 mL, 5.97 mmol) in toluene (5 mL) was added phosgene (20% solution in toluene, 0.91 mL, 1.85 mmol). The reaction mixture heated at reflux for 16 h and then was cooled to rt. 4-(4-Aminophenoxy)-N-methyl-2-pyridinecarboxamide, (0.32 g, 1.32 mmol) was added and the reaction mixture was heated at reflux for 2 h. After that the reaction mixture was quenched with water (5 mL) in a fume-hood, extracted with EtOAc (2×20 mL). The ethyl acetate extract was washed with saturated aqueous NaCl (15 mL), was dried over $Na_2SO_4$ and was concentrated under reduced pressure to 0.62 g of the title compound.

4-(4-(3-(4-Acrylamido-3-(trifluoromethyl)phenyl)ureido)phenoxy)-N-methylpicolinamide XVIII-11

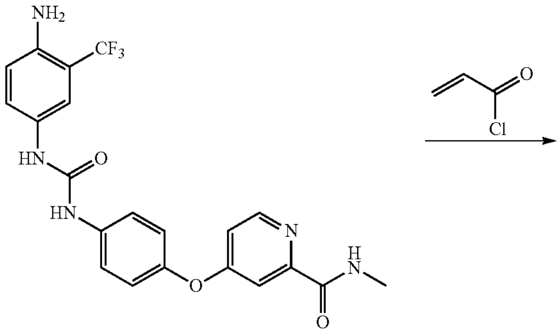

-continued

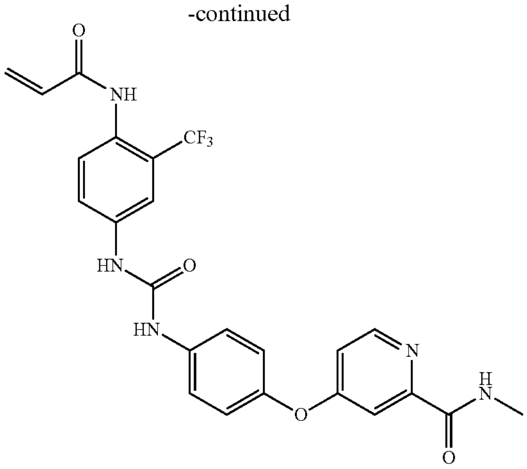

To a stirred solution of 4-(4-(3-(4-amino-3-(trifluoromethyl)phenyl)ureido)phenoxy)-N-methylpicolinamide (0.1 g, 0.22 mmol) and pyridine (0.035 g, 0.45 mmol) in DMF (5 mL) was added acryloyl chloride (0.03 g, 0.33 mmol) at 0° C. The reaction was allowed to come to rt and further stirred for 12 h, quenched with ice-cold water (10 mL) and extracted with EtOAc (2×20 mL). The ethyl acetate extract was washed with saturated aqueous NaCl solution (5 mL), dried over $Na_2SO_4$ and concentrated under reduced pressure to get crude XVIII-11. The crude product was purified initially by neutral alumina column chromatography and then by prep. HPLC to give 18 mg of the title compound as a white solid. $^1$H NMR (MeOD) δ ppm: 2.94 (s, 3H), 5.82 (d, J=10.0 Hz, 1H), 6.37 (dd, J=1.76 & 17.16 Hz, 1H), 6.50 (dd, J=10.28 & 17.16 Hz, 1H), 7.06 (dd, J=2.6 & 5.94 Hz, 1H), 7.11-7.15 (m, 2H), 7.45 (d, J=8.64 Hz, 1H), 7.56-7.61 (m, 3H), 7.67 (dd, J=2.24 & 8.48 Hz, 1H), 8.0 (s, 1H), 8.45-8.55 (m, 1H); LCMS: m/e 501 (M+2)

Example 8

(E)-4-(4-(3-(4-(Dimethylamino)but-2-enamido)-3-(trifluoromethyl)phenyl)ureido)phenoxy)-N-methylpicolinamide XVIII-12

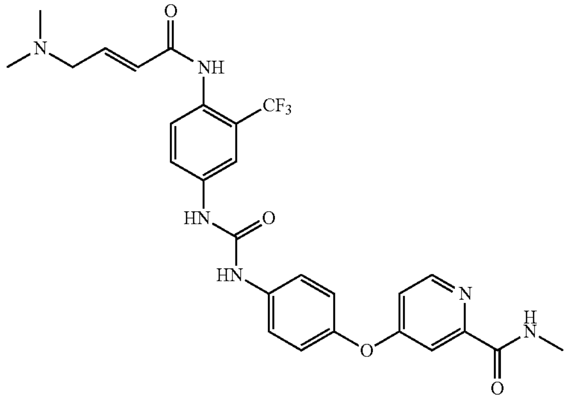

To a stirred solution of 4-dimethylamino-2-butenoic acid (0.186 g, 1.12 mmol) in $CH_3CN$ (2.0 mL) was added oxalyl chloride (0.171 g, 1.34 mmol) at 0° C. The reaction mixture was allowed to stir at 0° C. for ½ h and then at rt for 2 h. Finally it was heated at 45° C. for 5 min, cooled and the reaction mixture was taken for next step without further purification.

To a stirred solution of 4-(4-(3-(4-amino-3-(trifluoromethyl)phenyl)ureido)phenoxy)-N-methylpicolinamide (0.1 g, 0.224 mmol) in NMP (2.0 mL) at 0° C. was added the 4-dimethylaminobut-2-enoyl chloride from above. The reaction mixture was stirred at 0° C. to 10° C. for 2 h, quenched with cold water (10 mL), basified with triethylamine, and extracted with dichloromethane (3×10 mL). The combined organic extract was washed successively with water (10 mL) and saturated aqueous NaCl solution (10 mL) and was dried over $Na_2SO_4$. Concentration under reduced pressure followed by purification by column chromatography (neutral $Al_2O_3$, $CHCl_3$/MeOH, 99/1) gave the title compound (0.04 g) as a light yellow solid. $^1$H NMR (DMSO-$d_6$) δ ppm: 2.17 (s, 6H), 2.77 (d, J=4.84 Hz, 3H), 3.04 (d, J=5.8 Hz, 2H), 6.32 (d, J=14.84 Hz, 1H), 6.69 (td, J=5.92 & 15.44 Hz, 1H), 7.13-7.18 (m, 3H), 7.37-7.40 (m, 2H), 7.58-7.60 (m, 3H), 8.00 (d, J=2.36 Hz, 1H), 8.49 (d, J=5.6 Hz, 1H), 8.77 (q, J=4.52 Hz, 1H), 8.95 (s, 1H), 9.10 (s, 1H), 9.55 (s, 1H); LCMS m/e 557.2 (M+1).

Example 9

4-(4-(3-(4-(2-Chloroacetamido)-3-(trifluoromethyl)phenyl)ureido)phenoxy)-N-methylpicolinamide XVIII-13

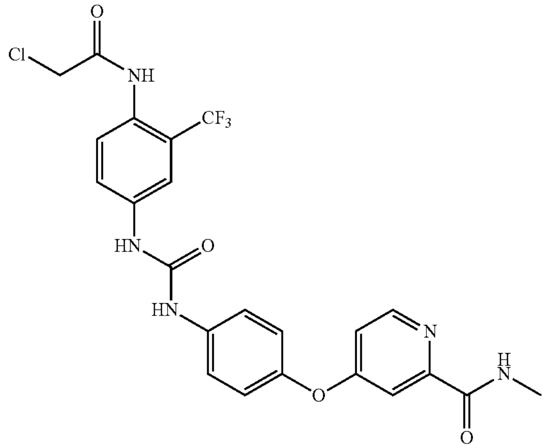 [SMILES: CNC(=O)c1cc(Oc2ccc(NC(=O)Nc3ccc(NC(=O)CCl)c(C(F)(F)F)c3)cc2)ccn1]

To a stirred solution of 4-(4-(3-(4-amino-3-(trifluoromethyl)phenyl)ureido)phenoxy)-N-methylpicolinamide (0.15 g, 0.34 mmol) and $Et_3N$ (0.05 g, 0.51 mmol) in dry THF (10 mL), was added chloroacetyl chloride (0.045 g, 0.404 mmol), dropwise at 0° C. under $N_2$. The reaction mixture was allowed to come to rt and stirred at this temperature for 12 h. It was concentrated under reduced pressure, quenched with water (10 mL) and the mixture was extracted with EtOAc (2×25 mL). The combined EtOAc extract was washed with water (10 mL), saturated aqueous NaCl (10 mL), dried over $Na_2SO_4$ and concentrated under reduced pressure to get a residue. It was further purified by column chromatography (neutral $Al_2O_3$, $CHCl_3$/MeOH mixtures) to the title compound (0.025 g) as a cream colored solid. $^1$H NMR (DMSO-$d_6$) δ ppm: 2.77 (d, J=4.8 Hz, 3H), 4.28 (s, 2H), 7.13-7.18 (m, 3H), 7.37-7.39 (m, 2H), 7.58-7.63 (m, 3H), 8.20 (d, J=2.28 Hz, 1H), 8.50 (d, J=5.6 Hz, 1H), 8.70-8.80 (m, 1H), 8.96 (s, 1H), 9.13 (s, 1H), 9.83 (s, 1H); LCMS: m/e 522.2 (M+1).

Example 10

4-(4-(3-(4-(2-Chloropropionamido)-3-(trifluoromethyl)phenyl)ureido)phenoxy)-N-methylpicolinamide XVIII-14

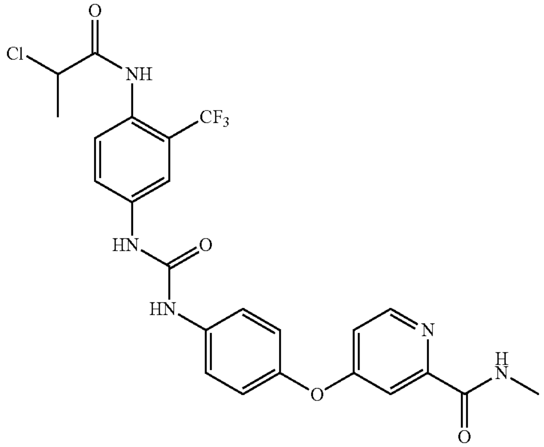 [SMILES: CNC(=O)c1cc(Oc2ccc(NC(=O)Nc3ccc(NC(=O)C(C)Cl)c(C(F)(F)F)c3)cc2)ccn1]

To a stirred solution of 4-(4-(3-(4-amino-3-(trifluoromethyl)phenyl)ureido)phenoxy)-N-methylpicolinamide (0.15 g, 0.34 mmol) in THF (5 mL) was added $Et_3N$ (0.07 mL, 0.51 mmol) and the reaction mixture was cooled to 0° C. To it was added 2-chloropropionyl chloride (0.064 g, 0.51 mmol) dropwise, at the same temperature. The reaction mixture was allowed to come to rt and then stir for 12 h at the same temperature. It was diluted with ethyl acetate (5 mL), washed with water (2 mL), saturated aqueous NaCl solution (2 mL) and was dried over $Na_2SO_4$. Filtration followed by concentration under reduced pressure offered a residue which was purified by column chromatography ($SiO_2$, 60-120, chloroform/methanol, 9/1) to give the title compound (0.01 g) as a white solid. $^1H$ NMR (DMSO-$d_6$) δ ppm: 1.61 (d, J=6.8 Hz, 3H), 2.79 (d, J=5.2 Hz, 3H), 4.75 (q, J=6.8 Hz, 1H), 7.14-7.19 (m, 3H), 7.35-7.39 (m, 2H), 7.59-7.65 (m, 3H), 8.02 (d, J=2.4 Hz, 1H), 8.51 (d, J=5.6 Hz, 1H), 8.70-8.80 (m, 1H), 8.98 (s, 1H), 9.15 (s, 1H), 9.85 (s, 1H); LCMS: m/e 536.1 (M+1).

Reversible Reference Compound 3

4-(4-(3-(4-(Propionamido)-3-(trifluoromethyl)phenyl)ureido)phenoxy)-N-methylpicolinamide

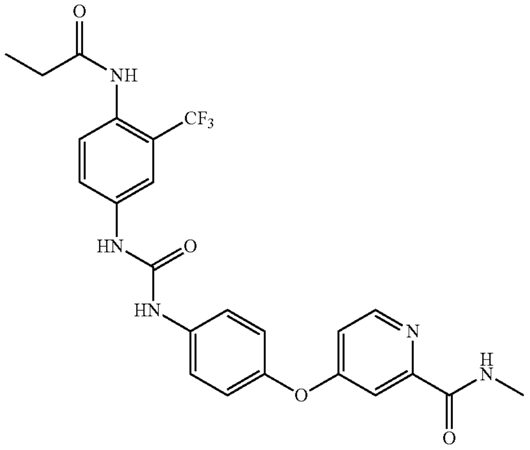 [SMILES: CCC(=O)Nc1ccc(NC(=O)Nc2ccc(Oc3ccnc(C(=O)NC)c3)cc2)cc1C(F)(F)F]

To a stirred solution of 4-(4-(3-(4-amino-3-(trifluoromethyl)phenyl)ureido)phenoxy)-N-methylpicolinamide (0.1 g, 0.23 mmol) and $Et_3N$ (0.04 g, 0.43 mmol) in DMF (2 mL) was added propionyl chloride (0.023 g, 0.25 mmol) dropwise at 0° C. The reaction was allowed to come to rt and stirred for additional 16 h. It was concentrated under reduced pressure and the residue was taken in water (2 mL) and extracted with EtOAc (2×20 mL). The EtOAc extract was washed with saturated aqueous NaCl solution (5 mL) and was dried over $Na_2SO_4$. Concentration under reduced pressure followed by purification by chromatography ($SiO_2$, 230-400, mixtures of $CHCl_3$/MeOH) yielded the title compound (0.024 g) as an off-white solid. $^1H$ NMR (MeOD) δ ppm: 1.23 (t, J=7.6 Hz, 3H), 2.35-2.55 (m, 2H), 2.94 (s, 3H), 7.05-7.07 (m, 1H), 7.11-7.15 (m, 2H), 7.39 (d, J=8.7 Hz, 1H), 7.56-7.60 (m, 3H), 7.63-7.66 (dd, J=2.32 & 8.44 Hz, 1H), 7.98 (d, J=2.36 Hz, 1H), 8.47 (d, J=5.64 Hz, 1H); LCMS: m/e 503.2 (M+1)

Example 11

4-(4-(3-(3-acrylamido)-4-chlorophenyl)ureido)phenoxy)-N-methylpicolinamide XVIII-15

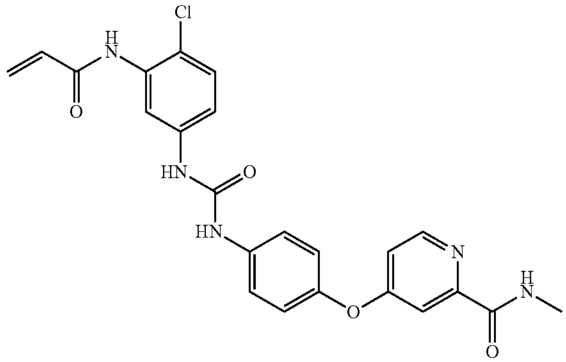 [SMILES: C=CC(=O)Nc1cc(NC(=O)Nc2ccc(Oc3ccnc(C(=O)NC)c3)cc2)ccc1Cl]

C,C'-Bis-tert-butyl N-3-nitro-5-chlorophenyl)iminodicarbonate

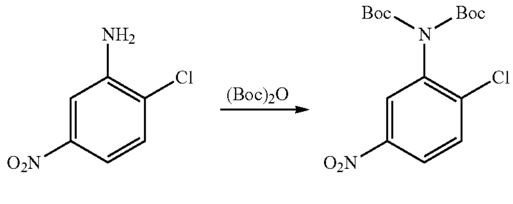 [SMILES: "(Boc)2O" ; Nc1cc([N+](=O)[O-])ccc1Cl ; CC(C)(C)OC(=O)N(C(=O)OC(C)(C)C)c1cc([N+](=O)[O-])ccc1Cl]

To a stirred solution of 3-nitro-5-chloroaniline (3 g, 17.4 mmol) in 1,4-dioxane (50 mL) was added 4-DMAP (1 g, 8.7 mmol) and Boc anhydride (9.5 g, 43.6 mmol) at room temperature. The reaction mixture was heated at 110° C. for 2 h. The reaction mixture was cooled, was concentrated under reduced pressure and the residue was dissolved in EtOAc (25 mL). It was washed with 10% citric acid solution (5 mL), water (5 mL) and saturated aqueous NaCl (2 mL). Drying over $Na_2SO_4$ followed by concentration under reduced pressure offered a residue which was purified by column chromatography ($SiO_2$, 60-120, pet ether/ethyl acetate, 6/4) to give 4.2 g of the title compound as faint yellow solid.

(2) C,C'-Bis-tert-butyl N-3-amino-5-chlorophenyl) iminodicarbonate

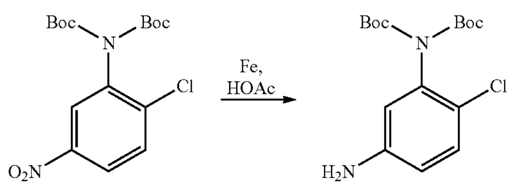

To a stirred solution of C,C'-bis-tert-butyl N-3-nitro-5-chlorophenyl)iminodicarbonate (1.9 g, 5.1 mmol) in methanol (25 mL) was added acetic acid (2.5 mL), followed by iron powder (0.45 g, 7.6 g-atom) under nitrogen atmosphere. The reaction mixture was heated at 70° C. for 2 h, cooled to room temperature and filtered through a Celite® bed. The filtrate was concentrated under reduced pressure and the residue was diluted with EtOAc (10 mL). It was washed successively with water (2 mL) and saturated aqueous NaCl solution (2 mL). Drying over $Na_2SO_4$ followed by concentration under reduced pressure offered a residue which was further purified by column chromatography ($SiO_2$, 60-120, pet ether/ethyl acetate, 6/4) to give 1.1 g of the title compound as an off white solid.

4-(4-(3-(3-bis-tert-butoxycarbonylamino)-4-chlorophenyl)ureido)phenoxy)-N-methylpicolinamide

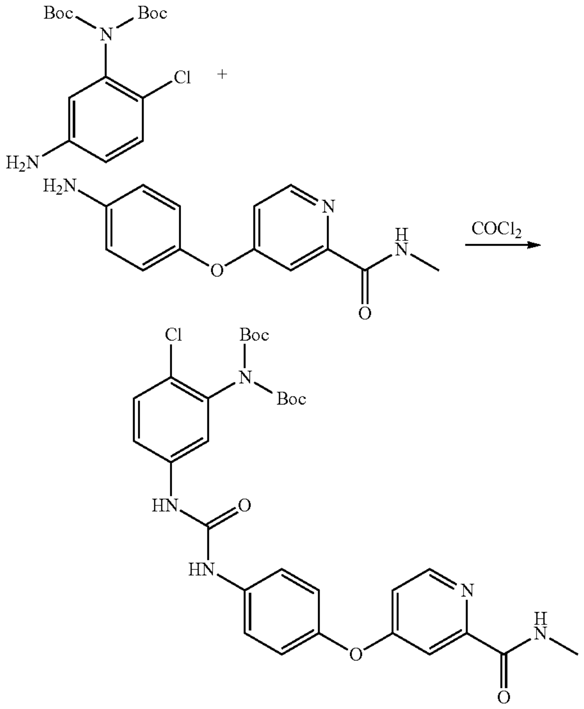

To a stirred solution of 4-(4-aminophenoxy)-N-methyl-2-pyridinecarboxamide (0.36 g, 1.4 mmol) in $CH_2Cl_2$ (5 mL) was added phosgene solution (20% solution in toluene, 1.01 g, 2.19 mmol) at 0° C. and the reaction mixture was stirred at room temperature for 15 min. It was again cooled to 0° C. and $Et_3N$ (0.44 g, 4.38 mmol) was added to it. The reaction mixture was then stirred at 35° C. for 3 h when TLC analysis showed that there was no starting material. The reaction mixture was again cooled to 0° C. and C,C'-bis-tert-butyl N-3-amino-5-chlorophenyl)iminodicarbonate (0.5 g, 1.4 mmol) was added to it. The reaction mixture was allowed to come to rt and then was heated at reflux for 16 h. The mixture was cooled to rt, was quenched with water (2 mL) and the dichloromethane layer was separated and was dried over $Na_2SO_4$. Filtration followed by concentration under reduced pressure offered a residue which was purified by column chromatography ($SiO_2$, 60-120, chloroform/methanol, 9/1) to give 0.4 g of the title compound as a brown solid.

4-(4-(3-(3-acrylamido)-4-chlorophenyl)ureido)phenoxy)-N-methylpicolinamide XVIII-15

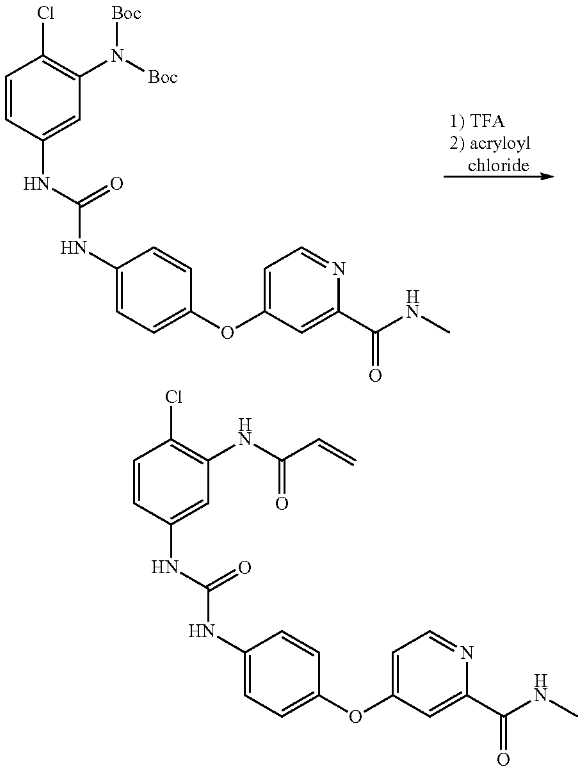

To a stirred solution of 4-(4-(3-(3-bis-tert-butoxycarbonylamino)-4-chlorophenyl)ureido)phenoxy)-N-methylpicolinamide (0.35 g, 0.59 mmol) in $CH_2Cl_2$ (5 mL) was added TFA (0.195 g, 1.71 mmol) at 0° C. The reaction mixture was allowed to come to rt and was stirred at this temperature for 3 h. It was quenched with $NaHCO_3$ solution (5 mL), organic layer was separated and dried over $Na_2SO_4$. Filtration followed by concentration under reduced pressure offered a residue which was purified by column chromatography ($SiO_2$, 60-120, chloroform/methanol, 9/1) to give the amino intermediate (0.15 g) as a light brown solid. This material was dissolved in NMP (3 mL) and acryloyl chloride (0.05 g, 0.54 mmol) was added at 0° C. The reaction mixture was allowed to come to rt and was stirred at this temperature for 1 h. It was diluted with $CH_2Cl_2$ (2 mL), was washed with $NaHCO_3$ solution (1 mL), water (1 mL), saturated aqueous NaCl solution (1 mL) and was dried over $Na_2SO_4$. Filtration followed by concentration under reduced pressure gave a residue, which was purified by column chromatography ($SiO_2$, 60-120, chloroform/methanol, 9/1) to give 0.07 g of the title compound as a white solid. $^1H$ NMR (DMSO-$d_6$) δ ppm: 2.77 (d, J=4.84 Hz, 3H), 5.78 (dd, J=1.8 & 10.12 Hz, 1H), 6.28 (dd, J=1.84 & 16.96 Hz, 1H), 6.62 (dd, J=10.16 & 16.92 Hz, 1H), 7.12-7.17 (m, 3H), 7.35-7.41 (m, 3H), 7.56-7.58 (m, 2H), 7.95 (d, J=1.96 Hz, 1H), 8.49 (d, J=5.6 Hz, 1H), 8.76-8.81 (m, 2H), 8.95 (s, 1H), 9.85 (s, 1H); LCMS: m/e 464 (M+1).

Example 12

4-(4-(3-(4-(N-methylacrylamido)phenyl)ureido)phenoxy)-N-methylpicolinamide XVIII-16

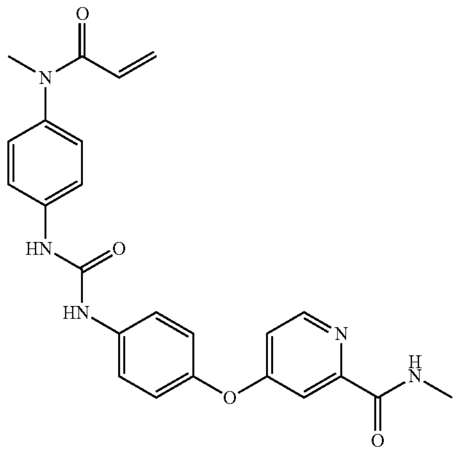 [SMILES: C=CC(=O)N(C)c1ccc(NC(=O)Nc2ccc(Oc3ccnc(C(=O)NC)c3)cc2)cc1]

Tert-butyl N-methyl-N-(4-nitrophenyl)carbamate

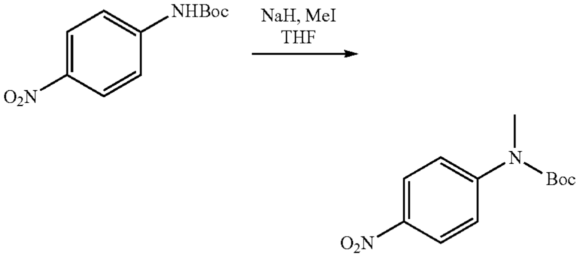

To a stirred solution of NaH (60% dispersion in paraffin oil) (251 mg, 6.28 mmol) in THF (6.0 mL) at 0° C. was added a solution of tert-butyl N-(4-nitrophenyl)carbamate (1.0 g, 4.19 mmol) in THF (4.0 mL) over a period of 15 min. The reaction mixture was stirred at this temperature for 15 min and to it was added methyl iodide (590.8 mg, 4.19 mmol). The reaction mixture was warmed to rt, and was stirred at 50° C. for 16 h. The mixture was cooled, was quenched with ice cold water (10.0 mL), and was extracted with EtOAc (3×50 mL). The combined EtOAc extract was washed with water (50 mL), saturated aqueous NaCl (50 mL), dried over $Na_2SO_4$ and concentrated and reduced pressure. The residue was further purified by column chromatography ($SiO_2$, 60-120, hexane/ethylacetete 90/10) to give the title compound (300 mg) as a yellow solid.

Tert-butyl N-methyl-N-(4-aminophenyl)carbamate

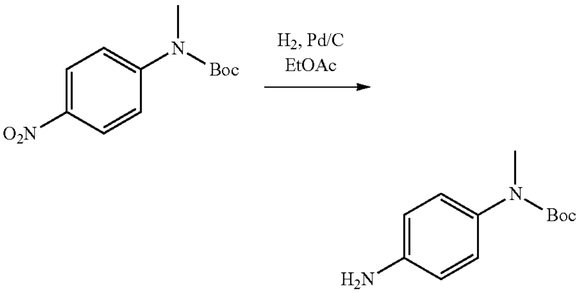

To a solution of tert-butyl N-methyl-N-(4-nitrophenyl) carbamate (0.090 g, 0.356 mmol) in EtOAc (5 mL)) was added 10% Pd/C (0.012 g) and the reaction mixture was allowed to stir under $H_2$ atmosphere (1.5 Kg hydrogen pressure) at rt for 16 h. The reaction mixture was filtered through a pad of Celite® and concentrated under reduced pressure to give the title compound (42 mg) as a brownish viscous oil.

4-(4-(3-(4-tert-butoxylcarbonylmethylaminophenyl) ureido)phenoxy)-N-methylpicolinamide

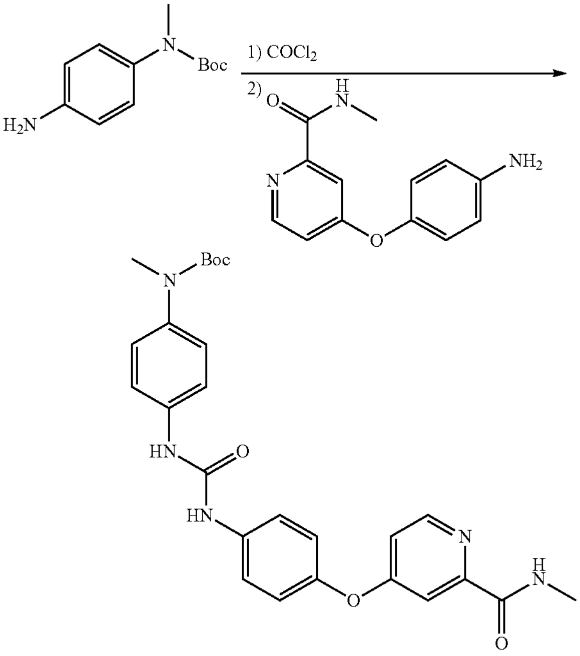

To a stirred solution of tert-butyl N-methyl-N-(4-aminophenyl)carbamate (0.2 g, 0.89 mmol) and $Et_3N$ (318 mg, 3.14 mmol) in toluene (4 mL) was added phosgene (20% solution in toluene, 0.85 mL, 1.61 mmol) at 0° C. The reaction mixture was allowed to reflux for 16 h, cooled to rt and to it was added 4-(4-aminophenoxy)-N-methyl-2-pyridinecarboxamide (0.218 g, 0.89 mmol) and the reaction mixture was again refluxed for 4 h. After that the reaction mixture was quenched with water (5 mL) in a fume-hood, was extracted with EtOAc (2×20 mL) and the ethyl acetate extract was washed with saturated aqueous NaCl (15 mL), was dried over $Na_2SO_4$ and was concentrated under reduced pressure. The residue was further purified by column chromatography ($SiO_2$, 60-120, hexane/ethyl acetete: 60/40) to give the title compound (78 mg) as an off-white solid.

4-(4-(3-(4-methylaminophenyl)ureido)phenoxy)-N-methylpicolinamide

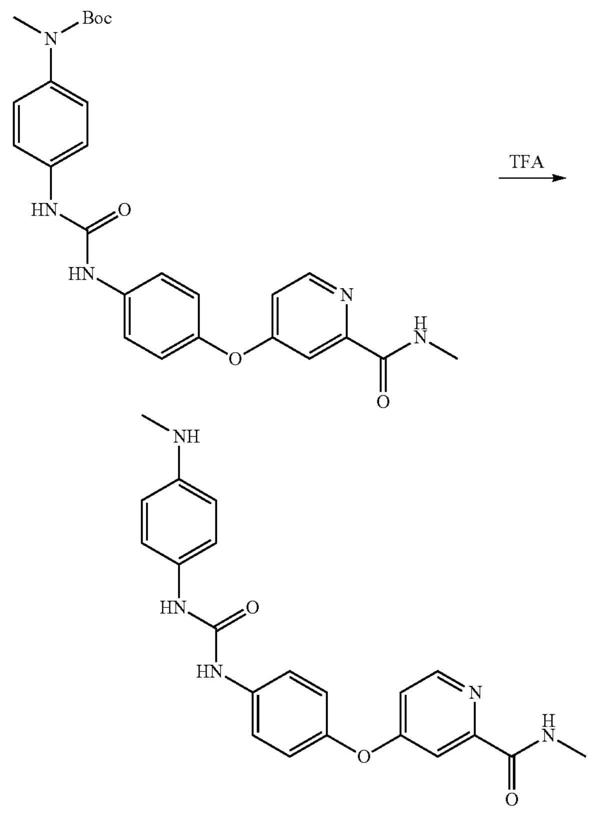

To a stirred solution of 4-(4-(3-(4-tert-butoxylcarbonylmethylaminophenyl)ureido)phenoxy)-N-methylpicolinamide (76 mg, 0.154 mmol) in $CH_2Cl_2$ (2.5 mL) was added trifluoroacetic acid (0.38 mL) at 0° C. The reaction mixture was allowed to come to rt and was stirred for additional 16 h. It was then quenched with ice-cold water (3 mL) and was basified with 10% $NaHCO_3$. It was extracted with EtOAc (2×25 mL). The combined EtOAc extract was washed with saturated aqueous NaCl (5 mL), was dried over $Na_2SO_4$ and was concentrated under reduced pressure to give the title compound (24 mg).

4-(4-(3-(4-(N-methylacrylamido)phenyl)ureido)phenoxy)-N-methylpicolinamide XVIII-16

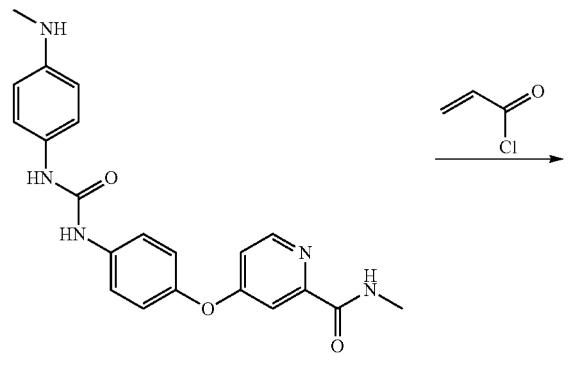

-continued

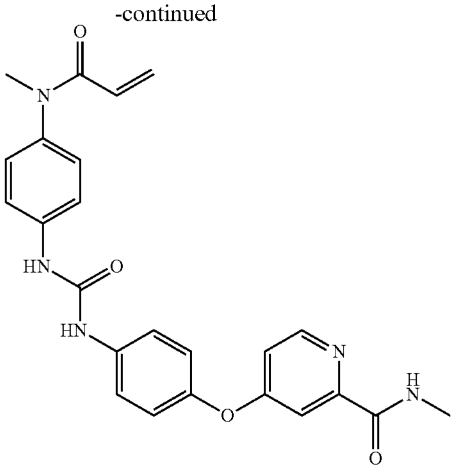

To a stirred solution of 4-(4-(3-(4-methylaminophenyl)ureido)phenoxy)-N-methylpicolinamide (20 mg, 0.051 mmol) in NMP (1.0 mL) at 0° C. was added acryloyl chloride (11.53 mg, 0.127 mmol). The reaction mixture was stirred at 0° C. for 30 min, was allowed to come to rt and was stirred for 90 min at this temperature. The reaction mixture was quenched with water (2 mL), was basified with 10% $NaHCO_3$ soln. and extracted with dichloromethane (2×10 mL). The combined $CH_2Cl_2$ extract was washed with water (5 mL), then with saturated aqueous NaCl (5 mL), was dried over $Na_2SO_4$ and was concentrated under reduced pressure. The residue obtained was further purified by column chromatography ($SiO_2$, 230-400, MeOH/$CHCl_3$: 1/99) to give the title compound (5 mg) as an off-white solid. $^1H$ NMR ($CDCl_3$) δ ppm: 3.05 (d, J=5.2 Hz, 3H), 3.33 (s, 3H), 5.51 (d, J=9.6 Hz, 1H), 6.08-6.15 (m, 1H), 6.35 (bd, J=17.2 Hz, 1H), 6.98 (d, J=8.44 Hz, 2H), 7.07-7.12 (m, 3H), 7.39 (d, J=8.4 Hz, 2H), 7.49 (d, J=6.8 Hz, 2H), 7.64 (s, 1H), 8.16 (s, 1H), 8.25 (s, 1H), 8.43 (d, J=5.6 Hz, 1H); LCMS: m/e 446 (M+1).

Example 13

4-{4-[4-(2-Chloro-acetyl)-piperazin-1-yl]-5-trifluoromethyl-pyrimidin-2-ylamino}-3-methoxy-N-(1-methyl-piperidin-4-yl)-benzamide (III-26)

The title compound was prepared according to the steps and intermediates as described below.

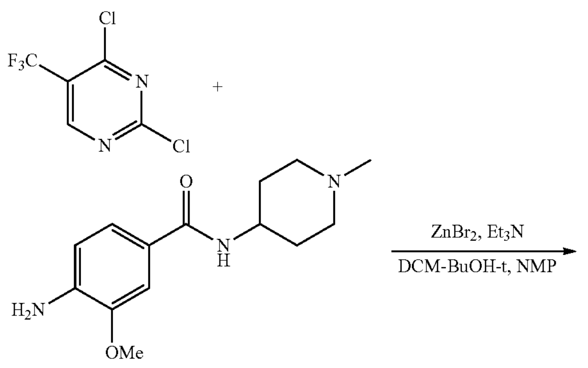

-continued

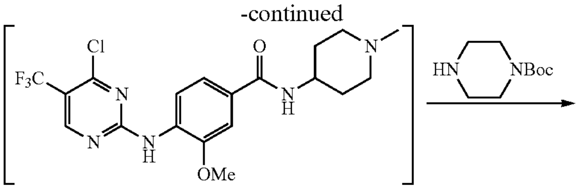

13a

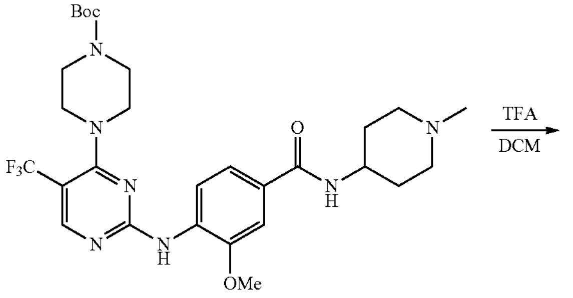

13b

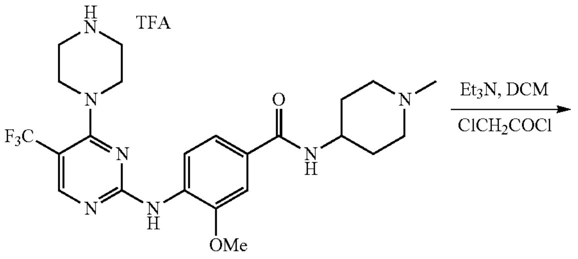

13c

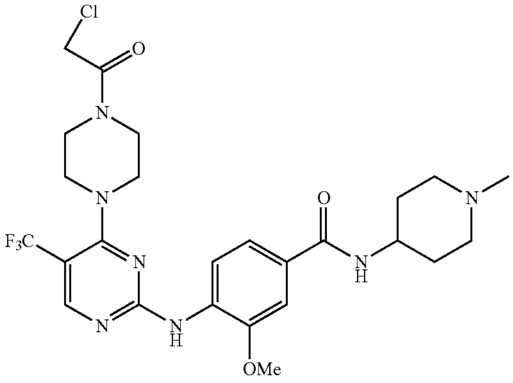

III-26

Step 1: Intermediate 13a

13a

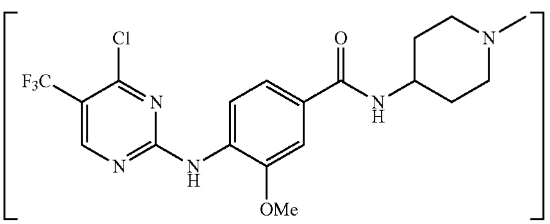

Under $N_2$, to a stirring solution of 500 mg of 2,4-dichloro-5-trifluoromethyl-pyrimidine (2.31 mmol) and 780 mg of zinc bromide (3.46 mmol) in 20 mL of dichloromethane-methanol (v/v 1/1) at 0° C., was added 526 mg of 4-amino-3-methoxy-N-(1-methyl-piperidin-4-yl)-benzamide (2.0 mmol) in 10 mL of N-methyl-pyrrolidinone (NMP). After stirring 30 min at 0° C., LC-MS showed completion of step 1 reaction with desired MS m/z=444.1 (ES+). Due to the moisture sensitivity of intermediate 13a, the reaction mixture was split into four aliquots (0.5 mmol each), and used directly for next step.

Step 2: Intermediate 13b

13b

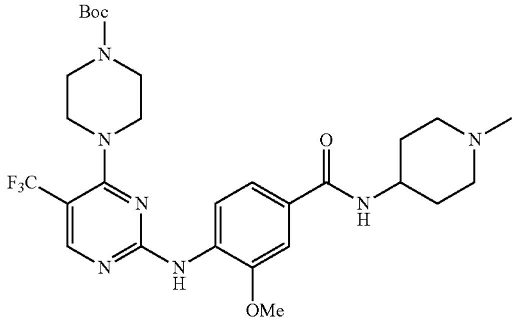

To one aliquot, was added N-Boc-piperizine (0.75 mmol) and 100 mg of anhydrous $K_2CO_3$. The reaction mixture was stirred at rt overnight. The reaction mixture was extracted with 50 mL of EtOAc, washed by water, brine, and dried over anhydrous sodium sulfate. After concentration, the residue was suspended into ether-heptane. The white solid was filtered out as desired product 13b (120 mg), MS m/z=594.2 (ES+).

Step 3: Intermediate 13c

13c

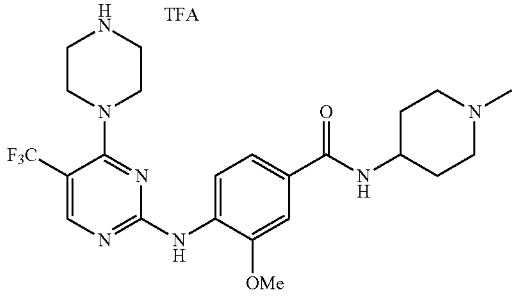

To a stirring solution of 120 mg of intermediate 13b (202 μmol) in 4 mL of anhydrous dichloromethane, was added 2 mL of trifluoroacetic acid. After 30 min, LC-MS showed completion of de-Boc protection, MS m/z=492.2 (ES+). The solvent was removed under reduced pressure, and co-evaporated with methanol/DCM several times to ensure the complete removal of trifluoroacetic acid. The residue was intermediate 13c, and can be used directly for next steps.

Step 4: 4-{4-[4-(2-Chloro-acetyl)-piperazin-1-yl]-5-trifluoromethyl-pyrimidin-2-ylamino}-3-methoxy-N-(1-methyl-piperidin-4-yl)-benzamide (III-26)

III-26

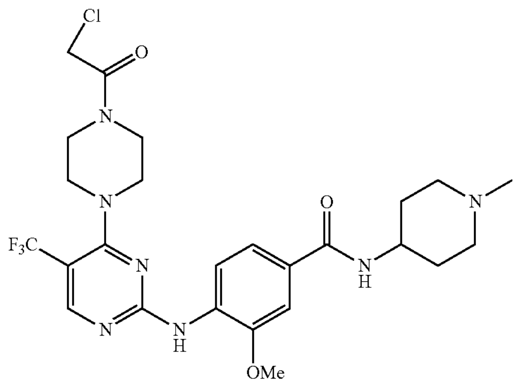

To a stirring solution of intermediate 13c (100 μmol), 250 μL of pyridine in 2 mL of anhydrous dichloromethane and 1 mL N,N-dimethylacetamide, was added 2-chloroacetyl chloride 150 μL. After 10 min, LC-MS showed completion of the acylation. The reaction mixture was concentrated, and purified by pre-HPLC, giving 39.5 mg of product III-26. MS m/z=570.2 (ES+), 568.2 (ES−).

Example 14

III-27

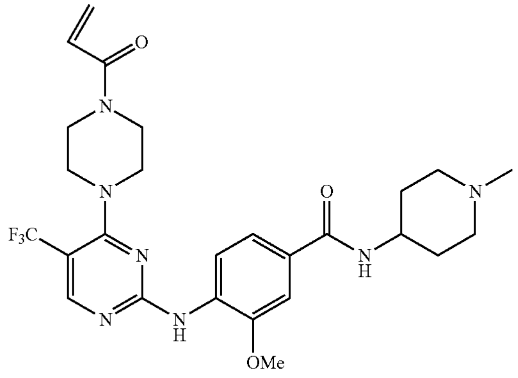

4-[4-(4-Acryloyl-piperazin-1-yl)-5-trifluoromethyl-pyrimidin-2-ylamino]-3-methoxy-N-(1-methyl-piperidin-4-yl)-benzamide (III-27)

At −20° C., to a stirring solution of intermediate 13c (100 μmol), 250 μL of pyridine in 2 mL of anhydrous dichloromethane and 1 mL N,N-dimethylacetamide, was added acryoyl chloride (1.2 equiv). After 10 min, the reaction was quenched by adding 200 μL of water. The reaction mixture was concentrated, and purified by pre-HPLC, giving III-27. MS m/z=548.3 (ES+), 546.2 (ES−).

Example 15

III-28

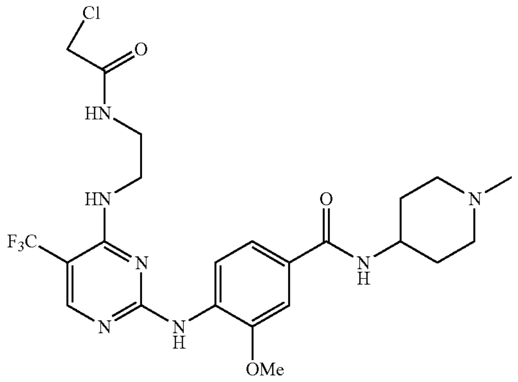

4-{4-[2-(2-Chloro-acetylamino)-ethylamino]-5-trifluoromethyl-pyrimidin-2-ylamino}-3-methoxy-N-(1-methyl-piperidin-4-yl)-benzamide (III-28)

The title compound was prepared in a similar way as III-26 through the following steps and intermediates as described below.

Step 1: Intermediate 15b

15b

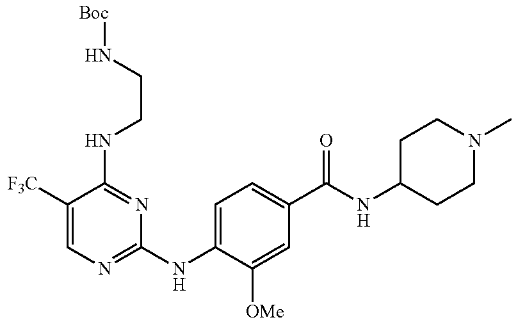

Intermediate 15b was synthesized in the same way as intermediate 13b but using 2-N-Boc-ethylamine instead of N-Boc-piperidine. MS m/z=568.2 (ES+), 566.2 (ES−).

Step 2: Intermediate 15c

15c

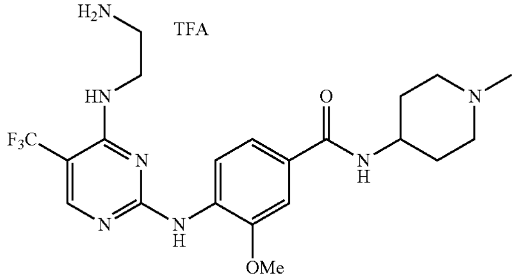

Intermediate 15c was prepared in the same way as intermediate 1c but starting with intermediate 15B. MS m/z: 468.2 (ES+).

Step 3: -{4-[2-(2-Chloro-acetylamino)-ethylamino]-5-trifluoromethyl-pyrimidin-2-ylamino}-3-methoxy-N-(1-methyl-piperidin-4-yl)-benzamide (III-28)

III-28

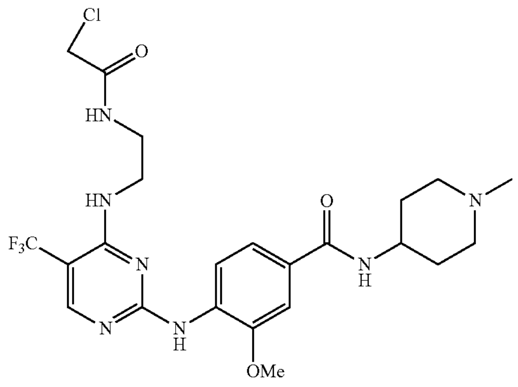

III-28 was synthesized in a similar way as of III-26 through intermediate 15c. MS m/z=544.2 (ES+), 542.3 (ES−)

Example 16

III-29

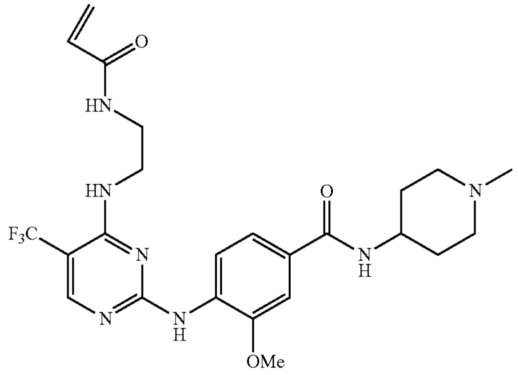

4-[4-(2-Acryloylamino-ethylamino)-5-trifluoromethyl-pyrimidin-2-ylamino]-3-methoxy-N-(1-methyl-piperidin-4-yl)-benzamide (III-29)

III-29 was synthesized in a similar way as of III-27 through intermediate 15c. MS m/z=522.3 (ES+), 520.2 (ES−).

Example 17

Biochemical Assays

A. KDR and FLT-3 Omnia Assay for Potency Assessment:

The protocol below describes a continuous-read kinase assay to measure inherent potency of Avila Therapeutics' compounds against active KDR and FLT-3 enzymes. The assay was performed substantially as described by the vendor (Invitrogen, Carlsbad, Calif. on their website.

Briefly, 10× stocks of KDR from Invitrogen or BPS Bioscience (PV3660 or 40301) and FLT-3 (PV3182) enzymes, 1.13×ATP (AS001A) and Y9-Sox or Y12-Sox peptide substrates (KCZ1001) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 μL of enzyme were pre-incubated in a Corning (#3574) 384-well, white, non-binding surface microtiter plate (Corning, N.Y.) for 30 min at 27° C. with a 0.5 μL volume of 50% DMSO and serially diluted compounds prepared in 50% DMSO. Kinase reactions were started with the addition of 45 μL of the ATP/Y9 or Y5-Sox peptide substrate mix and monitored every 30-90 seconds for 60 minutes at $\lambda_{ex}360/\lambda_{em}485$ in a Synergy[4] plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to 20+ minutes) from each reaction was determined from the slope of a plot of relative fluorescence units vs time (minutes) and then plotted against inhibitor concentration to estimate $IC_{50}$ from Log [Inhibitor] vs Response, Variable Slope model in GraphPad Prism from GraphPad Software (San Diego, Calif.).

[Reagent] Used in Optimized Protocols:

[PDGFRα]=2-5 nM, [ATP]=60 μM and [Y9-Sox peptide]=10 μM (ATP $K_{Mapp}$=61 μM)

[FLT-3]=15 nM, [ATP]=500 μM and [Y5-Sox peptide]=10 μM (ATP $K_{Mapp}$=470 μM)

B. Omnia Assay Protocol for Potency Assessment Against BTK

Below describes the protocol using EGFR-WT and EGFR-T790M/L858R and the protocol BTK-optimized reagent conditions then follow.

The mechanics of the assay platform are best described by the vendor (Invitrogen, Carlsbad, Calif.) on their website.

Briefly, 10× stocks of EGFR-WT (PV3872) from Invitrogen and EGFR-T790M/L858R (40350) from BPS Bioscience, San Diego, Calif., 1.13×ATP (AS001A) and appropriate Tyr-Sox conjugated peptide substrates (KCZ1001) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 μL of each enzyme were pre-incubated in a Corning (#3574) 384-well, white, non-binding surface microtiter plate (Corning, N.Y.) for 30 min. at 27° C. with a 0.5 μL volume of 50% DMSO and serially diluted compounds prepared in 50% DMSO. Kinase reactions were started with the addition of 45 μL of the ATP/Tyr-Sox peptide substrate mix and monitored every 30-90 seconds for 60 minutes at $\lambda_{ex}360/\lambda_{em}485$ in a Synergy[4] plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to ~30 minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.).

The modified BTK-optimized reagent conditions for the above protocol are: [BTK]=5 nM, [ATP]=40 mM, [Y5-Sox]=10 mM (ATP KMapp ~36 mM).

C. c-Kit (V654A and T670I) Omnia Assays for Potency Assessment:

Briefly, 10× stocks of c-Kit (V654A) from Millipore (14-733) or c-Kit (T670I) from Cell Signaling (7922), 1.13×ATP (AS001A) and Y9-Sox or Y12-Sox peptide substrates (KCZ1001) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 μL of each enzyme were pre-incubated in a Corning (#3574) 384-well, white, non-binding surface microtiter plate (Corning, N.Y.) for 30 min at 27° C. with a 0.5 volume of 50% DMSO and serially diluted compounds prepared in 50% DMSO. Kinase reactions were started with the addition of 45 μL of the Y9 or Y12-Sox peptide substrate and monitored every 30-90 seconds for 60 minutes at $\lambda_{ex}360/\lambda_{em}485$ in a Synergy[4] plate reader from BioTek (Winooski, Vt.). At the conclusion of each assay, progress curves from each well were examined for linear reaction kinetics and fit statistics ($R_2$, 95% confidence interval, absolute sum of squares). Initial velocity (0 minutes to 20+ minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.).

[c-Kit V654A]=5 nM, [ATP]=220 μM and [Y9-Sox]=10 μM (ATP $K_{Mapp}$=240 μM)

[c-Kit T670I]=5 nM, [ATP]=220 μM and [Y12-Sox]=10 μM (ATP $K_{Mapp}$=220 μm)

D. Assay for PDGFRA

Briefly, 10× stock of PDGFRα (PV3811) enzyme, 1.13× ATP (AS001A) and Y12-Sox peptide substrates (KCZ1001) was prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 μL of enzyme were pre-incubated in a Corning (#3574) 384-well, white, non-binding surface microtiter plate (Corning, N.Y.) for 30 min at 27° C. with a 0.5 μL volume of 50% DMSO and serially diluted compounds prepared in 50% DMSO. Kinase reactions were started with the addition of 45 μL of the ATP/Y9 or Y12-Sox peptide substrate mix and monitored every 30-9 seconds for 60 minutes at $\lambda_{ex}360/\lambda_{em}485$ in a Synergy[4] plate reader from BioTek (Winooski, Vt.). At the conclusion of each assay, progress curves from each well were examined for linear reaction kinetics and fit statistics ($R_2$, 95% confidence interval, absolute sum of squares). Initial velocity (0 minutes to 20+ minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.).

[PDGFRα]=2-5 nM, [ATP]=60 μM and [Y9-Sox peptide]=10 μM (ATP $K_{Mapp}$=61 μM)

The results of the biochemical assays are presented below. The reported IC50_APP and IC50 values are in units of nM.

II-53 inhibited FLT3 with an IC50_APP of 3.7625; KDR with an IC50_APP of 15.155, CKIT with an IC50_APP of 114.40, CKIT D816V with an IC50_APP of 127.13.

XVIII-11 inhibited FLT3 with an IC50_APP of 1.9935; KDR with an IC50_APP of 26.923, CKIT with an IC50_APP of 31.129, CKIT D816V with an IC50_APP of 3.4233.

XVIII-12 inhibited FLT3 with an IC50_APP of 1.0740; KDR with an IC50_APP of 148.50, CKIT with an IC50_APP of 10.450, CKIT D816V with an IC50_APP of 2.5040.

XVIII-13 inhibited FLT3 with an IC50_APP of 0.5080; KDR with an IC50_APP of 0.9499, PDGFRA with an IC50_APP of 0.5080.

XVIII-14 inhibited FLT3 with an IC50_APP of 106.90; KDR with an IC50_APP of 6.9410, PDGFRA with an IC50_APP of 1.5450.

XVIII-15 inhibited KDR with an IC50_APP of 462.50.

XVIII-16 inhibited KDR with an IC50_APP of 1335.0.

II-1 inhibited FLT3 with an IC50_APP of 3.1510; KDR with an IC50_APP of 39.259, BTK with an IC50_APP of 6169.5.

II-2 inhibited FLT3 with an IC50_APP of 0.5080; KDR with an IC50_APP of 51.384, BTK with an IC50_APP of 0.5715.

II-4 inhibited FLT3 KDR with and IC50_APP of 111.49, BTK with an IC50_APP of 05080.5.

II-3 inhibited KDR with an IC50_APP of 290.2, BTK with an IC50_APP of 458.50.

II-5 inhibited KDR with an IC50_APP of 39.700, BTK with an IC50_APP of 105.91.

Reversible Reference Compound 1 inhibited FLT3 with an IC50 of 5.8445; KDR with an IC50 of 253.89, BTK with an IC50 of 1640.5.

Reversible Reference Compound 2 inhibited KDR with an IC50 of 95.669; BTK with an IC50 of 183.69.

Reversible Reference Compound 3 inhibited CKIT with an IC50 of 16.309, PDGFRA with an IC50 of 4.1550, FLT3 with an IC50 of 0.4606, KDR with an IC50 of 39.375.

Example 18

EOL-1 Cell Washout Assay

EOL-1 cells purchased from DSMZ (ACC 386) were maintained in RPMI (Invitrogen #21870)+10% FBS+1% penicillin/streptomycin (Invitrogen #15140-122). EOL-1 cells were grown in suspension in complete media and compound was added to $2\times10^6$ cells per sample for 1 hour. After 1 hour, the cells were pelleted, the media was removed and replaced with compound-free media. Cells were washed every 2 hours and resuspended in fresh compound-free media. Cells were collected at specified time points, lysed in Cell Extraction Buffer and 15 μg total protein lysate was loaded in each lane. PDGFR phosphorylation was assay by western blot with Santa Cruz antibody sc-12910. The results of this experiment are depicted in FIG. 1 where it is shown that relative to DMSO control and to a reversible reference compound, XVIII-11 maintained enzyme inhibition of PDGFR in EOL-1 cells after "washout" after 0 hours and 4 hours.

Example 19 cKIT Washout Assay

GIST882 cells (See, Bauer et al., Cancer Research, 66(18):9153-9161 (2006)) were seeded in a 6 well plate at a density of $8\times10^5$ cells/well in complete media. The next day cells were treated with 1 uM compound diluted in complete media for 90 minutes. After 90 minutes, the media was removed and cells were washed with compound-free media. Cells were washed every 2 hours and resuspended in fresh compound-free media. Cells were collected at specified time points, lysed in Cell Extraction Buffer (Invitrogen FNN0011) supplemented with Roche complete protease inhibitor tablets (Roche 11697498001) and phosphatase inhibitors (Roche 04 906 837 001) and lysates were sheared by passing through a 28.5 gauge syringe 10 times each. Protein concentrations were measured and 10 ug total protein lysate was loaded in each lane. C-kit phosphorylation was assayed by western blot with pTyr (4G10) antibody and total kit antibody from Cell Signaling Technology.

Figure 2A:
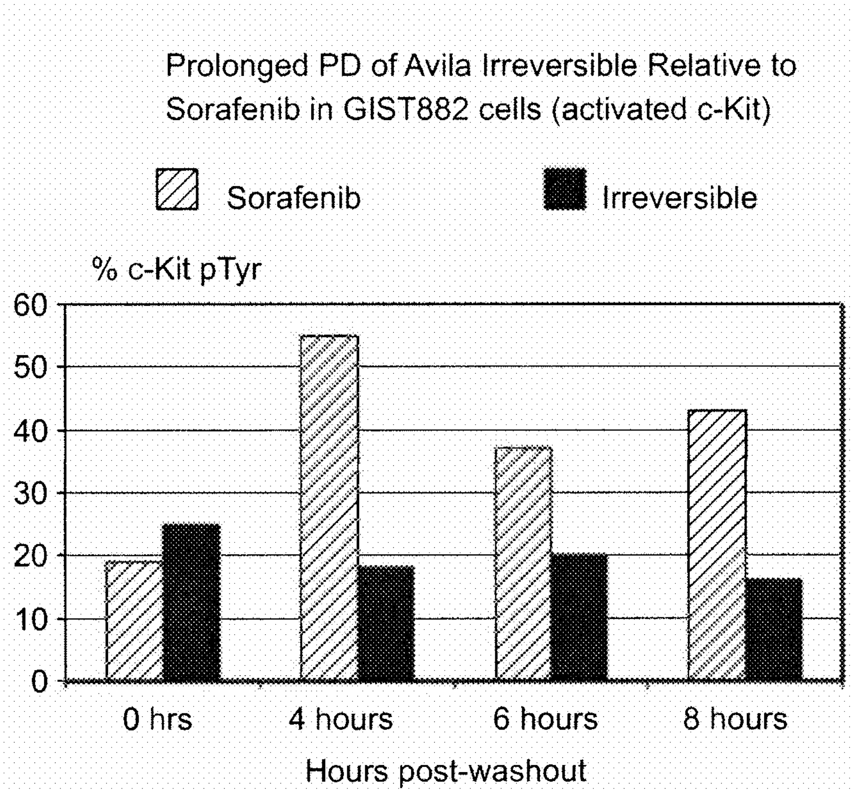
FIGS. 2A and 2B are histograms showing prolonged inhibition of cKIT activity by an irreversible inhibitor (XVIII-11) relative to sorafenib in a cKIT phosphorylation assay (2A) and downstream signaling assay that measured ERK phosphorylation (2B).
Figure 2B:
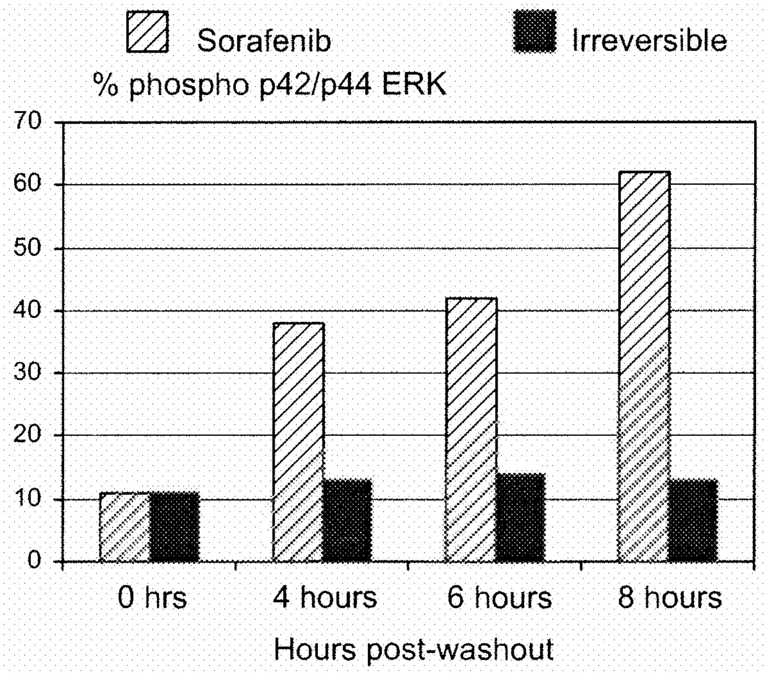

Sorafenib and XVIII-11 were tested for cellular activity in a GIST882 cell line at 1 micromolar. The results are depicted in FIGS. 2*a* and 2*b* where it is shown that XVIII-11 maintained c-KIT enzyme inhibition in GIST430 cells after "washout" for at least 8 hours. Both compounds inhibited cKIT autophosphorylation and also downstream signaling of ERK. In order to understand whether there was a prolonged inhibition with the irreversible inhibitor the cells were washed free of compound. For the reversible inhibitor, Sorafenib, the inhibitory activity of cKIT and downstream signaling was overcome whereas the irreversible inhibition of XVIII-11 persisted for at least 8 hours. These data support the superiority in duration of action of the irreversible inhibitor XVIII-11 over the reversible inhibitor Sorafenib

Example 20

Mass Spectral Analysis

A. C-KIT and XVIII-11

C-kit (15 pmols) was incubated with XVIII-11 (150 pmols) for 3 hrs at 10× access prior to tryptic digestion. Iodoacetamide was used as the alkylating agent after compound incubation. A control sample was also prepared which did not have the addition of XVIII-11. For tryptic digests a 2 ul aliquot (3.3 pmols) was diluted with 10 ul of 0.1% TFA prior to micro C18 Zip Tipping directly onto the MALDI target using alpha cyano-4-hydroxy cinnamic acid as the matrix (5 mg/ml in 0.1% TFA:Acetonitrile 50:50).

For tryptic digests the instrument was set in Reflectron mode with a pulsed extraction setting of 2200. Calibration was done using the Laser Biolabs Pep Mix standard (1046.54, 1296.69, 1672.92, 2093.09, 2465.20). For CID/PSD analysis the peptide was selected using cursors to set ion gate timing and fragmentation occurred at a laser power about 20% higher and He was used as the collision gas for CID. Calibration for fragments was done using the P14R fragmentation calibration for the Curved field Reflectron.

Figure 3:
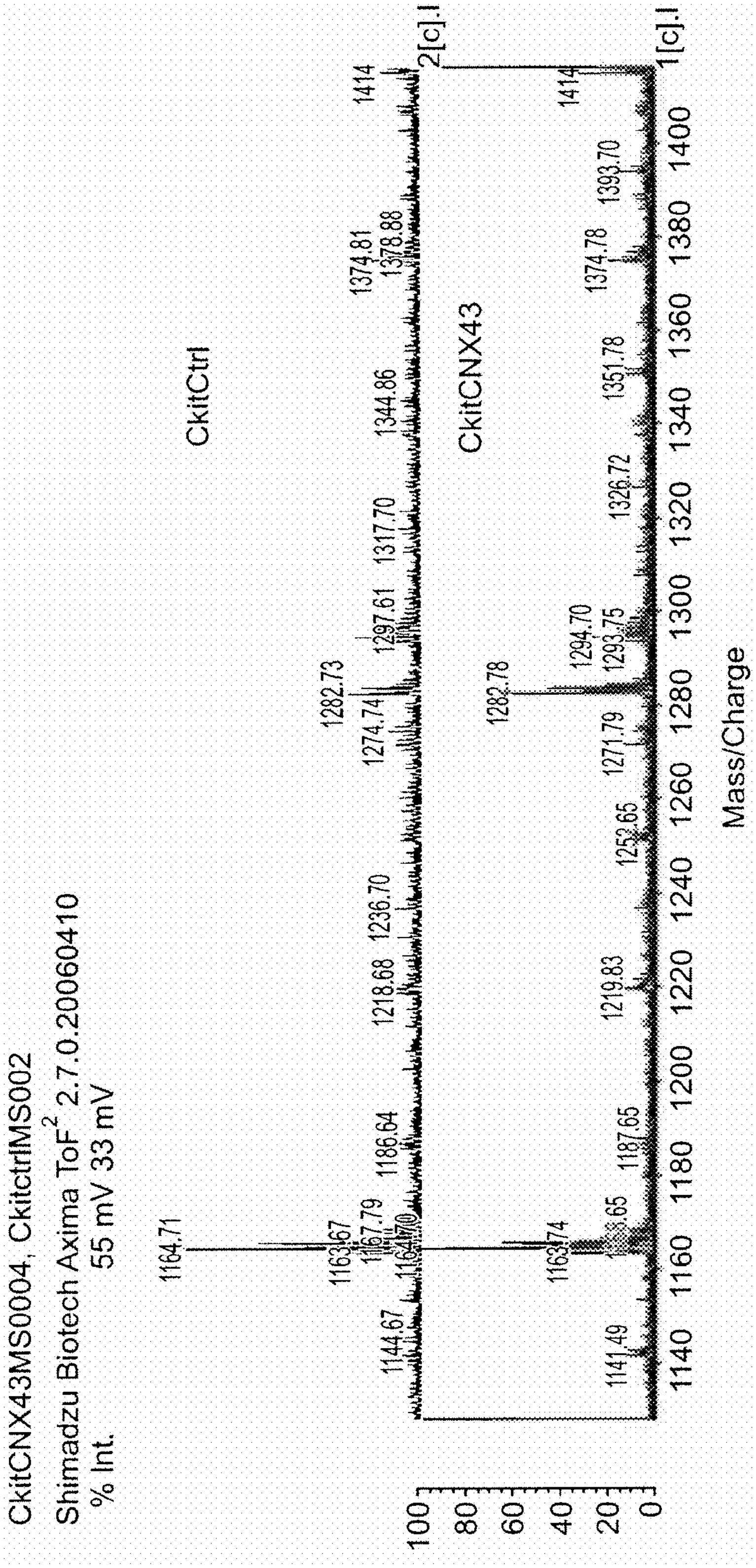
FIG. 3 shows the results of mass spectral analysis of a tryptic digest of C-KIT after inhibition with the reversible inhibitor XVIII-11.

A modified peptide of MH+ of 1141.49 (NCIHR; SEQ ID NO:46) was seen. (FIG. 3) This is the mass expected for the XVIII-11 compound at Mw of 499.15 Da. Attempts at fragmentation of the XVIII-11 modified peptide produced very weak CID spectra which provided some confirmatory evidence of the 1141.49 peptide via an Immonium ion for His at 110 and a C-terminal Arg at 175. There was also data to suggest that the Cys of ICDFGLAR may be modified.

B. KDR AND II-2

KDR kinase (40 pmols) was incubated with II-2 (395 pmols) for 3 hrs at 10× access prior to tryptic digestion. Iodoacetamide was used as the alkylating agent after compound incubation. For tryptic digests a 5 ul aliquot (6.7 pmols) was diluted with 10 ul of 0.1% TFA prior to micro C18 Zip Tipping directly onto the MALDI target using alpha cyano-4-hydroxy cinnamic acid as the matrix (5 mg/ml in 0.1% TFA:Acetonitrile 50:50).

For tryptic digests the instrument was set in Reflectron mode with a pulsed extraction setting of 1800. Calibration was done using the Laser Biolabs Pep Mix standard (1046.54, 1296.69, 1672.92, 2093.09, 2465.20). For CID/PSD analysis the peptide was selected using cursors to set ion gate timing and fragmentation occurred at a laser power about 20% higher and He was used as the collision gas for CID. Calibration for fragments was done using the P14R fragmentation calibration for the Curved field Reflectron.

Figure 4:
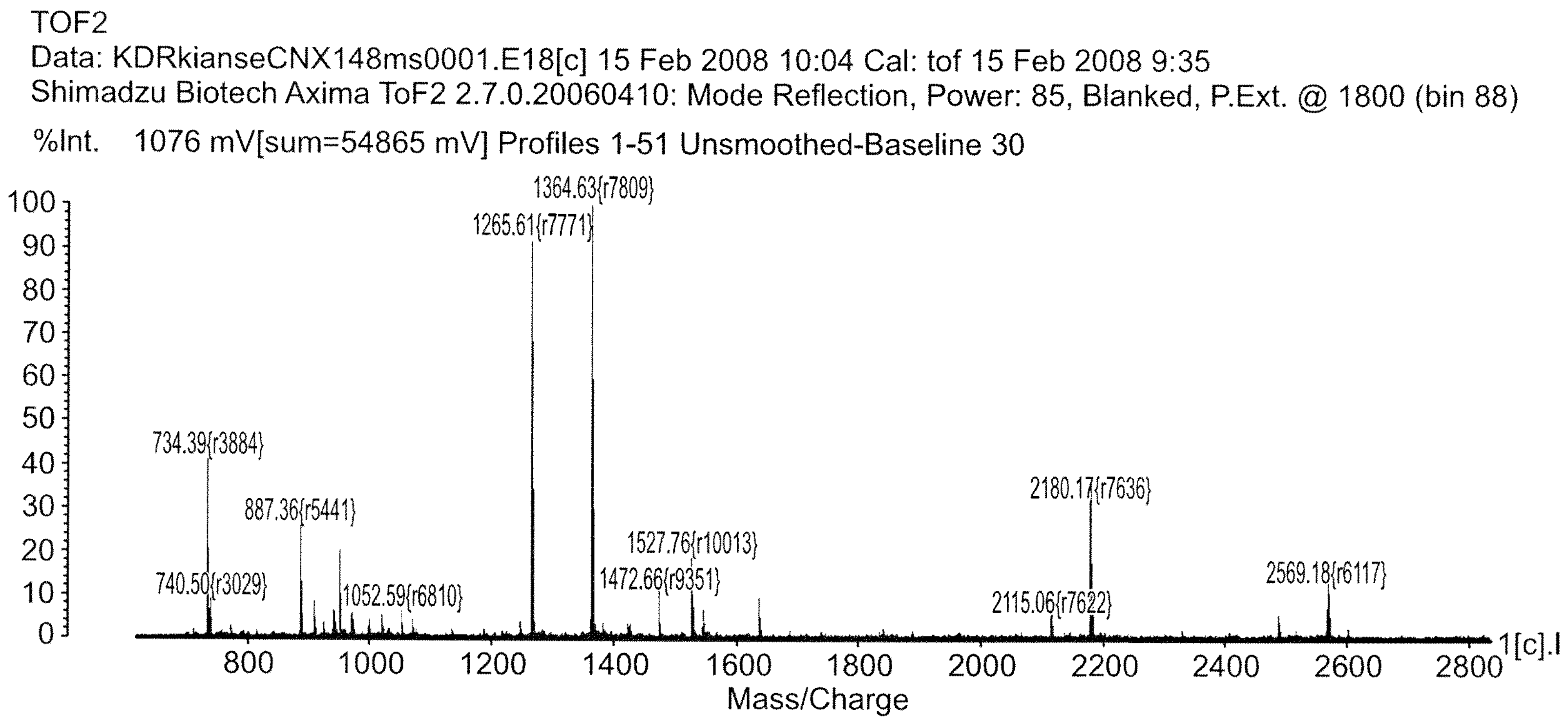
FIG. 4 shows the results of mass spectral analysis of a tryptic digest of KDR after inhibition with the reversible inhibitor II-2.

A modified peptide was seen at MH+ of 1364.63, which was predicted to be have the sequence ICDFGLAR (SEQ ID NO:47). (FIG. 4) This is the mass expected when the adduct mass of II-2 (470.17) is added to the peptide of 894.45. Evidence of the compound (II-2) was observed at MH+ of 471.27 in the low mass range of the spectra. In this case evidence of the compound was found in the PSD spectra of the 1364.63 peptide. Database searching also confirmed the modified peptide at 1364.63.

Preparative Example

The example shows general schemes used to prepare FAK inhibitors (IV-29-IV-31).

Scheme 1.

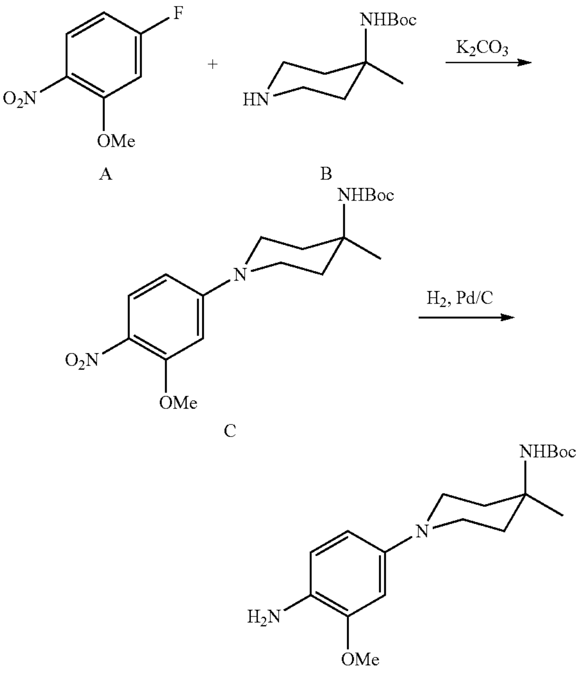

A B C D

Scheme 1 generally describes the synthesis of 2-methoxy-4-substituted amino anilines. 4-methyl-4-N-Boc-piperidine B was reacted with 4-fluoro-2-methoxy1-nitrobenzene A in the presence of potassium carbonate to give F-displaced product C., which was used as intermediates for the preparation of FAK inhibitors.

Scheme 2

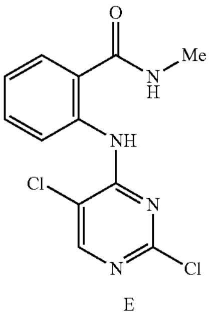

E

+

-continued

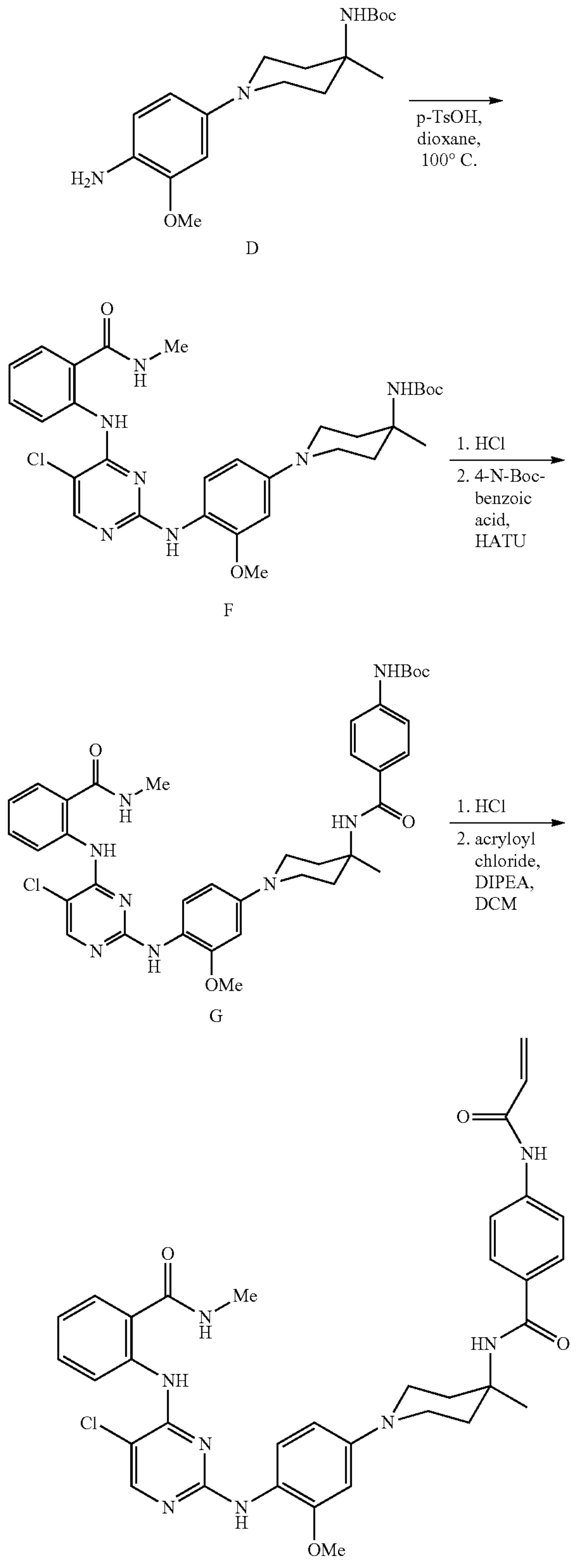

(IV-29)

Intermediate D was condensed with compound E catalyzed by p-TsOH. The Boc protection was then removed using HCl in dioxane, followed by the coupling of 4-N-Boc-benzoic acid to introduce the linkage. Final Boc-removal and installation of warhead with acryloyl chloride resulted in the final compound.

Example 21

2-(2-(4-(4-(4-acrylamidobenzamido)-4-methylpiperidin-1-yl)-2-methoxyphenylamino)-5-chloropyrimidin-4-ylamino)-N-methylbenzamide (IV-21)

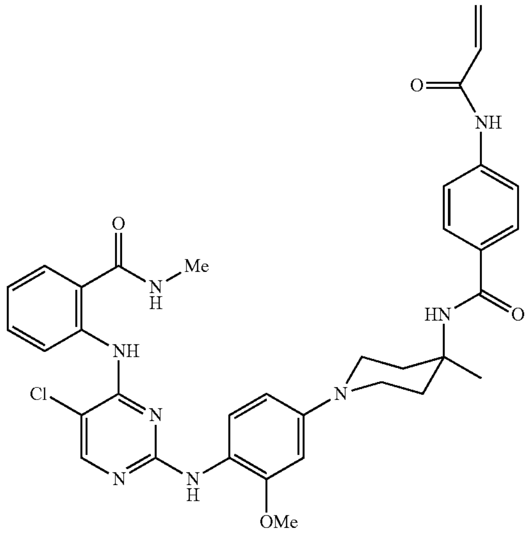 [SMILES: C=CC(=O)Nc1ccc(C(=O)NC2(C)CCN(c3ccc(Nc4ncc(Cl)c(Nc5ccccc5C(=O)NC)n4)c(OC)c3)CC2)cc1]

The title compound was prepared according to the steps and intermediates as described below.

Intermediate 21-1

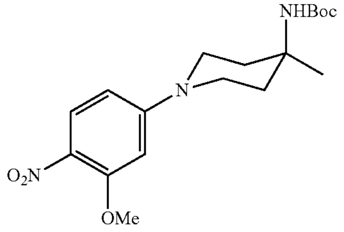

tert-Butyl 1-(3-methoxy-4-nitrophenyl)-4-methylpiperidin-4-ylcarbamate (C, in Preparative Example Scheme 1)

171 mg of 4-fluoro-2-methoxy-1-nitrobenzene (1 mmol), 214 mg of 4-N-Boc-4-methyl-piperidine (1 mmol), and 200 mg of $K_2CO_3$ were heated at 70° C. in 5 mL of N,N-dimethylacetamide (DMA) for 24 hr. After cooling down, the reaction mixture was diluted with 60 mL of EtOAc, washed with water 10 mL×2, brine 10 mL, and dried over anhydrous $Na_2SO_4$. After concentration, 350 mg the desired product was obtained as yellow solid after flash column chromatography on silica gel with eluent (heptane/EtOAc 2/1) (96%). LC-MS: m/z 366.2 (ES+).

Intermediate 21-2

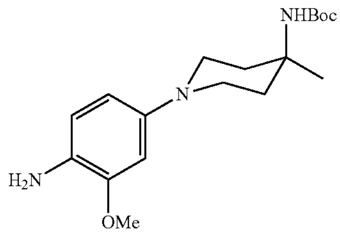

tert-Butyl[1-(4-Amino-3-methoxy-phenyl)-4-methyl-piperidin-4-yl]-ate (D, in Preparative Example Scheme 1)

350 mg of compound 21-1 was hydrogenated overnight under 1 atmosphere hydrogen with 50 mg of 10% Pd/C in 15 mL of MeOH. 300 mg of desired aniline 21-2 was obtained after filtration. LC-MS: m/z 336.2 (ES+).

Intermediate 21-3

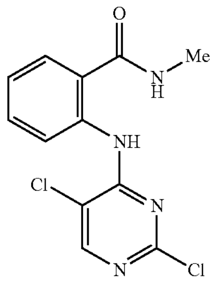

2-(2,5-Dichloro-pyrimidin-4-ylamino)-N-methyl-benzamide (E, in Preparative Example Scheme 2)

1.0 g of 2-Amino-N-methyl-benzamide (6.64 mmol), 1.22 g 2,4,5-trichloropyrimidine (6.64 mmol), and 1.3 g of $K_2CO_3$ were stirred in 5 mL of DMA at rt overnight. The reaction mixture was then poured into 50 mL of ice-water, the precipitate was filtered out, dried in vacuum giving slight yellow solid 1.7 g (86%). LC-MS: m/z 297.0 (ES+), 295.0 (ES−).

Intermediate 21-4

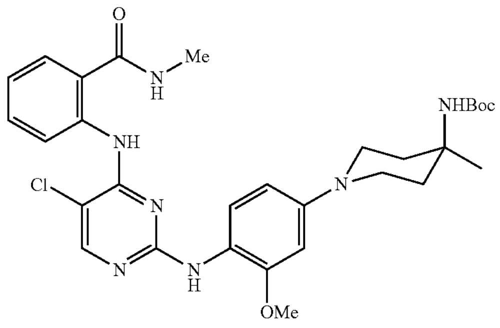

tert-Butyl(1-{4-[5-Chloro-4-(2-methylcarbamoyl-phenylamino)-pyrimidin-2-ylamino]-3-methoxy-phenyl}-4-methyl-piperidin-4-yl)-carbamate (F, in Preparative Example Scheme 2)

300 mg of intermediate 21-2 (0.895 mmol, 1.2 equiv.) and 220 mg of intermediate 21-3 (0.746 mmol, 1 equiv.) was heated in 6 mL of 0.1 M p-TsOH in dioxane (0.8 equiv) at 100° C. for 60 hrs. The reaction mixture was then extracted with EtOAc, washed with aq. $NaHCO_3$, and dried over sodium sulfate. After concentration, the desired intermediate was obtained after column chromatography on silica gel with eluent (heptane/EtOAc 1/1), giving yellow solid 100 mg (20%). LC-MS: m/z 596.3 (ES+), 594.2 (ES−).

Intermediate 21-5

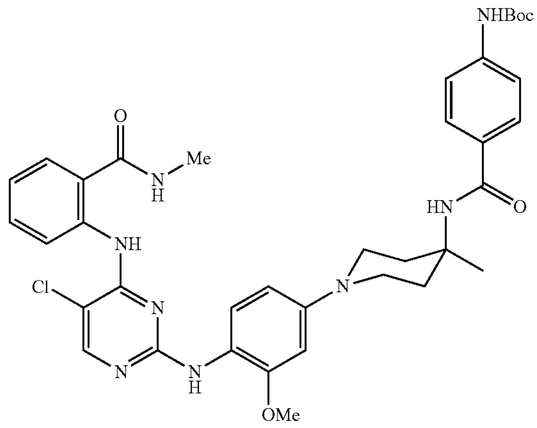

tert-Butyl[4-(1-{4-[5-Chloro-4-(2-methylcarbamoyl-phenylamino)-pyrimidin-2-ylamino]-3-methoxy-phenyl}-4-methyl-piperidin-4-ylcarbamoyl)-phenyl]-carbamate (G, in Preparative Example Scheme 2)

To a solution of 100 mg of intermediate 21-4 in 1 mL of anhydrous dichloromethane was added 2 mL of 4 M HCl in dioxane. After stirring at rt for 30 min, the solvent was removed under reduced pressure, giving the desired de-Boc intermediate which was used directly for the following coupling step. LC-MS: m/z: 496.2 (ES+), 494.2 (ES−).

27 mg of the de-Boc intermediate reacted with 12 mg of 4-N-Boc-benzoic acid in the presence of 50 uL of DIPEA, 40 mg of HATU in 2 mL of acetonitrile at rt for 2 hr. The reaction mixture was diluted with 40 mL of EtOAc, washed with aq. $NaHCO_3$, dried over $Na_2SO_4$. After concentration, 29 mg of intermediate 21-5 was obtained as slight yellow solid after column chromatography on silica gel using heptane/EtOAc (1/3 v/v) as eluent. LC-MS: m/z 715.2 (ES+), 713.3 (ES−).

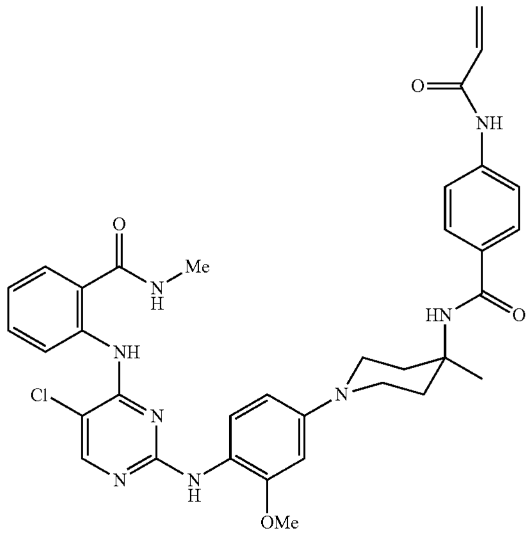 [SMILES: C=CC(=O)Nc1ccc(C(=O)NC2(C)CCN(c3ccc(Nc4ncc(Cl)c(Nc5ccccc5C(=O)NC)n4)c(OC)c3)CC2)cc1]

2-(2-(4-(4-(4-acrylamidobenzamido)-4-methylpiperidin-1-yl)-2-methoxyphenylamino)-5-chloropyrimidin-4-ylamino)-N-methylbenzamide (IV-29)

To a solution of 29 mg of intermediate 21-5 in 0.5 mL of anhydrous dichloromethane was added 1 mL of 4 M HCl in dioxane. After stirring at rt for 1 hr, the solvent was removed under reduced pressure, giving desire de-Boc intermediate which was used directly for the following coupling step.

To the de-Boc intermediate in 2 mL of dichloromethane and 100 uL of DIPEA at −20° C., was added 55 uL of 1.1 M acryloyl chloride solution in dichloromethane (1.3 equiv). After 5 min, the reaction was quenched with water, and the reaction mixture was concentrated and subject to prep-HPLC purification, giving 6 mg of final product. LC-MS: m/z 669.3 (ES+), 667.2 (ES−).

Example 22

2-{2-[4-(9-Acryloyl-2,9-diaza-spiro[5.5]undec-2-yl)-2-methoxy-phenylamino]-5-chloro-pyrimidin-4-ylamino}-N-methyl-benzamide (IV-30)

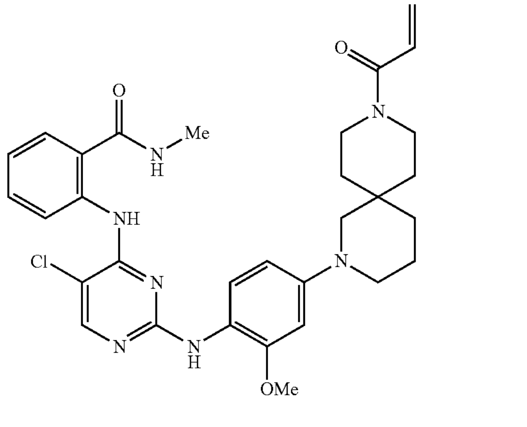 [SMILES: C=CC(=O)N1CCC2(CCCN(c3ccc(Nc4ncc(Cl)c(Nc5ccccc5C(=O)NC)n4)c(OC)c3)C2)CC1]

The title compound was prepared in a process similar to that described in Example 21, but using 2,9-Diaza-spiro[5.5]undecane-9-carboxylic acid tert-butyl ester instead of 4-N-Boc-4-Me-piperidine as intermediate B in Preparative Example Scheme 1. The de-Boc and acylation with acryloyl chloride were done in the same way as in Example 21. LC-MS: m/z 590.2 (ES+), 588.3 (ES−).

Example 23

2-(2-{4-[4-(4-Acryloylamino-benzenesulfonyl)-piperazin-1-yl]-2-methoxy-phenylamino}-5-chloro-pyrimidin-4-ylamino)-N-methyl-benzamide (IV-31)

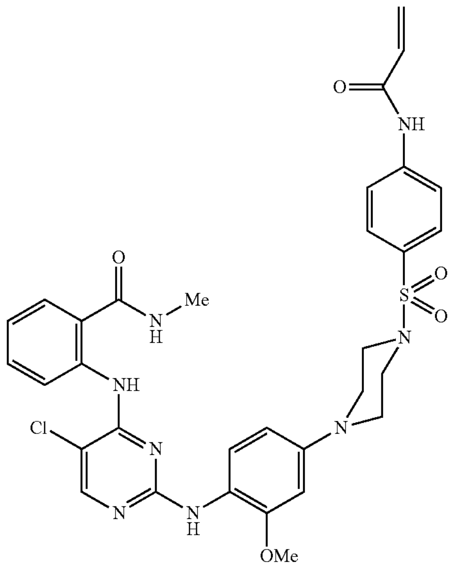 [SMILES: C=CC(=O)Nc1ccc(S(=O)(=O)N2CCN(c3ccc(Nc4ncc(Cl)c(Nc5ccccc5C(=O)NC)n4)c(OC)c3)CC2)cc1]

The title compound was prepared in a process similar to that described in Example 21, but using 4-N-Boc-piperizine instead of 4-N-Boc-4-Me-piperidine as intermediate B in Preparative Example Scheme 1, and 4-nitrobenzenesulfonyl chloride in stead of 4-N-Boc-benzoic acid in Preparative Example Scheme 2. The nitro reduction was accomplished with $SnCl_2$ in refluxing MeOH. The final acylation with acryloyl chloride was done in the same way as in Example 21. LC-MS: m/z 677.2 (ES+).

Example 24

FAK Biochemical Assay

Activities of FAK inhibitors were assessed in an OMNIA® kinase assay (Invitrogen, Carlsbad, Calif.) using pre-activated FAK enzyme. Briefly, a 10× stock of pre-activated FAK enzyme (M4446) from Invitrogen (Madison, Wis.), 1.13×ATP (AS001A) and Y3-Sox conjugated peptide substrate (YP003A) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 μL of enzyme were pre-incubated in a Corning (#3574) 384-well, white, non-binding surface microtiter plate (Corning, N.Y.) for 30 min at 27° C. with a 0.5 μL volume of 50% DMSO and serially diluted compounds prepared in 50% DMSO. Kinase reactions were started with the addition of 45 μL of ATP/Y3-Sox peptide substrate mix and monitored every 30-90 seconds for 60 minutes at $\lambda_{ex}360/\lambda_{485}$ in a Synergy[4]

plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to ~30 minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.). The assay was run using the following concentrations of reagents FAK=15 nM, Y3-Sox=10 μM, ATP=100 μM, (ATP $K_{Mapp}$ 92 μM).

Compound IV-29 had an $IC_{50}$ of 5.24 nM in the assay, and compound IV-30 had an $IC_{50}$ of 5.89 nM in the assay.

Example 25

Mass Spectral Analysis

Intact FAK (PTK2) was incubated for 1 hr at a 10× fold access of compound IV-29 to protein. 3 ul aliquots of the samples were diluted with 10 ul of 0.1% TFA prior to micro C4 ZipTipping directly onto the MALDI target using Sinapinic acid as the desorption matrix (10 mg/ml in 0.1% TFA:Acetonitrile 50:50). Mass spec analysis was run on intact FAK (PTK2) protein (m/z 146,672 Da), and on FAK that was incubated with compound IV-29 (mw=669.2). The centroid mass (m/z=147,037 Da) showed a positive shift of about 365 Da with minimal unmodified protein remaining indicating almost complete modification of FAK (PTK2) by compound IV-29. Compound IV-30 did not modify FAK as assessed by mass spec, and compound IV-31 showed partial modification of FAK.

The teachings of all patents, published applications and references cited herein are incorporated by reference in their entirety. While this invention has been particularly shown and described with reference to example embodiments thereof, it will be understood by those skilled in the art that various changes in form and details may be made therein without departing from the scope of the invention encompassed by the appended claims.

SEQUENCE LISTING

```
<160> NUMBER OF SEQ ID NOS: 47

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Cys Val His Arg Asp Leu
1               5


<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Cys Ile His Arg Asp Leu
1               5


<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Cys Ile His Arg Asp Leu
1               5


<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 4

Asn Cys Ile His Arg Asp Val
1 5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Asn Cys Val His Arg Asp Leu
1 5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Asn Cys Val His Arg Asp Ile
1 5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Ser Cys Val His Arg Asp Leu
1 5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Cys Cys Ile His Arg Asp Leu
1 5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Asn Cys Ile His Arg Asp Ile
1 5

```
<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Cys Asp Phe Gly
1               5


<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Cys Asp Phe Gly
1               5


<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gly Cys Leu Arg Asp Phe
1               5


<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Gly Cys Leu Leu Asp Phe
1               5


<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Thr Cys Ala Glu Lys Leu
1               5


<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 15

His Gly Cys Leu Ser Asp Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Gly Cys Leu Leu Asn Tyr
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Gly Cys Leu Leu Asn Phe Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Gly Cys Leu Leu Asn Tyr Leu
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Gly Cys Leu Leu Asp Tyr Val
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Gly Cys Leu Leu Asp His Val
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

His Gly Cys Leu Leu Glu Tyr Val
1 5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Tyr Gly Arg Cys Gln Lys
1 5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Phe Ala Arg Cys Tyr Glu
1 5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Phe Ala Lys Cys Tyr Glu
1 5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Phe Ala Lys Cys Phe Glu
1 5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Asp Leu Cys Gln Tyr Met Asp
1 5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Asn Leu Cys Gln Val Ile His
1 5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Asn Leu Cys Gln Val Ile Gln
1 5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Ser Leu Cys Lys Tyr Leu Ser Leu
1 5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Ser Gly Cys Phe Gly Val
1 5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Gln Gly Cys Phe Gly Glu
1 5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Gly Cys Phe Gly Asp
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Gly Cys Phe Gly Gln
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Gly Cys Phe Gly Gln
1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Arg Cys Ile Gly Glu Gly Gln Phe Gly Asp
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Glu Cys Val Gly Lys Gly Arg Tyr Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Glu Cys Val Gly Lys Gly Arg Tyr Gly
1 5 10

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gly Cys Gly Asn Phe
1 5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gly Cys Gly His Phe
1 5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Gly Cys Gly Gly Asn
1 5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Tyr Cys Cys Tyr Gly
1 5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Tyr Met Cys His Gly
1 5

```
<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Phe Met Cys His Gly
1               5


<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Ala Arg Asn Cys Leu Leu Thr Cys Pro Gly Pro Gly Arg Val Ala
1               5                   10                  15

Lys Ile Gly Asp
            20


<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Lys Pro Gln Leu Ala Ile Val Thr Gln Trp Cys Glu Gly Ser Ser
1               5                   10                  15

Leu Tyr His His
            20


<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asn Cys Ile His Arg
1               5


<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Cys Asp Phe Gly Leu Ala Arg
1               5
```

What is claimed is:

1. A protein kinase conjugate that has the formula,

X—M—S—$CH_2$-Prot wherein, Prot is a human protein kinase or portion thereof comprising a cysteine residue containing amino acid sequence selected from the group consisting of SEQ ID NOs: 1, 6, 7, 8, 9, 26, 27, 28, 29, 30, 31, 32, 33, 35, 36, 37, 38, 39, 40, 41, 42, 43, 44, and 45;

S—$CH_2$ is the sulfur atom and methylene group from the side chain of said cysteine residue;

M is a modifier moiety that is formed by the covalent bonding of a warhead group with the side chain of said cysteine residue;

X is a chemical moiety that binds in or near the ATP binding site of the protein kinase; and wherein the protein kinase conjugate is formed in association with a cell.

2. The conjugate of claim 1, wherein the warhead group is -L-Y, wherein

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —CH(OH)—, —C(O)O—, —S—, —SO—, —$SO_2$—, —C(═S)—, —C(═NR)—, —N═N—, or —C(═$N_2$)—;

Y is hydrogen, nitrile, $C_{1-6}$ aliphatic optionally substituted with one or more OH, NRxRy, oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and R, Rx and Ry are independently hydrogen, lower alkyl, lower haloalkyl, or lower cycloalkyl;

each $R^e$ is independently selected from -Q-Z, OH, oxo, $NO_2$, halogen, CN, a suitable leaving group, or a $C_{1-6}$ aliphatic optionally substituted with oxo, halogen, $NO_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

3. The conjugate of claim 1, wherein the warhead group is

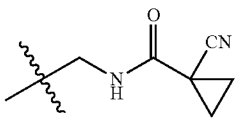
a

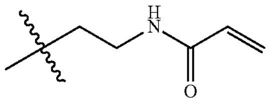
b

-continued

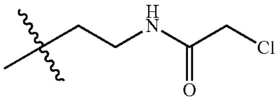
c

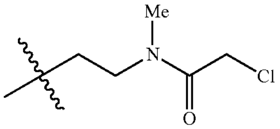
d

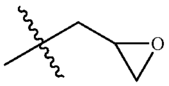
e

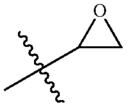
f

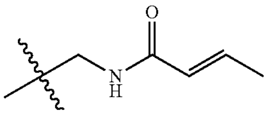
g

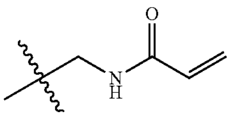
h

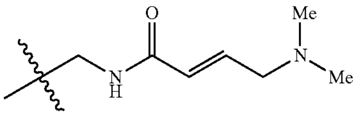
i

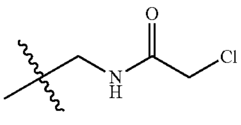
j

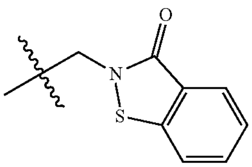
k

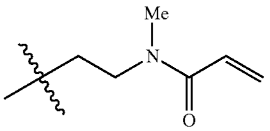
l

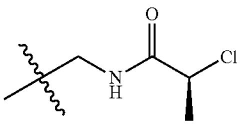
m

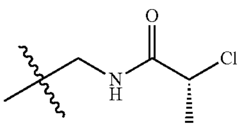
n

-continued
o
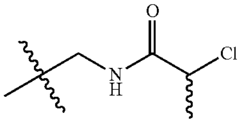
p
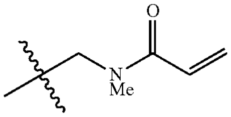
q
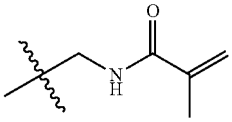
r
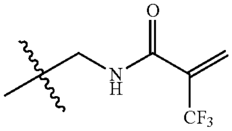
s
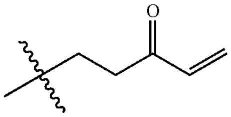
t
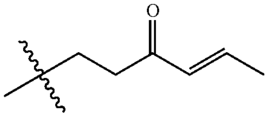
u
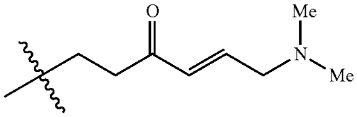
v
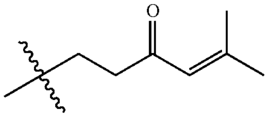
w
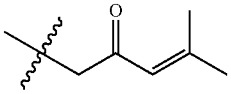
x
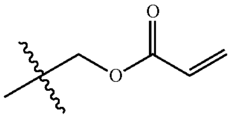
y
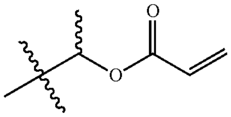
z
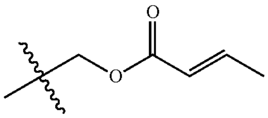
-continued
aa
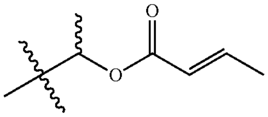
bb
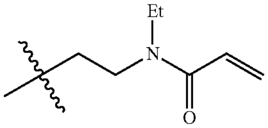
cc
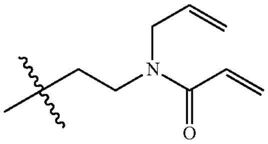
dd
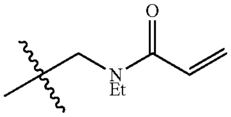
ee
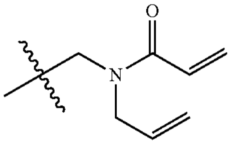
ff
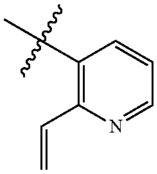
gg
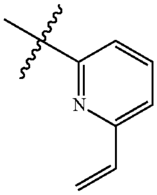
hh
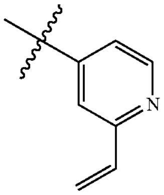
ii
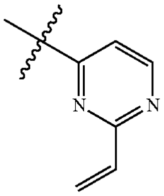

-continued
jj
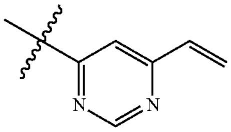
kk
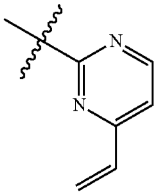
ll
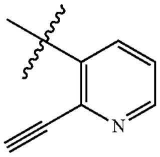
mm
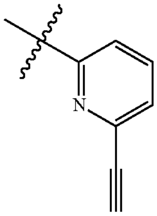
nn
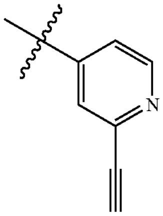
oo
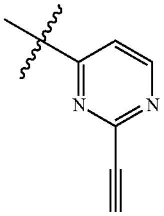
pp
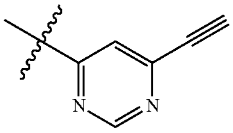
qq
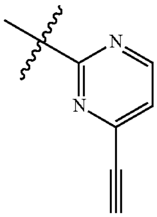
-continued
rr
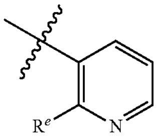
ss
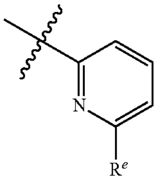
tt
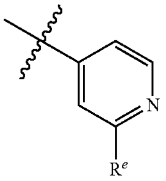
uu
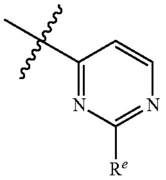
vv
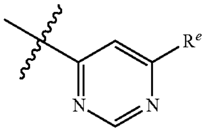
ww
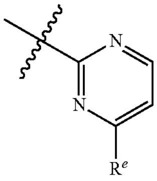
xx
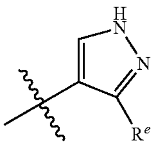
yy
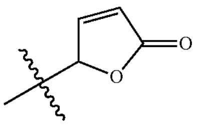
zz
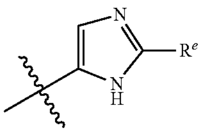

-continued
aaa
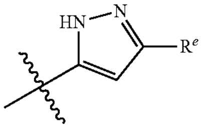
bbb
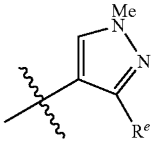
ccc
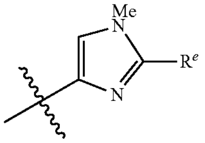
ddd
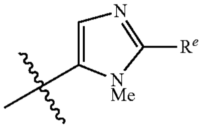
eee
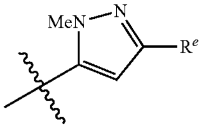
fff
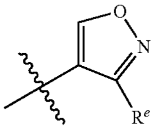
ggg
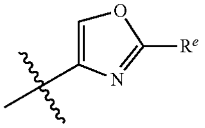
hhh
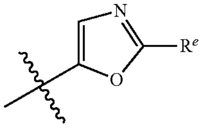
iii
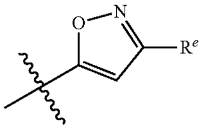
jjj
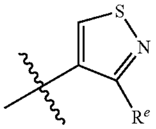
kkk
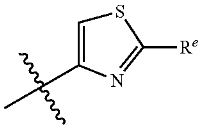
-continued
lll
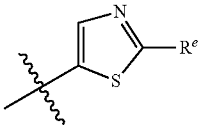
mmm
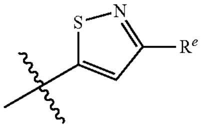
nnn
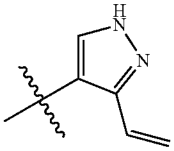
ooo
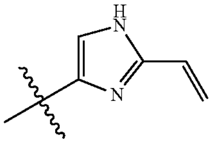
ppp
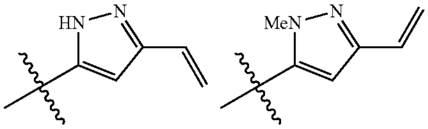
qqq
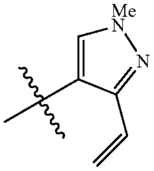
rrr
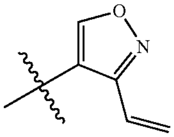
sss
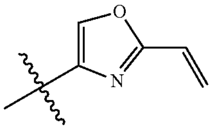
ttt
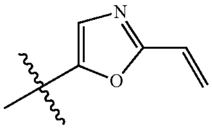
uuu
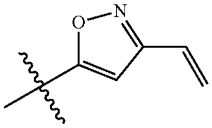

-continued
vvv
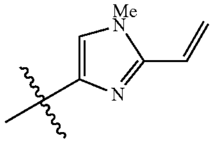
www
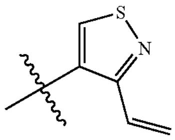
xxx
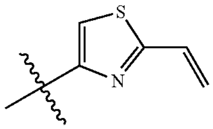
yyy
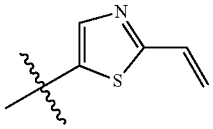
zzz
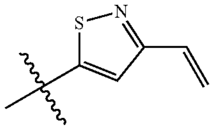
aaaa
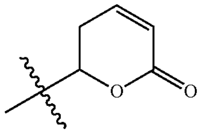
bbbb
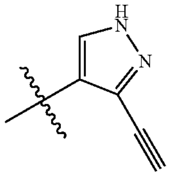
cccc
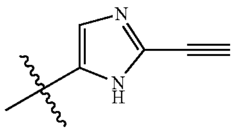
dddd
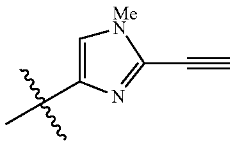
eeee
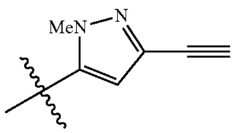
-continued
ffff
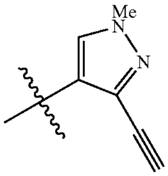
gggg
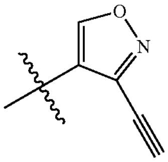
hhhh
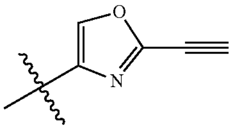
iiii
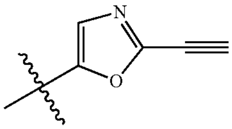
jjjj
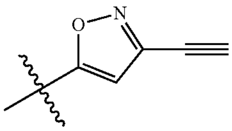
kkkk
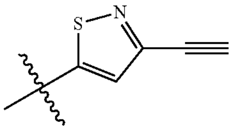
llll
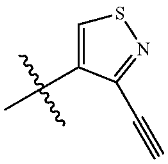
mmmm
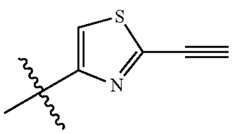
nnnn
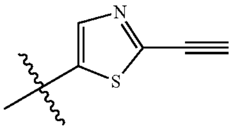
oooo
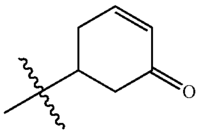

-continued
pppp
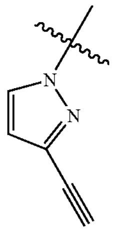
qqqq
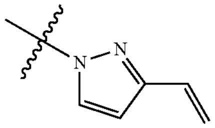
rrrr
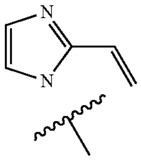
ssss
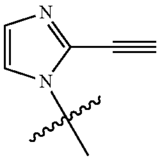
tttt
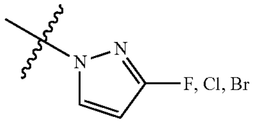
uuuu
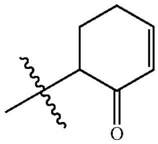
vvvv
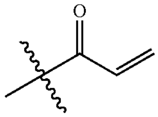
wwww
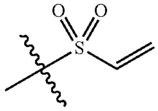
xxxx
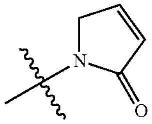
yyyy
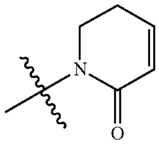
-continued
zzzz
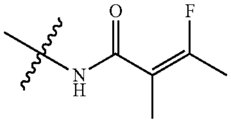
aaaaa
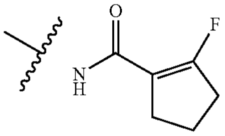
bbbbb
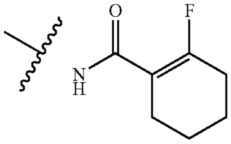
ccccc
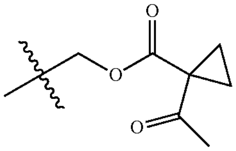
ddddd
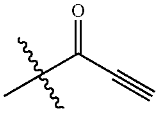
eeeee
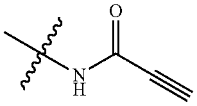
fffff
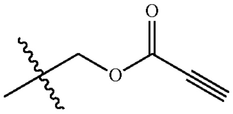
ggggg
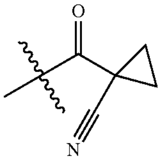
hhhhh
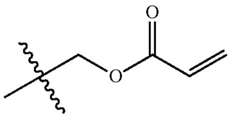
iiiii
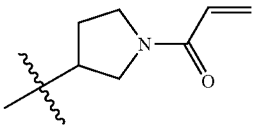
jjjjj
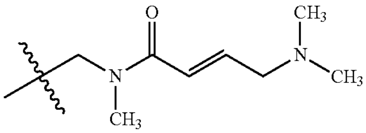

-continued
kkkkk
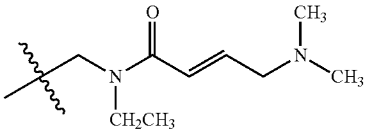
lllll
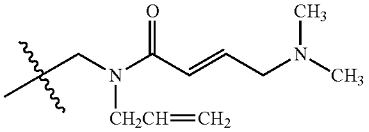
mmmmm
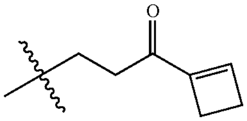
nnnnn
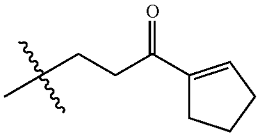
ooooo
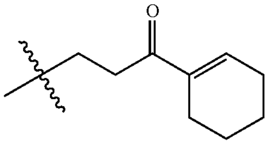
ppppp
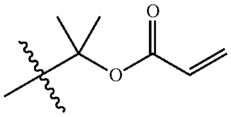
qqqqq
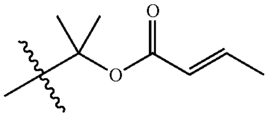
rrrrr
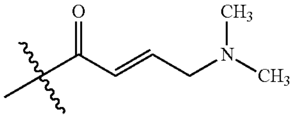
sssss
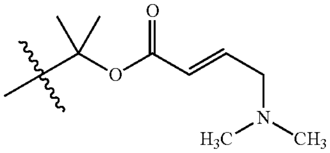
ttttt
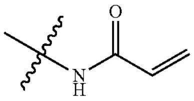
uuuuu
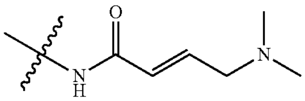
-continued
vvvvv
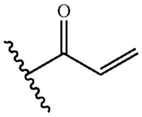
wwwww
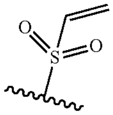
xxxxx
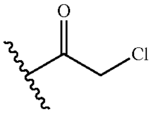
yyyyy
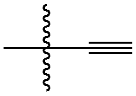
zzzzz
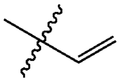
aaaaaa
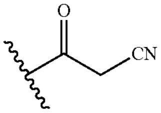
bbbbbb
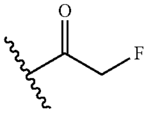
cccccc
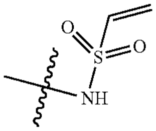
dddddd
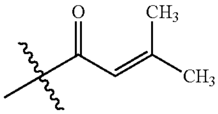
eeeeee
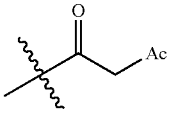
ffffff
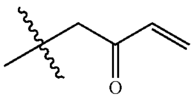
gggggg
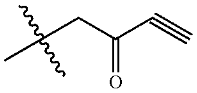
hhhhhh
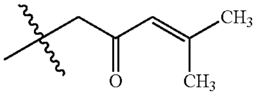

-continued iiiii

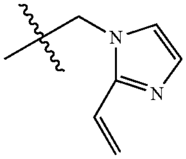

jjjjj

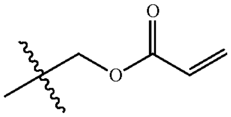

kkkkkk

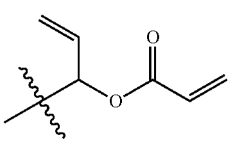

llllll

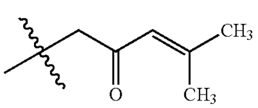

mmmmmm

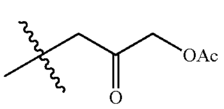

nnnnnn

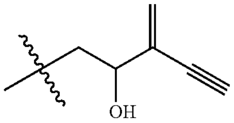

oooooo

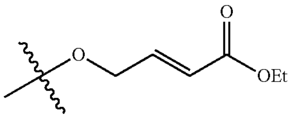

pppppp

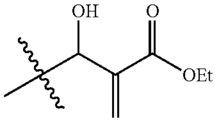

qqqqqq

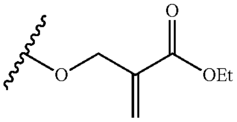

rrrrrr

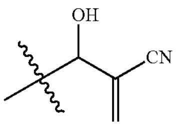

ssssss

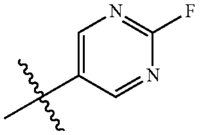

tttttt

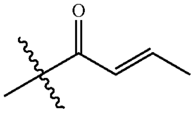

-continued uuuuuu

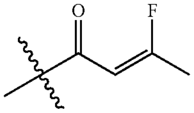

vvvvvv

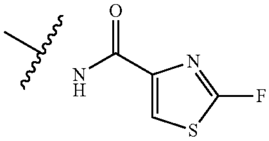

wwwwww

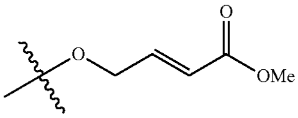

xxxxxx

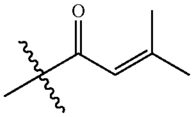

or yyyyyy

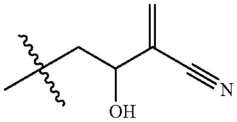

wherein each $R^e$ is independently a suitable leaving group, $NO_2$, CN, or oxo.

4. The conjugate of claim 1, wherein the modifier moiety taken together with the side chain Sulfur and methylene of the cysteine residue have a formula selected from the group consisting of a

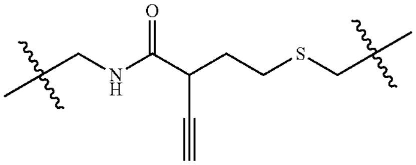

b

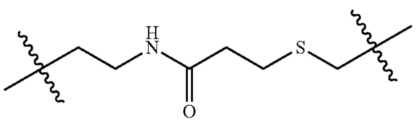

c

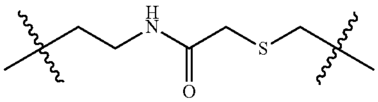

d

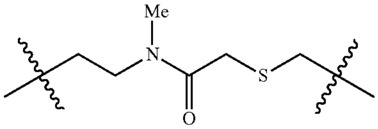

e

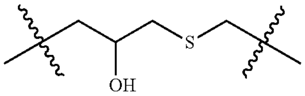

f
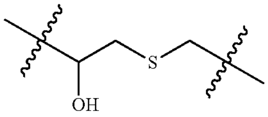
g
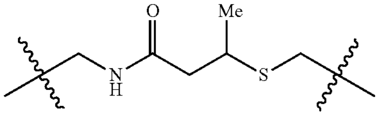
h
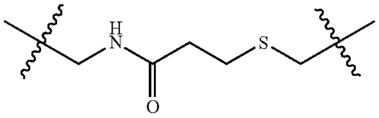
i
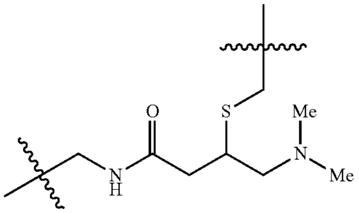
j
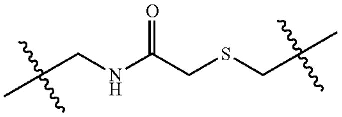
k
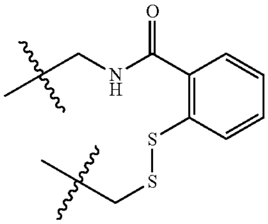
l
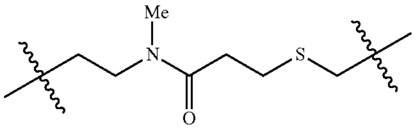
m
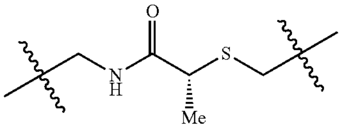
n
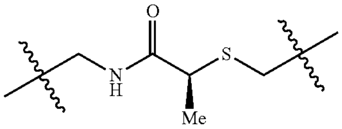
o
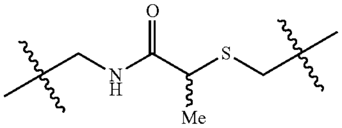
p
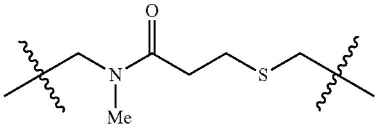
q
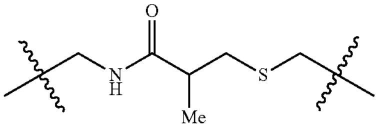
r
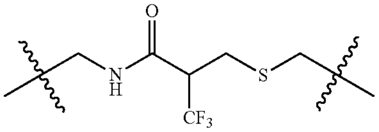
s
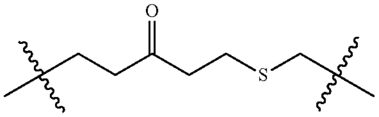
t
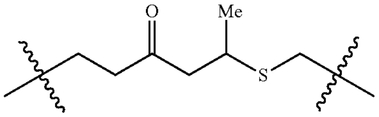
u
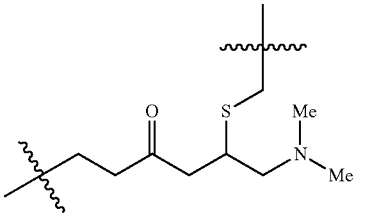
v
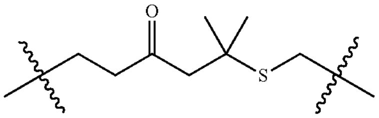
w
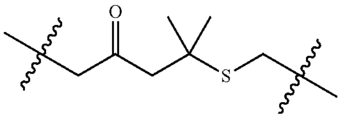
x
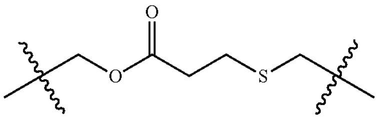
y
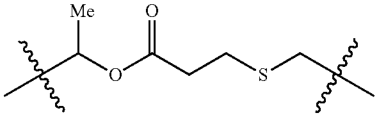
z
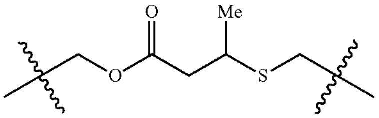

-continued
aa
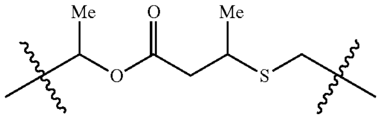
bb
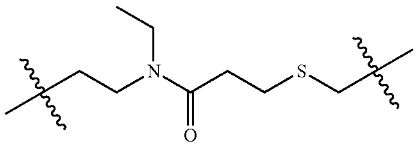
cc
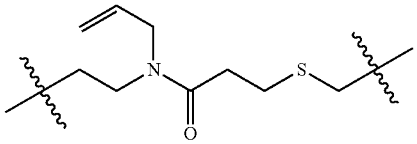
dd
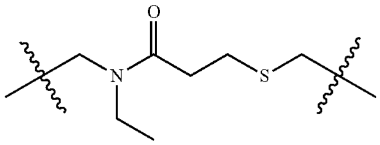
ee
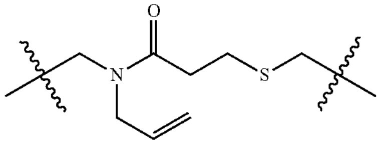
ff
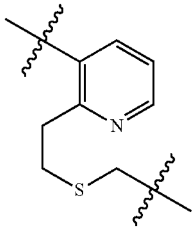
gg
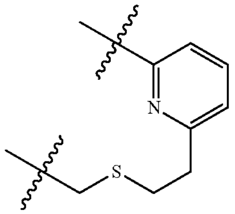
hh
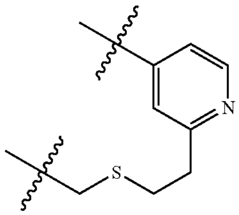
-continued
ii
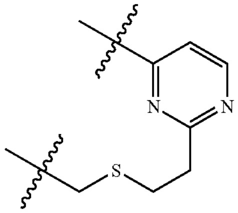
jj
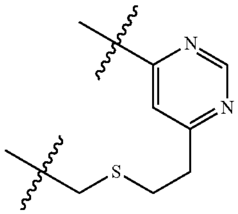
kk
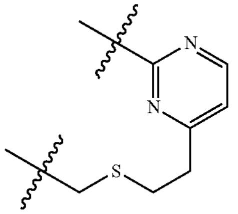
ll
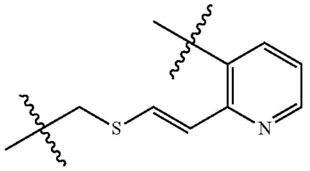
mm
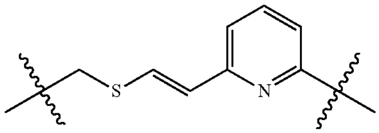
nn
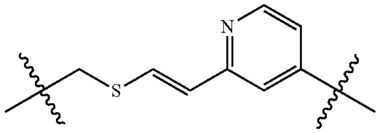
oo
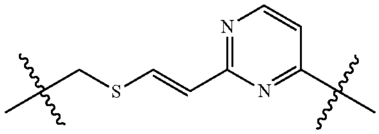
pp
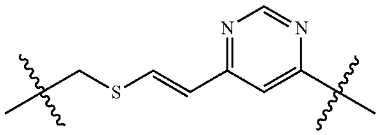
qq
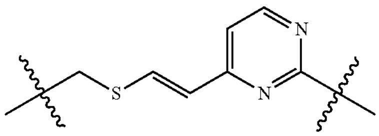

-continued
rr
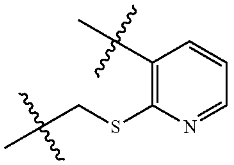
ss
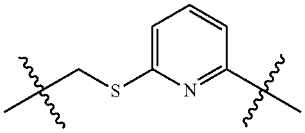
tt
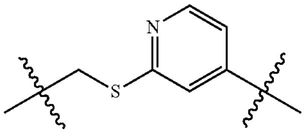
uu
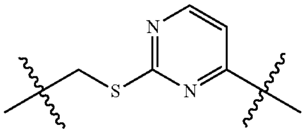
vv
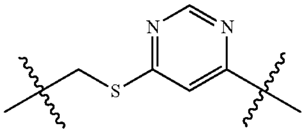
ww
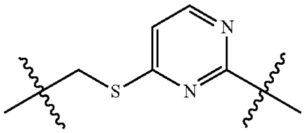
xx
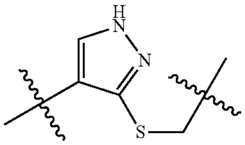
yy
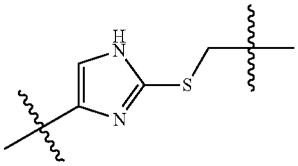
zz
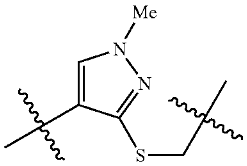
aaa
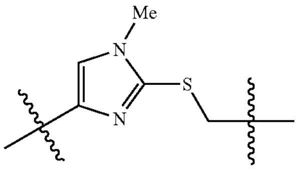
-continued
bbb
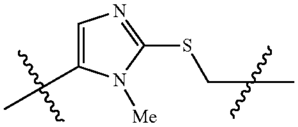
ccc
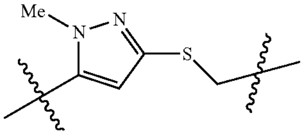
ddd
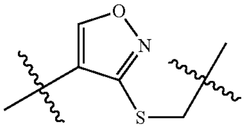
eee
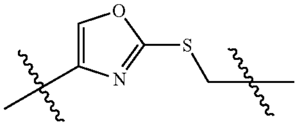
fff
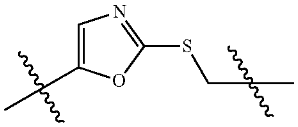
ggg
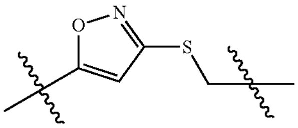
hhh
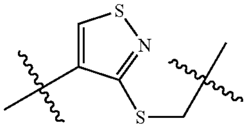
iii
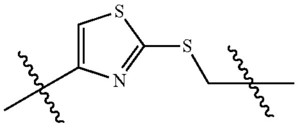
jjj
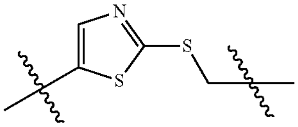
kkk
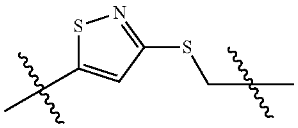
lll
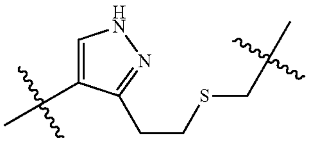

-continued
mmm
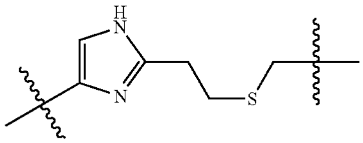
nnn
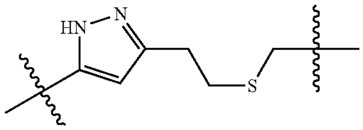
ooo
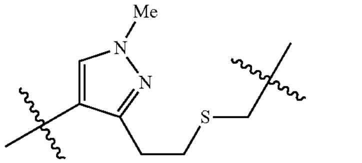
ppp
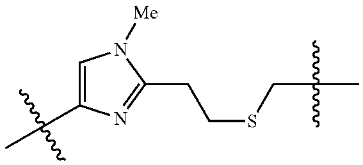
qqq
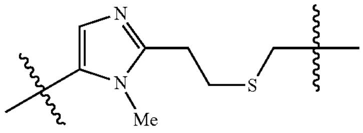
rrr
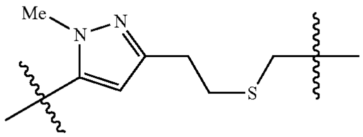
sss
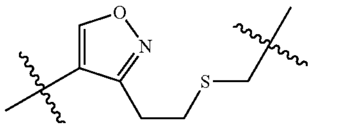
ttt
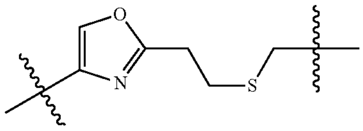
uuu
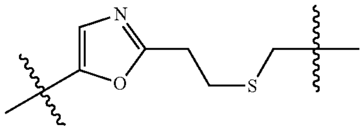
vvv
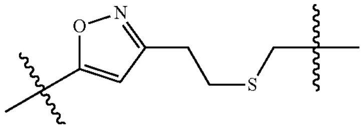
-continued
www
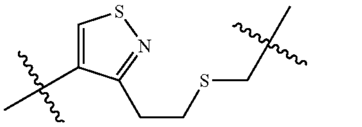
xxx
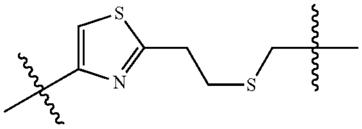
yyy
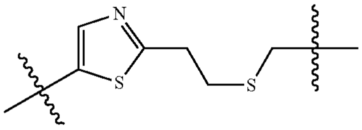
zzz
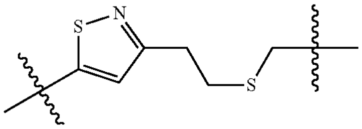
aaaa
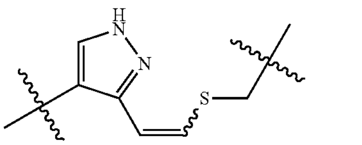
bbbb
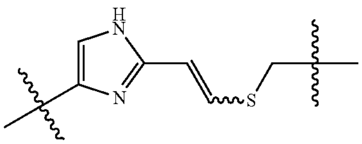
cccc
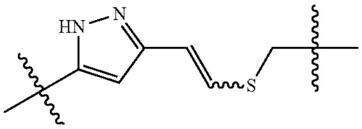
dddd
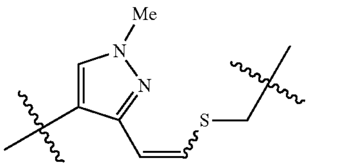
eeee
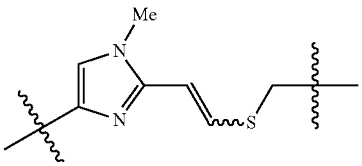
ffff
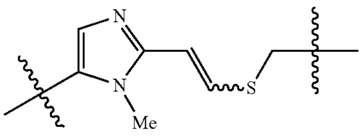

-continued
gggg
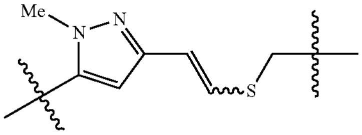
hhhh
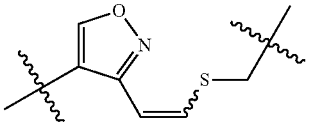
iiii
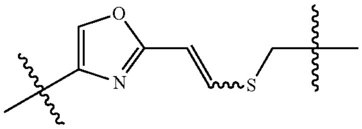
jjjj
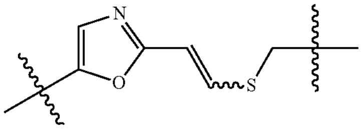
kkkk
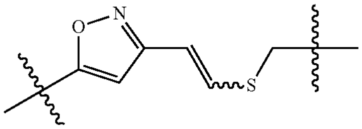
llll
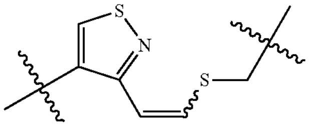
mmmm
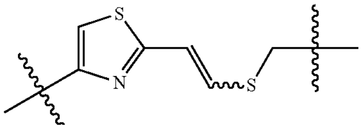
nnnn
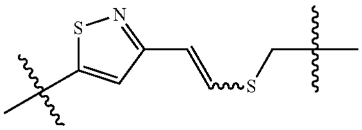
oooo
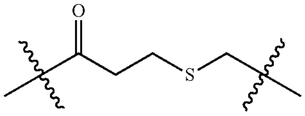
pppp
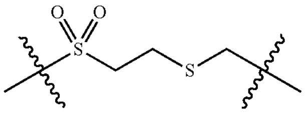
qqqq
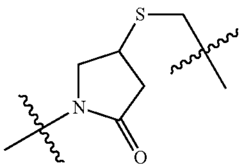
-continued
rrrr
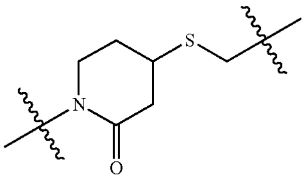
ssss
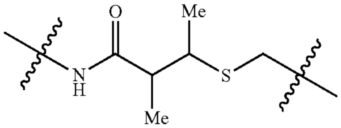
tttt
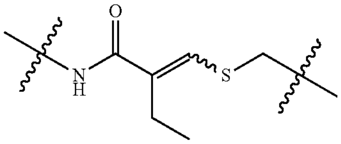
uuuu
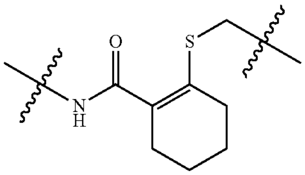
vvvv
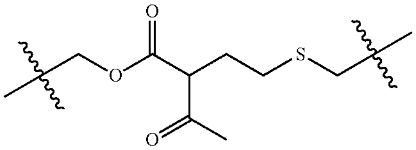
wwww
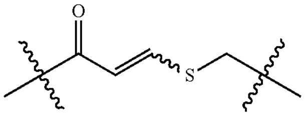
xxxx
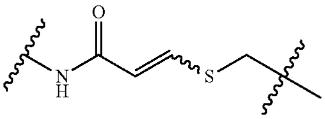
yyyy
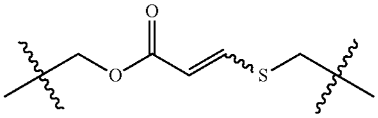
zzzz
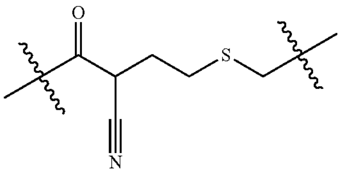
aaaaa
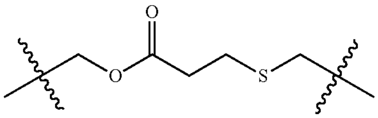

-continued

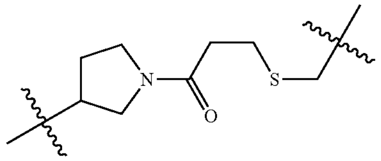

bbbbb

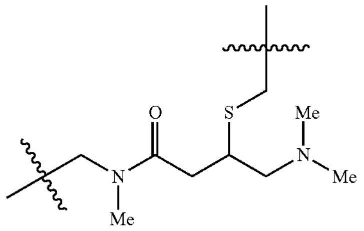

ccccc

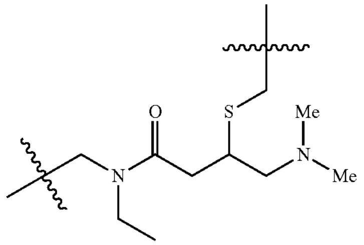

ddddd

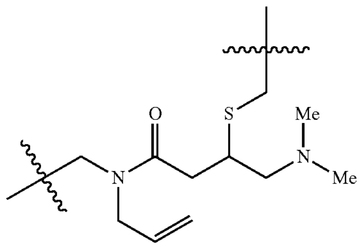

eeeee and

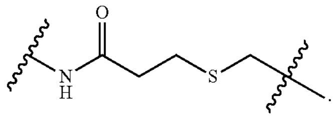

fffff

5. The conjugate of claim 1, wherein Prot is a kinase or portion of a kinase comprising an amino acid sequence selected from the group consisting of SEQ ID NOs: 1, 6, 7, 8, and 9.

6. The conjugate of claim 1, wherein Prot is a kinase selected from the group consisting of JAK3, C-KIT, FAK2, FLT3, FES, CDKL4, or wherein Prot is a portion of JAK3 wherein the portion of JAK3 comprises the amino acid sequence of SEQ ID NO:1, a portion of C-KIT wherein the portion of C-KIT comprises the amino acid sequence of SEQ ID NO: 41, a portion of FAK2 wherein the portion of FAK2 comprises the amino acid sequence of SEQ ID NO:6, a portion of FLT3 wherein the portion of FLT3 comprises the amino acid sequence of SEQ ID NO:7 or 41, a portion of FES wherein the portion of FES comprises the amino acid sequence of SEQ ID NO:8, or a portion of CDKL4 wherein the portion of CDLK4 comprises the amino acid sequence of SEQ ID NO:9.

7. The conjugate of claim 1, wherein Prot is a kinase or portion of a kinase comprising a cysteine residue containing amino acid sequence selected from the group consisting of SEQ ID NOs: 26, 27, 28 and 29.

8. The conjugate of claim 1, wherein Prot is a kinase selected from the group consisting of PFTAIRE1, JNK1, JNK2, JNK3, BMPR2, or wherein Prot is a portion of PFTAIRE1 wherein the portion of PFTAIRE1 comprises the amino acid sequence of SEQ ID NO:26, a portion of JNK1 wherein the portion of JNK1 comprises the amino acid sequence of SEQ ID NO:28, a portion of JNK2 wherein the portion of JNK2 comprises the amino acid sequence of SEQ ID NO:27, a portion of JNK3 wherein the portion of JNK3 comprises the amino acid sequence of SEQ ID NO:28, or a portion of BMPR2 wherein the portion of BMPR2 comprises the amino acid sequence of SEQ ID NO:29.

9. The conjugate of claim 1, wherein Prot is a kinase or portion of a kinase comprising a cysteine residue containing amino acid sequence selected from the group consisting of SEQ ID NOs: 30, 31, 32 and 33.

10. The conjugate of claim 1, wherein Prot is a kinase selected from the group consisting of TNK1, YES, FGR, SRC, LIMK1, or wherein Prot is a portion of TNK1 wherein the portion of TNK1 comprises the amino acid sequence of SEQ ID NO:30, a portion of YES wherein the portion of YES comprises the amino acid sequence of SEQ ID NO:31, a portion of FOR wherein the portion of FOR comprises the amino acid sequence of SEQ ID NO:32, a portion of SRC wherein the portion of SRC comprises the amino acid sequence of SEQ ID NO:31, or a portion of LIMK1 wherein the portion of LIMK1 comprises the amino acid sequence of SEQ ID NO:33.

11. The conjugate of claim 1, wherein Prot is a kinase or portion of a kinase comprising a cysteine residue containing amino acid sequence selected from the group consisting of SEQ ID NOs: 35, 36 and 37.

12. The conjugate of claim 1, wherein Prot is a kinase selected from the group consisting of FAK, ALK1, ALK2, or wherein Prot is a portion of FAK wherein the portion of FAK comprises the amino acid sequence of SEQ ID NO:35, a portion of ALK1 wherein the portion of ALK1 comprises the amino acid sequence of SEQ ID NO:36, a portion of ALK2 wherein the portion of ALK2 comprises the amino acid sequence of SEQ ID NO:37.

13. The conjugate of claim 1, wherein Prot is a kinase or portion of a kinase comprising a cysteine residue containing amino acid sequence selected from the group consisting of SEQ ID NOs: 38, 39 and 40.

14. The conjugate of claim 1, wherein Prot is a kinase selected from the group consisting of ZAP70, CRIK, ERK3, CK1g1, CK1g2, CK1g3, or wherein Prot is a portion of ZAP70 wherein the portion of ZAP70 comprises the amino acid sequence of SEQ ID NO:38, a portion of CRIK wherein the portion of CRIK comprises the amino acid sequence of SEQ ID NO:39, a portion of ERK3 wherein the portion of ERK3 comprises the amino acid sequence of SEQ ID NO:40, a portion of CK1g1 wherein the portion of CK1g1 comprises the amino acid sequence of SEQ ID NO:38, or a portion of CK1g2 wherein the portion of CK1g2 comprises the amino acid sequence of SEQ ID NO:38, or a portion of CK1g3 wherein the portion of CK1g3 comprises the amino acid sequence of SEQ ID NO:38.

15. The conjugate of claim 1, wherein Prot is a kinase or portion of a kinase comprising a cysteine residue containing amino acid sequence selected from the group consisting of SEQ ID NOs: 41, 42, and 43.

16. The conjugate of claim 1, wherein Prot is a kinase selected from the group consisting of FMS, RON, FGR, or wherein Prot is a portion of FMS wherein the portion of FMS comprises the amino acid sequence of SEQ ID NO:41, a portion of RON wherein the portion of RON comprises the amino acid sequence of SEQ ID NO:42, or a portion of FGR wherein the portion of FGR comprises the amino acid sequence of SEQ ID NO:43.

17. The conjugate of claim 1, wherein Prot is a kinase or portion of a kinase comprising a cysteine residue containing amino acid sequence of SEQ ID NO:44.

18. The conjugate of claim 1, wherein Prot is ALK or a portion thereof that comprises a cystein residue containing amino acid sequence of SEQ ID NO:44.

19. The conjugate of claim 1, wherein Prot is a kinase or portion of a kinase comprising a cysteine residue containing amino acid sequence of SEQ ID NO:45.

20. The conjugate of claim 1, wherein Prot is B-RAF or a portion thereof that comprises a cysteine residue containing amino acid sequence of SEQ ID NO:45.

21. The conjugate of claim 1, wherein, if the protein kinase is JAK3, the cysteine residue is Cys945.

22. The conjugate of claim 1, wherein Prot is C-KIT or a portion thereof, wherein the C-KIT or a portion thereof comprises the amino acid sequence SEQ ID NO: 41.

23. The conjugate of claim 6, wherein Prot is C-KIT or a portion thereof, wherein the C-KIT or a portion thereof comprises the amino acid sequence SEQ ID NO: 41.

24. The conjugate of claim 6, wherein Prot comprises the amino acid sequence SEQ ID NO:41.

25. The conjugate of claim 1, wherein the cysteine residue containing amino acid sequence is SEQ ID NO:1.

26. The conjugate of claim 1, wherein the cysteine residue containing amino acid sequence is SEQ ID NO:6.

27. The conjugate of claim 1, wherein the cysteine residue containing amino acid sequence is SEQ ID NO:7.

28. The conjugate of claim 1, wherein the cysteine residue containing amino acid sequence is SEQ ID NO:8.

29. The conjugate of claim 1, wherein the cysteine residue containing amino acid sequence is SEQ ID NO:9.

30. The conjugate of claim 1, wherein the cysteine residue containing amino acid sequence is SEQ ID NO:26.

31. The conjugate of claim 1, wherein the cysteine residue containing amino acid sequence is SEQ ID NO:27.

32. The conjugate of claim 1, wherein the cysteine residue containing amino acid sequence is SEQ ID NO:28.

33. The conjugate of claim 1, wherein the cysteine residue containing amino acid sequence is SEQ ID NO:29.

34. The conjugate of claim 1, wherein the cysteine residue containing amino acid sequence is SEQ ID NO:30.

35. The conjugate of claim 1. wherein the cysteine residue containing amino acid sequence is SEQ ID NO:31.

36. The conjugate of claim 1, wherein the cysteine residue containing amino acid sequence is SEQ ID NO:32.

37. The conjugate of claim 1, wherein the cysteine residue containing amino acid sequence is SEQ ID NO:33.

38. The conjugate of claim 1, wherein the cysteine residue containing amino acid sequence is SEQ ID NO:35.

39. The conjugate of claim 1, wherein the cysteine residue containing amino acid sequence is SEQ ID NO:36.

40. The conjugate of claim 1, wherein the cysteine residue containing amino acid sequence is SEQ ID NO:37.

41. The conjugate of claim 1, wherein the cysteine residue containing amino acid sequence is SEQ ID NO:38.

42. The conjugate of claim 1, wherein the cysteine residue containing amino acid sequence is SEQ ID NO:39.

43. The conjugate of claim 1, wherein the cysteine residue containing amino acid sequence is SEQ ID NO:40.

44. The conjugate of claim 1, wherein the cysteine residue containing amino acid sequence is SEQ ID NO:41.

45. The conjugate of claim 1, wherein the cysteine residue containing amino acid sequence is SEQ ID NO:42.

46. The conjugate of claim 1, wherein the cysteine residue containing amino acid sequence is SEQ ID NO:43.

47. The conjugate of claim 1, wherein the cysteine residue containing amino acid sequence is SEQ ID NO:44.

48. The conjugate of claim 1, wherein the cysteine residue containing amino acid sequence is SEQ ID NO:45.

* * * * *